US012617795B2

(12) United States Patent
Jarvis et al.

(10) Patent No.: US 12,617,795 B2
(45) Date of Patent: May 5, 2026

(54) SUBSTITUTED 6,7-DIHYDRO-5H-PYRROLO [3,4-D] PYRIMIDINES, 5,7-DIHYDROFURO [3,4-D]PYRIMIDINES, AND PYRIDO [2,3-D]PYRIMIDINES AS KCC2 MODULATORS

(71) Applicant: Astrazeneca AB, Södertälje (SE)

(72) Inventors: Rebecca Elizabeth Jarvis, Cambridge (GB); Roland Werner Bürli, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 673 days.

(21) Appl. No.: 17/911,051

(22) PCT Filed: Mar. 12, 2021

(86) PCT No.: PCT/EP2021/056393
§ 371 (c)(1),
(2) Date: Sep. 12, 2022

(87) PCT Pub. No.: WO2021/180952
PCT Pub. Date: Sep. 16, 2021

(65) Prior Publication Data

US 2023/0151013 A1 May 18, 2023

Related U.S. Application Data

(60) Provisional application No. 62/989,104, filed on Mar. 13, 2020.

(51) Int. Cl.
*A61K 31/519* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ A61K 31/519; C07D 487/04
USPC ........................................ 514/258.1; 544/253
See application file for complete search history.

(56) References Cited

FOREIGN PATENT DOCUMENTS

| | | | |
|---|---|---|---|
| WO | 9510506 | A1 | 4/1995 |
| WO | 2008136756 | A1 | 11/2008 |
| WO | 2010020905 | A1 | 2/2010 |
| WO | 2015131080 | A1 | 9/2015 |
| WO | 2018217766 | A1 | 11/2018 |
| WO | 2019045824 | A1 | 3/2019 |
| WO | 2019226643 | A1 | 11/2019 |

OTHER PUBLICATIONS

Examination Report for Australian application No. 2021234134, Apr. 2, 2025, 4 pages.

Delpire, Eric, et al., "Small-molecule screen identifies inhibitors of the neuronal K—Cl cotransporter KCC2," Proceedings of the National Academy of Sciences, Mar. 2009, pp. 5383-5388, 106.13.

International Search Report for PCT/EP2021/056393 dated May 4, 2021, 4 pages.

Galanopoulou, Aristea S., "Developmental patterns in the regulation of chloride homeostasis and GABAA receptor signaling by seizures," Epilepsia, Sep. 2007, pp. 14-18, 48.

Huberfeld, Gilles, et al., "Perturbed chloride homeostasis and GABAergic signaling in human temporal lobe epilepsy," Journal of Neuroscience, Sep. 2007, pp. 9866-9873, 27.37.

Price, Theodore J., et al., "Role of cation-chloride-cotransporters (CCC) in pain and hyperalgesia," Current topics In medicinal chemistry, Jun. 2005, pp. 547-555, 5.6.

Tang, Xin, et al., "Pharmacological enhancement of KCC2 gene expression exerts therapeutic effects on human Rett syndrome neurons and Mecp2 mutant mice," Science translational medicine, Jul. 2019, eaau0164, 11.503.

Tyzio, Roman, et al., "Oxytocin-mediated GABA inhibition during delivery attenuates autism pathogenesis in rodent offspring," Science, Feb. 2014, pp. 675-679, 343.6171.

Merner, Nancy D., et al., "Regulatory domain or CpG site variation in SLC12A5, encoding the chloride transporter KCC2, in human autism and schizophrenia," Frontiers in cellular neuroscience, Oct. 2015, 10 pages, 386.

Boulenguez, Pascale, et al., "Down-regulation of the potassium-chloride cotransporter KCC2 contributes to spasticity after spinal cord injury," Nature medicine, Mar. 2010, pp. 302-307, 16.3.

Fuchs, Andrea, et al., "Downregulation of the potassium chloride cotransporter KCC2 in vulnerable motoneurons in the SOD1-G93A mouse model of amyotrophic lateral sclerosis," Journal of Neuropathology & Experimental Neurology, Oct. 2010, pp. 1057-1070, 69.10.

Hubner, Christian A., et al., "Disruption of KCC2 reveals an essential role of K—Cl cotransport already in early synaptic inhibition," Neuron, May 2001, pp. 515-524, 30.2.

Woo, Nam-Sik, et al., "Hyperexcitability and epilepsy associated with disruption of the mouse neuronal-specific K—Cl cotransporter gene," Hippocampus, Feburary 2002, pp. 258-268, 12.2.

(Continued)

*Primary Examiner* — Douglas M Willis
(74) *Attorney, Agent, or Firm* — Carter, DeLuca & Farrell LLP

(57) ABSTRACT

The invention concerns compounds of Formula (I):

(I)

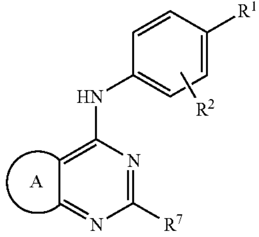

or pharmaceutically acceptable salts thereof, wherein $R^1$, $R^2$, $R^7$ and ring A have any of the meanings hereinbefore defined in the description; process for their preparation; pharmaceutical compositions containing them and their use in treating KCC2 mediated diseases.

35 Claims, No Drawings

(56) References Cited

OTHER PUBLICATIONS

Duy, Phan Q., et al., "Identification of KCC2 mutations in human epilepsy suggests strategies for therapeutic transporter modulation," Frontiers in Cellular Neuroscience, Nov. 2019, 6 pp. 13, 515.
De Araujo Furtado, Marcio, et al., "Exposure to nerve agents: from status epilepticus to neuroinflammation, brain damage, neurogenesis and epilepsy," Neurotoxicology, Dec. 2012, pp. 1476-1490, 33.6.
Moore, Yvonne E., et al., "Potentiating KCC2 activity is sufficient to limit the onset and severity of seizures," Proceedings of the National Academy of Sciences, Oct. 2018, pp. 10166-10171, 115. 40.
Cordshagen, Antje, et al., "Phosphoregulation of the intracellular termini of K+-Cl-cotransporter 2 (KCC2) enables flexible control of its activity," Journal of Biological Chemistry, Nov. 2018, pp. 16984-16993, 293.44.
Zhang, Di, et al., "A thallium transport FLIPR-based assay for the identification of KCC2-positive modulators," Journal of Biomolecular screening, Feb. 2010, pp. 177-184, 15.2.
English Translation of Japanese Office Action for application No. 2022-554784 Feb. 4, 2025, 8 pages.
Written Opinion for Singapore application No. 11202252597C, Aug. 15, 2025, 8 pages.
English Translation of Office Action for Columbian patent application No. NC2022/0012884, Sep. 30, 2025, 17 pages.
Examination Report for Indian application No. 202217052089, Jan. 15, 2026, 7 pages.

SUBSTITUTED 6,7-DIHYDRO-5H-PYRROLO[3,4-D]PYRIMIDINES, 5,7-DIHYDROFURO[3,4-D]PYRIMIDINES, AND PYRIDO[2,3-D]PYRIMIDINES AS KCC2 MODULATORS

FIELD

The specification generally relates to fused amino pyrimidine compounds and pharmaceutically acceptable salts thereof. These compounds and their pharmaceutically acceptable salts selectively modulate KCC2, and the specification therefore also relates to the use of such compounds and salts thereof to treat or prevent KCC2 mediated disease, including neurological disorders. The specification further relates to pharmaceutical compositions comprising such compounds and salts; methods of manufacture of such compounds and salts; and to methods of treating KCC2 mediated disease, including neurological disorders, using such compounds and salts.

BACKGROUND

KCC2 is an electro-neutral membrane transporter, encoded by the SLC12A5 gene, that plays a key role in inhibitory neurotransmission. KCC2 couples the efflux of $K^+$ and $Cl^-$ ions across the membrane of neurons, resulting in the maintenance of a low intracellular chloride concentration. Low intracellular levels of chloride are essential for $GABA_A$ receptor-mediated signalling, relying as it does on the ligand gated influx of $Cl^-$ ions to hyperpolarise the neuronal membrane, resulting in inhibition of action potential firing.

$GABA_A$ signalling is the major inhibitory neurotransmitter mechanism in the adult brain and consequently KCC2 has a key role in normal neurodevelopment and various neurological disorders. Decreased activity of KCC2 has been implicated in the pathogenesis of neurological disorders including epilepsy (Galanopoulou et al, Epilepsia 2007; 48:14-18; Huberfield et al, The Journal of Neuroscience (2007) 27, 9866-9873), neuropathic pain (Price et al, Curr Top Med Chem 2005; 5:547-555), Rett's syndrome (Tang et al, 2019, Translational Medicine, 11(503)), autism (Tyzio et al, Science 343, 675-679, Merner et al, Frontiers in cellular neuroscience 9, 2015), mental disorders, spinal cord injury (Boulenguez et al, Nature Medicine 2010, 16, 302-307) and conditions in which there is neuronal hyperexcitability such as ALS (Fuchs et al, Journal of Neuropathology & Experimental Neurology, Volume 69, Issue 10, October 2010, Pages 1057-1070).

Increasing the expression level or activity of KCC2 is a therapeutic approach to treat diseases linked to neuronal hyperexcitability. KCC2 is preferentially expressed in neurons, making it an ideal drug target for neurological disorders.

The genetic knockdown of KCC2 in mice leads to network hyperexcitability and spontaneous seizure activity (Hubner et al, Neuron 2001:30:515-524; Woo et al, Hippocampus 2002; 12:258-268).

Mutations in the KCC2 gene have been found in human patients with epilepsy (Duy et al, Front Cell Neurosci. 2019; 13: 515), reinforcing the link between KCC2 dysfunction and epilepsy and supporting the approach of KCC2 activation as a means to increase $Cl^-$ extrusion, restore GABA inhibition and treat disorders such as refractory epilepsy and status epilepticus.

Status epilepticus can be caused by nerve agents (de Araujo Furtado et al, 2012, *Neuro Toxicology,* 33(6), 1476-1490) and activation of KCC2 is a potential therapeutic option.

Recently it has been shown that potentiating KCC2 activity by genetic modification of its regulatory sites is sufficient to limit the onset and severity of seizures in mice (Moore et al, Proc Natl Acad Sci USA. 2018 Oct. 2; 115(40): 10166-10171).

KCC2 activity is modulated by phosphorylation at a number of regulation sites (Cordshagen et al, Journal of Biological Chemistry 2018, 293, 16984-16993) including phosphorylation at T1007 by STK39 and OSR1. KCC2 cell surface expression is regulated by phosphorylation at S940.

Direct modulation of KCC2 by interaction with small molecules has been reported. Delpire et al (Proc Natl Acad Sci USA. 2009 Mar. 31; 106(13): 5383-5388) describe an assay to identify small molecule inhibitors of KCC2 and Zhang et al (Journal of Biomolecular Screening 15(2): 2010) describe an assay used to identify positive modulators of KCC2.

There exists a need for new compounds which activate KCC2 and which are therefore useful in the treatment of neurological disorders.

SUMMARY

Briefly, this specification describes, in part, a compound of Formula (I):

(I)

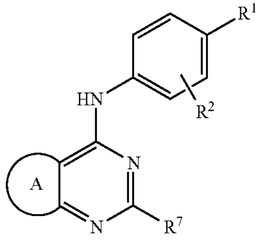

or a pharmaceutically acceptable salt thereof, wherein:

$R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{2-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$ and wherein aryl and heteroaryl are optionally substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl;

$R^2$ is selected from —H; -halo; and —$C_{1-3}$alkyl optionally substituted with 1, 2 or 3 substituents selected from —F and —$CF_3$;

A is selected from

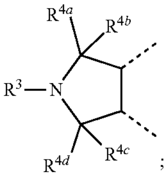
;
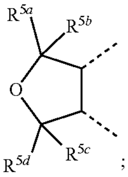
; and
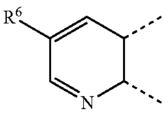

or a N-oxide thereof;

$R^3$ is selected from —H; —$C_{1-6}$alkyl; —$C_{2-6}$alkenyl; —$C_{2-6}$alkynyl; $C_{3-7}$cycloalkyl; and a 5 or 6 membered heterocycloalkyl; wherein the alkyl, alkenyl, alkynyl, cycloalkyl or heterocycloalkyl are optionally substituted by 1, 2 or 3 groups selected from —F, —$CF_3$, —$C_{1-3}$alkyl optionally substituted by 1 or 2 substituents selected from —F, —$CF_3$, —C(O)$NR^8R^9$ and —$NR^8R^9$;

$R^{4a}$ and $R^{4b}$ are each independently selected from —H and —$C_{1-3}$ alkyl optionally substituted with 1, 2 or 3 substituents selected from —F and $CF_3$;

$R^{4c}$ and $R^{4d}$ are each independently selected from —H and —$C_{1-3}$ alkyl optionally substituted with 1, 2 or 3 substituents selected from —F and $CF_3$, or $R^{4c}$ and $R^{4d}$ together with the carbon to which they are attached represent carbonyl;

$R^{5a}$, $R^{5b}$, $R^{5c}$ and $R^{5d}$ are each independently selected from —H and —$C_{1-3}$ alkyl optionally substituted with 1, 2 or 3 substituents selected from —F and $CF_3$;

$R^6$ is selected from —H; -halo; —$NH_2$; —CN; —$C_{1-3}$alkyl optionally substituted with 1, 2 or 3 substituents selected from —F and $CF_3$; —$C_{1-3}$alkoxy optionally substituted with 1, 2 or 3 substituents selected from —F and —$CF_3$; —C(O)O—$C_{1-3}$alkyl; —C(O)$NR^8R^9$; —C(O)OH; and —NHC(O)—$C_{1-3}$alkyl;

$R^7$ is selected from $NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1, 2 or 3 groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and $CF_3$; —C(O)OH; —$C_{1-3}$alkylene-NHC(O)$C_{1-6}$alkyl; —$C_{1-3}$alkylene-NHC(O)O$C_{1-6}$alkyl; $C_{3-5}$cycloalkyl; or the heterocycloalkyl is optionally substituted with two substituents on the same ring carbon which together with the carbon atom to which they are attached form a 5 to 7 membered monocyclic heterocycloalkyl; and wherein when $R^7$ is morpholinyl and $R^1$ is unsubstituted phenyl, $R^2$ is not —H;

$R^8$ and $R^9$ are each independently selected from —H and —$C_{1-6}$alkyl;

$R^{10}$ is —$C_{1-6}$alkyl;

$R^{11}$ is selected from —$C_{1-6}$alkyl optionally substituted with 1 or 2 substituents selected from —F and —$C_{1-3}$alkoxy; and —$(CH_2)R^{12}$;

$R^{12}$ is a 5 or 6 membered heteroaryl, a 3 to 5 membered cycloalkyl or a 3 to 6 membered heterocycloalkyl;

m is 0 or 1; and n is 1, 2 or 3.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of a neurological disorder.

This specification also describes, in part, a compound of Formula (I), or a pharmaceutically acceptable salt thereof, for the manufacture of a medicament for the treatment of a neurological disorder.

This specification also describes, in part, a method for treating a neurological disorder in a warm blooded animal in need of such treatment, which comprises administering to the warm-blooded animal a therapeutically effective amount of a compound of Formula (I), or a pharmaceutically acceptable salt thereof.

Further aspects of the disclosure will be apparent to one skilled in the art from reading this specification.

DESCRIPTION OF ILLUSTRATIVE EMBODIMENTS

Many embodiments are detailed throughout the specification and will be apparent to a reader skilled in the art. The specification is not to be interpreted as being limited to any particular embodiment(s) described herein.

In an embodiment there is provided a compound of Formula (I):

(I)

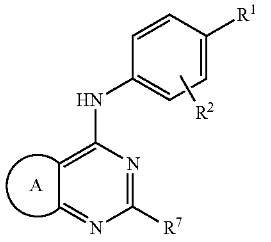

or a pharmaceutically acceptable salt thereof, wherein:

$R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{3-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$; and wherein aryl and heteroaryl are optionally substituted with 1 or 2 substituents selected from -halo, —$C_{1-3}$alkyl, —$C_{1-8}$alkoxy and —$C_{2-8}$alkynyloxy, wherein —$C_{1-3}$alkyl, —$C_{1-8}$alkoxy and —$C_{2-8}$alkynyloxy are optionally substituted with 1, 2, or 3 substituents selected from —F, —$CF_3$ and —NHC(O)O—$C_{1-6}$alkyl or two substituents together with the carbon to which they are attached form diazirinyl;

$R^2$ is selected from —H; -halo; and —$C_{1-3}$alkyl optionally substituted with 1, 2 or 3 substituents selected from —F and —$CF_3$;

A is selected from:

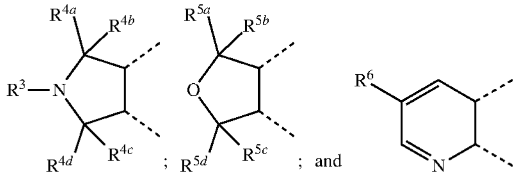

or a N-oxide thereof;

$R^3$ is selected from —H; —$C_{1-6}$alkyl; —$C_{2-6}$ alkenyl; —$C_{2-6}$ alkynyl; —$C_{3-7}$ cycloalkyl; and a 5 or 6 membered heterocycloalkyl; wherein the alkyl, alkenyl, alkynyl, cycloalkyl or heterocycloalkyl are optionally substituted by 1, 2 or 3 groups selected from —F, —$CF_3$, —$C_{1-3}$alkyl optionally substituted by 1 or 2 substituents selected from —F, —$CF_3$, —C(O)$NR^8R^9$ and —$NR^8R^9$;

$R^{4a}$ and $R^{4b}$ are each independently selected from —H and —$C_{1-3}$alkyl optionally substituted with 1, 2 or 3 substituents selected from —F and —$CF_3$;

$R^{4c}$ and $R^{4d}$ are each independently selected from hydrogen and —$C_{1-3}$ alkyl optionally substituted with 1, 2 or 3 substituents selected from —F and —$CF_3$; or $R^{4c}$ and $R^{4d}$ together with the carbon to which they are attached represent carbonyl;

$R^{5a}$, $R^{5b}$, $R^{5c}$ and $R^{5d}$ are each independently selected from —H and —$C_{1-3}$ alkyl optionally substituted with 1, 2 or 3 substituents selected from —F and $CF_3$;

$R^6$ is selected from —H; -halo; —$NH_2$; —CN; —$C_{1-3}$ alkyl optionally substituted with 1, 2 or 3 substituents selected from —F and $CF_3$; —$C_{1-3}$alkoxy optionally substituted with 1, 2 or 3 substituents selected from —F and —$CF_3$; —C(O)O—$C_{1-3}$alkyl; —C(O)$NR^8R^9$; —C(O)OH; and —NHC(O)—$C_{1-3}$alkyl;

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1, 2 or 3 groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$ alkyl; —$C_{1-3}$alkylene-NHC(O)O$C_{1-6}$alkyl; and $C_{3-5}$cycloalkyl; or the heterocycloalkyl is optionally substituted with two substituents on the same ring carbon which together with the carbon atom to which they are attached form a 5 to 7 membered monocyclic heterocycloalkyl; and wherein when $R^7$ is morpholinyl and $R^1$ is unsubstituted phenyl, $R^2$ is not —H;

$R^8$ and $R^9$ are each independently selected from —H and —$C_{1-6}$alkyl;

$R^{10}$ is —$C_{1-6}$alkyl;

$R^{11}$ is selected from —$C_{1-6}$alkyl optionally substituted with 1 or 2 substituents selected from —F and —$C_{1-3}$ alkoxy; and —$(CH_2)_nR^{12}$;

$R^{12}$ is a 5 or 6 membered heteroaryl, a 3 to 5 membered cycloalkyl or a 3 to 6 membered heterocycloalkyl;

m is 0 or 1; and n is 1, 2 or 3.

In the context of the present specification, unless otherwise indicated, the term "alkyl" includes both linear and branched chain alkyl groups. The prefix $C_{p-q}$ in $C_{p-q}$alkyl and other terms (where p and q are integers) indicates the range of carbon atoms that are present in the group, for example $C_{1-3}$alkyl includes $C_1$alkyl (methyl), $C_2$alkyl (ethyl) and $C_3$alkyl (propyl as n-propyl and isopropyl).

The term "$C_{p-q}$alkoxy" comprises —O—$C_{p-q}$alkyl groups and —$C_{p-q}$alkyl groups where the O atom is within the alkyl chain, for example, —$CH_2$—O—$CH_3$.

The term "$C_{p-q}$alkenyl" includes both linear and branched chain alkyl groups containing at least two carbon atoms and at least one double carbon-carbon bond.

The term "$C_{p-q}$alkenyloxy" comprises —O—$C_{p-q}$alkenyl groups and —$C_{p-q}$alkenyl groups where the O atom is within the alkenyl chain.

The term "$C_{p-q}$alkynyl" includes both linear and branched chain alkyl groups containing at least two carbon atoms and at least one triple carbon-carbon bond.

The term "$C_{p-q}$alkynyloxy" comprises —O—$C_{p-q}$alkynyl groups and —$C_{p-q}$alkynyl groups where the O atoms is within the alkynyl chain.

$C_{p-q}$cycloalkyl refers to a cyclic non-aromatic group of p-q carbon atoms and no heteroatoms. For example, a 3 to 7 membered cycloalkyl refers to a ring containing 3 to 7 carbon atoms. Suitable $C_{3-7}$cycloalkyl rings include cyclopropyl, cyclobutyl, cyclopentyl and cyclohexyl.

Aryl is a 6 to 10 membered monocyclic or bicyclic aromatic ring containing no heteroatoms. Aryl includes phenyl.

Heterocycloalkyl is a monocyclic saturated or partially unsaturated, non-aromatic ring having, for example, 3 to 7 members, such as 3 to 6 members, 5 to 7 members such as 5 or 6 members, where at least one member and up to 4 members, particularly 1, 2 or 3 members of the ring are heteroatoms selected from N, O and S, and the remaining ring atoms are carbon atoms, in stable combinations known to those of skill in the art. Heterocycloalkyl ring nitrogen and sulphur atoms are optionally oxidised. Suitable heterocycloalkyl rings include morpholinyl, thiazolidinyl, homomorpholine, tetrahydropyranyl, pyrrolyl, thiomorpholinyl and tetrahydrofuranyl. In one embodiment, when $R^7$ is heterocycloalkyl, optionally two substituents on the same ring carbon together with the carbon to which they are attached form a 5 to 7 membered heterocycloalkyl ring, thereby creating a spirocyclic ring system. For example, in one embodiment, $R^7$ is morpholinyl and two substituents on the same ring carbon together form a tetrahydropyran.

Heteroaryl is a polyunsaturated, monocyclic 5 or 6 membered aromatic ring containing at least one and up to 3 heteroatoms, particularly, 1 or 2 heteroatoms selected from N, O and S, and the remaining ring atoms are carbon atoms. Heteroaryl ring nitrogen and sulphur atoms are optionally oxidised. Suitable heteroaryl rings include pyridinyl, isoxazolyl, oxadiazolyl, imidazolyl, pyrazinyl, oxazolyl, thiophenyl and thiazolyl.

The term "halo" is fluorine, chlorine or bromine.

The use of the dashed bond------ in rings A of Formula (I) represents the fusion of the pyrimidine ring.

Where the term "optionally" is used, it is intended that the subsequent feature may or may not occur. As such, use of the term "optionally" includes instances where the feature is present, and also instances where the feature is not present. For example, a group "optionally substituted with 1, 2 or 3 —F substituents" includes group with and without an —F substituent.

The term "substituted" means that one or more hydrogens (for example 1 or 2 hydrogens, or alternatively 1 hydrogen) on the designated group is replaced by the indicated substituent(s) (for example 1, 2 or 3 substituents, or alternatively 1 or 2 substituents, or alternatively 1 substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002.

A suitable pharmaceutically acceptable salt of a compound of the Formula (I) is, for example, a salt formed within the human or animal body after administration of a compound of the Formula (I), to said human or animal body.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113 and 114 is individually disclaimed.

The following embodiments of moiety A may be applied to the description of the compounds of Formula (I), provided herein:

A is selected from:

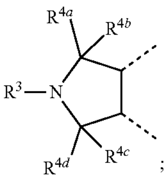 ; 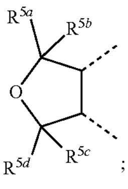 ; and 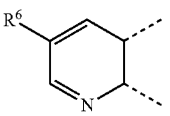

or a N-oxide thereof.

In one embodiment, A is

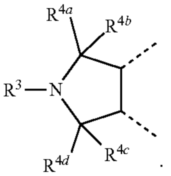

In one embodiment, A is

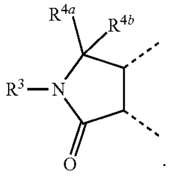

In one embodiment, A is

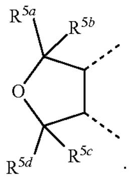

In one embodiment, A is

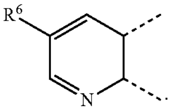

In one embodiment, A is

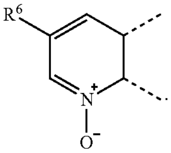

In an embodiment, there is provided a compound of Formula (II):

(II)

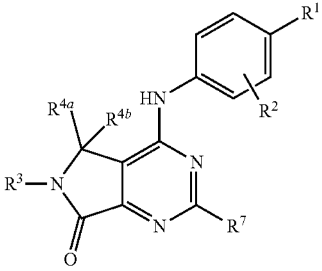

or a pharmaceutically acceptable salt thereof, wherein $R^1$, $R^2$, $R^3$, $R^{4a}$, $R^{4b}$ and $R^7$ are as defined for Formula (I).

In one embodiment, there is provided a compound of Formula (II) or a pharmaceutically acceptable salt thereof, wherein $R^1$, $R^2$, $R^3$, $R^{4a}$, $R^{4b}$ and $R^7$ are as defined for Formula (I) and when $R^7$ is morpholinyl, either:

$R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{3-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$; heteroaryl is optionally substituted with 1 or 2 substituents selected from -halo, —$C_{1-3}$alkyl, —$C_{1-8}$alkoxy and —$C_{2-8}$alkynyloxy, wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl; and aryl is substituted with 1 or 2 substituents selected from -halo, —$C_{1-3}$alkyl, —$C_{1-8}$alkoxy and —$C_{2-8}$alkynyloxy, wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl; and $R^2$ is selected from —H; -halo; and —$C_{1-3}$alkyl optionally substituted with 1, 2 or 3 substituents selected from —F and —$CF_3$; or $R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{3-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$; and heteroaryl is optionally substituted with 1 or 2 substituents selected from -halo, —$C_{1-3}$alkyl, —$C_{1-8}$alkoxy and —$C_{2-8}$alkynyloxy, wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl; and $R^2$ is selected from -halo and —$C_{1-3}$alkyl optionally substituted with 1, 2 or 3 substituents selected from —F and —$CF_3$.

In an embodiment, there is provided a compound of Formula (II) or a pharmaceutically acceptable salt thereof, wherein:

$R^1$ is selected from —$C_{2-6}$alkyl; —$C_{2-6}$alkoxy; $C_{3-2}$cycloalkyl; —O—$C_{3-7}$cycloalkyl; phenyl optionally substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl; —O-phenyl optionally substituted with 1 or 2-halo substituents; —O—$CH_2$-phenyl; and thiophenyl; wherein —$C_{2-6}$alkyl and —$C_{2-6}$alkoxy are optionally substituted with 1, 2 or 3 substituents selected from —F and —$CF_3$;

$R^2$ is selected from —H, —F and —$CH_3$;

$R^3$ is selected from —$C_{2-4}$alkynyl and —$C_{1-3}$alkyl optionally substituted with —$NR^8R^9$;

$R^{4a}$ and $R^{4b}$ are both —H;

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1 or 2 substituents selected from —CN; —$C_{1-3}$alkyl optionally substituted with 1, 2 or 3 substituents selected from —F, —$CF_3$ and —OH; —$C_{1-3}$alkoxy; cyclopropyl; —C(O)OH; —$C_{1-3}$alkylene-NHC(O)$C_{1-6}$alkyl; —$C_{1-3}$alkylene-NHC(O)O$C_{1-6}$alkyl; or the heterocycloalkyl is optionally substituted with two substituents on the same ring carbon which together with the carbon atom to which they are attached form a 6 membered monocyclic heterocycloalkyl;

$R^8$ and $R^9$ are each independently selected from —$C_{1-6}$alkyl;

$R^{10}$ is selected from —$C_{1-3}$alkyl;

$R^{11}$ is selected from —$C_{1-3}$alkyl optionally substituted with 1 or 2 substituents selected from —F and —$C_{1-3}$alkoxy; and —$(CH_2)$, $R^{12}$;

$R^{12}$ is selected from a 5 or 6 membered heteroaryl, a 3 to 5 membered cycloalkyl or a 3 to 6 membered heterocycloalkyl;

n is 1 or 2.

In one embodiment, there is provided a compound of Formula (II) or a pharmaceutically acceptable salt thereof, wherein:

$R^1$ is selected from —$C_{2-6}$alkyl; —$C_{2-6}$alkoxy; $C_{3-2}$cycloalkyl; —O—$C_{3-2}$cycloalkyl; phenyl substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$, —NHC(O)O—$C_{1-6}$alkyl or two substituents together with the carbon to which they are attached form diazirinyl; —O-phenyl optionally substituted with 1 or 2-halo substituents; —O—$CH_2$-phenyl; and thiophenyl; wherein —$C_{2-6}$alkyl and —$C_{2-6}$ alkoxy are optionally substituted with 1, 2 or 3 substituents selected from —F and —$CF_3$; and $R^2$ is selected from —H, —F and —$CH_3$; or $R^1$ is selected from —$C_{2-6}$alkyl; —$C_{2-6}$alkoxy; $C_{3-7}$cycloalkyl; —O—$C_{3-7}$cycloalkyl; unsubstituted phenyl; phenyl optionally substituted with 1 or 2-halo substituents; —O—$CH_2$-phenyl; and thiophenyl; wherein —$C_{2-6}$alkyl and —$C_{2-6}$alkoxy are optionally substituted with 1, 2 or 3 substituents selected from —F and —$CF_3$; and $R^2$ is selected from —F and —$CH_3$;

$R^3$ is selected from —$C_{2-4}$alkynyl and —$C_{1-3}$alkyl optionally substituted with —$NR^8R^9$;

$R^{4a}$ and $R^{4b}$ are both —H;

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1 or 2 substituents selected from —CN; —$C_{1-3}$alkyl optionally substituted with 1, 2 or 3 substituents selected from —F, —$CF_3$ and —OH; —$C_{1-3}$alkoxy; cyclopropyl; —C(O)OH; —$C_{1-3}$alkylene-NHC(O)$C_{1-6}$alkyl; —$C_{1-3}$alkylene-NHC(O)O$C_{1-6}$alkyl; or the heterocycloalkyl is optionally substituted with two substituents on the same ring carbon which together with the carbon atom to which they are attached form a 6 membered monocyclic heterocycloalkyl;

$R^8$ and $R^9$ are each independently selected from —$C_{1-6}$alkyl;

$R^{10}$ is selected from —$C_{1-3}$alkyl;

$R^{11}$ is selected from —$C_{1-3}$alkyl optionally substituted with 1 or 2 substituents selected from —F and —$C_{1-3}$alkoxy; and —$(CH_2)_6R^{12}$;

$R^{12}$ is selected from a 5 or 6 membered heteroaryl, a 3 to 5 membered cycloalkyl or a 3 to 6 membered heterocycloalkyl; and n is 1 or 2.

In one embodiment, there is provided a compound of Formula (III):

(III)

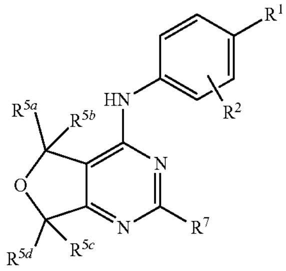

or a pharmaceutically acceptable salt thereof, wherein $R^1$, $R^2$, $R^{5a}$, $R^{5b}$, $R^{5c}$, $R^{5d}$ and $R^7$ are as defined for Formula (I).

In one embodiment, there is provided a compound of Formula (III) or a pharmaceutically acceptable salt thereof, wherein:

$R^1$ is selected from $C_{3-7}$cycloalkyl and $C_{6-10}$aryl, wherein the aryl is optionally substituted with a —$C_{2-8}$alkoxy substituent wherein the alkoxy is optionally substituted with 1 or 2 —$CF_3$ substituents;

$R^2$ is —H;

$R^{5a}$, $R^{5b}$, $R^{5c}$ and $R^{5d}$ are each —H;

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1, 2 or 3 groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$ alkyl; —$C_{1-3}$alkylene-NHC(O)O$C_{1-6}$alkyl; and $C_{3-5}$cycloalkyl; or the heterocycloalkyl is optionally substituted with two substituents on the same ring carbon which together with the carbon atom to which they are attached form a 5 to 7 membered monocyclic heterocycloalkyl; and wherein when $R^7$ is morpholinyl and 10 is unsubstituted phenyl, $R^2$ is not —H.

In one embodiment, there is provided a compound of Formula (III) or a pharmaceutically acceptable salt thereof, wherein:

$R^1$ is selected from $C_{3-7}$cycloalkyl and $C_{6-10}$aryl, wherein the aryl is optionally substituted with a —$C_{2-8}$alkoxy substituent wherein the alkoxy is optionally substituted with 1 or 2 —$CF_3$ substituents;

$R^2$ is —H;

$R^{5a}$, $R^{5b}$, $R^{5c}$ and $R^{5d}$ are each —H;

$R^7$ is a selected from a 5 to 7 membered monocyclic heterocycloalkyl and a 5 or 6 membered monocyclic heteroaryl, wherein the heterocycloalkyl and heteroaryl are optionally substituted with a substituent selected from —$C_{1-3}$alkyl optionally substituted with 1, 2 or 3 substituents selected from —F and —OH; and cyclopropyl.

In one embodiment, there is provided a compound of Formula (IV):

(IV)

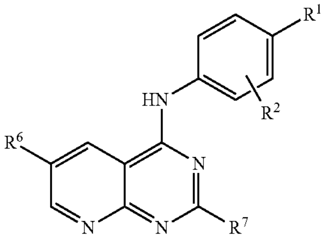

or a N-oxide or pharmaceutically acceptable salt thereof, wherein $R^1$, $R^2$, $R^6$ and $R^7$ are as defined for Formula (I).

In one embodiment, there is provided a compound of Formula (IV), or a N-oxide or pharmaceutically acceptable salt thereof, wherein:

$R^1$ selected from $C_{3-7}$cycloalkyl optionally substituted with 1, 2 or 3 substituents selected from —F and —$CF_3$;

$R^2$ is selected from —H; -halo; and —$C_{1-3}$alkyl optionally substituted with 1, 2 or 3 substituents selected from —F and —$CF_3$;

$R^6$ is selected from —H; -halo; —$NH_2$; —CN; —$C_{1-3}$ alkyl optionally substituted with 1, 2 or 3 substituents selected from —F and $CF_3$; —$C_{1-3}$alkoxy optionally substituted with 1, 2 or 3 substituents selected from —F and —$CF_3$; —C(O)O—$C_{1-3}$alkyl; —C(O)$NR^8R^9$; —C(O)OH; and —NHC(O)—$C_{1-3}$alkyl;

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1, 2 or 3 groups selected from —CN; —$C_{3-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$ alkyl; —$C_{1-3}$alkylene-NHC(O)O$C_{3-6}$alkyl; and $C_{3-5}$cycloalkyl; or the heterocycloalkyl is optionally substituted with two substituents on the same ring carbon which together with the carbon atom to which they are attached form a 5 to 7 membered monocyclic heterocycloalkyl;

$R^8$ and $R^9$ are each independently selected from —H and —$C_{3-6}$alkyl;

$R^{10}$ is —$C_{3-6}$alkyl;

$R^{11}$ is selected from —$C_{3-6}$alkyl optionally substituted with 1 or 2 substituents selected from —F and —$C_{1-3}$ alkoxy; and —$(CH_2)R^{12}$;

$R^{12}$ is a 5 or 6 membered heteroaryl, a 3 to 5 membered cycloalkyl or a 3 to 6 membered heterocycloalkyl;

n is 1, 2 or 3.

In one embodiment, there is provided a compound of Formula (IV), or a N-oxide or pharmaceutically acceptable salt thereof, wherein:

$R^1$ selected from $C_{3-7}$cycloalkyl optionally substituted with 1, 2 or 3 substituents selected from —F and —$CF_3$;

$R^2$ is —H;

$R^6$ is selected from —H; -halo; —$NH_2$; —CN; —$C_{1-3}$ alkyl optionally substituted with 1, 2 or 3 substituents selected from —F and $CF_3$; —$C_{1-3}$alkoxy optionally substituted with 1, 2 or 3 substituents selected from —F and —$CF_3$; —C(O)O—$C_{1-3}$alkyl; —C(O)N$R^8R^9$; —C(O)OH; and —NHC(O)—$C_{1-3}$alkyl;

$R^7$ is selected a 5 to 7 membered monocyclic heterocycloalkyl optionally substituted with 1, 2 or 3 groups selected from —$C_{1-6}$alkyl optionally substituted with 1, 2 or 3 substituents selected from —F, —$CF_3$ and —OH; and $C_{3-5}$cycloalkyl;

$R^8$ and $R^9$ are each independently selected from —H and —$C_{1-6}$alkyl.

The following embodiments of moieties $R^1$, $R^2$, $R^3$, $R^{4a}$, $R^{4b}$, $R^{4c}$, $R^{4d}$, $R^5$, $R^{6a}$, $R^{6b}$, $R^7$, $R^8$, $R^9$, $R^{10}$, $R^{11}$, $R^{12}$, m and n may be applied, alone or in combination, to the description of the compounds of Formula (I) provided herein. The following embodiments of moieties $R^1$, $R^2$, $R^3$, $R^{4a}$, $R^{4b}$, $R^7$, $R^8$, $R^9$, $R^{10}$, $R^{11}$, $R^{12}$, m and n may be applied, alone or in combination, to the description of the compounds of Formula (II) provided herein. The following embodiments of moieties $R^1$, $R^2$, $R^{5a}$, $R^{5b}$, $R^{5c}$, $R^{5d}$, $R^7$, $R^8$, $R^9$, $R^{10}$, $R^{11}$, $R^{12}$, m and n may be applied, alone or in combination, to the description of the compounds of Formula (III) provided herein. The following embodiments of moieties $R^1$, $R^2$, $R^6$, $R^7$, $R^8$, $R^9$, $R^{10}$, $R^{11}$, $R^{12}$, m and n may be applied, alone or in combination, to the descriptions of the compounds of Formula (IV) provided herein.

$R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{3-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$ and wherein aryl and heteroaryl are optionally substituted with 1 or 2 substituents selected from -halo, —$C_{1-3}$alkyl, —$C_{1-8}$alkoxy and —$C_{2-8}$ alkynyloxy wherein —$C_{1-3}$alkyl, —$C_{1-8}$alkoxy and —$C_{2-8}$ alkynyloxy are optionally substituted with 1, 2, or 3 substituents selected from —F, —$CF_3$ and —NHC(O)O—$C_{1-6}$alkyl or two substituents together with the carbon to which they are attached form diazirinyl.

In one embodiment, $R^1$ is selected from $C_{2-6}$alkyl; $C_{2-6}$alkenyl; $C_{2-6}$alkynyl; $C_{2-6}$alkoxy; $C_{2-6}$alkenyloxy; $C_{2-6}$alkynyloxy; $C_{3-7}$cycloalkyl; —O—$C_{3-7}$cycloalkyl; $C_{6-10}$aryl; —O—$(CH_2)_m$—$C_{6-10}$aryl; 6 membered heteroaryl; and thiophenyl; wherein alkyl, alkenyl, alkynyl, alkoxy, alkenyloxy, alkynyloxy and cycloalkyl are optionally substituted with 1, 2 or 3 substituents selected from —F and —$CF_3$ and wherein —O—$(CH_2)_m$—$C_{6-10}$aryl and heteroaryl are optionally substituted with 1 or 2 substituents selected from -halo, —$C_{1-3}$alkyl, —$C_{1-8}$alkoxy and —$C_{2-8}$ alkynyloxy wherein —$C_{1-3}$alkyl, —$C_{1-8}$alkoxy and —$C_{2-8}$ alkynyloxy are optionally substituted with 1, 2, or 3 substituents selected from —F, —$CF_3$ and —NHC(O)O—$C_{1-6}$ alkyl or two substituents together with the carbon to which they are attached form diazirinyl; and $C_{6-10}$aryl is substituted with 1 or 2 substituents selected from -halo, —$C_{1-3}$ alkyl, —$C_{1-8}$alkoxy and —$C_{2-8}$alkynyloxy wherein —$C_{1-3}$ alkyl, —$C_{1-8}$alkoxy and —$C_{2-8}$alkynyloxy are optionally substituted with 1, 2, or 3 substituents selected from —F, —$CF_3$ and —NHC(O)O—$C_{1-6}$alkyl or two substituents together with the carbon to which they are attached form diazirinyl.

In one embodiment, $R^1$ is selected from $C_{2-6}$alkyl; $C_{2-6}$alkoxy; $C_{3-7}$cycloalkyl; —O—$C_{3-7}$cycloalkyl; $C_{6-10}$aryl; —O—$(CH_2)_m$—$C_{6-10}$aryl and thiophenyl; wherein alkyl, alkoxy and cycloalkyl are optionally substituted with 1, 2 or 3 substituents selected from —F and —$CF_3$ and wherein aryl is optionally substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$ and —NHC(O)O—$C_{1-6}$alkyl or two substituents together with the carbon to which they are attached form diazirinyl.

In one embodiment, $R^3$ is selected from $C_{2-6}$alkyl optionally substituted with 1, 2 or 3 substituents selected from —F and —$CF_3$; $C_{2-4}$alkoxy; $C_{4-6}$cycloalkyl; —O—$C_{4-6}$cycloalkyl; phenyl; —O—$(CH_2)_m$-phenyl; and thiophenyl; wherein phenyl is optionally substituted with 1 or 2 substituents selected from -halo, —$C_{1-3}$alkyl, —$C_{1-8}$alkoxy and —$C_{2-8}$ alkynyloxy wherein —$C_{1-3}$alkyl, —$C_{1-8}$alkoxy and —$C_{2-8}$ alkynyloxy are optionally substituted with 1, 2, or 3 substituents selected from —F, —$CF_3$ and —NHC(O)O—$C_{1-6}$ alkyl or two substituents together with the carbon to which they are attached form diazirinyl.

In one embodiment, $R^1$ is selected from $C_{2-6}$alkyl optionally substituted with 1, 2 or 3 substituents selected from —F and —$CF_3$; $C_{2-4}$alkoxy; $C_{4-6}$cycloalkyl; —O—$C_{4-6}$cycloalkyl; phenyl; —O—$(CH_2)_m$-phenyl; and thiophenyl; wherein O—$(CH_2)_m$-phenyl is optionally substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$ and —NHC(O)O—$C_{1-6}$alkyl or two substituents together with the carbon to which they are attached form diazirinyl; and phenyl is substituted with 1 or 2 substituents selected from -halo, —$C_{1-3}$alkyl, —$C_{1-8}$alkoxy and —$C_{2-8}$alkynyloxy wherein —$C_{1-3}$alkyl, —$C_{1-8}$alkoxy and —$C_{2-8}$alkynyloxy are optionally substituted with 1, 2, or 3 substituents selected from —F, —$CF_3$ and —NHC(O)O—$C_{1-6}$alkyl or two substituents together with the carbon to which they are attached form diazirinyl.

In one embodiment, $R^1$ is selected from —$CF_2CF_3$; propyl; butyl; pentyl; propoxy; cyclobutyl; cyclohexyl; —O-cyclopentyl; thiophenyl; phenyl; —O-phenyl; —O—$CH_2$-phenyl; wherein phenyl is optionally substituted with 1 or 2 substituents selected from —F, —Cl, —$CH_3$, —O—$(CH_2)_5$C≡CH, —O—$(CH_2)_7$, —O—$(CH_2)_2$C(N═N)$(CH_2)_2$C≡CH, —O—$(CH_2)_2$NHC(O)OC$(CH_3)_3$, —O—$CH_2$C≡CH, —O—$(CH_2)_5CF_3$ and —O—$(CH_2)_7$.

In one embodiment, $R^1$ is selected from —$CF_2CF_3$; propyl; butyl; pentyl; propoxy; cyclobutyl; cyclohexyl; —O-cyclopentyl; thiophenyl; phenyl substituted with 1 or 2 substituents selected from —F, —Cl, —$CH_3$, —O—$(CH_2)_5$C≡CH, —O—$(CH_2)_7$, —O—$(CH_2)_2$C(N═N)$(CH_2)_2$C≡CH, —O—$(CH_2)_2$NHC(O)OC$(CH_3)_3$, —O—$CH_2$C≡CH, —O—$(CH_2)_5CF_3$ and —O—$(CH_2)_7$; —O-phenyl; —O—$CH_2$-phenyl; wherein —O-phenyl and —O—$CH_2$-phenyl is optionally substituted with 1 or 2 substituents selected from —F, —Cl, —$CH_3$, —O—$(CH_2)_5$C≡CH, —O—$(CH_2)_7$, —O—$(CH_2)_2$C(N═N)$(CH_2)_2$C≡CH, —O—$(CH_2)_2$NHC(O)OC$(CH_3)_3$, —O—$CH_2$C≡CH, —O—$(CH_2)_5$ $CF_3$ and —O—$(CH_2)_7$.

In one embodiment, $R^1$ is cyclohexyl. In another embodiment, $R^3$ is phenyl substituted with —F, —Cl, —$CH_3$, —O—$(CH_2)_5$C≡CH, —O—$(CH_2)_7$, —O—$(CH_2)_2$C(N═N)$(CH_2)_2$C≡CH, —O—$(CH_2)_2$NHC(O)OC$(CH_3)_3$, —O—$CH_2$C≡CH, —O—$(CH_2)_5CF_3$ and —O—$(CH_2)_7$. In another embodiment, $R^3$ is phenyl.

$R^2$ is selected from —H, -halo and —$C_{1-3}$alkyl optionally substituted with 1, 2 or 3 substituents selected from —F and —$CF_3$. In one embodiment, $R^2$ is —H. In another embodiment, $R^2$ is -halo. In one embodiment, $R^2$ is —F. In another embodiment, $R^2$ is —$C_{1-3}$alkyl. In one embodiment, $R^2$ is methyl.

$R^3$ is selected from —H; —$C_{1-6}$alkyl; —$C_{2-6}$alkenyl; —$C_{2-6}$alkynyl; —$C_{3-7}$cycloalkyl; and a 5 or 6 membered heterocycloalkyl; wherein the alkyl, alkenyl, alkynyl, cycloalkyl or heterocycloalkyl are optionally substituted by 1, 2 or 3 groups, for example 1 or 2 groups, selected from —$C_{1-3}$alkyl optionally substituted with 1, 2 or 3 substituents selected from —F, —$CF_3$, —C(O)$NR^8R^9$ and —$NR^8R^9$.

In one embodiment, $R^3$ is selected from —H; —$C_{2-4}$ alkynyl; —$C_{1-3}$alkyl optionally substituted with —C(O)$NR^8R^9$ or —$NR^8R^9$; and a 5 or 6 membered heterocycloalkyl optionally substituted with $C_{1-3}$alkyl.

In one embodiment, $R^3$ is selected from —H; —$C_{2-4}$alkynyl; —$C_{1-3}$alkyl optionally substituted with —C(O)$NR^8R^9$ or —$NR^8R^9$; and a 5 or 6 membered nitrogen containing heterocycloalkyl optionally substituted with $C_{1-3}$alkyl.

In one embodiment, $R^3$ is selected from —H; —$C_{2-4}$alkynyl; —$C_{1-3}$alkyl optionally substituted with —C(O)$NR^8R^9$ or —$NR^8R^9$; and piperidinyl optionally substituted with $C_{1-3}$alkyl.

In one embodiment, $R^3$ is selected from methyl, ethyl, i-propyl, —$(CH_2)_2N(CH_3)_2$, —$(CH_2)_3N(CH_3)_2$, —$CH_2C{\equiv}CH$, —$CH_2C(O)N(CH_3)_2$ and N-methylpiperidine. In one embodiment, $R^3$ is selected from ethyl, i-propyl, —$(CH_2)_2N(CH_3)_2$, —$(CH_2)_3N(CH_3)_2$, —$CH_2C{\equiv}CH$, —$CH_2C(O)N(CH_3)_2$ and N-methylpiperidine.

In one embodiment, $R^3$ is selected from —$C_{2-4}$alkynyl and —$C_{1-3}$alkyl optionally substituted with —$NR^8R^9$.

In one embodiment, $R^3$ is selected from ethyl, i-propyl, —$(CH_2)_2N(CH_3)_2$, —$(CH_2)_3N(CH_3)_2$ and —$CH_2C{\equiv}CH$.

In one embodiment, $R^3$ is i-propyl.

$R^{4a}$ and $R^{4b}$ are each independently selected from —H and —$C_{1-3}$alkyl optionally substituted with 1, 2 or 3 substituents selected from —F and —$CF_3$. In one embodiment, $R^{4a}$ is methyl and $R^{4b}$ is —H. In one embodiment, $R^{4a}$ and $R^{4b}$ are both —H.

$R^{4c}$ and $R^{4d}$ are each independently selected from —H and $C_{1-3}$ alkyl optionally substituted with 1, 2 or 3 substituents selected from —F and —$CF_3$; or $R^{46}$ and $R^{4d}$ together with the carbon to which they are attached represent carbonyl. In one embodiment, $R^{4c}$ and $R^{4d}$ together with the carbon to which they are attached represent carbonyl. In another embodiment, $R^{4c}$ and $R^{4d}$ are each independently selected from —H and $C_{1-3}$ alkyl optionally substituted with 1, 2 or 3 substituents selected from —F and —$CF_3$. In another embodiment, $R^{4c}$ and $R^{4d}$ are both —H or together with the carbon to which they are attached represent carbonyl. In yet another embodiment, $R^{46}$ and $R^{4d}$ are both —H.

$R^{5a}$, $R^{5b}$, $R^{5c}$ and $R^{5d}$ are each independently selected from —H and —$C_{1-3}$ alkyl optionally substituted with 1, 2 or 3 substituents selected from —F and —$CF_3$. In one embodiment, $R^{5a}$, $R^{5b}$, $R^{5c}$ and $R^{5d}$ are each independently selected from —H and —$C_{1-3}$ alkyl optionally substituted with 1, 2 or 3 substituents selected from —F and —$CF_3$. In one embodiment, $R^{5a}$, $R^{5b}$, $R^{5c}$ and $R^{5d}$ are each independently selected from —H and —$C_{1-3}$ alkyl. In one embodiment, $R^{5a}$ is methyl and $R^{5b}$, $R^{5c}$ and $R^{5d}$ are each —H. In one embodiment, $R^{5a}$, $R^{5b}$ and $R^{5c}$ are each —H and $R^{5d}$ is methyl. In one embodiment, $R^{5a}$, $R^{5b}$, $R^{5c}$ and $R^{5d}$ each represent —H.

$R^6$ is selected from —H; -halo; —$NH_2$; —CN; —$C_{1-3}$ alkyl optionally substituted with 1, 2 or 3 substituents selected from —F and $CF_3$; —$C_{1-3}$alkoxy optionally substituted with 1, 2 or 3 substituents selected from —F and —$CF_3$; —C(O)O—$C_{1-3}$alkyl; —C(O)$NR^8R^9$; —C(O)OH; and —NHC(O)—$C_{1-3}$alkyl. In one embodiment, $R^6$ is selected from —H; —Br; —$NH_2$; —CN; methoxy; ethyl; —$C(O)OCH_3$; —$C(O)NH_2$; —C(O)OH; and —NHC(O)$CH_3$.

$R^7$ is selected from —$NR^{10}R^{11}$; a 5 to 7 membered monocyclic heterocycloalkyl; and a 5 or 6 membered monocyclic heteroaryl; wherein the heterocycloalkyl and heteroaryl are optionally substituted with 1, 2 or 3 (for example, 1 or 2) groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$alkyl; —$C_{1-3}$alkylene-NHC(O)O$C_{1-6}$alkyl; and $C_{3-5}$cycloalkyl; or the heterocycloalkyl is optionally substituted with two substituents on the same ring carbon which together with the carbon atom to which they are attached form a 5 to 7 membered monocyclic heterocycloalkyl.

In one embodiment, $R^7$ is selected from $NR^{10}R^{11}$; a 5 to 7 membered monocylic heterocycloalkyl selected from morpholinyl, thiazolidinyl, tetrahydropyranyl, pyrrolyl, thiomorpholinyl and 3,4-dihydro-2H-pyranyl; a 5 or 6 membered monocyclic heteroaryl selected from pyridinyl, dihydropyranyl, imidazolyl, oxazolyl, imidazolyl and thiazolyl; wherein the heterocycloalkyl and heteroaryl are optionally substituted with 1, 2 or 3 (for example, 1 or 2) groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$alkyl; —$C_{1-3}$alkylene-NHC(O)O$C_{1-6}$ alkyl; and $C_{3-5}$cycloalkyl; or the heterocycloalkyl is optionally substituted with two substituents on the same ring carbon which together with the carbon atom to which they are attached form a 5 to 7 membered monocyclic heterocycloalkyl.

In one embodiment, $R^7$ is selected from $NR^{10}R^{11}$; a 5 to 7 membered monocylic heterocycloalkyl selected from morpholinyl, thiazolidinyl, tetrahydropyranyl, pyrrolyl, thiomorpholinyl and 3,4-dihydro-2H-pyranyl; a 5 or 6 membered monocyclic heteroaryl selected from pyridinyl, dihydropyranyl, imidazolyl, oxazolyl, imidazolyl and thiazolyl; wherein the heterocycloalkyl and heteroaryl are optionally substituted with 1, 2 or 3 (for example, 1 or 2) groups selected from —CN, methyl, ethyl, propyl, cyclopropyl, methoxy, —$CH_2CF_3$, —$CH_2OH$, —$CH_2CH_2OH$, —C(O)OH, —$(CH_2)_2NHC(O)CH_3$ and —$CH_2NHC(O)OC(CH_3)_3$; or the heterocycloalkyl is optionally substituted with two substituents on the same ring carbon which together with the carbon atom to which they are attached form a 6 membered monocyclic heterocycloalkyl.

In one embodiment, $R^7$ is selected from $NR^{10}R^{11}$ wherein $R^{10}$ is selected from methyl, ethyl or propyl and $R^{11}$ is selected from ethyl, propyl, $CH_2CHF_2$, $CH_2CH_2OCH_2CH_3$ and —$(CH_2)_pR^{12}$; a 5 to 7 membered monocyclic heterocycloalkyl selected from morpholinyl, thiazolidinyl, tetrahydropyranyl, pyrrolyl, thiomorpholinyl and 3,4-dihydro-2H-pyranyl; a 5 or 6 membered monocyclic heteroaryl selected from pyridinyl, dihydropyranyl, imidazolyl, oxazolyl, imidazolyl and thiazolyl; wherein the heterocycloalkyl and heteroaryl are optionally substituted with 1 or 2 groups selected from —CN, methyl, ethyl, propyl, cyclopropyl, methoxy, —$CH_2CF_3$, —$CH_2OH$, —$CH_2CH_2OH$, —C(O)OH, —$(CH_2)_2NHC(O)CH_3$ and —$CH_2NHC(O)OC(CH_3)_3$; or the heterocycloalkyl is optionally substituted with two substituents on the same ring carbon which together with the carbon atom to which they are attached form tetrahydropyranyl.

In one embodiment, $R^7$ is selected from $NR^{10}R^{11}$ wherein $R^{10}$ is selected from methyl, ethyl or propyl and $R^{11}$ is selected from ethyl, propyl, $CH_2CHF_2$, $CH_2CH_2OCH_2CH_3$ and —$(CH_2)_n$ $R^{12}$.

In one embodiment, $R^7$ is selected from $NR^{10}R^{11}$ wherein $R^{10}$ is selected from methyl, ethyl or propyl; $R^{11}$ is selected from ethyl, propyl, $CH_2CHF_2$, $CH_2CH_2OCH_2CH_3$ and —$(CH_2)_n$ $R^{12}$; n is 1 or 2; and $R^{12}$ is selected from isoxazolyl, oxadiazolyl, cyclopropyl, pyrazinyl, tetrahydrofuranyl and pyridinyl.

In one embodiment, $R^7$ is selected from a 5 to 7 membered monocyclic heterocycloalkyl optionally substituted with 1, 2 or 3 (for example, 1 or 2) groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$C_{1-3}$alkylene-NHC(O)$C_{1-6}$alkyl; —$C_{1-3}$alkylene-NHC(O)O$C_{1-6}$alkyl and $C_{3-5}$cycloalkyl; or the heterocycloalkyl is optionally substituted with two substituents on the same ring carbon which together with the carbon atom to which they are attached form a 5 to 7 membered monocyclic heterocycloalkyl.

In one embodiment, $R^7$ is a 5 to 7 membered monocyclic heterocycloalkyl selected from morpholinyl, thiazolidinyl, tetrahydropyranyl, pyrrolyl, thiomorpholinyl and 3,4-dihydro-2H-pyranyl wherein the heterocycloalkyl is optionally substituted with 1 or 2 groups selected from —CN; —$C_{1-6}$alkyl optionally substituted with 1, 2 or 3 substituents selected from —F, —$CF_3$ and —OH; —$C_{1-3}$alkoxy optionally substituted with 1, 2 or 3 substituents selected from —F and —$CF_3$; —C(O)OH; —$CH_2NHC(O)CH_3$; —$CH_2NHC(O)OC(CH_3)_3$; and $C_{3-5}$cycloalkyl; or the heterocycloalkyl is optionally substituted with two substituents on the same ring carbon which together with the carbon atom to which they are attached form a 6 membered monocyclic heterocycloalkyl;

In one embodiment, $R^7$ is a 5 to 7 membered monocyclic heterocyclalkyl optionally substituted with 1 or 2 substituents selected from methyl, ethyl, propyl, cyclopropyl, —$CH_2CH_2OH$, —$CH_2OH$, —C(O)OH, —$CH_2CF_3$, and —$CH_2NHC(O)OC(CH_3)_3$; or the heterocycloalkyl is optionally substituted with two substituents on the same ring carbon which together with the carbon atom to which they are attached form tetrahydropyran.

In one embodiment, $R^7$ is morpholinyl optionally substituted with 1 or 2 substituents selected from methyl, ethyl, propyl, cyclopropyl, —$CH_2CH_2OH$, —$CH_2OH$, —C(O)OH, —$CH_2CF_3$, and —$CH_2NHC(O)OC(CH_3)_3$; or optionally substituted with two substituents on the same ring carbon which together with the carbon atom to which they are attached form tetrahydropyran (i.e. $R^7$ becomes a spirocyclic group).

In one embodiment, $R^7$ is 2-methylmorpholin-4-yl.

$R^8$ is selected from —H and —$C_{1-6}$alkyl. In one embodiment, $R^8$ is selected from —H and —$C_{1-3}$alkyl. In one embodiment, $R^8$ is —H. In one embodiment, $R^8$ is —$C_{1-3}$ alkyl. In one embodiment, $R^8$ is methyl.

$R^9$ is selected from —H and —$C_{1-6}$alkyl. In one embodiment, $R^9$ is selected from —H and —$C_{1-3}$alkyl. In one embodiment, $R^9$ is —H. In one embodiment, $R^9$ is —$C_{1-3}$ alkyl. In one embodiment, $R^9$ is methyl.

$R^{10}$ is —$C_{1-6}$alkyl. In one embodiment, $R^{10}$ is —$C_{1-3}$ alkyl. In one embodiment, $R^{10}$ is methyl. In another embodiment, $R^{10}$ is ethyl. In another embodiment, $R^{10}$ is propyl.

$R^{11}$ is selected from —$C_{1-6}$alkyl optionally substituted with 1 or 2 substituents selected from —F and —$C_{1-3}$alkoxy; or —$(CH_2)_n R^{12}$. In one embodiment, $R^{11}$ is selected from —$C_{1-6}$alkyl optionally substituted with 1 or 2 substituents selected from —F and ethoxy. In one embodiment, $R^{11}$ is selected from ethyl, propyl, $CH_2CHF_2$, $CH_2CH_2OCH_2CH_3$ and —$(CH_2)_n R^{12}$. In one embodiment, $R^{11}$ is selected from —$(CH_2)_n R^{12}$.

$R^{12}$ is selected from a 5 or 6 membered heteroaryl, a 3 to 5 membered cycloalkyl or a 3 to 6 membered heterocycloalkyl. In one embodiment, $R^{11}$ is selected from isoxazolyl, oxadiazolyl, cyclopropyl, pyrazinyl, tetrahydrofuranyl and pyridinyl.

m is 0 or 1. In one embodiment, m is 0. In another embodiment, m is 1.

n is 1, 2 or 3. In one embodiment, n is 1 or 2. In another embodiment, n is 1. In another embodiment, n is 2. In another embodiment, n is 3.

In an embodiment, the compound of Formula (I) is selected from:

2-(diethylamino)-6-(propan-2-yl)-4-{[4-(propan-2-yl)phenyl]amino}-5,6-dihydro-7H-pyrrolo[3,4-d]pyrimidin-7-one;

4-[(4-cyclohexylphenyl)amino]-2-(2-cyclopropylmorpholin-4-yl)-6-(propan-2-yl)-5,6-dihydro-7H-pyrrolo[3,4-d]pyrimidin-7-one;

6-(propan-2-yl)-4-{[4-(propan-2-yl)phenyl]amino}-2-(1,3-thiazolidin-3-yl)-5,6-dihydro-7H-pyrrolo[3,4-d]pyrimidin-7-one;

2-[(2R,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one;

6-(propan-2-yl)-4-{[4-(propan-2-yl)phenyl]amino}-2-(thiomorpholin-4-yl)-5,6-dihydro-7H-pyrrolo[3,4-d]pyrimidin-7-one;

2-[(2S)-2-methylmorpholin-4-yl]-6-(propan-2-yl)-4-{[4-(propan-2-yl)phenyl]amino}-5,6-dihydro-7H-pyrrolo[3,4-d]pyrimidin-7-one;

2-[(2R)-2-methylmorpholin-4-yl]-6-(propan-2-yl)-4-{[4-(propan-2-yl)phenyl]amino}-5,6-dihydro-7H-pyrrolo[3,4-d]pyrimidin-7-one;

2-[(2S,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one;

2-(3-methylmorpholin-4-yl)-6-(propan-2-yl)-4-{[4-(propan-2-yl)phenyl]amino}-5,6-dihydro-7H-pyrrolo[3,4-d]pyrimidin-7-one;

2-(2-cyclopropylmorpholin-4-yl)-6-(propan-2-yl)-4-{[4-(propan-2-yl)phenyl]amino}-5,6-dihydro-7H-pyrrolo[3,4-d]pyrimidin-7-one;

4-[(4-cyclohexylphenyl)amino]-2-(morpholin-4-yl)-6-(propan-2-yl)-5,6-dihydro-7H-pyrrolo[3,4-d]pyrimidin-7-one;

4-[(4-cyclohexylphenyl)amino]-2-(2-methylmorpholin-4-yl)-6-(propan-2-yl)-5,6-dihydro-7H-pyrrolo[3,4-d]pyrimidin-7-one;

4-[(4-cyclohexylphenyl)amino]-2-[(2R)-2-methylmorpholin-4-yl]-6-(propan-2-yl)-5,6-dihydro-7H-pyrrolo[3,4-d]pyrimidin-7-one;

4-[(4-cyclohexylphenyl)amino]-2-((2R)-cyclopropylmorpholin-4-yl)-6-(propan-2-yl)-5,6-dihydro-7H-pyrrolo[3,4-d]pyrimidin-7-one;

4-[(4-cyclohexylphenyl)amino]-2-((2S)-cyclopropylmorpholin-4-yl)-6-(propan-2-yl)-5,6-dihydro-7H-pyrrolo[3,4-d]pyrimidin-7-one;

4-[(4-cyclohexylphenyl)amino]-6-(propan-2-yl)-2-[2-(2,2,2-trifluoroethyl)morpholin-4-yl]-5,6-dihydro-7H-pyrrolo[3,4-d]pyrimidin-7-one;

tert-butyl {[2R)-4-{4-[(4-cyclohexylphenyl)amino]-7-oxo-6-(propan-2-yl)-6,7-dihydro-5H-pyrrolo[3,4-d]pyrimidin-2-yl}morpholin-2-yl]methyl}carbamate;

4-[(4-cyclohexylphenyl)amino]-6-(propan-2-yl)-2-[2-(propan-2-yl)morpholin-4-yl]-5,6-dihydro-7H-pyrrolo[3,4-d]pyrimidin-7-one;

4-[(4-cyclohexylphenyl)amino]-6-(propan-2-yl)-2-(1,3-thiazolidin-3-yl)-5,6-dihydro-7H-pyrrolo[3,4-d]pyrimidin-7-one;

4-[(4-cyclohexylphenyl)amino]-2[(2-ethoxyethyl)(methyl)amino]-6-(propan-2-yl)-5,6-dihydro-7H-pyrrolo[3,4-d]pyrimidin-7-one;

4-[(4-cyclohexylphenyl)amino]-2-(2-ethylmorpholin-4-yl)-6-(propan-2-yl)-5,6-dihydro-7H-pyrrolo[3,4-d]pyrimidin-7-one;

4-[(4-cyclohexylphenyl)amino]-2-{methyl[(1,2-oxazol-3-yl)methyl]amino}-6-(propan-2-yl)-5,6-dihydro-7H-pyrrolo[3,4-d]pyrimidin-7-one;

4-[(4-cyclohexylphenyl)amino]-2-{methyl[2-(1,2,4-oxadiazol-3-yl)ethyl]amino}-6-(propan-2-yl)-5,6-dihydro-7H-pyrrolo[3,4-d]pyrimidin-7-one;

4-[(4-cyclohexylphenyl)amino]-2-(1,4-oxazepan-4-yl)-6-(propan-2-yl)-5,6-dihydro-7H-pyrrolo[3,4-d]pyrimidin-7-one;

4-[(4-cyclohexylphenyl)amino]-2-(1,9-dioxa-4-azaspiro[5.5]undecan-4-yl)-6-(propan-2-yl)-5,6-dihydro-7H-pyrrolo[3,4-d]pyrimidin-7-one;

4-[(4-cyclohexylphenyl)amino]-2-(3-methoxypyrrolidin-1-yl)-6-(propan-2-yl)-5,6-dihydro-7H-pyrrolo[3,4-d]pyrimidin-7-one;

4-[(4-cyclohexylphenyl)amino]-2-[2-(2-hydroxyethyl)morpholin-4-yl]-6-(propan-2-yl)-5,6-dihydro-7H-pyrrolo[3,4-d]pyrimidin-7-one;

4-[(4-cyclohexylphenyl)amino]-2-(dipropylamino)-6-(propan-2-yl)-5,6-dihydro-7H-pyrrolo[3,4-d]pyrimidin-7-one;

4-[(4-cyclohexylphenyl)amino]-2-[(cyclopropylmethyl)(methyl)amino]-6-(propan-2-yl)-5,6-dihydro-7H-pyrrolo[3,4-d]pyrimidin-7-one;

4-[(4-cyclohexylphenyl)amino]-2-[2-(hydroxymethyl)morpholin-4-yl]-6-(propan-2-yl)-5,6-dihydro-7H-pyrrolo[3,4-d]pyrimidin-7-one;

4-[(4-cyclohexylphenyl)amino]-2-[3-hydroxymethyl)morpholin-4-yl]-6-(propan-2-yl)-5,6-dihydro-7H-pyrrolo[3,4-d]pyrimidin-7-one;

4-[(4-cyclohexylphenyl)amino]-2-{methyl[(pyrazin-2-yl)methyl]amino}-6-(propan-2-yl)-5,6-dihydro-7H-pyrrolo[3,4-d]pyrimidin-7-one;

4-[(4-cyclohexylphenyl)amino]-2-(diethylamino)-6-(propan-2-yl)-5,6-dihydro-7H-pyrrolo[3,4-d]pyrimidin-7-one;

4-[(4-cyclohexylphenyl)amino]-2-{methyl[(oxolan-2-yl)methyl]amino}-6-(propan-2-yl)-5,6-dihydro-7H-pyrrolo[3,4-d]pyrimidin-7-one;

4-[(4-cyclohexylphenyl)amino]-2-[(2,2-difluoro ethyl)(methyl)amino]-6-(propan-2-yl)-5,6-dihydro-7H-pyrrolo[3,4-d]pyrimidin-7-one;

4-[(4-cyclohexylphenyl)amino]-2-{methyl[2-(pyridin-2-yl)ethyl]amino}-6-(propan-2-yl)-5,6-dihydro-7H-pyrrolo[3,4-d]pyrimidin-7-one;

(3S)-4-{4-[(4-cyclohexylphenyl)amino]-7-oxo-6-(propan-2-yl)-6,7-dihydro-5H-pyrrolo[3,4-d]pyrimidin-2-yl}morpholine-3-carboxylic acid;

N-[2-(4-{4-[(4-cyclohexylphenyl)amino]-7-oxo-6-(propan-2-yl)-6,7-dihydro-5H-pyrrolo[3,4-d]pyrimidin-2-yl}morpholin-2-yl)ethyl]acetamide;

6-(propan-2-yl)-4-{[4-(propan-2-yl)phenyl]amino}-2-(pyridin-4-yl)-5,6-dihydro-7H-pyrrolo[3,4-d]pyrimidin-7-one;

4-{4-[(4-cyclohexylphenyl)amino]-7-oxo-6-(propan-2-yl)-6,7-dihydro-5H-pyrrolo[3,4-d]pyrimidin-2-yl}pyridine-2-carbonitrile;

4-[(4-cyclohexylphenyl)amino]-2-(2-cyclopropylpyridin-4-yl)-6-(propan-2-yl)-5,6-dihydro-7H-pyrrolo[3,4-d]pyrimidin-7-one;

4-[(4-cyclohexylphenyl)amino]-2-(2-methoxypyridin-4-yl)-6-(propan-2-yl)-5,6-dihydro-7H-pyrrolo[3,4-d]pyrimidin-7-one;

4-[(4-cyclohexylphenyl)amino]-2-(2-methylpyridin-4-yl)-6-(propan-2-yl)-5,6-dihydro-7H-pyrrolo[3,4-d]pyrimidin-7-one;

4-[(4-cyclohexylphenyl)amino]-2-(3,6-dihydro-2H-pyran-4-yl)-6-(propan-2-yl)-5,6-dihydro-7H-pyrrolo[3,4-d]pyrimidin-7-one;

4-[(4-cyclohexylphenyl)amino]-6-(propan-2-yl)-2-(pyridin-4-yl)-5,6-dihydro-7H-pyrrolo[3,4-d]pyrimidin-7-one;

4-[(4-cyclohexylphenyl)amino]-2-(1-methyl-1H-pyrazol-4-yl)-6-(propan-2-yl)-5,6-dihydro-7H-pyrrolo[3,4-d]pyrimidin-7-one;

4-[(4-cyclohexylphenyl)amino]-2-(1,3-oxazol-5-yl)-6-(propan-2-yl)-5,6-dihydro-7H-pyrrolo[3,4-d]pyrimidin-7-one;

4-[(4-cyclohexylphenyl)amino]-6-(propan-2-yl)-2-(1,3-thiazol-5-yl)-5,6-dihydro-7H-pyrrolo[3,4-d]pyrimidin-7-one;

2-(3,6-dihydro-2H-pyran-4-yl)-6-(propan-2-yl)-4-{[4-(propan-2-yl)phenyl]amino}-5,6-dihydro-7H-pyrrolo[3,4-d]pyrimidin-7-one;

4-{[4-(4-fluorophenoxy)phenyl]amino}-2-[(2R)-2-methylmorpholin-4-yl]-6-(propan-2-yl)-5,6-dihydro-7H-pyrrolo[3,4-d]pyrimidin-7-one;

2-(2-cyclopropylmorpholin-4-yl)-4-({4'-[(hept-6-yn-1-yl)oxy][1,1'-biphenyl]-4-yl}amino)-6-(propan-2-yl)-5,6-dihydro-7H-pyrrolo[3,4-d]pyrimidin-7-one;

2-(2-cyclopropylmorpholin-4-yl)-4-{[4'-(heptyloxy)-[1,1'-biphenyl]-4-yl]amino}-6-(propan-2-yl)-5,6-dihydro-7H-pyrrolo[3,4-d]pyrimidin-7-one;

4-[(4'-{2-[3-(but-3-yn-1-yl)-3H-diaziren-3-yl]ethoxy}[1,1'-biphenyl]-4-yl)amino]-2-(2-cyclopropyl-morpholin-4-yl)-6-(propan-2-yl)-5,6-dihydro-7H-pyrrolo[3,4-d]pyrimidin-7-one;

2-[(2R)-2-methylmorpholin-4-yl]-4-[(4-pentylphenyl)amino]-6-(propan-2-yl)-5,6-dihydro-7H-pyrrolo[3,4-d]pyrimidin-7-one;

4-{[4-(butan-2-yl)phenyl]amino}-2-[(2R)-2-methylmorpholin-4-yl]-6-(propan-2-yl)-5,6-dihydro-7H-pyrrolo[3,4-d]pyrimidin-7-one;

4-{[4-(benzyloxy)phenyl]amino}-2-[(2R)-2-methylmorpholin-4-yl]-6-(propan-2-yl)-5,6-dihydro-7H-pyrrolo[3,4-d]pyrimidin-7-one;

2-(2-cyclopropylmorpholin-4-yl)-4-{[4-(pentafluoroethyl)phenyl]amino}-6-(propan-2-yl)-5,6-dihydro-7H-pyrrolo[3,4-d]pyrimidin-7-one;

2-(2-cyclopropylmorpholin-4-yl)-6-(propan-2-yl)-4-[(4-propylphenyl)amino]-5,6-dihydro-7H-pyrrolo[3,4-d]pyrimidin-7-one;

2-[(2R)-2-methylmorpholin-4-yl]-6-(propan-2-yl)-4-[(4-propylphenyl)amino]-5,6-dihydro-7H-pyrrolo[3,4-d]pyrimidin-7-one;

2-[(2R)-2-methylmorpholin-4-yl]-4-{[4-(pentafluoroethyl)phenyl]amino}-6-(propan-2-yl)-5,6-dihydro-7H-pyrrolo[3,4-d]pyrimidin-7-one;

2-(2-cyclopropylmorpholin-4-yl)-6-(propan-2-yl)-4-({4[(propan-2-yl)oxy]phenyl}amino)-5,6-dihydro-7H-pyrrolo[3,4-d]pyrimidin-7-one;

4-[(4-cyclobutylphenyl)amino]-2-(morpholin-4-yl)-6-(propan-2-yl)-5,6-dihydro-7H-pyrrolo[3,4-d]pyrimidin-7-one;

4-{[4-(cyclopentyloxy)phenyl]amino}-2-[(2R)-2-methylmorpholin-4-yl]-6-(propan-2-yl)-5,6-dihydro-7H-pyrrolo[3,4-d]pyrimidin-7-one;

2-[(2R)-2-methylmorpholin-4-yl]-6-(propan-2-yl)-4-{[4-(2,2,2-trifluoroethyl)phenyl]amino}-5,6-dihydro-7H-pyrrolo[3,4-d]pyrimidin-7-one;

tert-butyl {2-[(4'{[2-(2-cyclopropylmorpholin-4-yl)-7-oxo-6-(propan-2-yl)-6,7-dihydro-5H-pyrrolo[3,4-d]pyrimidin-4-yl]amino}[1,1'-biphenyl]-4-yl)oxy]ethyl}carbamate;

6-ethyl-2-[(2R)-2-methylmorpholin-4-yl]-4-{[4-(propan-2-yl)phenyl]amino}-5,6-dihydro-7H-pyrrolo[3,4-d]pyrimidin-7-one;

4-[(4-cyclohexylphenyl)amino]-6-ethyl-2-[(2R)-2-methylmorpholin-4-yl]-5,6-dihydro-7H-pyrrolo[3,4-d]pyrimidin-7-one;

tert-butyl {2-[(4'{[2-(morpholin-4-yl)-7-oxo-6-(propan-2-yl)-6,7-dihydro-5H-pyrrolo[3,4-d]pyrimidin-4-yl]amino}[1,1'-biphenyl]-4-yl)oxy]ethyl}carbamate;

4-[(4'-{2-[3-(but-3-yn-1-yl)-3H-diaziren-3-yl]ethoxy}-[1,1'-biphenyl]-4-yl)amino]-2-(morpholin-4-yl)-6-(propan-2-yl)-5,6-dihydro-7H-pyrrolo[3,4-d]pyrimidin-7-one;

2-(morpholin-4-yl)-6-(propan-2-yl)-4-({4'4[(prop-2-yn-1-yl)oxy]-[1,1'-biphenyl]-4-yl}amino)-5,6-dihydro-7H-pyrrolo[3,4-d]pyrimidin-7-one;

4-[(4-cyclohexylphenyl)amino]-6-[3-dimethylamino)propyl]-2-[(2R)-2-methylmorpholin-4-yl]-5,6-dihydro-7H-pyrrolo[3,4-d]pyrimidin-7-one;

4-[(4-cyclohexylphenyl)amino]-6[2-(dimethylamino)ethyl]-2-[(2R)-2-methylmorpholin-4-yl]-5,6-dihydro-7H-pyrrolo[3,4-d]pyrimidin-7-one;

4-[(4-cyclobutylphenyl)amino]-6-[3-24(2R)-2-methylmorpholin-4-yl]-5,6-dihydro-7H-pyrrolo[3,4-d]pyrimidin-7-one;

4-[(4-cyclobutylphenyl)amino]-6-[2-(dimethylamino)ethyl]-2-[(2R)-2-methylmorpholin-4-yl]-5,6-dihydro-7H-pyrrolo[3,4-d]pyrimidin-7-one;

2-(morpholin-4-yl)-4-{[4-(propan-2-yl)phenyl]amino}-6-(prop-2-yn-1-yl)-5,6-dihydro-7H-pyrrolo[3,4-d]pyrimidin-7-one;

4-[(4-cyclohexylphenyl)amino]-2-(oxan-4-yl)-6-(propan-2-yl)-5,6-dihydro-7H-pyrrolo[3,4-d]pyrimidin-7-one;

4-[(4-cyclohexylphenyl)amino]-2-(1H-imidazol-1-yl)-6-(propan-2-yl)-5,6-dihydro-7H-pyrrolo[3,4-d]pyrimidin-7-one;

2-(3,6-dihydro-2H-pyran-4-yl)-4-[(2'-methyl[1,1'-biphenyl]-4-yl)amino]-6-(propan-2-yl)-5,6-dihydro-7H-pyrrolo[3,4-d]pyrimidin-7-one;

4-[(4'-{2-[3-(but-3-yn-1-yl)-3H-diaziren-3-yl]ethoxy}[1,1'-biphenyl]-4-yl)amino]-2-(3,6-dihydro-2H-pyran-4-yl)-6-(propan-2-yl)-5,6-dihydro-7H-pyrrolo[3,4-d]pyrimidin-7-one;

2-(3,6-dihydro-2H-pyran-4-yl)-4-[(2-fluoro[1,1'-biphenyl]-4-yl)amino]-6-(propan-2-yl)-5,6-dihydro-7H-pyrrolo[3,4-d]pyrimidin-7-one;

2-(morpholin-4-yl)-4-{[4-(pentafluoroethyl)phenyl]amino}-6-(propan-2-yl)-5,6-dihydro-7H-pyrrolo[3,4-d]pyrimidin-7-one;

4-[(2-fluoro[1,1'-biphenyl]-4-yl)amino]-2-(morpholin-4-yl)-6-(propan-2-yl)-5,6-dihydro-7H-pyrrolo[3,4-d]pyrimidin-7-one;

4-[(3,4'-dichloro[1,1'-biphenyl]-4-yl)amino]-2-(morpholin-4-yl)-6-(propan-2-yl)-5,6-dihydro-7H-pyrrolo[3,4-d]pyrimidin-7-one;

2-(morpholin-4-yl)-6-(propan-2-yl)-4-{[4-(propan-2-yl)phenyl]amino}-5,6-dihydro-7H-pyrrolo[3,4-d]pyrimidin-7-one;

4-[(4-tert-butylphenyl)amino]-2-(morpholin-4-yl)-6-(propan-2-yl)-5,6-dihydro-7H-pyrrolo[3,4-d]pyrimidin-7-one;

4-[(2-methyl[1,1'-biphenyl]-4-yl)amino]-2-(morpholin-4-yl)-6-(propan-2-yl)-5,6-dihydro-7H-pyrrolo[3,4-d]pyrimidin-7-one;

4-[(4'-chloro[1,1'-biphenyl]-4-yl)amino]-2-(morpholin-4-yl)-6-(propan-2-yl)-5,6-dihydro-7H-pyrrolo[3,4-d]pyrimidin-7-one;

N-(4-cyclohexylphenyl)-2-[(2R)-2-methylmorpholin-4-yl]-5,7-dihydrofuro[3,4-d]pyrimidin-4-amine;

N-(4-cyclobutylphenyl)-2-(3,6-dihydro-2H-pyran-4-yl)-5,7-dihydrofuro[3,4-d]pyrimidin-4-amine;

N-(4-cyclohexylphenyl)-2-(2-cyclopropylmorpholin-4-yl)-5,7-dihydrofuro[3,4-d]pyrimidin-4-amine;

2-(2-cyclopropylmorpholin-4-yl)-N-[4'-(heptyloxy)-[1,1'-biphenyl]-4-yl]-5,7-dihydrofuro[3,4-d]pyrimidin-4-amine;

2-[(2R)-2-methylmorpholin-4-yl]-N-{4'-[(6,6,6-trifluorohexyl)oxy]-[1,1'-biphenyl]-4-yl}-5,7-dihydrofuro[3,4-d]pyrimidin-4-amine;

N-(4-cyclohexylphenyl)-2-(2-methylpyridin-4-yl)-5,7-dihydrofuro[3,4-d]pyrimidin-4-amine;

N-(4-cyclohexylphenyl)-2-[(2R)-2-methylmorpholin-4-yl]pyrido[2,3-d]pyrimidin-4-amine;

6-bromo-N-(4-cyclohexylphenyl)-2-[(2R)-2-methylmorpholin-4-yl]pyrido[2,3-d]pyrimidin-4-amine;

N-(4-cyclohexylphenyl)-2-(3,6-dihydro-2H-pyran-4-yl)pyrido[2,3-d]pyrimidin-4-amine;

N-(4-cyclohexylphenyl)-2-[(2R)-2-methylmorpholin-4-yl]-8-oxo-8lambda~5~-pyrido[2,3-d]pyrimidin-4-amine;

N-(4-cyclohexylphenyl)-6-ethyl-2-[(2R)-2-methylmorpholin-4-yl]pyrido[2,3-d]pyrimidin-4-amine;

4-[(4-cyclohexylphenyl)amino]-2-[(2R)-2-methylmorpholin-4-yl]pyrido[2,3-d]pyrimidine-6-carbonitrile;

methyl 4-[(4-cyclohexylphenyl)amino]-2-[(2R)-2-methylmorpholin-4-yl]pyrido[2,3-d]pyrimidine-6-carboxylate;

4-[(4-cyclohexylphenyl)amino]-2-[(2R)-2-methylmorpholin-4-yl]pyrido[2,3-d]pyrimidine-6-carboxylic acid;

4-[(4-cyclohexylphenyl)amino]-2-[(2R)-2-methylmorpholin-4-yl]pyrido[2,3-d]pyrimidine-6-carboxamide;

4-[(4-cyclohexylphenyl)amino]-2-(2-cyclopropylmorpholin-4-yl)pyrido[2,3-d]pyrimidine-6-carboxamide;

N-(4-cyclohexylphenyl)-6-methoxy-2-[(2R)-2-methylmorpholin-4-yl]pyrido[2,3-d]pyrimidin-4-amine;

N-{4-[(4-cyclohexylphenyl)amino]-2-[(2R)-2-methylmorpholin-4-yl]pyrido[2,3-d]pyrimidin-6-yl}acetamide;

N-4-(4-cyclohexylphenyl)-2-[(2R)-2-methylmorpholin-4-yl]pyrido[2,3-d]pyrimidine-4,6-diamine;

N-(4-cyclohexylphenyl)-2-(morpholin-4-yl)-6-(propan-2-yl)-6,7-dihydro-5H-pyrrolo[3,4-d]pyrimidin-4-amine;

N-(4-cyclohexylphenyl)-2-[(2R)-2-methylmorpholin-4-yl]-6-(propan-2-yl)-6,7-dihydro-5H-pyrrolo[3,4-d]pyrimidin-4-amine;

2-{4-[(4-cyclohexylphenyl)amino]-2-(3,6-dihydro-2H-pyran-4-yl)-5,7-dihydro-6H-pyrrolo[3,4-d]pyrimidin-6-yl}-N,N-dimethylacetamide;

N-(4-cyclohexylphenyl)-2-(2-cyclopropylmorpholin-4-yl)-6-(1-methylpiperidin-4-yl)-6,7-dihydro-5H-pyrrolo[3,4-d]pyrimidin-4-amine;

2-(morpholin-4-yl)-6-(propan-2-yl)-4-{[4-(thiophen-2-yl)phenyl]amino}-5,6-dihydro-7H-pyrrolo[3,4-d]pyrimidin-7-one;

2-(morpholin-4-yl)-6-(propan-2-yl)-4-{[4-(thiophen-3-yl)phenyl]amino}-5,6-dihydro-7H-pyrrolo[3,4d]pyrimidin-7-one;

and pharmaceutically acceptable salts thereof.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example one or two hydrogens, or alternatively one hydrogen) on the designated group is replaced by the indicated substituent(s) (for example one or two substituents, or alternatively one substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002.

A suitable pharmaceutically acceptable salt of a compound of Formula (I) is, for example, an acid addition salt. An acid addition salt of a compound of Formula (I) may be formed by bringing the compound into contact with a suitable inorganic or organic acid under conditions known to the skilled person.

Compounds described in this specification may form base addition salts. A base-addition salt of a compound of Formula (I) may be formed by bringing the compound into contact with a suitable inorganic or organic base under conditions known to the skilled person.

In one embodiment there is provided a compound of Formula (I), or a pharmaceutically acceptable salt thereof.

In one embodiment there is provided a compound of Formula (I).

In one embodiment there is provided a pharmaceutically acceptable salt of a compound of Formula (I).

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The invention encompasses all such solvated and unsolvated forms of compounds of Formula (I), particularly to the extent that such forms possess KCC2 modulating activity, as for example measured using the tests described herein.

Atoms of the compounds and salts described in this specification may exist as their isotopes. All compounds of Formula (I) where an atom is replaced by one or more of its isotopes (for example a compound of Formula (I) where one or more carbon atom is an $^{11}C$ or $^{13}C$ carbon isotope, or where one or more hydrogen atoms is a $^{2}H$ or $^{3}H$ isotope, or where one or more nitrogen atoms is a $^{15}N$ isotope or where one of more oxygen atoms is an $^{17}O$ or $^{18}O$ isotope) are encompassed herein.

Compounds of the application may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof where appropriate such isomers can be separated from their mixtures by the application or adaptation of known methods (e.g. chromatographic techniques and recrystallisation techniques). Where appropriate such isomers can be prepared by the application or adaptation of known methods. In some embodiments, a single stereoisomer is obtained by isolating it from a mixture of isomers (e.g., a racemate) using, for example, chiral chromatographic separation. In other embodiments, a single stereoisomer is obtained through direct synthesis from, for example, a chiral starting material.

In an embodiment there is provided a compound of Formula (I), or a pharmaceutically acceptable salt thereof, which is a single optical isomer being in an enantiomeric excess (% e.e.) of ≥95%, ≥98% or ≥99%. In one embodiment, the single optical isomer is present in an enantiomeric excess (% e.e.) of ≥99%.

In one embodiment there is provided an N-oxide of a compound of Formula (I) as herein defined, or a pharmaceutically acceptable salt thereof.

Compounds of Formula (I), where $R^7$ is —$NR^{10}R^{11}$ (i.e. $R^7$ is linked by an aliphatic N atom), may for example be prepared by the reaction of a compound of Formula (V):

(V)

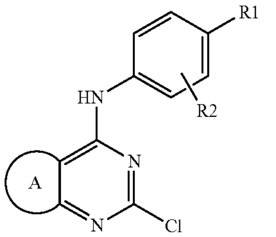

or a salt thereof, where $R^1$, $R^2$ and A are as defined in any of the embodiments herein, with an amine. The reaction is conveniently performed in a suitable solvent and at a suitable temperature, for example, di-isopropylethylamine in dimethylsulfoxide at a temperature of 20-100° C., or TsOH in butanol at 80° C.

When $R^7$ is attached via a carbon atom, the compound of Formula (I) can be made by the reaction of a compound of Formula (V) with a boronic acid or ester of the Formula (VI), where $R^7$ is as defined in any of the embodiments herein and each R is the same or different and represents —H, an aliphatic chain, or where together the two R groups form a ring with the boron and two oxygen atoms. The reaction is conveniently performed with a suitable base in the presence of a palladium catalyst and a solvent at a suitable temperature. For example, cesium carbonate or sodium carbonate and a palladium catalyst such as Pd $(PPh_3)_4$, in aqueous dioxane at a temperature in the range of 80-100° C.

(VI)

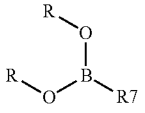

When $R^7$ is linked via an aromatic N atom, the compound of Formula (I) can be made by reaction of a compound of Formula (V) with the anion of $R^7$. For example, by reaction of the anion of imidazole, generated by treatment with a suitable base (for example) sodium hydride, in a suitable solvent (for example dimethylformamide), with a compound of Formula (V).

A compound of the Formula (V) may be prepared from a compound of Formula (VII), or a salt thereof, where A is as defined in any of the embodiments herein, and a compound of Formula (VIII), or a salt thereof, where $R^1$ and $R^2$ are as defined in any of the embodiments herein, in the presence of a base in a suitable solvent (for example, di-isopropylethylamine in tert butanol or dimethylsulfoxide) and at a suitable temperature (for example 20-100° C.).

(VII)

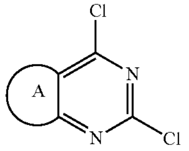

(VIII)

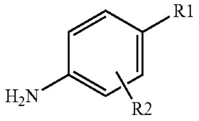

A compound of Formula (I) may also be made in one pot from the reaction between a compound of Formula (VII) with the stepwise addition of a compound of Formula (VIII) and an amine $R^7$. The reaction is conveniently performed in the presence of a base (for example, di-isopropylethylamine) in a suitable solvent (dimethylsulfoxide) at a suitable temperature (for example, a temperature of 20-100° C.).

A compound of Formula (VII) may be made, for example, from a compound of Formula (IX). Suitable conditions for this transformation are heating at a temperature of about 80° C. in $POCl_3$ in the presence of an amine base such as diethylphenylamine.

(IX)

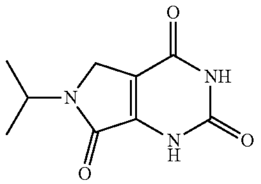

A compound of the Formula (IX) may, for example, be prepared from a compound of the Formula (X) by reaction with propan-2-amine and formaldehyde in a suitable solvent (for example, ethanol) at a suitable temperature (for example, a temperature of 0-80° C.).

(X)

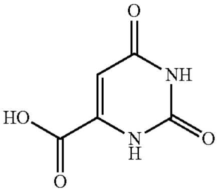

A compound of the Formula (I), when $R^{5a}$ and $R^{5b}$ are both H, may also be made from reaction of a compound of the Formula (XI), or a salt thereof, where $R^1$, $R^2$ and $R^7$ are as defined in any of the embodiments herein, with a suitable amine, for example N,N-dimethylpropane-1,3-diamine. Suitable conditions for this reaction are HCl in ethanol at a temperature of about 190° C. in a sealed tube.

(XI)

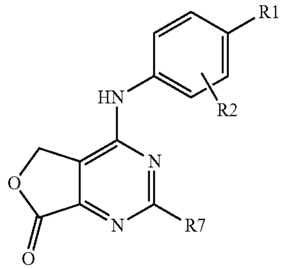

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example, compounds of Formula (I) may be converted into further compounds of Formula (I) by conventional functional group modifications. Such reactions and modifications include, for example, introduction of a substituent by means of an aromatic substitution reaction, C—H activation reaction, reduction of substituents, alkylation of substituents and oxidation of substituents. The reagents and reaction conditions for such procedures are well known in the chemical art. Particular examples of aromatic substitution reactions include the introduction of a halogen group.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

Compounds of Formula (I), (II), (III) and (IV), and any intermediates used to make these, can be prepared by methods similar to those shown in the Examples section.

Compounds may be further selected on the basis of further biological or physical properties which may be measured by techniques known in the art and which may be used in the assessment or selection of compounds for therapeutic or prophylactic application.

As a result of their KCC2 activation activity, the compounds of Formula (I), and pharmaceutically acceptable salts thereof are expected to be useful in therapy, for example, in the treatment of diseases or medical conditions mediated at least in part by KCC2, including neurological disorders such as epilepsy, pain, autism spectrum disorders, cognition, anxiety and amyotrophic lateral sclerosis.

Certain compounds described herein may be selective against other targets, including P2X3.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of a compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by KCC2. In one embodiment, the disease mediated by KCC2 is a neurological disorder.

In one embodiment, there is provided a compound of Formula (I), or a pharmaceutically acceptable salt thereof, for use in the treatment of epilepsy. In one embodiment, the epilepsy is selected from the group consisting of treatment-refractory epilepsy, status epilepticus, status epilepticus resistant to benzodiazepines (e.g. lorazepam or diazepam), status epilepticus caused by nerve agents or organophosphorous compounds (e.g. soman), Dravet syndrome, Lennox-Gastaut syndrome, Doose syndrome, Jeavons syndrome and myoclonic absence epilepsy.

In one embodiment, there is provided a compound of Formula (I), or a pharmaceutically acceptable salt thereof, for use in the treatment of pain. In one embodiment, said pain is selected from the group consisting of widespread pain, localized pain, nociceptive pain, central pain, central and peripheral neuropathic pain, diabetic neuropathic pain, central and peripheral neurogenic pain, central and peripheral neuralgia, low back pain, postoperative pain, visceral pain, pelvic pain, allodynia, anesthesia dolorosa, causalgia, dysesthesia, fibromyalgia, hyperalgesia, hyperesthesia, hyperpathia, ischemic pain, sciatic pain, burn-induced pain, pain associated with multiple sclerosis, pain associated with arthritis, pain associated with pancreatitis, pain associated with psoriasis, pain associated with fibromyalgia, pain associated with IBS, and pain associated with cancer.

In one embodiment, there is provided a compound of Formula (I), or a pharmaceutically acceptable salt thereof, for use in the treatment of autism spectrum disorders. In one embodiment, the autism spectrum disorder is selected from autism, Asperger syndrome, childhood disintegrative disorder and Rett's syndrome.

In one embodiment, there is provided a compound of Formula (I), or a pharmaceutically acceptable salt thereof, for use in the treatment of a cognition disorder. In one embodiment, the cognition disorder is selected from the group consisting of amnesia, dementia and delirium.

In one embodiment, there is provided a compound of Formula (I), or a pharmaceutically acceptable salt thereof, for use in the treatment of anxiety.

In one embodiment, there is provided a compound of Formula (I), or a pharmaceutically acceptable salt thereof, for use in the treatment of motor neuron disease. In one embodiment, the motor neuron disease is amyotrophic lateral sclerosis.

In one embodiment, there is provided the use of the compound of Formula (I), or a pharmaceutically acceptable salt thereof, for the manufacture of a medicament for the treatment of a disease or disorder mediated by KCC2. In one embodiment, said disease or disorder mediated by KCC2 is epilepsy. In another embodiment, said disease or disorder mediated by KCC2 is pain. In another embodiment, said disease or disorder mediated by KCC2 is an autism spectrum disorder. In another embodiment, said disease or disorder mediated by KCC2 is a cognition disorder. In another embodiment, said disease or disorder mediated by KCC2 is anxiety. In another embodiment, said disease or disorder mediated by KCC2 is amyotrophic lateral sclerosis.

The term "therapeutically effective amount" refers to an amount of a compound of Formula (I) as described in any of the embodiments herein which is effective to provide "therapy" in a subject, or to "treat" a disease or disorder in a subject. In the case of neurological disorders, the therapeutically effective amount may cause any of the changes observable or measurable in a subject as described in the definition of "therapy", "treatment" and "prophylaxis" above. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease or disorder responsive to activation of KCC2 as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Subjects" include, for example, humans.

In one embodiment there is provided a method for treating a neurological disease or disorder selected from epilepsy, pain, autism spectrum disorders, cognition, anxiety and amyotrophic lateral sclerosis, in a subject in need of such treatment, which comprises administering to said subject a therapeutically effective amount of a compound of Formula (I), or a pharmaceutically acceptable salt thereof.

In one embodiment there is provided a method for treating epilepsy in a subject in need of such treatment, which comprises administering to said subject a therapeutically effective amount of a compound of Formula (I), or a pharmaceutically acceptable salt thereof. In one embodiment there is provided a method for treating pain in a subject in need of such treatment, which comprises administering to said subject a therapeutically effective amount of a compound of Formula (I), or a pharmaceutically acceptable salt thereof.

In one embodiment there is provided a method for treating an autism spectrum disorder in a subject in need of such treatment, which comprises administering to said subject a therapeutically effective amount of a compound of Formula (I), or a pharmaceutically acceptable salt thereof.

In one embodiment there is provided a method for treating a cognition disorder in a subject in need of such treatment, which comprises administering to said subject a therapeutically effective amount of a compound of Formula (I), or a pharmaceutically acceptable salt thereof.

In one embodiment there is provided a method for treating anxiety in a subject in need of such treatment, which comprises administering to said subject a therapeutically effective amount of a compound of Formula (I), or a pharmaceutically acceptable salt thereof.

In one embodiment there is provided a method for treating amyotrophic lateral sclerosis in a subject in need of such treatment, which comprises administering to said subject a therapeutically effective amount of a compound of Formula (I), or a pharmaceutically acceptable salt thereof.

In any embodiment where epilepsy is mentioned in a general sense, said epilepsy may be selected from the group consisting of treatment-refractory epilepsy, status epilepticus, status epilepticus resistant to benzodiazepines (e.g. lorazepam or diazepam), status epilepticus caused by nerve agents or organophosphorous compounds (e.g. soman), Dravet syndrome, Lennox-Gastaut syndrome, Doose syndrome, Jeavons syndrome and myoclonic absence epilepsy.

In any embodiment where epilepsy is mentioned in a general sense the following embodiments may apply:

In one embodiment the epilepsy is treatment-refractory epilepsy.

In one embodiment the epilepsy is status epilepticus.

In one embodiment the epilepsy is status epilepticus resistant to benzodiazepines (e.g. lorazepam or diazepam).

In one embodiment the epilepsy is status epilepticus caused by nerve agents or organophosphorous compounds (e.g. soman).

In one embodiment the epilepsy is Dravet syndrome.

In one embodiment the epilepsy is Lennox-Gastaut syndrome.

In one embodiment the epilepsy is Doose syndrome.

In one embodiment the epilepsy is Jeavons syndrome.

In one embodiment the epilepsy is myoclonic absence epilepsy.

In any embodiment where pain is mentioned in a general sense, said pain may be selected from the group consisting of widespread pain, localized pain, nociceptive pain, central pain, central and peripheral neuropathic pain, diabetic neuropathic pain, central and peripheral neurogenic pain, central and peripheral neuralgia, low back pain, postoperative pain, visceral pain, pelvic pain, allodynia, anesthesia dolorosa, causalgia, dysesthesia, fibromyalgia, hyperalgesia, hyperesthesia, hyperpathia, ischemic pain, sciatic pain, burn-induced pain, pain associated with multiple sclerosis, pain associated with arthritis, pain associated with pancreatitis, pain associated with psoriasis, pain associated with fibromyalgia, pain associated with IBS, and pain associated with cancer.

In any embodiment where pain is mentioned in a general sense the following embodiments may apply:

In one embodiment the pain is widespread pain.

In one embodiment the pain is localized pain.

In one embodiment the pain is nociceptive pain.

In one embodiment the pain is central pain.

In one embodiment the pain is central and peripheral neuropathic pain.

In one embodiment the pain is diabetic neuropathic pain.

In one embodiment the pain is central and peripheral neurogenic pain.

In one embodiment the pain is central and peripheral neuralgia.

In one embodiment the pain is low back pain.

In one embodiment the pain is postoperative pain.

In one embodiment the pain is visceral pain.

In one embodiment the pain is pelvic pain.

In one embodiment the pain is allodynia.

In one embodiment the pain is anesthesia dolorosa.

In one embodiment the pain is causalgia.

In one embodiment the pain is dysesthesia.

In one embodiment the pain is fibromyalgia.

In one embodiment the pain is hyperalgesia.

In one embodiment the pain is hyperesthesia.

In one embodiment the pain is hyperpathia.

In one embodiment the pain is ischemic pain.

In one embodiment the pain is sciatic pain.

In one embodiment the pain is burn-induced pain.

In one embodiment the pain is pain associated with multiple sclerosis.

In one embodiment the pain is pain associated with arthritis.

In one embodiment the pain is pain associated with pancreatitis.

In one embodiment the pain is pain associated with psoriasis.

In one embodiment the pain is pain associated with fibromyalgia.

In one embodiment the pain is pain associated with IBS.

In one embodiment the pain is pain associated with cancer.

In any embodiment where autism spectrum disorders are mentioned in a general sense, said autism spectrum disorder may be selected from the group consisting of autism, Asperger syndrome, childhood disintegrative disorder and Rett's syndrome.

In any embodiment where autism spectrum disorders are mentioned in a general sense the following embodiments may apply:

In one embodiment the autism spectrum disorder is autism.

In one embodiment the autism spectrum disorder is Asperger syndrome.

In one embodiment the autism spectrum disorder is childhood disintegrative disorder.

In one embodiment the autism spectrum disorder is Rett's syndrome.

In any embodiment where cognition disorders are mentioned in a general sense, said cognition disorder may be selected from the group consisting of amnesia, dementia and delirium.

In any embodiment where anxiety is mentioned in a general sense, said anxiety may be selected from the group consisting of generalised anxiety disorder, panic disorder, obsessive-Compulsive disorder and posttraumatic stress disorder.

In any embodiment where motor neuron disease is mentioned in a general sense, said motor neuron disease may be amyotrophic lateral sclerosis.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the *Handbook of Pharmaceutical Excipients*, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The pharmaceutical compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution or suspension for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

The compound of Formula (I) will normally be administered to a warm-blooded animal at a unit dose within the range 2.5-5000 $mg/m^2$ body area of the animal, or approximately 0.05-100 mg/kg, and this normally provides a therapeutically-effective dose. A unit dose form such as a tablet or capsule will usually contain, for example 0.1-250 mg of active ingredient. The daily dose will necessarily be varied depending upon the host treated, the particular route of administration, any therapies being co-administered, and the severity of the illness being treated.

The pharmaceutical compositions described herein comprise compounds of Formula (I), or a pharmaceutically acceptable salt thereof, and are therefore expected to be useful in therapy.

As such, in one embodiment there is provided a pharmaceutical composition for use in therapy, comprising a compound of Formula (I), or a pharmaceutically acceptable salt thereof, and at least one pharmaceutically acceptable excipient.

In one embodiment there is provided a pharmaceutical composition for use in the treatment of a disease or condition in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of epilepsy, comprising a compound of Formula (I), or a pharmaceutically acceptable salt thereof, and at least one pharmaceutically acceptable excipient.

In one embodiment there is provided a pharmaceutical composition for use in the treatment of epilepsy in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of treatment-refractory epilepsy, status epilepticus, status epilepticus resistant to benzodiazepines (e.g. lorazepam or diazepam), status epilepticus caused by nerve agents or organophosphorous compounds (e.g. soman), Dravet syndrome, Lennox-Gastaut syndrome, Doose syndrome, Jeavons syndrome or myoclonic absence epilepsy, comprising a compound of Formula (I), or a pharmaceutically acceptable salt thereof, and at least one pharmaceutically acceptable excipient.

In one embodiment there is provided a pharmaceutical composition for use in the treatment of pain, comprising a compound of Formula (I), or a pharmaceutically acceptable salt thereof, and at least one pharmaceutically acceptable excipient.

In one embodiment there is provided a pharmaceutical composition for use in the treatment of pain in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of widespread pain, localized pain, nociceptive pain, central pain, central and peripheral neuropathic pain, diabetic neuropathic pain, central and peripheral neurogenic pain, central and peripheral neuralgia, low back pain, postoperative pain, visceral pain, pelvic pain, allodynia, anesthesia dolorosa, causalgia, dysesthesia, fibromyalgia, hyperalgesia, hyperesthesia, hyperpathia, ischemic pain, sciatic pain, burn-induced pain, pain associated with multiple sclerosis, pain associated with arthritis, pain associated with pancreatitis, pain associated with psoriasis, pain associated with IBS, or pain associated with cancer, comprising a compound of Formula (I), or a pharmaceutically acceptable salt thereof, and at least one pharmaceutically acceptable excipient.

In one embodiment there is provided a pharmaceutical composition for use in the treatment of autism spectrum disorders, comprising a compound of Formula (I), or a pharmaceutically acceptable salt thereof, and at least one pharmaceutically acceptable excipient.

In one embodiment there is provided a pharmaceutical composition for use in the treatment of autism spectrum disorders in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of autism, Asperger syndrome, childhood disintegrative disorder or Rett's syndrome, comprising a compound of Formula (I), or a pharmaceutically acceptable salt thereof, and at least one pharmaceutically acceptable excipient.

In one embodiment there is provided a pharmaceutical composition for use in the treatment of cognition disorders, comprising a compound of Formula (I), or a pharmaceutically acceptable salt thereof, and at least one pharmaceutically acceptable excipient.

In one embodiment there is provided a pharmaceutical composition for use in the treatment of cognition disorders in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of amnesia, dementia or delirium, comprising a compound of Formula (I), or a pharmaceutically acceptable salt thereof, and at least one pharmaceutically acceptable excipient.

In one embodiment there is provided a pharmaceutical composition for use in the treatment of anxiety, comprising a compound of Formula (I), or a pharmaceutically acceptable salt thereof, and at least one pharmaceutically acceptable excipient.

In one embodiment there is provided a pharmaceutical composition for use in the treatment of anxiety in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of generalised anxiety disorder, panic disorder, obsessive-Compulsive disorder or posttraumatic stress disorder.

In one embodiment there is provided a pharmaceutical composition for use in the treatment of amyotrophic lateral sclerosis, comprising a compound of Formula (I), or a pharmaceutically acceptable salt thereof, and at least one pharmaceutically acceptable excipient.

In one embodiment there is provided a pharmaceutical composition for use in the treatment of amyotrophic lateral sclerosis in which activation of KCC2 is beneficial, comprising a compound of Formula (I), or a pharmaceutically acceptable salt thereof, and at least one pharmaceutically acceptable excipient.

In one embodiment there is provided a pharmaceutical composition for use in the treatment of amyotrophic lateral sclerosis, comprising a compound of Formula (I), or a pharmaceutically acceptable salt thereof, and at least one pharmaceutically acceptable excipient.

EXAMPLES

The various embodiments of the specification are illustrated by the following Examples. The specification is not to be interpreted as being limited to the Examples.

General Experimental Details

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work up procedures were carried out after removal of residual solids by filtration;

(iii) flash column chromatography was performed on Merck Kieselgel silica (Art. 9385) or on reversed phase silica (Fluka silica gel 90 C18) or on Silicycle cartridges (40-63 μm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 μm silica) either manually or automated using an Isco Combi-Flash Companion system or similar system;

(iv) Preparative HPLC conditions A: Xselect CSH OBD Column 30×150 mm, 5 μm; Mobile Phase A: Water (0.1% formic acid), Mobile Phase B: acetonitrile; Row rate: 60 mL/min; Gradient elution; detection at 254/220 nm.

Preparative HPLC conditions B: XBridge Prep OBD C18 Column 30×150 μm, 5 μm; Mobile Phase A: Water (10 mM $NH_4HCO_3$+0.1% $NH_3·H_2O$), Mobile Phase B: acetonitrile; Flow rate: 60 mL/min; Gradient elution; detection at 254/220 nm.

Preparative HPLC conditions C: XBridge Prep OBD C18 Column 30×150 mm, 5 μm; Mobile Phase A: Water (0.05% $NH_3·H_2O$), Mobile Phase B: acetonitrile, Flow rate: 60 mL/min; Gradient elution; detection at 254/220 nm.

Preparative HPLC conditions D: XBridge Prep OBD C18 Column 30×150 mm, 5 μm; Mobile Phase A: Water (10 mL $NH_4HCO_3$), Mobile Phase B: acetonitrile; Flow rate: 60 mL/min; Gradient elution; detection at 254/220 nm.

(v) yields, where present, are not necessarily the maximum attainable;

(vi) $^1$H NMR spectra were obtained using a Braker 300 MHz, 400 MHz or 500 MHz spectrometer at 25° C. unless otherwise noted; chemical shifts are expressed in parts per million (ppm, δ units) and are referenced to the residual mono-1H isotopomer of the solvent ($CHCl_3$: 7.24 ppm; $CHDCl_2$: 5.32 ppm; $CD_3S({=}O)CD_2H$: 2.49 ppm). Coupling constants are given in units of hertz (Hz). Splitting patterns describe apparent multiplicities and are designated as s (singlet), d (doublet), t (triplet), q (quartet), m (multiplet) and brs (broad singlet).

(vii) in general, end products of Formula (I) were also characterized by mass spectroscopy following liquid chromatography (LCMS or UPLC); in general, reverse-phase C18 silica was used with a flow rate of 1 mL minute and detection was by Electrospray Mass Spectrometry and by UV absorbance recording a wavelength range of 220-320 nm. Analytical UPLC was performed on CSH C18 reverse-phase silica, using a Waters XSelect. CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the $[M+H]^+$ unless otherwise specified; for molecules with multiple isotopic patterns (Br, Cl, etc.) the reported value is the one obtained for the lowest isotope mass unless otherwise specified;

(viii) where reactions refer to the use of a microwave, one of the following microwave reactors were used: Biotage Initiator, Personal Chemistry Emrys Optimizer, Personal Chemistry Smithcreator or CEM Explorer;

(ix) intermediate purity was assessed by thin layer chromatographic, mass spectroscopy. LCMS, UPLC/MS, HPLC and/or NMR analysis;

(x) where compounds are presented as single stereoisomers, it will be understood that the absolute stereochemistry has not been determined and that reference to each individual stereoisomer equally encompasses reference to the alternate stereoisomer and the racemic form;

(xi) the following abbreviations have been used:

Abbreviations

| | |
|---|---|
| AcOH | acetic acid |
| aq | aqueous; |
| $(BPin)_2$ | bis(pinacolato)diboron |
| DCM | dichloromethane |
| DIEA | di-isopropyl ethylamine |
| DMEM | Dulbecco's Modified Eagle's Medium |
| DMF | N,N-dimethyl formamide; |
| DMSO | dimethyl sulfoxide; |
| ee | enantiomeric excess |
| $Et_2O$ | diethyl ether |
| EtOAc | ethyl acetate |
| EtOH | ethanol |
| eq. or equiv. | equivalent |
| h | hours |
| HPLC | high performance liquid chromatography |
| LCMS | liquid chromatography mass spectrometry |
| LiHMDS | lithium bis(trimethylsilyl)amide |
| MeOH | methanol |
| min | minutes |
| Ms | methanesulfonate |
| MS | mass spectrometry |
| NaHMDS | sodium bis(trimethylsilyl)amide |
| NMP | N-methylpyrrolidone |
| NMR | nuclear magnetic resonance |
| $Pd(dppf)Cl_2$ | Palladium (II) chloride [1,1'-Bis(diphenylphosphino)ferrocene] |
| rt or RT | 23° C. |
| SFC | supercritical fluid chromatography |
| STAB | Sodium triacetoxy borohydride |
| THF | tetrahydrofuran |
| $t_R$ | Retention time |
| TsOH | 4-methylbenzenesulfonic acid |
| 3rd Generation | BrettPhos Pd G3 , |
| Brettphos pre-catalyst | CAS No. 1470372-59-8. |

Synthesis of Intermediates

Intermediate 1: 2,4-dichloro-6-isopropyl-5,6-dihydro-7H-pyrrolo[3,4-d]pyrimidin-7-one

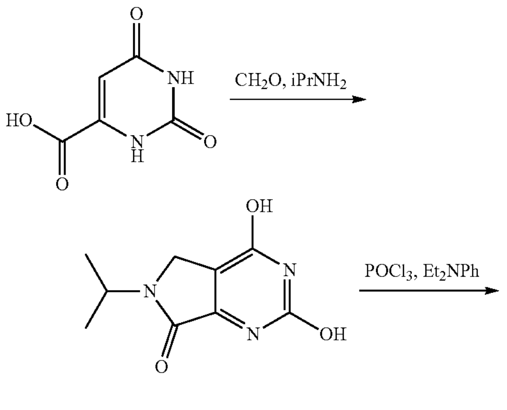

-continued

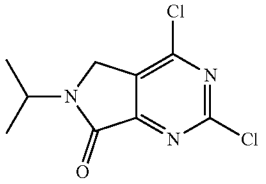

Intermediate 1, Step 1: 2,4-dihydroxy-6-isopropyl-5,6-dihydro-7H-pyrrolo[3,4-d] pyrimidin-7-one

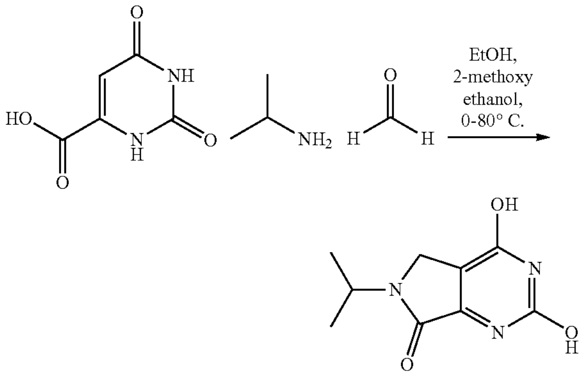

Propan-2-amine (136 mL, 1601.57 mmol) was added dropwise to 2,6-dioxo-1,2,3,6-tetrahydropyrimidine carboxylic acid (50 g, 320.31 mmol) and formaldehyde solution (120 mL, 1601.57 mmol) in ethanol (800 mL) at 0° C. The resulting solution was stirred at 80° C. for 16 h. The reaction mixture was cooled in an ice bath, the white solid was collected by filtration and washed with ethanol to give the crude intermediate (45 g) as a solid. To the above crude intermediate (45 g) was added 2-methoxy ethanol (250 mL) and 12 N HCl (25 mL, 822.86 mmol). The reaction mixture was refluxed for 16 h, cooled in an ice bath, and the solid was collected by filtration and washed with ethanol to give 2,4-dihydroxy-6-isopropyl-5,6-dihydro-7H-pyrrolo[3,4-d] pyrimidin-7-one (35.0 g, 52.2%) as a solid. $^1H$ NMR (400 MHz, DMSO-d6) δ 11.81 (s, 1H), 11.26 (s, 1H), 4.27 (p, J=6.7 Hz, 1H), 4.14 (s, 2H), 1.20 (d, J=6.7 Hz, 6H).

Intermediate 1, Step 2: 2,4-dichloro-6-isopropyl-5,6-dihydro-7H-pyrrolo[3,4-d]pyrimidin-7-one

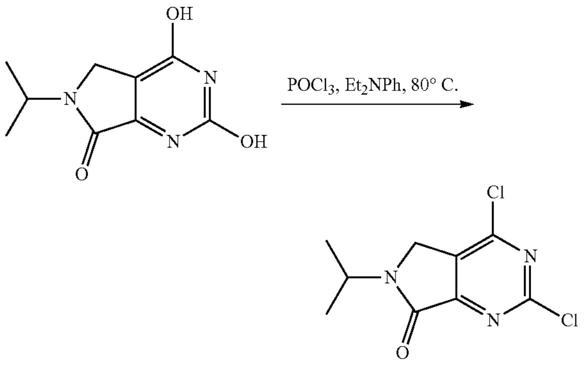

N,N-diethylaniline (67.1 mL, 418.25 mmol) was added dropwise to 2,4-dihydroxy-6-isopropyl-5,6-dihydro-7H-pyrrolo[3,4-d]pyrimidin-7-one (35 g, 167.30 mmol) in $POCl_3$ (300 mL) at 0° C. over a period of 20 minutes under nitrogen. The resulting solution was stirred at 80° C. for 2.5 hours and then concentrated under reduced pressure, with toluene co-evaporation to remove any trace of phosphorus oxychloride. The residue was poured onto crushed ice, and the pH of the mixture was adjusted to pH 6 using 30% $NH_4OH$ at 0° C. and extracted with EtOAc (3×400 mL). The organic layers were combined and washed with brine (200 mL). The organic layer was dried over $Na_2SO_4$, filtered and evaporated to afford dark oil. The crude product was purified by flash silica chromatography, elution gradient 25 to 30% EtOAc in petroleum ether. Pure fractions were evaporated to dryness to afford 2,4-dichloro-6-isopropyl-5,6-dihydro-7H-pyrrolo[3,4-d]pyrimidin-7-one (23.40 g, 56.8%) as a white solid. $^1$H NMR (400 MHz, DMSO-d6) δ 4.58 (s, 2H), 4.45 (p, J=6.7 Hz, 1H), 1.27 (d, J=6.8 Hz, 6H). ES+ m/z $[M+H]^+$: 246, HPLC $t_R$=0.92 min (99.0%).

Intermediate 2: 2,4-dichloro-6-ethyl-5,6-dihydro-7H-pyrrolo[3,4-d]pyrimidin-7-one

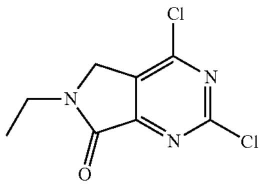

2,4-Dichloro-6-ethyl-5,6-dihydro-7H-pyrrolo[3,4-d]pyrimidin-7-one was made using the method described for Intermediate $^1$H NMR (300 MHz, CD3OD) δ 1.31 (t, J=7.3, 7.3 Hz, 3H), 3.73 (q, J=7.3, 7.3, 7.3 Hz, 2H), 4.63 (s, 2H). ES+ m/z $[M+H]^+$: 232, HPLC $t_R$=1.10 min (99.0%).

Intermediate 3: 2-chloro-4-((4-cyclohexylphenyl)amino)-6-isopropyl-5,6-dihydro-7H-pyrrolo[3,4-d]pyrimidin-7-one

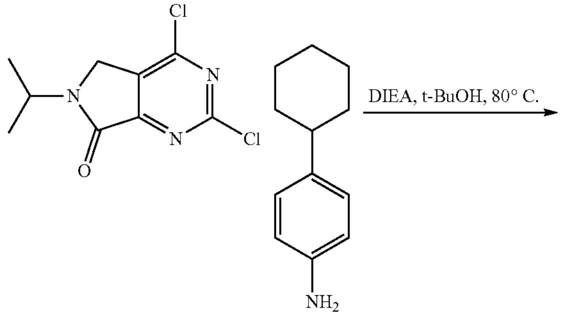

-continued

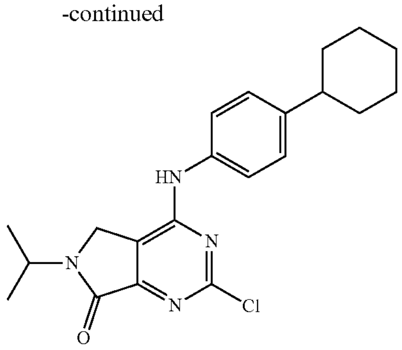

DIEA (3.55 mL, 20.32 mmol) was added to 2,4-dichloro-6-isopropyl-5,6-dihydro-7H-pyrrolo[3,4-d]pyrimidin-7-one (5.0 g, 20.32 mmol) and 4-cyclohexylaniline (3.56 g, 20.32 mmol) in tBuOH (100 mL) at rt. The resulting solution was stirred at 80° C. for 3 h. The reaction mixture was cooled to room temperature. The precipitate was collected by filtration, washed with water (100 mL) and $Et_2O$ (50 mL) and dried under vacuum to afford 2-chloro-4-((4-cyclohexylphenyl)amino)-6-isopropyl-5,6-dihydro-7H-pyrrolo[3,4-d]pyrimidin-7-one (7.00 g, 90%) as a white solid, which was used without further purification. $^1$H NMR (400 MHz, DMSO) δ 1.25 (m, 8H), 1.32-1.47 (m, 4H), 1.72 (d, J=12.7 Hz, 1H), 1.81 (d, J=9.6 Hz, 4H), 4.37 (s, 2H), 4.36-4.47 (m, 1H), 7.23-7.31 (m, 2H), 7.56-7.62 (m, 2H), 9.93 (s, 1H). ES+ m/z $[M+H]^+$: 385, HPLC $t_R$=1.32 min (98.0%).

Intermediate 4: 2-chloro-6-isopropyl-4-((4-isopropylphenyl)amino)-5,6-dihydro-7H-pyrrolo[3,4-d]pyrimidin-7-one

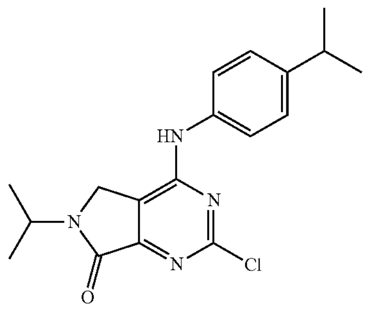 [SMILES: CC(C)c1ccc(Nc2nc(Cl)nc3c2CN(C(C)C)C3=O)cc1]

2-chloro-6-isopropyl-4-((4-isopropylphenyl)amino)-5,6-dihydro-7H-pyrrolo[3,4-d]pyrimidin-7-one was made using the method described for Intermediate 3. $^1$H NMR (400 MHz, DMSO) δ 1.22 (d, J=6.8 Hz, 6H), 1.25 (d, J=6.7 Hz, 6H), 2.82-2.97 (m, 1H), 4.36 (s, 2H), 4.36-4.47 (m, 1H), 7.25-7.32 (m, 2H), 7.56-7.63 (m, 2H), 9.94 (s, 1H). ES+ m/z $[M+H]^+$: 345, HPLC $t_R$=0.98 min (84.3%).

Intermediate 5: 4'-(hept-6-yn-1-yloxy)-[1,1'-biphenyl]-4-amine

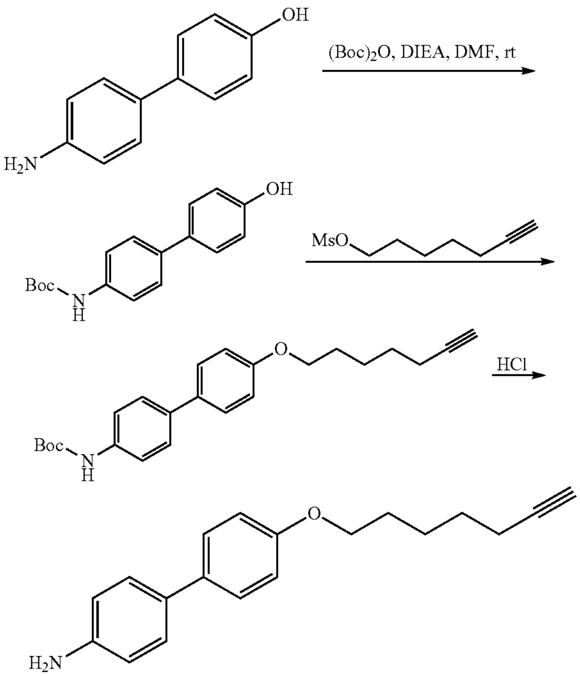

Intermediate 5, Step 1: tert-butyl (4'-hydroxy-[1,1'-biphenyl]-4-yl)carbamate

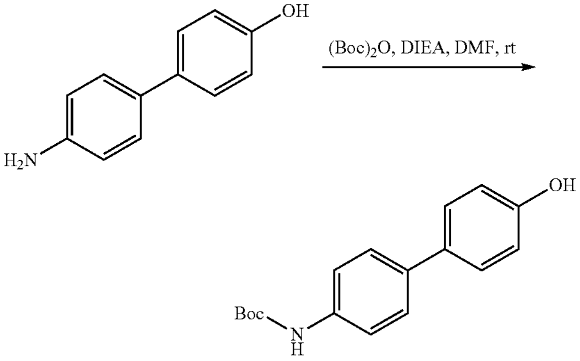

Di-tert-butyl dicarbonate (0.860 g, 3.94 mmol) was added to 4'-amino-[1,1'-biphenyl]-4-ol (0.73 g, 3.94 mmol), DIEA (2.065 mL, 11.82 mmol) in DMF (10 mL) at 0° C. under nitrogen. The resulting mixture was stirred at rt for 16 h. The reaction mixture was concentrated and diluted with DCM (50 mL) then washed sequentially with water (3×50 mL) and saturated brine (50 mL). The organic layer was dried over $Na_2SO_4$, filtered and evaporated to afford crude product. The crude product was purified by flash silica chromatography, elution gradient 0 to 20% MeOH in DCM. Pure fractions were evaporated to dryness to afford tert-butyl (4'-hydroxy-[1,1'-biphenyl]-4-yl)carbamate (0.462 g, 41.1%) as a yellow solid. $^1$H NMR (300 MHz, DMSO) δ 1.46 (s, 9H), 6.74-6.83 (m, 2H), 7.36-7.51 (m, 6H), 9.35 (s, 1H), 9.44 (s, 1H). ES$^+$ m/z [M−tBu]$^+$: 230, HPLC $t_R$=1.33 min (97.0%).

Intermediate 5, Step 2: tert-butyl (4'-(hept-6-yn-1-yloxy)-[1,1'-biphenyl]-4-yl)carbamate

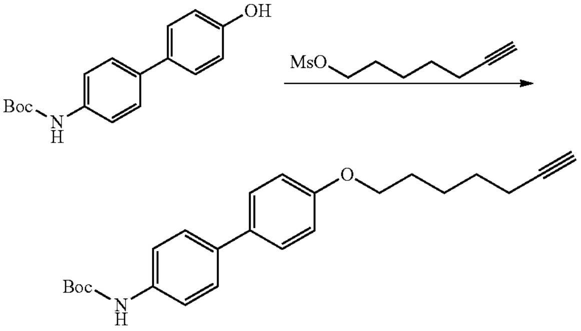

Hept-6-yn-1-yl methanesulfonate (160 mg, 0.84 mmol) was added to tert-butyl (4'-hydroxy-[1,1'-biphenyl]-4-yl) carbamate (200 mg, 0.70 mmol), and $K_2CO_3$ (194 mg, 1.40 mmol) in DMF (2 mL). The resulting mixture was stirred at 60° C. for 14 h. The reaction mixture was diluted with water, extracted with DCM, the organic layer was dried over $Na_2SO_4$, filtered and evaporated to afford yellow liquid. The crude product was purified by flash silica chromatography, elution gradient 0 to 30% EtOAc in petroleum ether. Pure fractions were evaporated to dryness to afford tert-butyl (4'-(hept-6-yn-1-yloxy)[1,1'-biphenyl]-4-yl)carbamate (300 mg, 113%) as a yellow solid. $^1$H NMR (300 MHz, DMSO) δ 1.47 (s, 9H), 1.45-1.55 (m, 4H), 1.68-1.74 (m, 3H), 2.14-2.22 (m, 1H), 2.75 (t, J=2.7 Hz, 1H), 3.97 (t, J=6.4 Hz, 2H), 6.91-7.01 (m, 2H), 7.45-7.56 (m, 6H), 9.37 (s, 1H). ES+ m/z [M−tBu]$^+$: 324, HPLC $t_R$=1.56 min (97.0%).

Intermediate 5, Step 3: 4'-(hept-6-yn-1-yloxy)-[1,1'-biphenyl]-4-amine

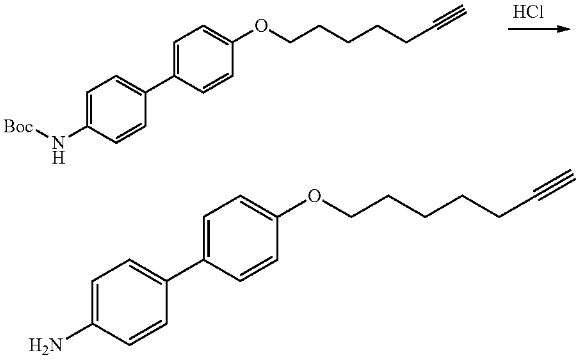

tert-Butyl (4'-(hept-6-yn-1-yloxy)[1,1'-biphenyl]-4-yl) carbamate (300 mg, 0.79 mmol) was added in HCl in 1,4-dioxane (10 mL). The resulting mixture was stirred at rt for 2 h. The solid was dried under vacuum and afford 4'-(hept-6-yn-1-yloxy)-[1,1'-biphenyl]-4-amine (290 mg, 116%) as a yellow solid. ES+ m/z [M+H]$^+$: 280, HPLC $t_R$=1.17 min (95.4%).

Intermediate 6: 4'-(heptyloxy)-[1,1'-biphenyl]-4-amine

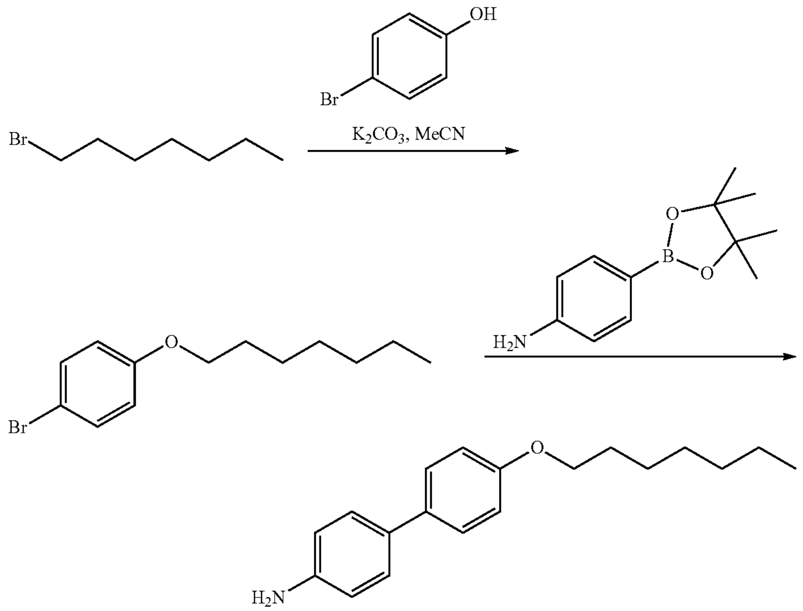

Intermediate 6, Step 1: 1-bromo-4-(heptyloxy)benzene

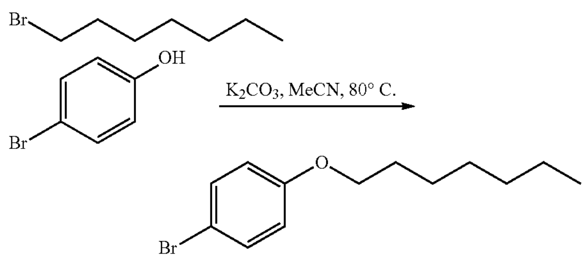

4-Bromophenol (1.932 g, 11.17 mmol) was added to 1-bromoheptane (2 g, 11.17 mmol) and $K_2CO_3$ (1.543 g, 11.17 mmol) in MeCN (30 mL) at rt. The resulting mixture was stirred at 80° C. for 16 h. The crude product was purified by flash silica chromatography, elution gradient 0 to 10% EtOAc in petroleum ether. Pure fractions were evaporated to dryness to afford 1-bromo-4-(heptyloxy)benzene (2.80 g, 92%) as a yellow oil. $^1$H NMR (400 MHz, $CDCl_3$) δ 0.89-0.97 (m, 3H), 1.27-1.37 (m, 4H), 1.33-1.42 (m, 2H), 1.39-1.51 (m, 2H), 1.74-1.85 (m, 2H), 3.94 (t, J=6.6 Hz, 2H), 6.76-6.83 (m, 2H), 7.34-7.43 (m, 2H).

Intermediate 6, Step 2: 4'-(heptyloxy)-[1,1'-biphenyl]-4-amine

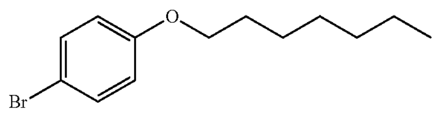

-continued

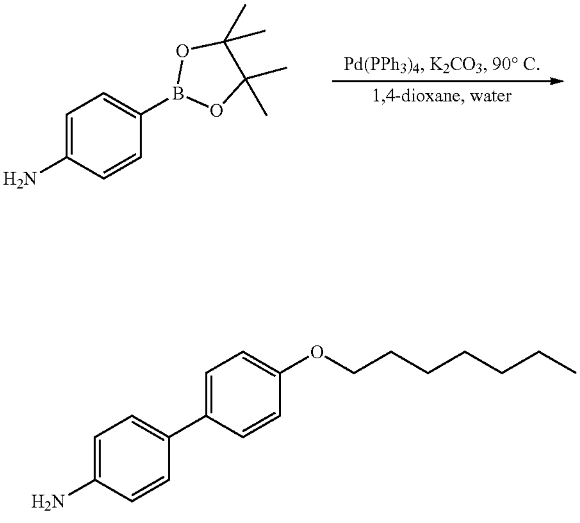

$Pd(PPh_3)_4$ (0.426 g, 0.37 mmol) was added to 1-bromo-4-(heptyloxy)benzene (1 g, 3.69 mmol), 4-(4,4,5,5-tetramethyl-1,3,2-dioxaborolan-2-yl)aniline (0.808 g, 3.69 mmol) and $K_2CO_3$ (1.529 g, 11.06 mmol) in 1,4-dioxane (15 mL) and water (3 mL) at rt under nitrogen. The resulting mixture was stirred at 90° C. for 16 h. The crude product was purified by flash silica chromatography, elution gradient 0 to 20% EtOAc in petroleum ether. Pure fractions were evaporated to dryness to afford 4'-(heptyloxy)-[1,1'-biphenyl]-4-amine (0.302 g, 28.9%) as a yellow solid. $^1$H NMR (300 MHz, DMSO) δ 0.80-0.88 (m, 2H), 1.24-1.30 (m, 8H), 1.62-1.77 (m, 3H), 3.94 (t, J=6.5 Hz, 2H), 5.10 (s, 2H), 6.58 (d, J=8.5 Hz, 2H), 6.90 (d, J=8.8 Hz, 2H), 7.25 (d, J=8.5 Hz, 2H), 7.40 (d, J=8.8 Hz, 2H). $ES^+$ m/z $[M+H]^+$: 284, HPLC $t_R$=1.18 min (97.2%).

Intermediate 7: 4'-(2-(3-(but-3-yn-1-yl)-3H-diazirin-3-yl)ethoxy)-[1,1'-biphenyl]-4-amine

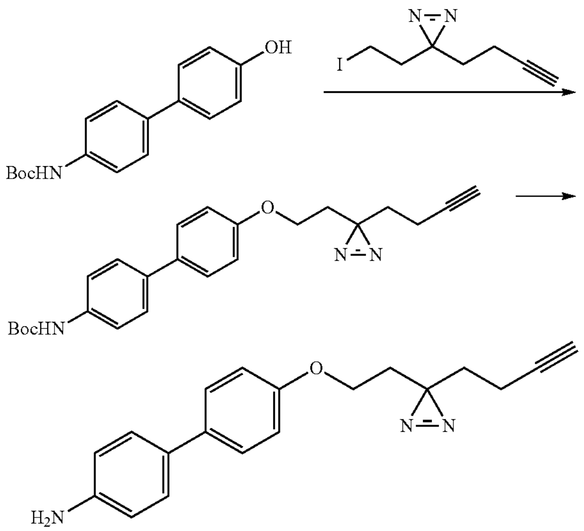

Intermediate 7, Step 1: tert-butyl (4'-(2-(3-(but-3-yn-1-yl)-3H-diazirin-3-yl) ethoxy)-[1,1'-biphenyl]-4-yl)carbamate

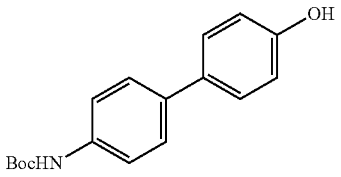

-continued

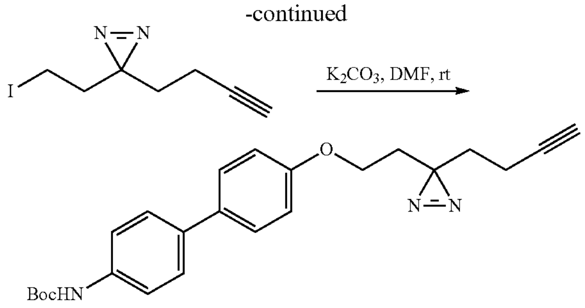

3-(But-3-yn-1-yl)-3-(2-iodoethyl)-3H-diazirine (300 mg, 1.21 mmol) was added to tert-butyl (4'-hydroxy-[1,1'-biphenyl]-4-yl)carbamate (414 mg, 1.45 mmol), and $K_2CO_3$ (334 mg, 2.42 mmol) in DMF (2 mL). The resulting mixture was stirred at RT for 14 h. The reaction mixture was diluted with water. The aqueous layers were combined and washed with EtOAc (3×50 mL). The solvent was removed under reduced pressure to give the crude product. The crude product was purified by flash silica chromatography, elution gradient 0 to 9.8% EtOAc in petroleum ether. Pure fractions were evaporated to dryness to afford tert-butyl (4'-(2-(3-(but-3-yn-1-yl)-3H-diazirin-3-yl)ethoxy)-[1,1'-biphenyl]-4-yl)carbamate (110 mg, 22%) as a yellow solid. $^1$H NMR (400 MHz, DMSO) δ 1.49 (s, 9H), 1.68 (t, J=7.4 Hz, 2H), 1.90 (t, J=6.1 Hz, 2H), 2.03-2.09 (m, 2H), 2.85 (t, J=2.6 Hz, 1H), 3.86 (t, J=6.1 Hz, 2H), 6.94-7.02 (m, 2H), 7.49-7.53 (m, 4H), 7.56 (d, J=2.9 Hz, 2H), 9.40 (s, 1H). $ES^+$ m/z $[M-tBu]^+$: 350, HPLC $t_R$=1.17 min (89.1%).

Intermediate 7, Step 2: 4'-(2-(3-(but-3-yn-1-yl)-3H-diazirin-3-yl)ethoxy)-[1,1'-biphenyl]-4-amine

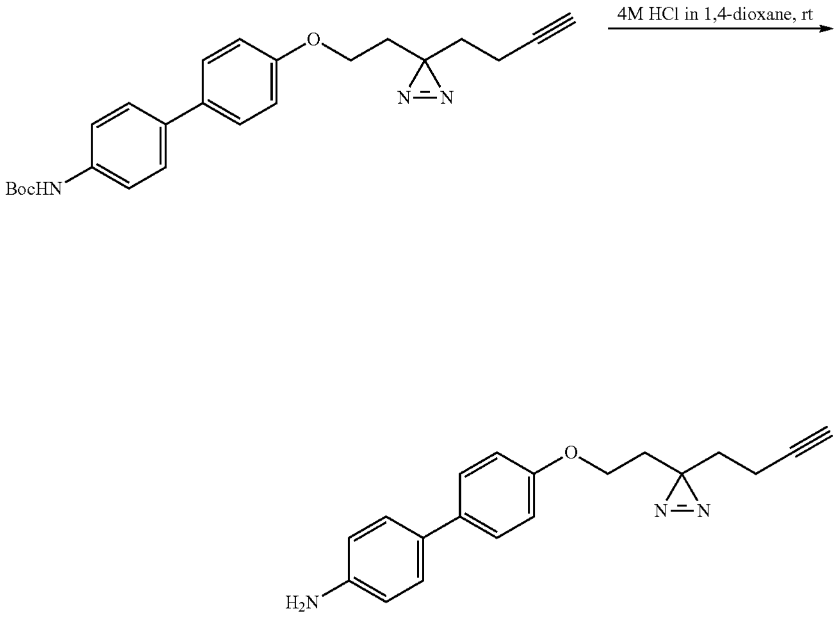

tert-Butyl (4'-(2-(3-(but-3-yn-1-yl)-3H-diazirin-3-yl) ethoxy)-[1,1'-biphenyl]-4-yl) carbamate (110 mg, 0.27 mmol) was added to 4 M HCl/dioxane (2 mL). The resulting mixture was stirred at RT for 4 h. The solvent was removed under reduced pressure to give the crude product 4'-(2-(3-(but-3-yn-1-yl)-3H-diazirin-3-yl)ethoxy)-[1,1'-biphenyl]-4-amine (100 mg, 121%) as a white solid. $^1$H NMR (400 MHz, DMSO) δ 1.68 (t, J=7.4 Hz, 2H), 1.91 (t, J=6.1 Hz, 2H), 2.01-2.10 (m, 2H), 2.86 (t, J=2.7 Hz, 1H), 3.87 (t, J=6.0 Hz, 2H), 6.99-7.06 (m, 2H), 7.33 (d, J=3.7 Hz, 2H), 7.59-7.62 (m, 2H), 7.67 (d, J=2.1 Hz, 2H). ES+ m/z $[M+H]^+$: 306, HPLC $t_R$=1.16 min (58.2%). The product was used without further purification.

Intermediate 8: tert-butyl (2-(4'-amino-[1,1'-biphenyl]-4-yl)oxy)ethyl)carbamate

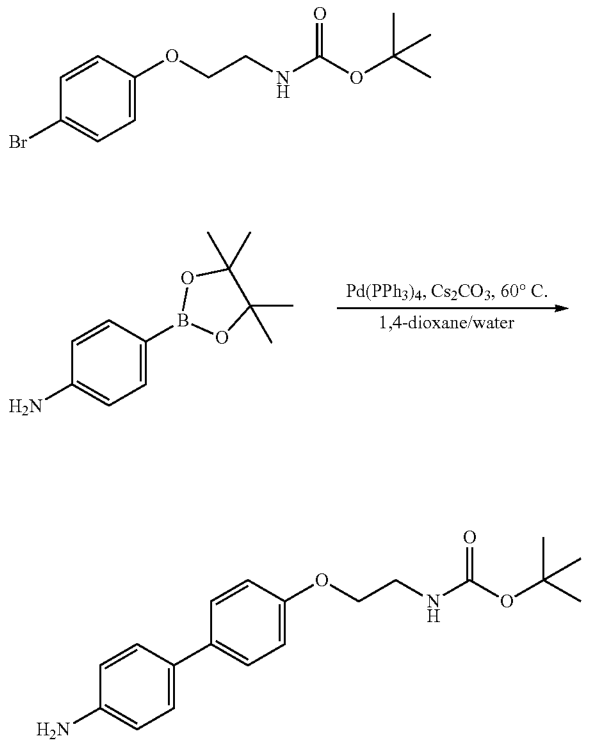

$Pd(PPh_3)_4$ (0.731 g, 0.63 mmol) was added to 4-(4,4,5,5-tetramethyl-1,3,2-dioxaborolan-2-yl)aniline (2.77 g, 12.65 mmol), tert-butyl (2-(4-bromophenoxy) ethyl)carbamate (4 g, 12.65 mmol) and $Cs_2CO_3$ (8.24 g, 25.30 mmol) in 1,4-dioxane (50 mL), water (10 mL) at rt under nitrogen. The resulting mixture was stirred at 80° C. for 16 hours. The crude product was purified by flash silica chromatography, elution gradient 40 to 55% EtOAc in petroleum ether. Pure fractions were evaporated to dryness to afford tert-butyl (24(4'-amino-[1,1'-biphenyl]-4-yl)oxy)ethyl)carbamate (3.57 g, 86%) as a yellow solid. $^1$H NMR (400 MHz, DMSO) δ 1.40 (s, 9H), 3.31 (p, J=5.2, 5.8 Hz, 2H), 3.97 (t, J=5.9 Hz, 2H), 5.12 (s, 2H), 6.58-6.68 (m, 2H), 6.89-6.97 (m, 2H), 7.00 (t, J=5.7 Hz, 1H), 7.23-7.34 (m, 2H), 7.40-7.48 (m, 2H). ES+ m/z $[M+H]^+$: 329, HPLC $t_R$=1.08 min (95.0%).

Intermediate 9: 2-chloro-6-isopropyl-4-((4-(4,4,5,5-tetramethyl-1,3,2-dioxa borolan-2-yl)phenyl)amino)-5,6-dihydro-7H-pyrrolo[3,4-d]pyrimidin-7-one

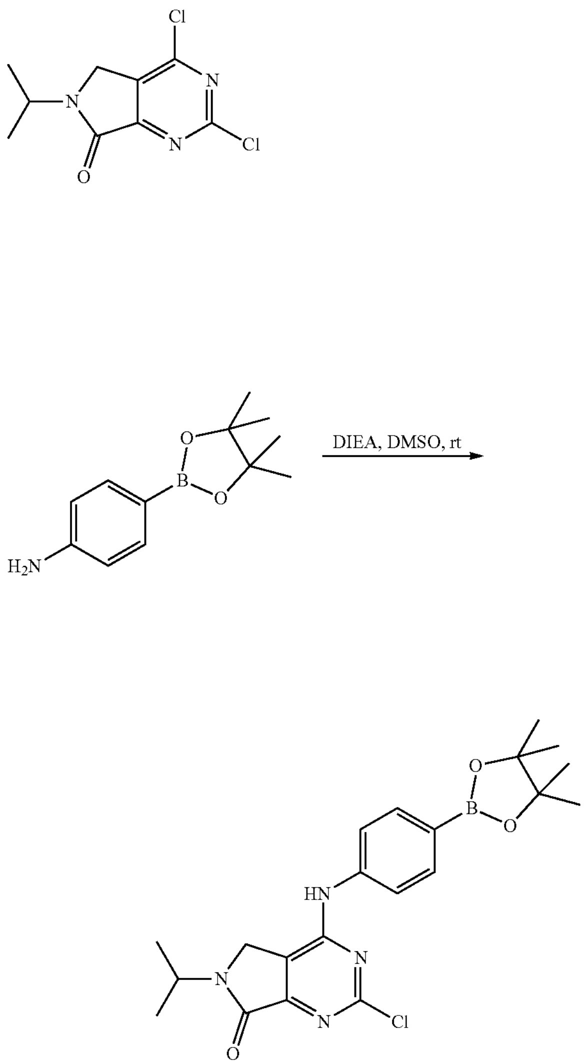

4-(4,4,5,5-Tetramethyl-1,3,2-dioxaborolan-2-yl)aniline (0.890 g, 4.06 mmol) was added to 2,4-dichloro-6-isopropyl-5,6-dihydro-7H-pyrrolo[3,4-d]pyrimidin-7-one (1 g, 4.06 mmol) and DIEA (1.419 mL, 8.13 mmol) in DMSO (10 mL) at 25'C and stirred at RT for 16 h. The reaction mixture was quenched with water (50 mL), extracted with EtOAc (3×50 mL), the organic layer was dried over $Na_2SO_4$, filtered and evaporated to afford yellow residue. The crude product was purified by flash silica chromatography, elution gradient 0 to 5% MeOH in DCM. Pure fractions were evaporated to dryness to afford 2-chloro-6-isopropyl-4-((4-(4,4,5,5-tetramethyl-1,3,2-dioxaborolan-2-yl) phenyl) amino)-5,6-dihydro-7H-pyrrolo[3,4-d]pyrimidin-7-one (1.070 g, 61%) as a yellow solid. $^1$H NMR (400 MHz, $CDCl_3$) δ 1.24 (d, J=6.7 Hz, 6H), 1.37 (s, 12H), 4.25 (s, 2H), 4.63 (p, J=6.8 Hz, 1H), 7.61 (d, J=8.0 Hz, 2H), 7.85 (d, J=8.1 Hz, 2H), 7.97 (s, 1H). ES+ m/z $[M+H]^+$: 429, HPLC $t_R$=1.38 min (71%).

Intermediate 10: 2-(3,6-dihydro-2H-pyran-4-yl)-6-isopropyl-4-((4-(4,4,5,5-tetramethyl-1,3,2-dioxaborolan-2-yl)phenyl)amino)-5,6-dihydro-7H-pyrrolo[3,4-d]pyrimidin-7-one

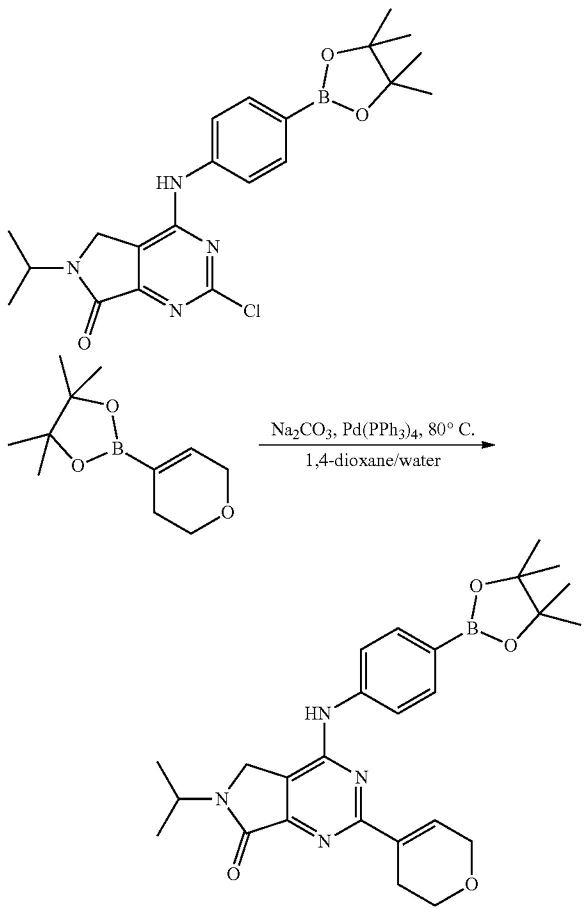

$Pd(PPh_3)_4$ (256 mg, 0.22 mmol) was added to 2-chloro-6-isopropyl-4-((4-(4,4,5,5-tetramethyl-1,3,2-dioxaborolan-2-yl)phenyl)amino)-5,6-dihydro-7H-pyrrolo[3,4-d]pyrimidin-7-one (950 mg, 2.22 mmol), dihydro-2H-pyran-4-yl)-4,4,5,5-tetramethyl-1,3,2-dioxaborolane (698 mg, 3.32 mmol) and $Na_2CO_3$ (470 mg, 4.43 mmol) in 1,4-dioxane (10 mL) and water (2 mL) at rt under nitrogen. The resulting mixture was stirred at 80° C. for 3 hours. The solvent was removed by distillation under vacuum. The crude product was purified by flash silica chromatography, elution gradient 0 to 5% MeOH in DCM. Pure fractions were evaporated to dryness to afford 2-(3,6-dihydro-2H-pyran-4-yl)-6-isopropyl-4(4-(4,4,5,5-tetramethyl-1,3,2-dioxaborolan-2-yl)phenyl)amino)-5,6-dihydro-7H-pyrrolo[3,4-d]pyrimidin-7-one (650 mg, 61.6%) as a yellow solid. $^1$H NMR (400 MHz, $CDCl_3$) δ 1.29 (s, 12H), 1.38 (s, 6H), 2.77 (s, 2H), 3.78 (t, J=5.4 Hz, 1H), 3.94 (t, J=5.5 Hz, 2H), 4.22 (q, J=2.8 Hz, 1H), 4.42 (d, J=3.0 Hz, 2H), 4.63-4.77 (m, 1H), 6.55 (s, 1H), 7.55-7.60 (m, 2H), 7.82-7.89 (m, 2H). ES+ m/z $[M+H]^+$: 477, HPLC $t_R$=1.21 min (76.4%).

Intermediate 11: 6-isopropyl-2-morpholino-4-((4-(4,4,5,5-tetramethyl-1,3,2-dioxaborolan-2-yl)phenyl)amino)-5,6-dihydro-7H-pyrrolo[3,4-d]pyrimidin-7-one

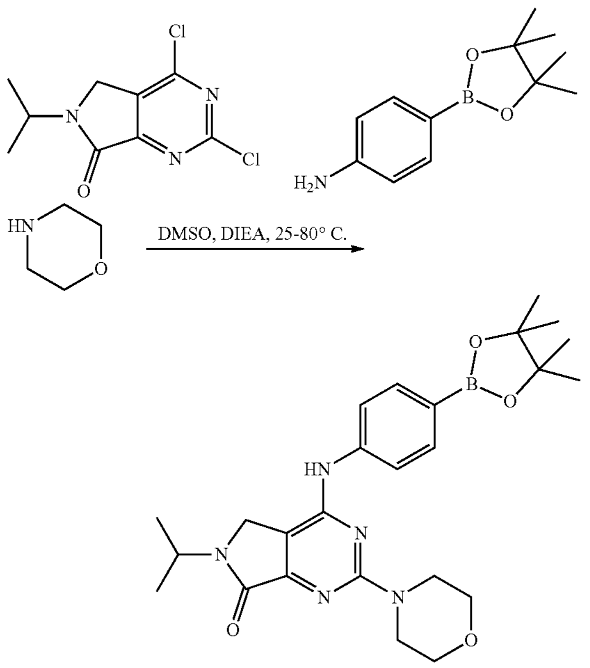

4-(4,4,5,5-Tetramethyl-1,3,2-dioxaborolan-2-yl)aniline (0.890 g, 4.06 mmol) was added to 2,4-dichloro-6-isopropyl-5,6-dihydro-7H-pyrrolo[3,4-d]pyrimidin-7-one (1 g, 4.06 mmol) and DIEA (1.419 mL, 8.13 mmol) in DMSO (6 mL) at 25° C. After stirring at RT for 16 hours, morpholine (0.708 g, 8.13 mmol) was added. The resulting mixture was stirred at 80° C. for 2 hours. The reaction mixture was quenched with water (20 mL), extracted with EtOAc (3×50 mL), the organic layer was dried over $Na_2SO_4$, filtered and evaporated to afford yellow residue. The crude product was purified by flash silica chromatography, elution gradient 0 to 8% MeOH in DCM. Pure fractions were evaporated to dryness to afford 6-isopropyl-2-morpholino-4-((4-(4,4,5,5-tetramethyl-1,3,2-dioxaborolan-2-yl)phenyl)amino)-5,6-dihydro-7H-pyrrolo[3,4-d]pyrimidin-7-one (1.477 g, 76%) as a yellow solid. $^1$H NMR (400 MHz, DMSO) δ 1.24 (d, J=6.7 Hz, 6H), 1.29 (s, 12H), 3.64-3.70 (m, 9H), 4.29 (s, 2H), 7.63-7.70 (m, 2H), 7.74-7.81 (m, 2H), 9.41 (s, 1H). ES+ m/z $[M+H]^+$: 480, HPLC $t_R$=1.30 min (70.9%).

Intermediate 12: 1-bromo-4-(prop-2-yn-1-yloxy)benzene

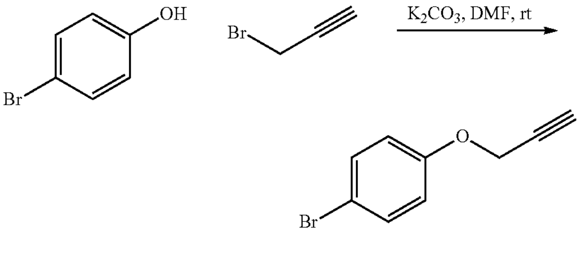

3-Bromoprop-1-yne (0.825 g, 6.94 mmol) was added to 4-bromophenol (1.0 g, 5.78 mmol) and $K_2CO_3$ (1.598 g, 11.56 mmol) in DMF (10 mL) at rt. The resulting mixture was stirred at rt for 16 hours. The reaction mixture was poured into water (50 mL) and extracted with EtOAc (3×50 mL). The organic layers were combined and washed with water (2×50 mL) and brine (50 mL). The organic layer was dried over $Na_2SO_4$, filtered and evaporated. The crude product was purified by flash silica chromatography, elution gradient 0 to 6% EtOAc in petroleum ether. Pure fractions were evaporated to dryness to afford 1-bromo-4-(prop-2-yn-1-yloxy)benzene (0.598 g, 49.0%) as a colourless oil. $^1H$ NMR (400 MHz, $CDCl_3$) δ 2.55 (t, J=2.4 Hz, 1H), 4.70 (d, J=2.4 Hz, 2H), 6.85-6.93 (m, 2H), 7.38-7.47 (m, 2H).

Intermediate 13: 3-(2-(4-bromophenoxy)ethyl)-3-(but-3-yn-1-yl)-3H-diazirine

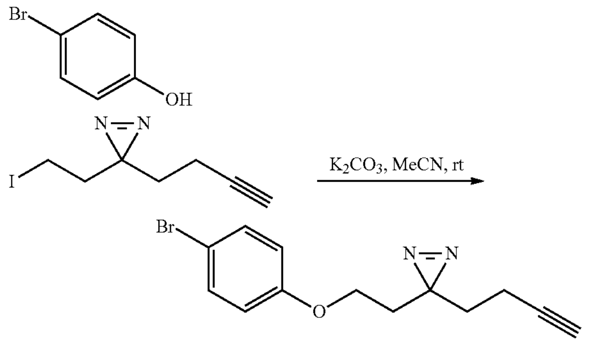

3-(But-3-yn-1-yl)-3-(iodoethyl)-3H-diazirine (300 mg, 1.28 mmol) was added to $K_2CO_3$ (531 mg, 3.85 mmol) and 4-bromophenol (244 mg, 1.41 mmol) in MeCN (3 mL). The resulting solution was stirred at RT for 1 hour. The reaction mixture was filtered through celite. The solvent was removed under reduced pressure. The crude product was purified by flash silica chromatography, elution gradient 0 to 10% EtOAc in petroleum ether. Pure fractions were evaporated to dryness to afford 3-(2-(4-bromophenoxy)ethyl)-3-(but-3-yn-1-yl)-3H-diazirine (100 mg, 26.6%) as a brown oil. $^1H$ NMR (300 MHz, $CDCl_3$) δ 1.75 (t, J=7.4 Hz, 2H), 1.91 (t, J=6.2 Hz, 2H), 2.01 (t, J=2.6 Hz, 1H), 2.05-2.13 (m, 2H), 3.81 (t, J=6.2 Hz, 2H), 6.74-6.86 (m, 2H), 7.34-7.45 (m, 2H). ES+ m/z $[M+H]^+$: No Mass, HPLC $t_R$=1.30 min (99.0%).

Intermediate 14: tert-butyl (2-(4-bromophenoxy)ethyl)carbamate

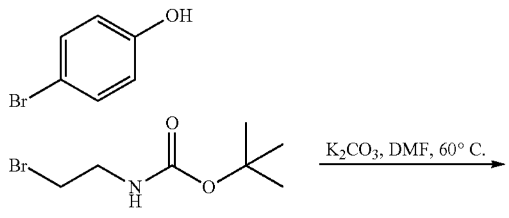

-continued

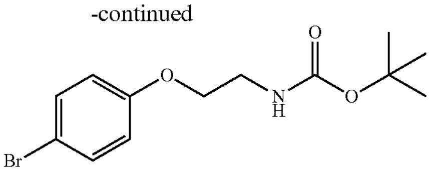

$K_2CO_3$ (3.00 g, 21.68 mmol) was added to 4-bromophenol (2.5 g, 14.45 mmol) and tert-butyl (2-bromoethyl)carbamate (3.89 g, 17.34 mmol) in DMF (30 mL) at rt. The resulting mixture was stirred at 60° C. for 16 hours. The reaction mixture was poured into water (150 mL) and extracted with EtOAc (3×50 mL). The organic layers were combined and washed with water (2×100 mL). The organic layer was dried over $Na_2SO_4$, filtered and evaporated to afford a colourless oil. The crude product was purified by flash silica chromatography, elution gradient 0 to 30% EtOAc in petroleum ether. Pure fractions were evaporated to dryness to afford tert-butyl (2-(4-bromophenoxy)ethyl)carbamate (4.37 g, 96%) as a white solid. $^1H$ NMR (400 MHz, $CDCl_3$) δ 1.47 (s, 9H), 3.54 (q, J=5.3 Hz, 2H), 4.00 (t, J=5.2 Hz, 2H), 4.98 (s, 1H), 6.72-6.83 (m, 2H), 7.37-7.41 (m, 2H). ES+ m/z $[M-tBu]^+$: 260, HPLC $t_R$=1.46 min (92%).

Intermediate 15 (R)-4-((4-cyclohexylphenyl)amino)-2-(2-methylmorpholino) furo[3,4-d]pyrimidin-7(5H)-one

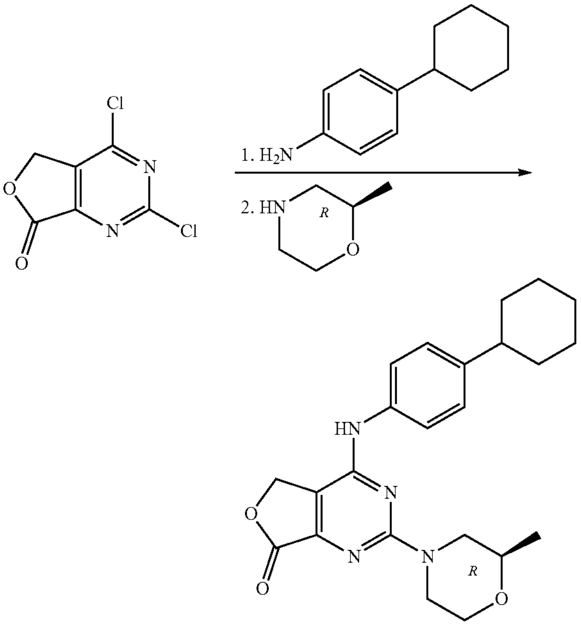

DIEA (0.598 mL, 3.42 mmol) was added to 2,4-dichlorofuro[3,4-d]pyrimidin-7(5H)-one (234 mg, 1.14 mmol) and 4-cyclohexylaniline (200 mg, 1.14 mmol) in DMSO (2 mL) at rt. The resulting mixture was stirred at rt for 16 h. (R)-2-methylmorpholine (115 mg, 1.14 mmol) was added to above mixture. The resulting mixture was stirred at 100° C. for 16 h. The reaction mixture was filtered with water and ethyl acetate and evaporated to afford (R)-4-((4-cyclohexylphenyl)amino)-2-(2-methylmorpholino)furo[3,4-d]pyrimidin-7(5H)-one (412 mg, 88%) as a yellow solid. $^1H$ NMR (400 MHz, DMSO) δ 1.16 (d, J=6.1 Hz, 3H), 1.31-

1.46 (m, 5H), 1.77-1.82 (m, 5H), 2.60-2.71 (m, 1H), 2.99 (t, J=11.4 Hz, 1H), 3.43-3.55 (m, 3H), 3.91 (d, J=10.8 Hz, 1H), 4.40 (dd, J=13.2, 30.2 Hz, 2H), 5.23 (s, 2H), 7.23 (d, J=8.3 Hz, 2H), 7.62 (d, J=8.2 Hz, 2H), 9.53 (s, 1H). ES+ m/z $[M+H]^+$: 409, HPLC $t_R$=1.50 min (81.4%).

Intermediate 16: (R)-4-((4-cyclobutylphenyl) amino)-2-(2-methylmorpholino) furo[3,4-d]pyrimidin-7(5H)-one

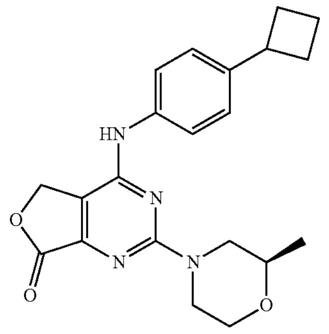 [SMILES: C[C@@H]1CN(c2nc(Nc3ccc(C4CCC4)cc3)c3c(n2)C(=O)OC3)CCO1]

(R)-4-((4-cyclobutylphenyl)amino)-2-(2-methylmorpholino)furo[3,4-d]pyrimidin-7(5H)-one was made from 2,4-dichlorofuro[3,4-d]pyrimidin-7(5H)-one using a method analogous to that described for Intermediate 15. $^1$H NMR (400 MHz, DMSO) δ 1.16 (d, J=6.2 Hz, 3H), 1.75-1.87 (m, 1H), 1.88-2.04 (m, 1H), 2.01-2.16 (m, 2H), 2.22-2.34 (m, 2H), 2.65 (dd, J=10.4, 13.1 Hz, 1H), 2.92-3.04 (m, 1H), 3.47-3.51 (m, 3H), 3.86-3.94 (m, 1H), 4.36 (d, J=13.1 Hz, 1H), (d, J=13.1 Hz, H), 5.22 (s, 2H), 7.22-7.27 (m, 2H), 7.63 (d, J=8.4 Hz, 2H), 9.53 (s, 1H). ES+ m/z $[M+H]^+$: 381, HPLC $t_R$=1.58 min (90.7%).

Intermediate 17: 4-((4-isopropylphenyl)amino)-2-morpholinofuro[3,4-d]pyrimidin-7(5H)-one

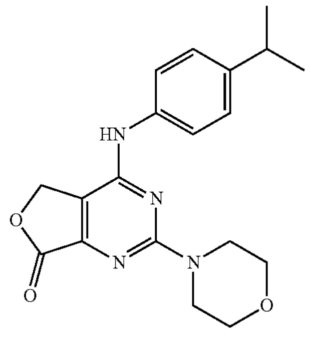 [SMILES: CC(C)c1ccc(Nc2nc(N3CCOCC3)nc3c2COC3=O)cc1]

4-((4-Isopropylphenyl)amino)-2-morpholinofuro[3,4-d]pyrimidin-7(5H)-one was made using a method analogous to that described for Intermediate 15. $^1$H NMR (400 MHz, DMSO) δ 1.21 (d, J=6.9 Hz, 6H), 2.88 (p, J=6.9 Hz, 1H), 3.63-3.75 (m, 8H), 5.23 (s, 2H), 7.21-7.29 (m, 2H), 7.61-7.67 (m, 2H), 9.51 (s, 1H). ES+ m/z $[M+H]^+$: 355, HPLC $t_R$=1.46 min (97.3%).

Synthesis of Examples

Example 1: 2-(Diethylamino)-6-isopropyl-4-((4-isopropylphenyl)amino)-5,6-dihydro-7H-pyrrolo[3,4-d]pyrimidin-7-one

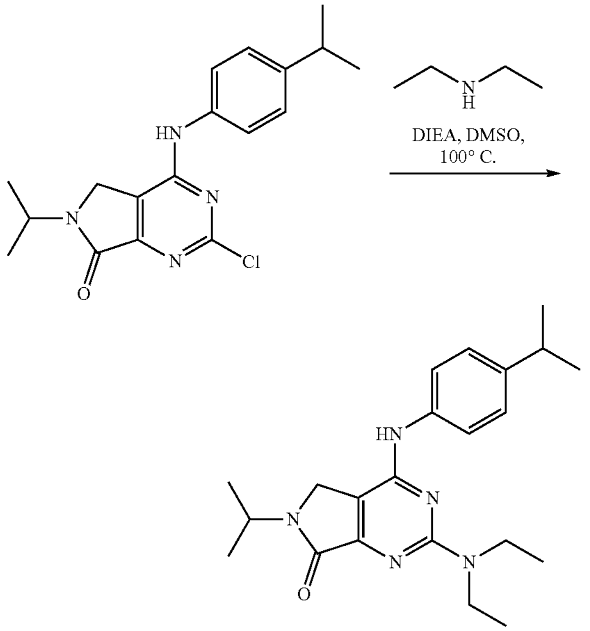

DIEA (0.152 mL, 0.87 mmol) was added to diethylamine (63.6 mg, 0.87 mmol), and 2-chloro-6-isopropyl-4-((4-isopropylphenyl)amino)-5,6-dihydro-7H-pyrrolo[3,4-d]pyrimidin-7-one (100 mg, 0.29 mmol) in DMSO (5 mL). The resulting mixture was stirred at 100° C. for 4 hours. The crude product was purified by preparative HPLC conditions B. Fractions containing the desired compound were evaporated to dryness to afford 2-(diethylamino)-6-isopropyl-4-((4-isopropylphenyl)amino)-5,6-dihydro-7H-pyrrolo[3,4-d]pyrimidin-7-one (70.0 mg, 63%) as a white solid. $^1$H NMR (400 MHz, DMSO) δ 1.14 (t, J=6.9 Hz, 6H), 1.22 (m, 12H), 2.79-2.92 (m, 1H), 3.60 (q, J=7.0 Hz, 4H), 4.24 (s, 2H), 4.36-4.48 (m, 1H), 7.20 (d, 2H), 7.75 (d, 2H), 9.03 (s, 1H). m/z (ES+), $[M+H]^{30}$ : 382; HPLC $t_R$=1.73 min.

Example 2: 4-((4-cyclohexylphenyl)amino)-2-(2-cyclopropylmorpholino)-6-isopropyl-5,6-dihydro-7H-pyrrolo[3,4-d]pyrimidin-7-one

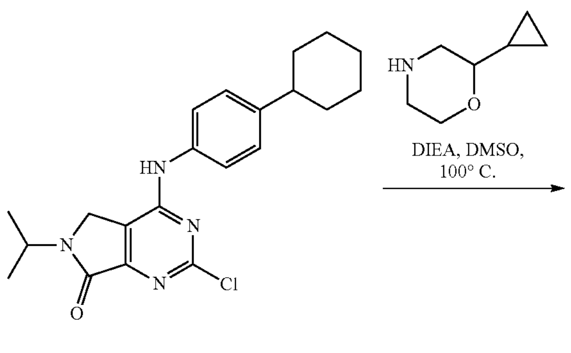

-continued

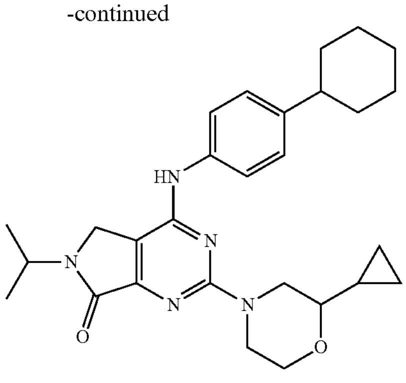

2-cyclopropylmorpholine (49.6 mg, 0.39 mmol) was added to 2-chloro-4-((4-cyclohexylphenyl)amino)-6-isopropyl-5,6-dihydro-7H-pyrrolo[3,4-d]pyrimidin-7-one (100 mg, 0.26 mmol) and DIEA (0.091 mL, 0.52 mmol) in DMSO (2 mL) at rt. The resulting mixture was stirred at 100° C. for 16 hours. The crude product was purified by preparative HPLC conditions D. Fractions containing the desired compound were evaporated to dryness to afford 4-((4-cyclohexylphenyl)amino)-2-(2-cyclopropylmorpholino)-6-isopropyl-5,6-dihydro-7H-pyrrolo[3,4-d]pyrimidin-7-one (60.0 mg, 48.6%) as a white solid. $^1H$ NMR (400 MHz, DMSO) δ 0.22-0.37 (m, 2H), 0.44-0.55 (m, 2H), 0.84-0.96 (m, 1H), 1.23 (d, J=6.8 Hz, 7H), 1.30-1.47 (m, 4H), 1.75 (dd, J=35.9, 10.9 Hz, 5H), 2.47 (s, 1H), 2.70-2.86 (m, 2H), 2.98 (td, J=12.5, 11.8, 3.4 Hz, 1H), 3.40 (td, 1H), 3.90 (dd, 1H), 4.25 (s, 2H), 4.33 (d, J=13.1 Hz, 1H), 4.37-4.47 (m, 1H), 4.52 (d, J=12.5 Hz, 1H), 7.19 (d, 2H), 7.63 (d, 2H), 9.19 (s, 1H). m/z (ES+), $[M+H]^+$: 476; HPLC $t_R$=2.37 min (99.8%).

The enantiomers of 4-((4-cyclohexylphenyl)amino)-2-(2-cyclopropylmorpholino)-6-isopropyl-5,6-dihydro-7H-pyrrolo[3,4-d]pyrimidin-7-one were separated using preparative chiral-HPLC: Column: (R, R)WHELK-01, 5/100 Kromasil, 2.11 cm×25 cm (5 μm); Mobile Phase A: Hex (8 mM $NH_3$·MeOH), Mobile Phase B: EtOH; Flow rate: 20 mL/min; 40% B over 20 min; detection at 254/220 nm; Isomer 1, $t_R$1=13.818 min; Isomer 2, $t_R$2=16.895 min. Data for isomer 1 (Example 15) and isomer 2 (Example 14) is shown in Table 1.

The Examples in Table 1 were made from Intermediates 3 and 4 in a manner analogous to Examples 1 and 2.

TABLE 1

| Example | Name | Structure | Analytical data |
|---|---|---|---|
| 3 | 6-(propan-2-yl)-4-{[4-(propan-2-yl)phenyl]amino}-2-(1,3-thiazolidin-3-yl)-5,6-dihydro-7H-pyrrolo[3,4-d]pyrimidin-7-one | 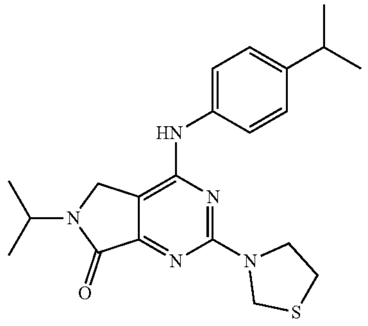 [SMILES: CC(C)c1ccc(Nc2nc(N3CCSC3)nc3c2CN(C(C)C)C3=O)cc1] | $^1H$ NMR (400 MHz, DMSO) δ 1.23 (dd, J = 11.2, 6.8 Hz, 12H), 2.82-2.93 (m, 1H), 3.08 (t, J = 6.3 Hz, 2H), 3.91 (t, J = 6.3 Hz, 2H), 4.28 (s, 2H), 4.36-4.48 (m, 1H), 4.73 (s, 2H), 7.24 (d, 2H), 7.72 (d, 2H), 9.24 (s, 1H). m/z (ES+), $[M + H]^+$ = 398; HPLC $t_R$ = 1.806 min (98.6%) |
| 4 | 2-[(2R,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one | 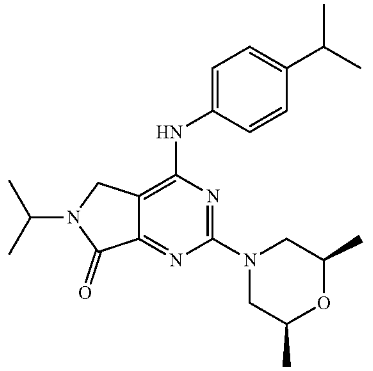 | $^1H$ NMR (400 MHz, DMSO) δ 1.14 (d, J = 6.4 Hz, 6H), 1.18-1.27 (m, 12H), 2.82-2.93 (m, 1H), 3.46 (s, 2H), 3.84 (d, J = 13.1 Hz, 2H), 3.95-4.04 (m, 2H), 4.25 (s, 2H), 4.36-4.47 (m, 1H), 7.23 (d, J = 8.6 Hz, 2H), 7.65 (d, J = 8.6 Hz, 2H), 9.17 (s, 1H). m/z (ES+), $[M + H]^+$: 345; HPLC $t_R$ = 1.379 min (100%) |

TABLE 1-continued

| Example | Name | Structure | Analytical data |
|---|---|---|---|
| 5 | 6-(propan-2-yl)-4-{[4-(propan-2-yl)phenyl]amino}-2-(thiomorpholin-4-yl)-5,6-dihydro-7H-pyrrolo[3,4-d]pyrimidin-7-one | 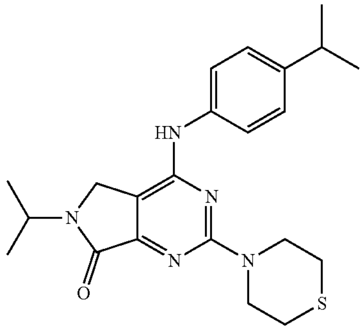 [SMILES: CC(C)c1ccc(Nc2nc(N3CCSCC3)nc3c2CN(C(C)C)C3=O)cc1] | $^1$H NMR (400 MHz, DMSO) δ 1.22 (dd, J = 10.2, 6.8 Hz, 12H), 2.58-2.65 (m, 4H), 2.81-2.93 (m, 1H), 4.03-4.10 (m, 4H), 4.25 (s, 2H), 4.36-4.47 (m, 1H), 7.22 (d, J = 8.5 Hz, 2H), 7.63 (d, 2H), 9.19 (s, 1H). m/z (ES+), [M + H]$^+$: 412; HPLC $t_R$ = 1.828 min (99.8%) |
| 6 | 2-[(2S)-2-methylmorpholin-4-yl]-6-(propan-2-yl)-4-{[4-(propan-2-yl)phenyl]amino}-5,6-dihydro-7H-pyrrolo[3,4-d]pyrimidin-7-one | 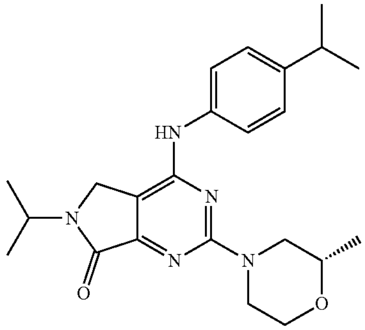 [SMILES: CC(C)c1ccc(Nc2nc(N3CCO[C@@H](C)C3)nc3c2CN(C(C)C)C3=O)cc1] | $^1$H NMR (400 MHz, DMSO) δ 1.16 (d, J = 6.2 Hz, 3H), 1.22 (dd, J = 9.9, 6.9 Hz, 12H), 2.62 (dd, J = 13.1, 10.4 Hz, 1H), 2.81-3.01 (m, 2H), 3.43-3.55 (m, 2H), 3.90 (dd, J = 11.5, 3.2 Hz, 1H), 4.25 (s, 2H), 4.33-4.49 (m, 3H), 7.23 (d, J = 8.5 Hz, 2H), 7.65 (d, 2H), 9.19 (s, 1H). m/z (ES+), [M + H]$^+$: 410; HPLC $t_R$ = 1.749 min (99.9%) |
| 7 | 2-[(2R)-2-methylmorpholin-4-yl]-6-(propan-2-yl)-4-{[4-(propan-2-yl)phenyl]amino}-5,6-dihydro-7H-pyrrolo[3,4-d]pyrimidin-7-one | 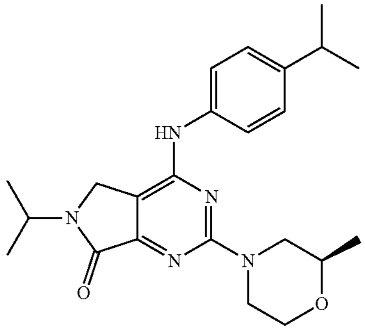 [SMILES: CC(C)c1ccc(Nc2nc(N3CCO[C@H](C)C3)nc3c2CN(C(C)C)C3=O)cc1] | $^1$H NMR (400 MHz, DMSO) δ 1.12-1.26 (m, 15H), 2.61 (dd, J = 13.1, 10.4 Hz, 1H), 2.79-3.01 (m, 2H), 3.42-3.55 (m, 2H), 3.89 (dd, J = 11.4, 3.0 Hz, 1H), 4.24 (s, 2H), 4.32-4.49 (m, 3H), 7.22 (d, 2H), 7.65 (d, 2H), 9.18 (s, 1H). m/z (ES+), [M + H]$^+$: 410; HPLC $t_R$ = 1.695 min (99.6%) |
| 8 | 2-[(2S,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one | 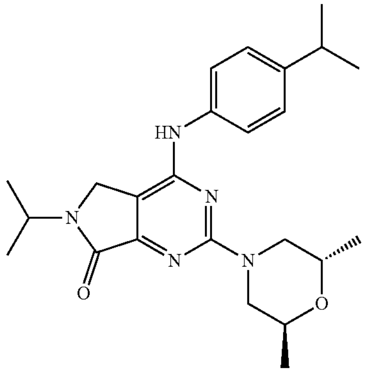 [SMILES: CC(C)c1ccc(Nc2nc(N3C[C@H](C)O[C@@H](C)C3)nc3c2CN(C(C)C)C3=O)cc1] | $^1$H NMR (400 MHz, DMSO) δ 1.14 (d, J = 6.4 Hz, 6H), 1.18-1.27 (m, 12H), 2.81-2.93 (m, 1H), 3.45 (s, 1H), 3.83 (d, J = 13.1 Hz, 2H), 3.95-4.04 (m, 2H), 4.25 (s, 2H), 4.36-4.47 (m, 1H), 7.23 (d, J = 8.6 Hz, 2H), 7.65 (d, 2H), 9.17 (s, 1H). m/z (ES+), [M + H]$^+$: 424; HPLC $t_R$ = 1.773 min (99.3%) |

TABLE 1-continued

| Example | Name | Structure | Analytical data |
|---|---|---|---|
| 9 | 2-(3-methylmorpholin-4-yl)-6-(propan-2-yl)-4-{[4-(propan-2-yl)phenyl]amino}-5,6-dihydro-7H-pyrrolo[3,4-d]pyrimidin-7-one | 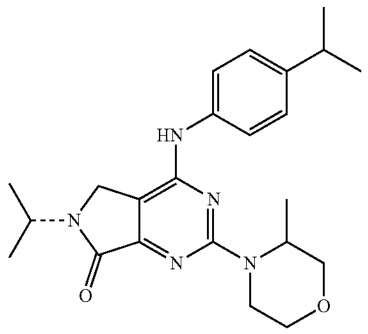 | $^1$H NMR (400 MHz, DMSO) δ 1.17-1.27 (m, 15H), 2.81-2.92 (m, 1H), 3.15 (td, J = 12.9, 3.6 Hz, 1H), 3.42 (td, 1H), 3.58 (dd, J = 11.4, 3.2 Hz, 1H), 3.73 (d, J = 11.3 Hz, 1H), 3.93 (dd, J = 11.2, 3.5 Hz, 1H), 4.17-4.28 (m, 3H), 4.36-4.47 (m, 1H), 4.59 (d, J = 6.0 Hz, 1H), 7.22 (d, J = 8.6 Hz, 2H), 7.67 (d, 2H), 9.17 (s, 1H). m/z (ES+), $[M + H]^+$: 410; HPLC $t_R$ = 1.734 min (99.1%) |
| 10 | 2-(2-cyclopropylmorpholin-4-yl)-6-(propan-2-yl)-4-{[4-(propan-2-yl)phenyl]amino}-5,6-dihydro-7H-pyrrolo[3,4-d]pyrimidin-7-one | 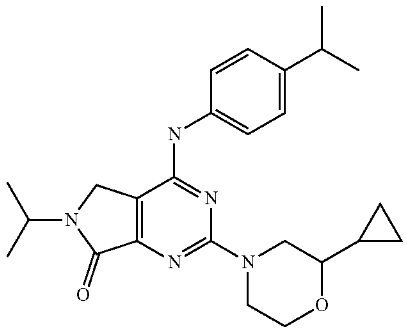 [SMILES: CC(C)c1ccc(Nc2nc(N3CCOC(C4CC4)C3)nc3c2CN(C(C)C)C3=O)cc1] | $^1$H NMR (400 MHz, MeOD) δ 0.29-0.36 (m, 1H), 0.36-0.44 (m, 1H), 0.57 (dd, J = 8.4, 2.0 Hz, 2H), 0.88-0.99 (m, 1H), 1.28 (d, J = 6.9 Hz, 6H), 1.34 (d, J = 6.8 Hz, 6H), 2.73-2.82 (m, 1H), 2.84-2.97 (m, 2H), 3.01-3.13 (m, 1H), 3.55 (td, J = 11.6, 2.7 Hz, 1H), 3.93-4.00 (m, 1H), 4.30 (s, 2H), 4.49-4.62 (m, 2H), 4.74 (d, J = 13.0 Hz, 1H), 7.23 (d, J = 8.5 Hz, 2H), 7.57-7.64 (m, 2H). m/z (ES+), $[M + H]^+$: 436; HPLC $t_R$ = 1.814 min (99.1%) |
| 11 | 4-[(4-cyclohexylphenyl) amino]-2-(morpholin-4-yl)-6-(propan-2-yl)-5,6-dihydro-7H-pyrrolo[3,4-d]pyrimidin-7-one | 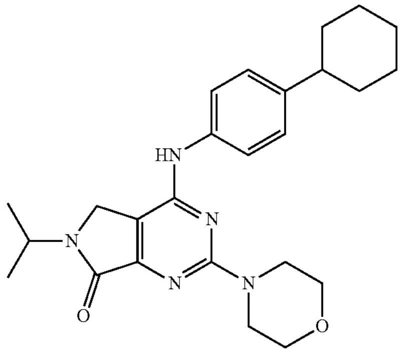 [SMILES: CC(C)N1Cc2c(Nc3ccc(C4CCCCC4)cc3)nc(N3CCOCC3)nc2C1=O] | $^1$H NMR (400 MHz, $CDCl_3$) δ 1.22 (d, J = 6.7, 1.8 Hz, 6H), 1.28 (d, J = 7.4 Hz, 1H), 1.35-1.48 (m, 4H), 1.80 (s, 1H), 1.90 (d, J = 10.6 Hz, 4H), 2.54 (t, 1H), 3.75 (t, J = 5.5, 4.0 Hz, 4H), 3.81-4.03 (m, 6H), 4.59-4.70 (m, 1H), 6.71 (s, 1H), 7.24 (d, 2H), 7.45 (dd, J = 8.4, 3.1 Hz, 2H). m/z (ES+), $[M + H]^+$: 436; HPLC $t_R$ = L6 min (99.5%) |
| 12 | 4-[(4-cyclohexylphenyl) amino]-2-(2-methylmorpholin-4-yl)-6-(propan-2-yl)-5,6-dihydro-7H-pyrrolo[3,4-d]pyrimidin-7-one | 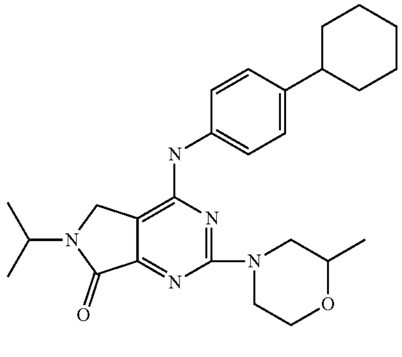 [SMILES: CC1CN(c2nc(Nc3ccc(C4CCCCC4)cc3)c3c(n2)C(=O)N(C(C)C)C3)CCO1] | $^1$H NMR (400 MHz, DMSO) δ 1.23 (d, J = 6.7 Hz, 7H), 1.33-1.45 (m, 4H), 1.75 (dd, J = 34.5, 11.3 Hz, 5H), 2.46 (d, 2H), 2.73 (t, J = 6.3, 3.8 Hz, 4H), 3.66 (t, J = 5.0 Hz, 4H), 4.24 (s, 2H), 4.36-4.47 (m, 1H), 7.19 (dd, 2H), 7.65 (dd, 2H), 9.11 (s, 1H). m/z (ES+), $[M + H]^+$: 450; HPLC $t_R$ = 1.89 min (99.9%). |

TABLE 1-continued

| Example | Name | Structure | Analytical data |
|---|---|---|---|
| 13 | 4-[(4-cyclohexylphenyl)amino]-2-[(2R)-2-methylmorpholin-4-yl]-6-(propan-2-yl)-5,6-dihydro-7H-pyrrolo[3,4-d]pyrimidin-7-one | 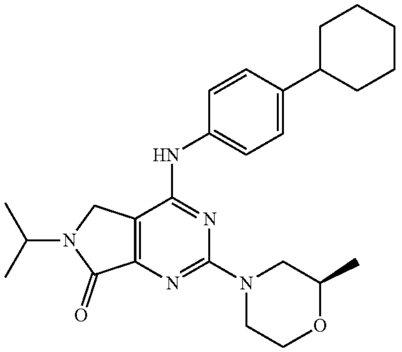 [SMILES: CC(C)N1Cc2c(Nc3ccc(C4CCCCC4)cc3)nc(N3CCO[C@H](C)C3)nc2C1=O] | $^1H$ NMR (400 MHz, DMSO) δ 1.16 (d, J = 6.2 Hz, 3H), 1.23 (d, J = 6.7 Hz, 7H), 1.29-1.47 (m, 4H), 1.71 (d, J = 12.6 Hz, 1H), 1.79 (d, J = 9.7 Hz, 4H), 2.47 (s, 1H), 2.62 (dd, J = 13.1, 10.4 Hz, 1H), 2.89-3.00 (m, 1H), 3.43-3.53 (m, 2H), 3.90 (d, J = 9.2 Hz, 1H), 4.25 (s, 2H), 4.32-4.49 (m, 3H), 7.20 (d, J = 8.5 Hz, 2H), 7.64 (d, J = 8.6 Hz, 2H), 9.18 (s, 1H). m/z (ES+), $[M + H]^+$: 450; HPLC $t_R$ = 2.996 min (99.9%). |
| 14 | 4-[(4-cyclohexylphenyl)amino]-2-(2-cyclopropylmorpholin-4-yl)-6-(propan-2-yl)-5,6-dihydro-7H-pyrrolo[3,4-d]pyrimidin-7-one (isomer 2) | 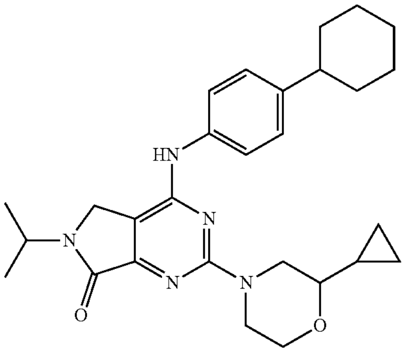 [SMILES: CC(C)N1Cc2c(Nc3ccc(C4CCCCC4)cc3)nc(N3CCOC(C4CC4)C3)nc2C1=O] | $^1H$ NMR (400 MHz, DMSO) δ 0.28 (s, 1H), 0.30-0.37 (m, 1H), 0.51 (d, J = 8.3 Hz, 2H), 0.91 (d, J = 7.9 Hz, 1H), 1.23 (d, J = 6.7 Hz, 8H), 1.33-1.47 (m, 4H), 1.71 (d, J = 12.2 Hz, 1H), 1.80 (d, J = 9.1 Hz, 3H), 2.74 (t, J = 9.6 Hz, 1H), 2.78-2.86 (m, 1H), 2.93-3.01 (m, 1H), 3.41 (t, J = 10.8 Hz, 1H), 3.91 (d, J = 11.4 Hz, 1H), 4.25 (s, 2H), 4.33 (d, J = 13.6 Hz, 1H), 4.39-4.45 (m, 1H), 4.52 (d, J = 12.6 Hz, 1H), 7.19 (d, J = 8.6 Hz, 2H), 7.63 (d, J = 8.6 Hz, 2H), 9.19 (s, 1H). m/z (ES+), $[M + H]^+$: 476; HPLC $t_R$ = 2.372 min (99.93%). ee = >99.5. |
| 15 | 4-[(4-cyclohexylphenyl)amino]-2-(2-cyclopropylmorpholin-4-yl)-6-(propan-2-yl)-5,6-dihydro-7H-pyrrolo[3,4-d]pyrimidin-7-one (isomer 1) | 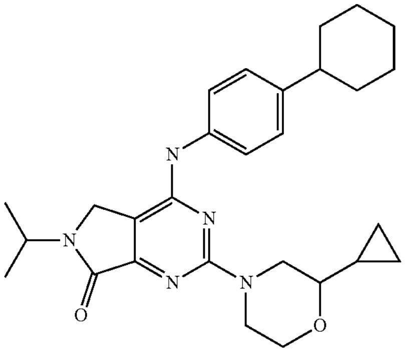 [SMILES: CC(C)N1Cc2c(Nc3ccc(C4CCCCC4)cc3)nc(N3CCOC(C4CC4)C3)nc2C1=O] | $^1H$ NMR (400 MHz, DMSO) δ 0.23-0.37 (m, 1H), 0.51 (d, J = 8.2 Hz, 1H), 0.91 (d, J = 7.9 Hz, 1H), 1.23 (d, J = 6.7 Hz, 8H), 1.40 (dd, J = 9.6, 6.2 Hz, 3H), 1.71 (d, J = 13.1 Hz, 1H), 1.80 (d, J = 9.2 Hz, 3H), 2.74 (t, J = 9.4 Hz, 1H), 2.79-2.87 (m, 1H), 2.93-3.03 (m, 1H), 3.41 (t, J = 11.6 Hz, 1H), 3.91 (d, J = 11.3 Hz, 1H), 4.25 (s, 1H), 4.33 (d, J = 13.1 Hz, 1H), 4.36-4.47 (m, 1H), 4.52 (d, J = 12.5 Hz, 1H), 7.19 (d, J = 8.6 Hz, 2H), 7.63 (d, J = 8.5 Hz, 1H), 9.19 (s, 1H). m/z (ES+), $[M + H]^+$: 476; HPLC $t_R$ = 2.370 min (99.7%). ee = 99.5. |
| 16 | 4-[(4-cyclohexylphenyl)amino]-6-(propan-2-yl)-2-[2-(2,2,2-trifluoroethyl)morpholin-4-yl]-5,6-dihydro-7H-pyrrolo[3,4-d]pyrimidin-7-one | 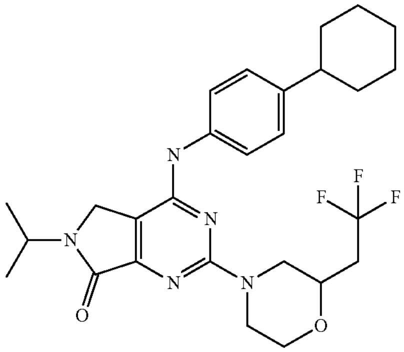 [SMILES: CC(C)N1Cc2c(Nc3ccc(C4CCCCC4)cc3)nc(N3CCOC(CC(F)(F)F)C3)nc2C1=O] | $^1H$ NMR (400 MHz, DMSO) δ 1.24 (d, J = 6.7 Hz, 7H), 1.33-1.42 (m, 4H), 1.75 (dd, J = 34.7, 10.8 Hz, 5H), 2.47 (s, 1H), 2.53-2.59 (m, 1H), 2.60-2.74 (m, 1H), 2.80 (dd, J = 13.2, 10.4 Hz, 1H), 2.99 (td, J = 12.6, 11.8, 3.5 Hz, 1H), 3.54 (td, J = 11.6, 2.8 Hz, 1H), 3.73 (q, J = 3.1 Hz, 1H), 3.96 (dd, J = 11.5, 3.1 Hz, 1H), 4.26 (s, 2H), 4.33-4.47 (m, 2H), 4.54 (d, J = 13.0 Hz, 1H), 7.19 (d, 2H), 7.64 (d, 2H), 9.21 (s, 1H). m/z (ES+), $[M + H]^+$: 518; HPLC $t_R$ = 1.776 min (99.8%). |

TABLE 1-continued

| Example | Name | Structure | Analytical data |
| --- | --- | --- | --- |
| 17 | tert-butyl {[(2R)-4-{4-[(4-cyclohexylphenyl)amino]-7-oxo-6-(propan-2-yl)-6,7-dihydro-5H-pyrrolo[3,4-d]pyrimidin-2-yl}morpholin-2-yl]methyl}carbamate | 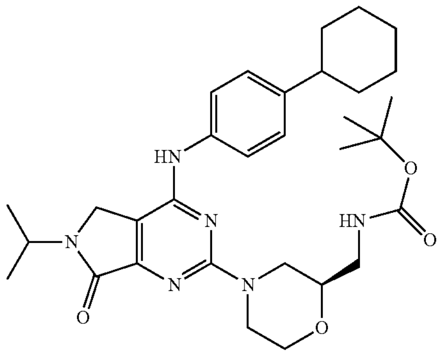 [SMILES: CC(C)N1Cc2c(Nc3ccc(C4CCCCC4)cc3)nc(N3CCO[C@H](CNC(=O)OC(C)(C)C)C3)nc2C1=O] | $^1$H NMR (400 MHz, DMSO) δ 1.23 (d, J = 6.7 Hz, 7H), 1.30-1.59 (m, 12H), 1.75 (dd, J = 35.3, 11.4 Hz, 5H), 2.45 (d, J = 10.8 Hz, 1H), 2.66 (t, 1H), 2.91-3.06 (m, 2H), 3.10-3.20 (m, 1H), 3.40-3.51 (m, 2H), 3.93 (dd, 1H), 4.26 (s, 2H), 4.33-4.47 (m, 2H), 4.51 (d, J = 13.0 Hz, 1H), 7.00 (t, J = 5.9 Hz, 1H), 7.23 (d, J = 8.5 Hz, 2H), 7.67 (d, J = 8.2 Hz, 2H), 9.17 (s, 1H). m/z (ES+), $[M + H]^+$ : 565; HPLC $t_R$ = 1.872 min (99.68%) |
| 18 | 4-[(4-cyclohexylphenyl)amino]-6-(propan-2-yl)-2-[2-(propan-2-yl)morpholin-4-yl]-5,6-dihydro-7H-pyrrolo[3,4-d]pyrimidin-7-one | 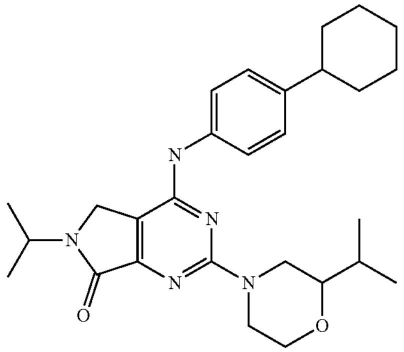 [SMILES: CC(C)C1CN(c2nc(Nc3ccc(C4CCCCC4)cc3)c3c(n2)C(=O)N(C(C)C)C3)CCO1] | $^1$H NMR (400 MHz, DMSO) δ 0.95 (dd, J = 11.2, 6.8 Hz, 6H), 1.23 (d, J = 6.7 Hz, 7H), 1.29-1.45 (m, 4H), 1.67-1.76 (m, 2H), 1.79 (d, J = 9.2 Hz, 4H), 2.46 (s, 1H), 2.67 (dd, J = 13.0, 10.6 Hz, 1H), 2.93 (td, J = 15.2, 12.3, 3.5 Hz, 1H), 3.05 (td, 1H), 3.44 (td, J = 11.6, 2.7 Hz, 1H), 3.94 (dd, J = 11.5, 3.2 Hz, 1H), 4.25 (s, 2H), 4.35-4.47 (m, 2H), 4.56 (d, J = 13.2 Hz, 1H), 7.17 (d, J = 8.4 Hz, 2H), 7.63 (d, 2H), 9.20 (s, 1H). m/z (ES+), $[M + H]^+$: 478; HPLC $t_R$ = 1.9 min (99.9%). |
| 19 | 4-[(4-cyclohexylphenyl)amino]-6-(propan-2-yl)-2-(1,3-thiazolidin-3-yl)-5,6-dihydro-7H-pyrrolo[3,4-d]pyrimidin-7-one | 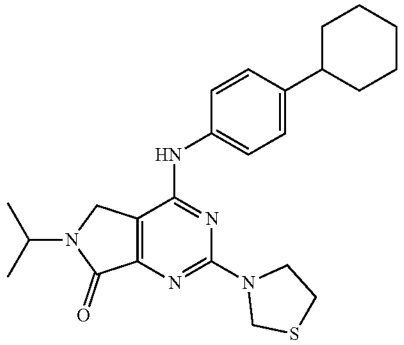 [SMILES: CC(C)N1Cc2c(Nc3ccc(C4CCCCC4)cc3)nc(N3CCSC3)nc2C1=O] | $^1$H NMR (400 MHz, DMSO) δ 1.24 (d, J = 6.8 Hz, 6H), 1.30-1.48 (m, 4H), 1.71 (d, J = 12.7 Hz, 1H), 1.80 (d, J = 9.5 Hz, 4H), 2.47 (s, 1H), 3.08 (t, J = 6.3 Hz, 2H), 3.91 (t, J = 6.3 Hz, 2H), 4.27 (s, 2H), 4.36-4.48 (m, 1H), 4.73 (s, 2H), 7.21 (d, J = 8.6 Hz, 2H), 7.71 (d, J = 8.6 Hz, 2H), 9.23 (s, 1H). m/z (ES+), $[M + H]^+$: 438; HPLC $t_R$ = 1.8 min (98.6%). |
| 20 | 4-[(4-cyclohexylphenyl)amino]-2-[(2-ethoxyethyl)(methyl)amino]-6-(propan-2-yl)-5,6-dihydro-7H-pyrrolo[3,4-d]pyrimidin-7-one | 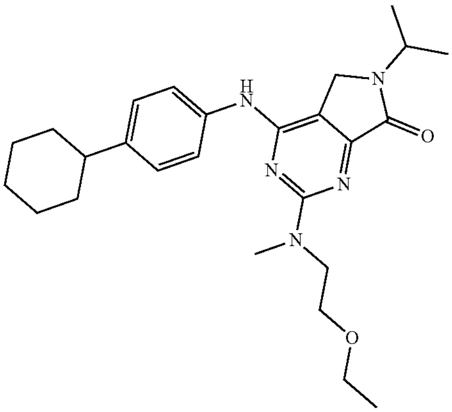 [SMILES: CCOCCN(C)c1nc(Nc2ccc(C3CCCCC3)cc2)c2c(n1)C(=O)N(C(C)C)C2] | $^1$H NMR (400 MHz, DMSO) δ 1.09 (t, J = 7.0 Hz, 3H), 1.23 (d, J = 6.8 Hz, 7H), 1.29-1.46 (m, 4H), 1.71 (d, J = 12.6 Hz, 1H), 1.79 (d, J = 9.1 Hz, 4H), 2.46 (s, 1H), 3.15 (s, 3H), 3.43 (q, J = 7.0 Hz, 2H), 3.56 (t, J = 6.1 Hz, 2H), 3.75 (t, J = 6.1 Hz, 2H), 4.24 (s, 2H), 4.36-4.47 (m, 1H), 7.17 (d, 2H), 7.71 (d, 2H), 9.08 (s, 1H). m/z (ES+), $[M + H]^+$: 452.4; HPLC $t_R$ = 2.161 min (99%). |

TABLE 1-continued

| Example | Name | Structure | Analytical data |
|---|---|---|---|
| 21 | 4-[(4-cyclohexylphenyl)amino]-2-(2-ethylmorpholin-4-yl)-6-(propan-2-yl)-5,6-dihydro-7H-pyrrolo[3,4-d]pyrimidin-7-one | 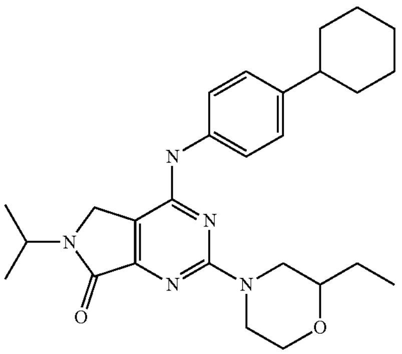 [SMILES: CCC1CN(c2nc(Nc3ccc(C4CCCCC4)cc3)c3c(n2)C(=O)N(C(C)C)C3)CCO1] | $^1$H NMR (400 MHz, DMSO) δ 0.94 (t, J = 7.5 Hz, 3H), 1.23 (d, J = 6.7 Hz, 7H), 1.29-1.43 (m, 4H), 1.43-1.59 (m, 2H), 1.75 (dd, J = 33.9, 11.1 Hz, 5H), 2.46 (s, 1H), 2.63 (dd, J = 13.1, 10.4 Hz, 1H), 2.96 (td, J = 12.3, 11.8, 3.5 Hz, 1H), 3.23-3.33 (m, 1H), 3.46 (td, J = 11.6, 2.7 Hz, 1H), 3.92 (dd, 1H), 4.25 (s, 2H), 4.34-4.45 (m, 2H), 4.49 (d, J = 13.3 Hz, 1H), 7.18 (d, 2H), 7.63 (d, 2H), 9.19 (s, 1H). m/z (ES+), [M + H]$^+$: 464; HPLC $t_R$ = 1.88 min (98.8%). |
| 22 | 4-[(4-cyclohexylphenyl)amino]-2-{methyl[(1,2-oxazol-3-yl)methyl]amino}-6-(propan-2-yl)-5,6-dihydro-7H-pyrrolo[3,4-d]pyrimidin-7-one | 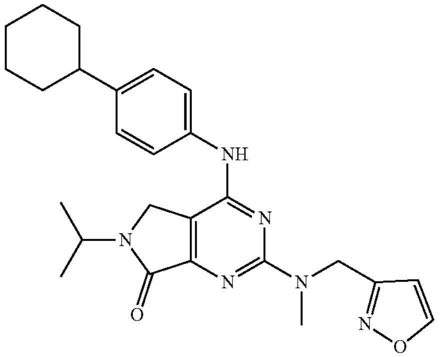 [SMILES: CC(C)N1Cc2c(Nc3ccc(C4CCCCC4)cc3)nc(N(C)Cc3ccon3)nc2C1=O] | $^1$H NMR (400 MHz, DMSO) δ 1.24 (d, J = 6.8 Hz, 7H), 1.32-1.44 (m, 4H), 1.74 (dd, J = 32.2, 11.4 Hz, 5H), 2.45 (s, 1H), 3.16 (s, 3H), 4.26 (s, 2H), 4.36-4.48 (m, 1H), 4.92 (s, 2H), 6.38 (d, J = 1.7 Hz, 1H), 7.15 (d, J = 8.2 Hz, 2H), 7.63 (d, 2H), 8.82 (d, J = 1.7 Hz, 1H), 9.16 (s, 1H). m/z (ES+), [M + H]$^+$: 461; HPLC $t_R$ = 2.22 min (98%). |
| 23 | 4-[(4-cyclohexylphenyl)amino]-2-{methyl[2-(1,2,4-oxadiazol-3-yl)ethyl]amino}-6-(propan-2-yl)-5,6-dihydro-7H-pyrrolo[3,4-d]pyrimidin-7-one | 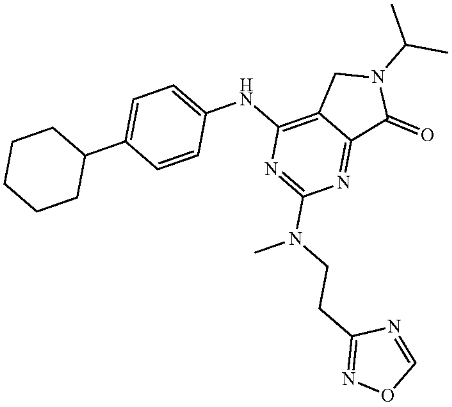 [SMILES: CC(C)N1Cc2c(Nc3ccc(C4CCCCC4)cc3)nc(N(C)CCc3ncon3)nc2C1=O] | $^1$H NMR (300 MHz, DMSO) δ 1.22 (d, J = 6.7 Hz, 7H), 1.35 (t, J = 10.1 Hz, 3H), 1.73 (dd, J = 23.1, 10.2 Hz, 5H), 2.49 (s, 1H), 3.01-3.12 (m, 5H), 3.95 (t, J = 7.3 Hz, 2H), 4.23 (s, 2H), 4.32-4.47 (m, 1H), 7.12 (d, J = 8.1 Hz, 2H), 7.68 (d, 2H), 9.09 (s, 1H), 9.55 (s, 1H). m/z (ES+), [M + H]$^+$: 476.2; HPLC $t_R$ = 1.6 min (99.3%). |
| 24 | 4-[(4-cyclohexylphenyl)amino]-2-(1,4-oxazepan-4-yl)-6-(propan-2-yl)-5,6-dihydro-7H-pyrrolo[3,4-d]pyrimidin-7-one | 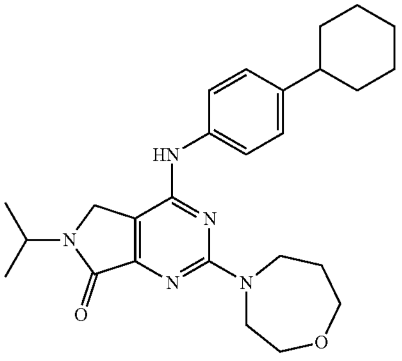 [SMILES: CC(C)N1Cc2c(Nc3ccc(C4CCCCC4)cc3)nc(N3CCCOCC3)nc2C1=O] | $^1$H NMR (400 MHz, DMSO) δ 1.24 (d, J = 6.8 Hz, 7H), 1.32-1.47 (m, 4H), 1.71 (d, J = 12.9 Hz, 1H), 1.79 (d, J = 9.5 Hz, 4H), 1.89 (t, 2H), 2.46 (s, 1H), 3.57-3.65 (m, 2H), 3.73 (t, J = 5.0 Hz, 2H), 3.80-3.91 (m, 4H), 4.25 (s, 2H), 4.36-4.47 (m, 1H), 7.18 (d, 2H), 7.65-7.72 (m, 2H), 9.09 (s, 1H). m/z (ES+), [M + H]$^+$: 450; HPLC $t_R$ = 1.830 min (100%). |

TABLE 1-continued

| Example | Name | Structure | Analytical data |
|---|---|---|---|
| 25 | 4-[(4-cyclohexylphenyl) amino]-2-(1,9-dioxa-4-azaspiro [5.5]undecan-4-yl)-6-(propan-2-yl)-5,6-dihydro-7H-pyrrolo[3,4-d]pyrimidin-7-one | 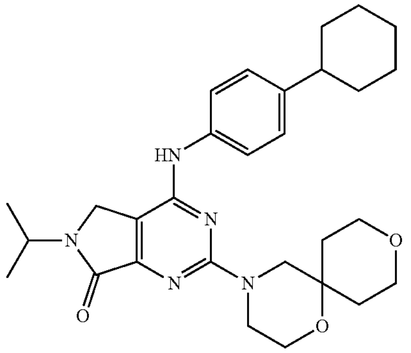 [SMILES: CC(C)N1Cc2c(Nc3ccc(C4CCCCC4)cc3)nc(N3CCOC4(CCOCC4)C3)nc2C1=O] | $^1$H NMR (400 MHz, DMSO) δ 1.23 (d, J = 6.8 Hz, 7H), 1.33-1.44 (m, 4H), 1.49-1.59 (m, 2H), 1.60-1.75 (m, 3H), 1.80 (d, J = 9.3 Hz, 4H), 2.47 (s, 1H), 3.50 (s, 2H), 3.55-3.64 (m, 2H), 3.66-3.80 (m, 6H), 4.24 (s, 2H), 4.34-4.47 (m, 1H), 7.20 (d, 2H), 7.62 (d, 2H), 9.19 (s, 1H). m/z (ES+), $[M + H]^+$: 506; HPLC $t_R$ = 2.962 min (99.2%). |
| 26 | 4-[(4-cyclohexylphenyl) amino]-2-(3-methoxypyrrolidin-1-yl)-6-(propan-2-yl)-5,6-dihydro-7H-pyrrolo[3,4-d]pyrimidin-7-one | 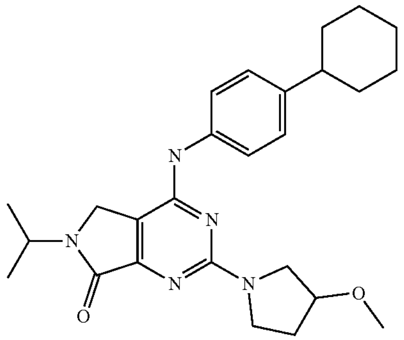 [SMILES: COC1CCN(c2nc(Nc3ccc(C4CCCCC4)cc3)c3c(n2)C(=O)N(C(C)C)C3)C1] | $^1$H NMR (400 MHz, DMSO) δ 1.23 (d, J = 6.7 Hz, 7H), 1.33-1.44 (m, 4H), 1.75 (dd, J = 34.2, 11.1 Hz, 5H), 1.99-2.09 (m, 2H), 2.46 (s, 1H), 3.28 (s, 3H), 3.44-3.66 (m, 4H), 4.03-4.09 (m, 1H), 4.25 (s, 2H), 4.36-4.47 (m, 1H), 7.19 (d, 2H), 7.79 (d, 2H), 9.07 (s, lH).m/z (ES+), $[M + H]^+$: 450; HPLC $t_R$ = 1.612 min (99.3%). |
| 27 | 4-[(4-cyclohexylphenyl) amino]-2-[2-(2-hydroxyethyl)morpholin-4-yl]-6-(propan-2-yl)-5,6-dihydro-7H-pyrrolo[3,4-d]pyrimidin-7-one | 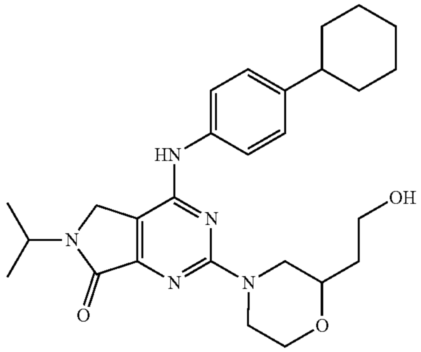 [SMILES: CC(C)N1Cc2c(Nc3ccc(C4CCCCC4)cc3)nc(N3CCOC(CCO)C3)nc2C1=O] | $^1$H NMR (400 MHz, DMSO) δ 1.23 (d, J = 6.7 Hz, 7H), 1.30-1.47 (m, 4H), 1.54-1.75 (m, 3H), 1.80 (d, J = 9.6 Hz, 3H), 2.47 (s, 1H), 2.68 (dd, J = 13.1, 10.4 Hz, 1H), 2.97 (td, 1H), 3.42-3.59 (m, 4H), 3.91 (d, J = 9.9 Hz, 1H), 4.25 (s, 2H), 4.34-4.54 (m, 4H), 7.20 (d, J = 8.5 Hz, 2H), 7.65 (d, 2H), 9.18 (s, 1H). m/z (ES+), $[M + H]^+$: 480; HPLC $t_R$ = 1.637 min (99.8%). |
| 29 | 4-[(4-cyclohexylphenyl) amino]-2-(dipropylamino)-6-(propan-2-yl)-5,6-dihydro-7H-pyrrolo[3,4-d]pyrimidin-7-one | 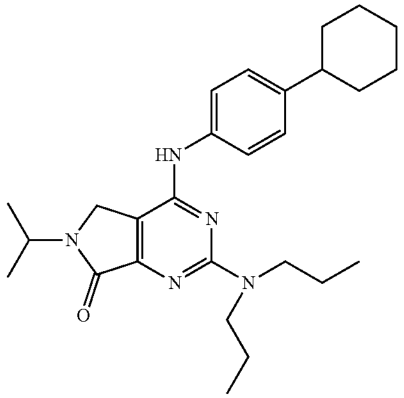 [SMILES: CCCN(CCC)c1nc(Nc2ccc(C3CCCCC3)cc2)c2c(n1)C(=O)N(C(C)C)C2] | $^1$H NMR (400 MHz, DMSO) δ 0.88 (t, J = 7.3 Hz, 6H), 1.23 (d, J = 6.7 Hz, 7H), 1.33-1.46 (m, 4H), 1.51-1.65 (m, 4H), 1.70 (d, J = 12.8 Hz, 1H), 1.79 (d, J = 9.2 Hz, 4H), 2.46 (s, 1H), 3.49 (s, 4H), 4.23 (s, 2H), 4.36-4.47 (m, 1H), 7.16 (d, 2H), 7.71 (d, 2H), 9.02 (s, 1H). m/z (ES+), $[M + H]^+$: 450; HPLC $t_R$ = 2.005 min (99.9%). |

TABLE 1-continued

| Example | Name | Structure | Analytical data |
|---|---|---|---|
| 30 | 4-[(4-cyclohexylphenyl)amino]-2-[(cyclopropylmethyl)(methyl)amino]-6-(propan-2-yl)-5,6-dihydro-7H-pyrrolo[3,4-d]pyrimidin-7-one | 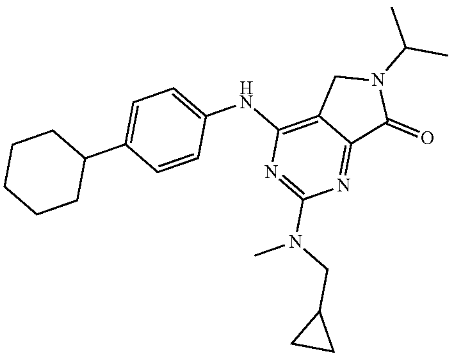 [SMILES: CC(C)N1Cc2c(Nc3ccc(C4CCCCC4)cc3)nc(N(C)CC3CC3)nc2C1=O] | $^1$H NMR (400 MHz, DMSO) δ 0.22-0.30 (m, 2H), 0.39-0.48 (m, 2H), 1.03-1.13 (m, 1H), 1.23 (d, J = 6.8 Hz, 7H), 1.33-1.46 (m, 4H), 1.71 (d, J = 12.6 Hz, 1H), 1.80 (d, J = 9.7 Hz, 4H), 2.46 (s, 1H), 3.16 (s, 3H), 3.52 (d, J = 6.8 Hz, 2H), 4.24 (s, 2H), 4.36-4.47 (m, 1H), 7.18 (d, 2H), 7.71 (d, J = 8.3 Hz, 2H), 9.07 (s, 1H). m/z (ES+), [M + H]$^+$: 434.4; HPLC $t_R$ = 2.20 min (99%). |
| 31 | 4-[(4-cyclohexylphenyl)amino]-2-[2-(hydroxymethyl)morpholin-4-yl]-6-(propan-2-yl)-5,6-dihydro-7H-pyrrolo[3,4-d]pyrimidin-7-one | 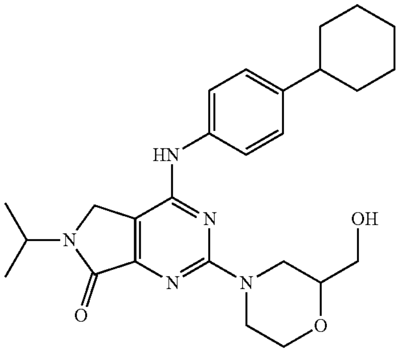 [SMILES: CC(C)N1Cc2c(Nc3ccc(C4CCCCC4)cc3)nc(N3CCOC(CO)C3)nc2C1=O] | $^1$H NMR (300 MHz, DMSO) δ 1.20 (s, 3H), 1.22 (s, 4H), 1.36 (s, 3H), 1.71 (s, 1H), 1.77 (d, J = 8.8 Hz, 4H), 2.67 (s, 2H), 3.48 (d, J = 11.0 Hz, 4H), 3.90 (d, J = 11.2 Hz, 1H), 4.23 (s, 2H), 4.31-4.44 (m, 2H), 4.57 (d, J = 13.0 Hz, 1H), 4.82 (d, J = 5.6 Hz, 1H), 7.17 (d, J = 8.4 Hz, 2H), 7.63 (d, J = 8.3 Hz, 2H), 9.15 (s, 1H). m/z (ES+), [M + H]$^+$: 466; HPLC $t_R$ = 1.772 min (99%). |
| 32 | 4-[(4-cyclohexylphenyl)amino]-2-[3-(hydroxymethyl)morpholin-4-yl]-6-(propan-2-yl)-5,6-dihydro-7H-pyrrolo[3,4-d]pyrimidin-7-one | 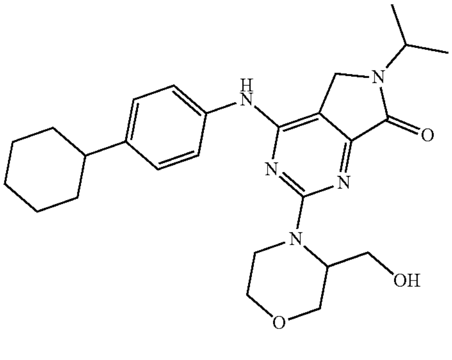 [SMILES: CC(C)N1Cc2c(Nc3ccc(C4CCCCC4)cc3)nc(N3CCOCC3CO)nc2C1=O] | $^1$H NMR (400 MHz, DMSO) δ 1.24 (dd, J = 6.7, 2.0 Hz, 7H), 1.33-1.43 (m, 4H), 1.75 (dd, J = 34.1, 11.0 Hz, 5H), 2.46 (s, 1H), 3.05-3.16 (m, 1H), 3.37-3.49 (m, 3H), 3.72-3.83 (m, 1H), 3.90 (dd, J = 9.5 Hz, 1H), 4.08 (d, J = 11.4 Hz, 1H), 4.23-4.29 (m, 3H), 4.36-4.47 (m, 2H), 4.88 (t, J = 5.1 Hz, 1H), 7.18 (d, 2H), 7.67 (d, 2H), 9.15 (s, 1H). m/z (ES+), [M + H]$^+$: 466; HPLC $t_R$ = 2.047 min (99%). |
| 33 | 4-[(4-cyclohexylphenyl)amino]-2-{methyl[(p razin-2-yl)methyl]amino}-6-(propan-2-yl)-5,6-dihydro-7H-pyrrolo[3,4-d]pyrimidin-7-one | 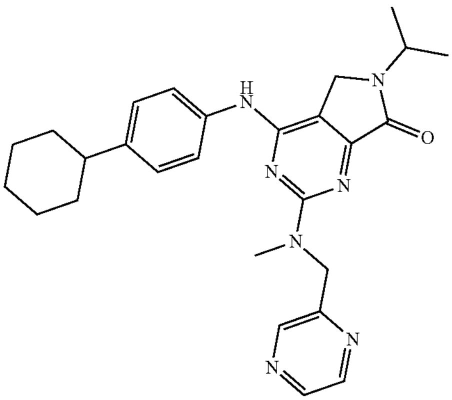 [SMILES: CC(C)N1Cc2c(Nc3ccc(C4CCCCC4)cc3)nc(N(C)Cc3cnccn3)nc2C1=O] | $^1$H NMR (400 MHz, DMSO) δ 1.23 (d, J = 6.7 Hz, 7H), 1.36 (dd, J = 11.7, 8.9 Hz, 4H), 1.74 (dd, J = 30.0, 11.2 Hz, 5H), 2.43 (s, 1H), 4.24 (s, 2H), 3.25 (s, 3H), 4.41 (p, J = 6.8 Hz, 1H), 4.97 (s, 2H), 7.09 (s, 2H), 7.50 (s, 2H), 8.45 (s, 1H), 8.49-8.60 (m, 2H), 9.09 (s, 1H). m/z (ES+), [M + H]$^+$: 472; HPLC $t_R$ = 1.808 min (99.3%). |

TABLE 1-continued

| Example | Name | Structure | Analytical data |
|---|---|---|---|
| 34 | 4-[(4-cyclohexylphenyl) amino]-2-(diethylamino)-6-(propan-2-yl)-5,6-dihydro-7H-pyrrolo[3,4-d]pyrimidin-7-one | 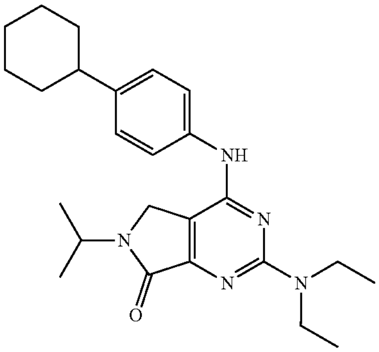 [SMILES: CCN(CC)c1nc(Nc2ccc(C3CCCCC3)cc2)c2c(n1)C(=O)N(C(C)C)C2] | $^{1}$H NMR (400 MHz, DMSO) δ 1.14 (t, J = 6.9 Hz, 6H), 1.23 (d, J = 6.7 Hz, 7H), 1.33-1.43 (m, 4H), 1.71 (d, J = 12.7 Hz, 1H), 1.79 (d, J = 9.7 Hz, 4H), 2.46 (s, 1H), 3.59 (q, J = 6.9 Hz, 4H), 4.23 (s, 2H), 4.36-4.47 (m, 1H), 7.17 (d, 2H), 7.73 (d, 2H), 9.03 (s, lH).m/z (ES+), $[M + H]^+$: 423; HPLC $t_R$ = 1.93 min (99.8%). |
| 35 | 4-[(4-cyclohexylphenyl) amino]-2-{methyl[(oxolan-2-yl)methyl]amino}-6-(propan-2-yl)-5,6-dihydro-7H-pyrrolo[3,4-dlpyrimidin-7-one | 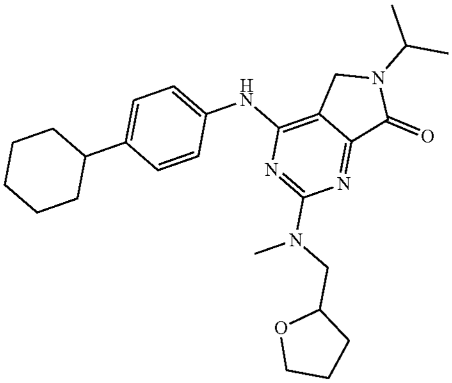 [SMILES: CC(C)N1Cc2c(Nc3ccc(C4CCCCC4)cc3)nc(N(C)CC3CCCO3)nc2C1=O] | $^{1}$H NMR (400 MHz, DMSO) δ 1.23 (d, J = 6.8 Hz, 7H), 1.33-1.42 (m, 4H), 1.48-1.58 (m, 1H), 1.69-1.87 (m, 8H), 2.46 (s, 1H), 3.15 (s, 3H), 3.52 (s, 1H), 3.57-3.64 (m, 1H), 3.71-3.83 (m, 2H), 4.03-4.14 (m, 1H), 4.24 (s, 2H), 4.35-4.47 (m, 1H), 7.17 (d, 2H), 7.68 (d, J = 8.0 Hz, 2H), 9.06 (s, 1H). m/z (ES+), $[M + H]^+$: 464; HPLC $t_R$ = 1.853 min (99.7%). |
| 36 | 4-[(4-cyclohexylphenyl) amino]-2-[(2,2-difluoroethyl)(methyl) amino]-6-(propan-2-yl)-5,6-dihydro-7H-pyrrolo[3,4-d]pyrimidin-7-one | 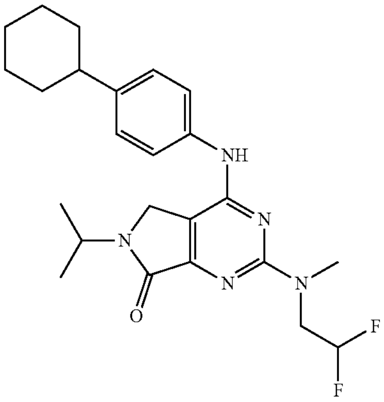 [SMILES: CC(C)N1Cc2c(Nc3ccc(C4CCCCC4)cc3)nc(N(C)CC(F)F)nc2C1=O] | $^{1}$H NMR (400 MHz, DMSO) δ 1.24 (d, J = 6.7 Hz, 7H), 1.35-1.44 (m, 4H), 1.75 (dd, J = 34.4, 11.2 Hz, 5H), 2.45(s, 1H), 3.19 (s, 3H), 4.01 (t, J = 14.6 Hz, 2H), 4.26 (s, 2H), 4.36-4.48 (m, 1H), 6.12-6.38 (m, 1H), 7.19 (d, J = 8.4 Hz, 2H), 7.67 (d, J = 8.0 Hz, 2H), 9.22 (s, 1H). m/z (ES+), $[M + H]^+$: 444; HPLC $t_R$ = 2.035 min (99%). |

TABLE 1-continued

| Example | Name | Structure | Analytical data |
|---|---|---|---|
| 37 | 4-[(4-cyclohexylphenyl)amino]-2-{methyl[2-(pyridin-2-yl)ethyl]amino}-6-(propan-2-yl)-5,6-dihydro-7H-pyrrolo[3,4-d]pyrimidin-7-one | 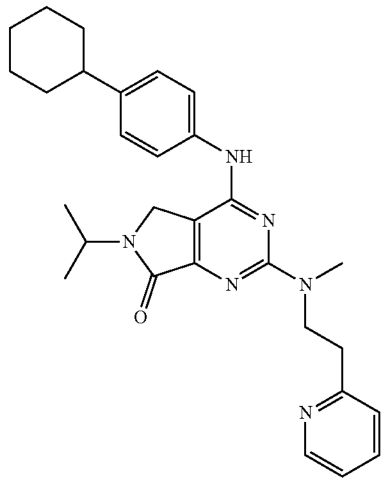 [SMILES: CC(C)N1Cc2c(Nc3ccc(C4CCCCC4)cc3)nc(N(C)CCc3ccccn3)nc2C1=O] | $^1$H NMR (400 MHz, DMSO) δ 1.24 (d, J = 6.8 Hz, 7H), 1.37 (t, J = 10.1 Hz, 4H), 1.74 (d, J = 35.6 Hz, 5H), 2.45 (s, 1H), 3.05 (d, J = 13.4 Hz, 5H), 3.96 (t, J = 7.6 Hz, 2H), 4.25 (s, 2H), 4.42 (p, J = 6.6 Hz, 1H), 7.11 (s, 2H), 7.25 (dd, J = 7.5, 4.0 Hz, 2H), 7.65-7.76 (m, 3H), 8.53 (d, J = 4.1 Hz, 1H), 9.08 (s, 1H). m/z (ES+), [M + H]$^+$: 485; HPLC $t_R$ = 1.673 min (97.2%). |
| 38 | (3S)-4-{4-[(4-cyclohexylphenyl)amino]-7-oxo-6-(propan-2-yl)-6,7-dihydro-5H-pyrrolo[3,4-d]pyrimidin-2-yl}morpholine-3-carboxylic acid | 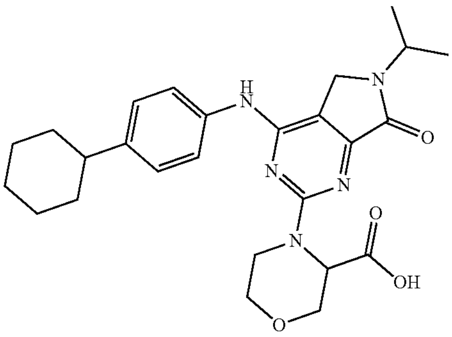 [SMILES: CC(C)N1Cc2c(Nc3ccc(C4CCCCC4)cc3)nc(N3CCOCC3C(=O)O)nc2C1=O] | $^1$H NMR (400 MHz, DMSO) rotamers δ 1.24 (d, J = 6.7 Hz, 6H), 1.36 (d, J = 12.8 Hz, 4H), 1.71 (d, J = 12.5 Hz, 1H), 1.79 (d, J = 9.3 Hz, 4H), 2.46 (s, 1H), 3.31 (s, 1H), 3.50 (s, 1H), 3.69 (s, 1H), 3.95 (d, J = 11.0 Hz, 1H), 4.28 (dd, J = 13.5, 9.0 Hz, 5H), 4.42 (s, 1H), 4.82-5.10 (m, 1H), 7.10-7.30 (m, 2H), 7.57-7.68 (m, 2H), 9.23 (s, 1H), 12.85 (brs, 1H). m/z (ES+), [M + H]$^+$: 480.2; HPLC $t_R$ = 2.085 min (98.9%). |
| 39 | N-[2-(4-{4-[(4-cyclohexylphenyl)amino]-7-oxo-6-(propan-2-yl)-6,7-dihydro-5H-pyrrolo[3,4-d]pyrimidin-2-yl}morpholin-2-yl)ethyl]acetamide | 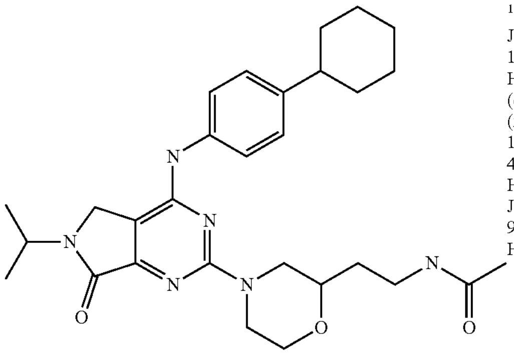 | $^1$H NMR (400 MHz, DMSO) δ 1.23 (d, J = 6.7 Hz, 7H), 1.38 (h, J = 12.2 Hz, 4H), 1.60 (q, J = 7.0 Hz, 2H), 1.71 (d, J = 12.7 Hz, 1H), 1.79 (d, J = 7.9 Hz, 7H), 2.68 (dd, J = 13.1, 10.4 Hz, 1H), 2.92-3.03 (m, 1H), 3.07-3.27 (m, 3H), 3.46 (d, J = 13.6 Hz, 2H), 3.92 (d, J = 10.7 Hz, 1H), 4.25 (s, 2H), 4.40 (td, J = 17.2, 15.9, 10.4 Hz, 3H), 7.20 (d, J = 8.5 Hz, 2H), 7.63 (d, J = 8.5 Hz, 2H), 7.87 (t, J = 5.6 Hz, 1H), 9.20 (s, 1H). m/z (ES+), [M + H]$^+$: 521; HPLC $t_R$ = 1.657 min (99%). |

Example 40: 6-isopropyl-4-((4-isopropylphenyl)amino)-2-(pyridin-4-yl)-5,6-dihydro-7H-pyrrolo[3,4-d]pyrimidin-7-one

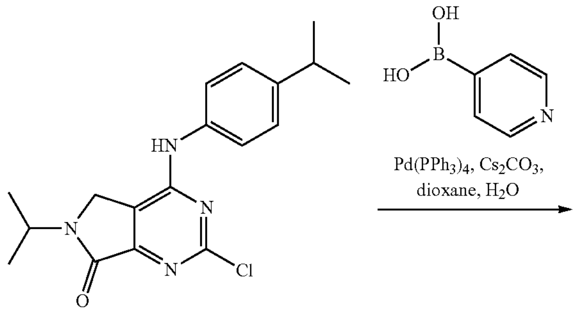

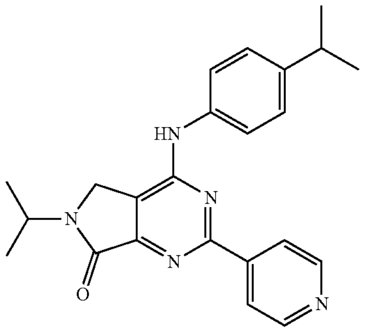

$Pd(PPh_3)_4$ (67.0 mg, 0.06 mmol) was added to 2-chloro-6-isopropyl-4-((4-isopropylphenyl)amino)-5,6-dihydro-7H-pyrrolo[3,4-d]pyrimidin-7-one (200 mg, 0.58 mmol), pyridin-4-ylboronic acid (86 mg, 0.70 mmol) and $Cs_2CO_3$ (378 mg, 1.16 mmol) in 1,4-dioxane (5 mL), water (1 mL) at rt under nitrogen. The resulting solution was stirred at 100° C. for 3 hours. The solvent was removed under reduced pressure. The crude product was purified by flash silica chromatography, elution gradient 3 to 5% DCM in MeOH. Pure fractions were evaporated to dryness to afford product as a yellow solid. The crude product was purified by preparative HPLC conditions B. Fractions containing the desired compound were evaporated to dryness to afford 6-isopropyl-4-((4-isopropylphenyl)amino)-2-(pyridin-4-yl)-5,6-dihydro-7H-pyrrolo[3,4-d]pyrimidin-7-one (100 mg, 44.5%) as a white solid. $^1H$ NMR (400 MHz, DMSO) δ 1.27 (dd, J=15.8, 6.8 Hz, 12H), 2.85-2.99 (m, 1H), 4.44-4.53 (m, 3H), 7.34 (dd, 2H), 7.81 (dd, 2H), 8.23 (dd, 2H), 8.77 (dd, 2H), 9.70 (s, 1H). m/z (ES+), $[M+H]^+$: 388; HPLC $t_R$=1.358 min (98.8%).

Example 41: 4-(4-((4-cyclohexylphenyl)amino)-6-isopropyl-7-oxo-6,7-dihydro-5H-pyrrolo[3,4-d]pyrimidin-2-yl)picolinonitrile

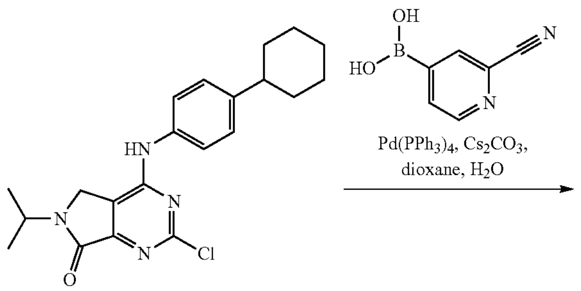

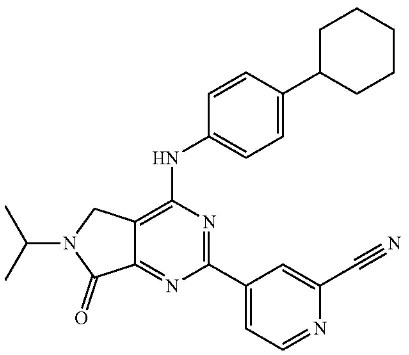

$Pd(PPh_3)_4$ (30.0 mg, 0.03 mmol) was added to $Cs_2CO_3$ (169 mg, 0.52 mmol), 2-chloro-4-((4-cyclohexylphenyl)amino)-6-isopropyl-5,6-dihydro-7H-pyrrolo[3,4-d]pyrimidin-7-one (100 mg, 0.26 mmol) and 4-(4,4,5,5-tetramethyl-1,3,2-dioxaborolan-2-yl)picolinonitrile (90 mg, 0.39 mmol) in 1,4-dioxane (2 mL) water (0.400 mL) at RT, under nitrogen. The resulting mixture was stirred at 100° C. for 6 hours. The solvent was removed under reduced pressure. The crude product was purified by flash silica chromatography, elution gradient 0 to 5% MeOH in DCM. Pure fractions were evaporated to dryness to afford 4-(4-((4-cyclohexylphenyl)amino)-6-isopropyl-7-oxo-6,7-dihydro-5H-pyrrolo[3,4-d]pyrimidin-2-yl)picolinonitrile as a crude product. The crude product was purified by preparative HPLC Conditions A. Fractions containing the desired compound were evaporated to dryness to afford 4-(4-((4-cyclohexylphenyl)amino)-6-isopropyl-7-oxo-6,7-dihydro-5H-pyrrolo[3,4-d]pyrimidin-2-yl)picolinonitrile (20.10 mg, 17%) as a yellow solid. $^1H$ NMR (400 MHz, DMSO) δ 1.29 (d, J=6.7 Hz, 7H), 1.36-1.51 (m, 4H), 1.73 (d, J=11.9 Hz, 1H), 1.83 (s, 4H), 4.42-4.54 (m, 3H), 7.31 (d, J=8.1 Hz, 2H), 7.74 (d, J=8.1 Hz, 2H), 8.49 (d, J=5.7 Hz, 1H), 8.62 (s, 1H), 8.95 (d, J=5.1 Hz, 1H), 9.80 (s, 1H). m/z (ES+) $[M+H]^+$: 453; HPLC $t_R$=2.976 min (99.3%).

The Examples in Table 2 were made from Intermediates 3 and 4 and the appropriate boronic esters or acids, according to the procedure of Examples 40 and 41.

TABLE 2

| Example | Name | Structure | Analytical data |
|---|---|---|---|
| 42 | 4-[(4-cyclohexylphenyl)amino]-2-(2-cyclopropylpyridin-4-yl)-6-(propan-2-yl)-5,6-dihydro-7H-pyrrolo[3,4-d]pyrimidin-7-one | 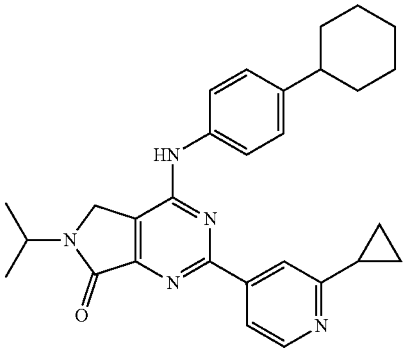 [SMILES: CC(C)N1Cc2c(Nc3ccc(C4CCCCC4)cc3)nc(-c3ccnc(C4CC4)c3)nc2C1=O] | $^1$H NMR (400 MHz, DMSO) δ 0.93-1.07 (m, 4H), 1.29 (t, J = 6.7 Hz, 7H), 1.33-1.51 (m, 4H), 1.73 (d, J = 12.4 Hz, 1H), 1.83 (s, 4H), 2.20-2.31 (m, 1H), 4.42-4.55 (m, 3H), 7.31 (d, J = 8.5 Hz, 2H), 7.79 (d, J = 8.4 Hz, 2H), 7.95 (dd, J = 5.1, 1.6 Hz, 1H), 8.12 (d, J = 1.5 Hz, 1H), 8.57 (d, J = 5.2 Hz, 1H), 9.69 (s, 1H). m/z (ES+), $[M + H]^+$: 468; HPLC $t_R$ = 1.841 min (99.6%). |
| 43 | 4-[(4-cyclohexylphenyl)amino]-2-(2-methoxypyridin-4-yl)-6-(propan-2-yl)-5,6-dihydro-7H-pyrrolo[3,4-d]pyrimidin-7-one | 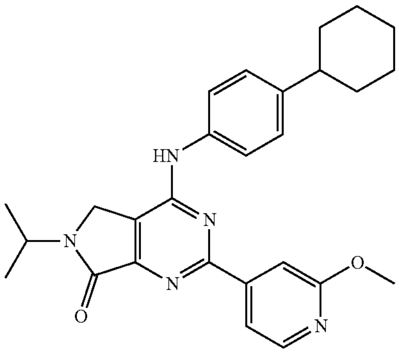 [SMILES: COc1cc(-c2nc(Nc3ccc(C4CCCCC4)cc3)c3c(n2)C(=O)N(C(C)C)C3)ccn1] | $^1$H NMR (400 MHz, DMSO) δ 1.28 (t, J = 6.8 Hz, 7H), 1.35-1.50 (m, 4H), 1.72 (d, J = 12.5 Hz, 1H), 1.77-1.88 (m, 4H), 2.54 (d, J = 4.8 Hz, 1H), 3.93 (s, 3H), 4.38-4.53 (m, 3H), 7.29 (d, J = 8.5 Hz, 2H), 7.60 (s, 1H), 7.75 (d, J = 8.5 Hz, 2H), 7.82 (dd, J = 5.3, 1.4 Hz, 1H), 8.33 (d, J = 5.3 Hz, 1H), 9.68 (s, 1H). m/z (ES+), $[M + H]^+$: 458; HPLC $t_R$ = 1.464 min (99.6%). |
| 44 | 4-[(4-cyclohexylphenyl)amino]-2-(2-methylpyridin-4-yl)-6-(propan-2-yl)-5,6-dihydro-7H-pyrrolo[3,4-d]pyrimidin-7-one | 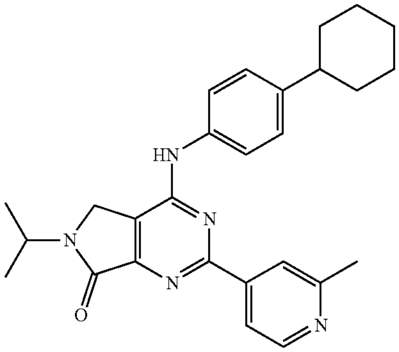 [SMILES: Cc1cc(-c2nc(Nc3ccc(C4CCCCC4)cc3)c3c(n2)C(=O)N(C(C)C)C3)ccn1] | $^1$H NMR (400 MHz, DMSO) δ 1.24 (s, 1H), 1.29 (d, J = 6.7 Hz, 6H), 1.36-1.51 (m, 4H), 1.73 (d, J = 12.3 Hz, 1H), 1.83 (s, 4H), 2.55 (s, 1H), 2.60 (s, 3H), 4.43-4.53 (m, 3H), 7.31 (d, J = 8.5 Hz, 2H), 7.79 (d, J = 8.4 Hz, 2H), 8.01 (dd, 1H), 8.10 (s, 1H), 8.63 (d, J = 5.2 Hz, 1H), 9.68 (s, 1H). m/z (ES+), $[M + H]^+$: 442; HPLC $t_R$ = 1.688 min (98.4%). |
| 45 | 4-[(4-cyclohexylphenyl)amino]-2-(3,6-dihydro-2H-pyran-4-yl)-6-(propan-2-yl)-5,6-dihydro-7H-pyrrolo[3,4-d]pyrimidin-7-one | 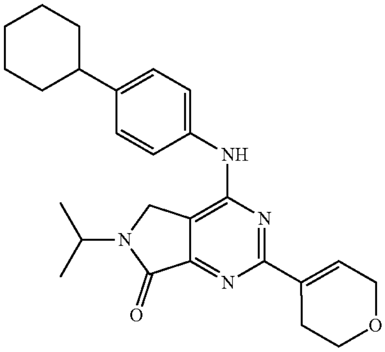 [SMILES: CC(C)N1Cc2c(Nc3ccc(C4CCCCC4)cc3)nc(C3=CCOCC3)nc2C1=O] | $^1$H NMR (400 MHz, DMSO) δ 1.26 (d, J = 6.7 Hz, 7H), 1.33-1.47 (m, 4H), 1.71 (d, J = 12.5 Hz, 1H), 1.80 (d, J = 9.6 Hz, 4H), 2.59 (s, 2H), 3.82(1, J = 5.4 Hz, 2H), 4.31 (d, J = 3.1 Hz, 2H), 4.39 (s, 2H), 4.41-4.51 (m, 1H), 7.14 (s, 1H), 7.23 (d, J = 8.5 Hz, 2H), 7.75 (d, J = 8.5 Hz, 2H), 9.43 (s, 1H). m/z (ES+), $[M + H]^+$: 433; HPLC $t_R$ = 1.691 min (99%). |

TABLE 2-continued

| Example | Name | Structure | Analytical data |
|---|---|---|---|
| 46 | 4-[(4-cyclohexylphenyl)amino]-6-(propan-2-yl)-2-(pyridin-4-yl)-5,6-dihydro-7H-pyrrolo[3,4-d]pyrimidin-7-one | 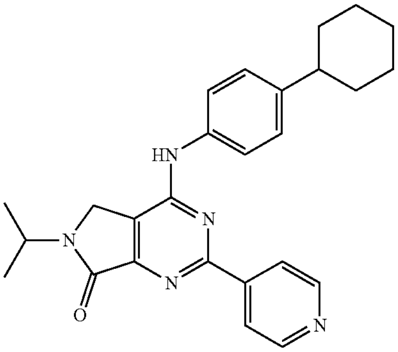 [SMILES: CC(C)N1Cc2c(Nc3ccc(C4CCCCC4)cc3)nc(-c3ccncc3)nc2C1=O] | $^1$H NMR (400 MHz, DMSO) δ 1.24 (s, 1H), 1.29 (d, J = 6.8 Hz, 6H), 1.36-1.51 (m, 4H), 1.73 (d, J = 12.5 Hz, 1H), 1.78-1.90 (m, 4H), 2.56 (s, 1H), 4.44-4.53 (m, 3H), 7.31 (d, 2H), 7.79 (d, 2H), 8.22 (dd, 2H), 8.77 (dd, 2H), 9.70 (s, 1H). m/z (ES+), $[M + H]^+$: 428; HPLC $t_R$ = 2.655 min (99.8%). |
| 47 | 4-[(4-cyclohexylphenyl)amino]-2-(1-methyl-1H-pyrazol-4-yl)-6-(propan-2-yl)-5,6-dihydro-7H-pyrrolo[3,4-d]pyrimidin-7-one | 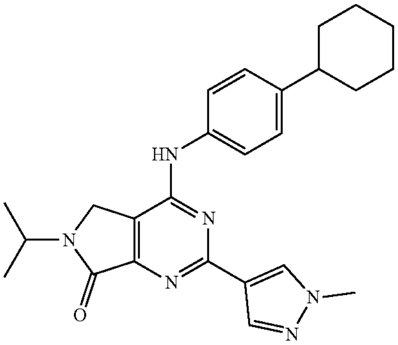 [SMILES: CC(C)N1Cc2c(Nc3ccc(C4CCCCC4)cc3)nc(-c3cnn(C)c3)nc2C1=O] | $^1$H NMR (400 MHz, DMSO) δ 1.27 (d, J = 6.7 Hz, 7H), 1.35-1.48 (m, 4H), 1.73 (d, J = 12.5 Hz, 1H), 1.82 (d, J = 7.7 Hz, 4H), 2.49 (s, 1H), 3.93 (s, 3H), 4.39 (s, 2H), 4.42-4.50 (m, 1H), 7.28 (d, J = 8.4 Hz, 2H), 7.82 (d, J = 8.4 Hz, 2H), 7.98 (s, 1H), 8.32 (s, 1H), 9.41 (s, 1H). m/z (ES+), $[M + H]^+$: 431; HPLC $t_R$ = 1.792 min (99%). |
| 48 | 4-[(4-cyclohexylphenyl)amino]-2-(1,3-oxazol-5-yl)-6-(propan-2-yl)-5,6-dihydro-7H-pyrrolo[3,4-d]pyrimidin-7-one | 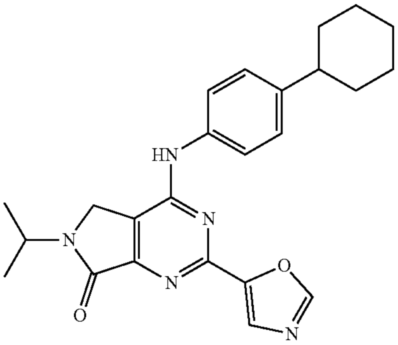 [SMILES: CC(C)N1Cc2c(Nc3ccc(C4CCCCC4)cc3)nc(-c3cnco3)nc2C1=O] | $^1$H NMR (400 MHz, DMSO) δ 1.19-1.34 (m, 8H), 1.35-1.49 (m, 4H), 1.72 (d, J = 12.4 Hz, 1H), 1.82 (d, J = 8.1 Hz, 4H), 4.40-4.51 (m, 3H), 7.24-7.31 (m, 2H), 7.81 (d, 2H), 7.89 (s, 1H), 8.61 (s, 1H), 9.66 (s, 1H). m/z (ES+), $[M + H]^+$: 418; HPLC $t_R$ = 1.954 min (97.3%). |
| 49 | 4-[(4-cyclohexylphenyl)amino]-6-(propan-2-yl)-2-(1,3-thiazol-5-yl)-5,6-dihydro-7H-pyrrolo[3,4-d]pyrimidin-7-one | 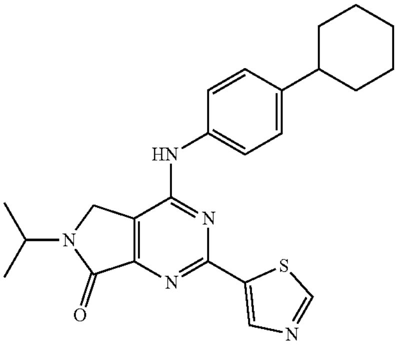 [SMILES: CC(C)N1Cc2c(Nc3ccc(C4CCCCC4)cc3)nc(-c3cncs3)nc2C1=O] | $^1$H NMR (400 MHz, DMSO) δ 1.22-1.31 (m, 7H), 1.35-1.50 (m, 4H), 1.72 (d, J = 12.5 Hz, 1H), 1.82 (d, J = 7.7 Hz, 4H), 4.40-4.52 (m, 3H), 7.29 (d, 2H), 7.78 (d, 2H), 8.57 (d, J = 0.8 Hz, 1H), 9.22 (d, J = 0.7 Hz, 1H), 9.66 (s, 1H). m/z (ES+), $[M + H]^+$: 434; HPLC $t_R$ = 1.657 min (99.3%). |

TABLE 2-continued

| Example | Name | Structure | Analytical data |
|---|---|---|---|
| 50 | 2-(3,6-dihydro-2H-pyran-4-yl)-6-(propan-2-yl)-4-{[4-(propan-2-yl)phenyl]amino}-5,6-dihydro-7H-pyrrolo[3,4-d]pyrimidin-7-one | 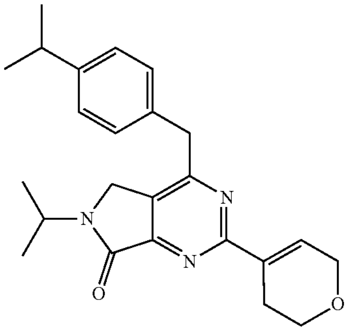 [SMILES: CC(C)c1ccc(Cc2nc(C3=CCOCC3)nc3c2CN(C(C)C)C3=O)cc1] | $^{1}H$ NMR (400 MHz, DMSO) δ 1.22 (d, J = 6.9 Hz, 6H), 1.26 (d, J = 6.8 Hz, 6H), 2.60 (s, 2H), 2.83-2.94 (m, 1H), 3.83 (t, J = 5.4 Hz, 2H), 4.32 (d, J = 2.9 Hz, 2H), 4.40 (s, 2H), 4.42-4.51 (m, 1H), 7.15 (s, 1H), 7.26 (d, 2H), 7.77 (d, 2H), 9.42 (s, 1H). m/z (ES+), $[M + H]^{+}$: 393; HPLC $t_R$ = 2.602 min (99.6%). |

Example 51: (R)-4-((4-(4-fluorophenoxy)phenyl)amino)-6-isopropyl-2-(2-methylmorpholino)-5,6-dihydro-7H-pyrrolo[3,4-d]pyrimidin-7-one

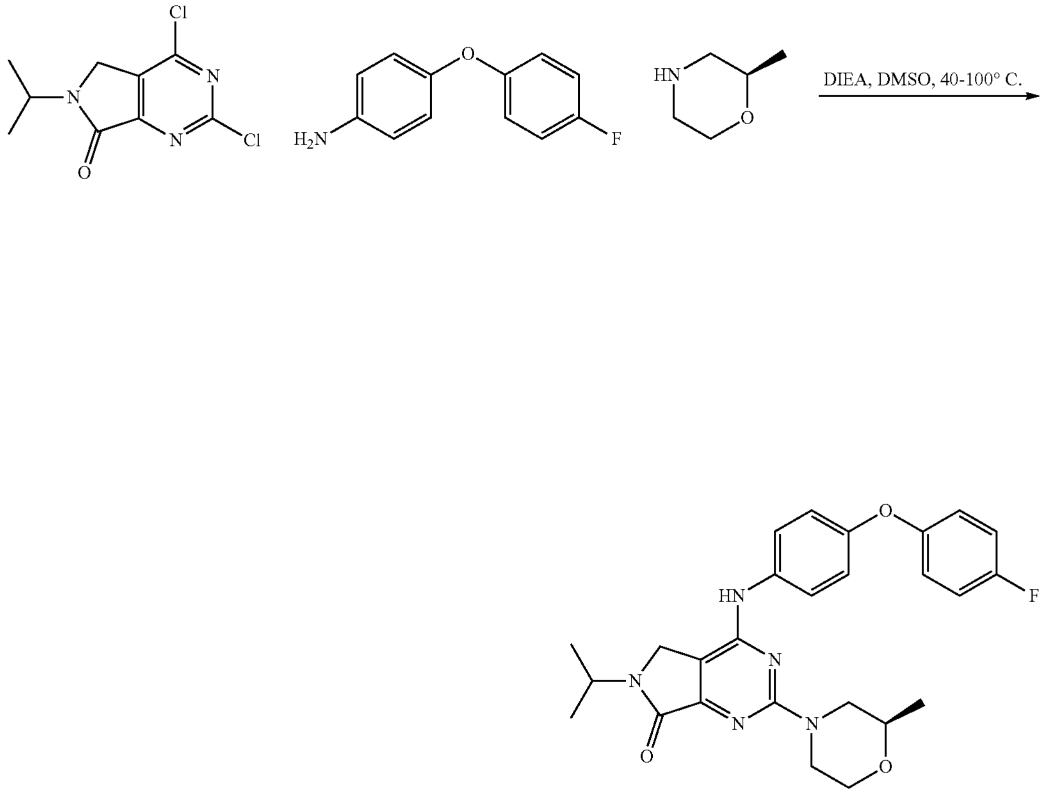

4-(4-Fluorophenoxy)aniline (83 mg, 0.41 mmol) was added to 2,4-dichloro-6-isopropyl-5,6-dihydro-7H-pyrrolo[3,4-d]pyrimidin-7-one (100 mg, 0.41 mmol) and DIEA (0.213 mL, 1.22 mmol) in DMSO (2 mL) at rt. The resulting mixture was stirred at 40° C. for 16 hours. (R)-2-methylmorpholine (41.1 mg, 0.41 mmol) was added to the reaction at rt. The resulting mixture was stirred at 100° C. for 16 hours. The crude product was purified by preparative HPLC conditions A. Fractions containing the desired compound were evaporated to dryness to afford (R)-4-((4-(4-fluorophenoxy)phenyl)amino)-6-isopropyl-2-(2-methylmorpholino)-5,6-dihydro-7H-pyrrolo[3,4-d]pyrimidin-7-one (63.0 mg, 32.5%) as a yellow solid. $^{1}H$ NMR (400 MHz, DMSO) δ 1.15 (d, J=6.2 Hz, 3H), 1.24 (d, J=6.7 Hz, 6H), 2.61 (dd, J=13.1, 10.4 Hz, 1H), 2.88-3.00 (m, 1H), 3.44-3.54 (m, 2H), 3.89 (d, J=9.3 Hz, 1H), 4.26 (s, 2H), 4.31-4.46 (m, 3H), 6.99-7.11 (m, 4H), 7.18-7.29 (m, 2H), 7.74 (dd, J=9.2, 3.0 Hz, 2H), 9.30 (s, 1H). m/z (ES+), $[M+H]^{+}$: 478; HPLC $t_R$=1.946 min (98%).

The Examples in Table 3 were made from Intermediate 1 or 2 and the appropriate amines, which are commercially available or described in the Intermediates section, according to procedures analogous to those described above.

TABLE 3

| Example | Name | Structure | Analytical Data |
|---|---|---|---|
| 52 | 2-(2-cyclopropylmorpholin-4-yl)-4-({4'-[(hept-6-yn-1-yl)oxy][1,1'-biphenyl]-4-yl}amino)-6-(propan-2-yl)-5,6-dihydro-7H-pyrrolo[3,4-d]pyrimidin-7-one | 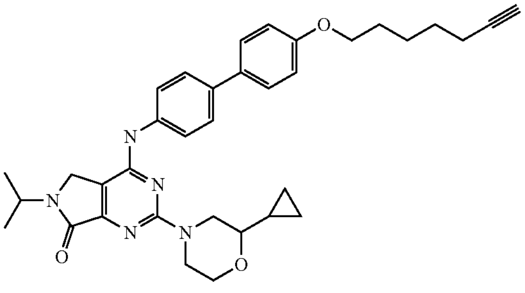 [SMILES: C#CCCCCCOc1ccc(-c2ccc(Nc3nc(N4CCOC(C5CC5)C4)nc4c3CN(C(C)C)C4=O)cc2)cc1] | $^1$H NMR (300 MHz, DMSO) δ 0.29 (t, J = 5.7 Hz, 2H), 0.49 (d, J = 6.2 Hz, 2H), 0.85-0.95 (m, 1H), 1.22 (d, J = 6.7 Hz, 6H), 1.51 (d, J = 6.4 Hz, 4H), 1.73 (s, 2H), 2.18 (d, J = 2.7 Hz, 2H), 2.72-2.90 (m, 3H), 2.98 (t, J = 11.0 Hz, 1H), 3.41 (s, 1H), 3.90 (d, J = 11.1 Hz, 1H), 3.99 (t, J = 6.4 Hz, 2H), 4.24-4.43 (m, 4H), 4.53 (d, J = 12.2 Hz, 1H), 6.99 (d, J = 8.8 Hz, 2H), 7.53-7.63 (m, 4H), 7.79 (d, J = 8.7 Hz, 2H), 9.32 (s, 1H). m/z (ES+), [M + H]$^+$: 580; HPLC $t_R$ = 2.05 min (99.3%). |
| 53 | 2-(2-cyclopropylmorpholin-4-yl)-4-{[4'-(heptyloxy)[1,1'-biphenyl]-4-yl]amino}-6-(propan-2-yl)-5,6-dihydro-7H-pyrrolo[3,4-d]pyrimidin-7-one | 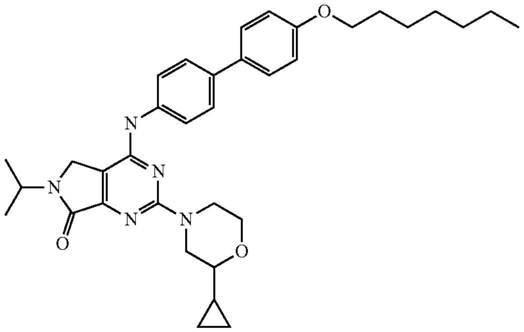 [SMILES: CCCCCCCOc1ccc(-c2ccc(Nc3nc(N4CCOC(C5CC5)C4)nc4c3CN(C(C)C)C4=O)cc2)cc1] | $^1$H NMR (400 MHz, DMSO) δ 0.22-0.40 (m, 2H), 0.43-0.60 (m, 2H), 0.84-0.99 (m, 4H), 1.20-1.38 (m, 12H), 1.43 (t, J = 7.8 Hz, 2H), 1.67-1.79 (m, 2H), 2.70-2.91 (m, 2H), 2.90-3.10 (m, 1H), 3.38-3.48 (m, 1H), 3.88-3.96 (m, 1H), 4.00 (t, J = 6.5 Hz, 2H), 4.29 (s, 2H), 4.32-4.48 (m, 2H), 4.55 (d, J = 12.5 Hz, 1H), 6.96-7.04 (m, 2H), 7.55-7.64 (m, 4H), 7.77-7.85 (m, 2H), 9.34 (s, 1H). m/z (ES+), [M + H]$^+$: 584; HPLC $t_R$ = 2.00 min (99.9%). |
| 54 | 4-[(4'-{2-[3-(but-3-yn-1-yl)-3H-diaziren-3-yl]ethoxy}[1,1'-biphenyl]-4-yl)amino]-2-(2-cyclopropyl-morpholin-4-yl)-6-(propan-2-yl)-5,6-dihydro-7H-pyrrolo[3,4-d]pyrimidin-7-one | 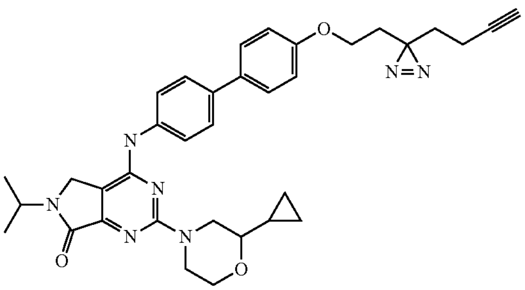 [SMILES: C#CCCC1(CCOc2ccc(-c3ccc(Nc4nc(N5CCOC(C6CC6)C5)nc5c4CN(C(C)C)C5=O)cc3)cc2)N=N1] | $^1$H NMR (400 MHz, DMSO) δ 0.26-0.37 (m, 2H), 0.43-0.59 (m, 2H), 0.86-0.99 (m, 1H), 1.24 (d, J = 6.8 Hz, 6H), 1.68 (t, J = 7.4 Hz, 2H), 1.90 (t, J = 6.1 Hz, 2H), 2.06-2.10(m, 2H), 2.72-2.91 (m, 3H), 2.95-3.06 (m, 1H), 3.38-3.48 (m, 1H), 3.87 (t, J = 6.1 Hz, 2H), 3.92 (d, J = 11.0 Hz, 1H), 4.29 (s, 2H), 4.31-4.48 (m, 2H), 4.55 (d, J = 12.3 Hz, 1H), 6.97-7.05 (m, 2H), 7.57-7.64 (m, 4H), 7.77-7.85 (m, 2H), 9.34 (s, 1H). m/z (ES+), [M + H]$^+$: 606; HPLC $t_R$ = 1.99 min (99.4%). |
| 55 | 2-[(2R)-2-methylmorpholin-4-yl]-4-[(4-pentylphenyl)amino]-6-(propan-2-yl)-5,6-dihydro-7H-pyrrolo[3,4-d]pyrimidin-7-one | 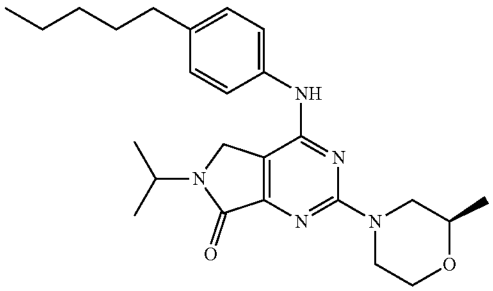 [SMILES: CCCCCc1ccc(Nc2nc(N3CCO[C@H](C)C3)nc3c2CN(C(C)C)C3=O)cc1] | $^1$H NMR (400 MHz, DMSO) δ 0.87 (t, J = 6.9 Hz, 3H), 1.15 (d, J = 6.1 Hz, 3H), 1.23 (d, J = 6.7 Hz, 6H), 1.25-1.35 (m, 4H), 1.51-1.63 (m, 2H), 2.52-2.66 (m, 4H), 2.88-3.00 (m, 1H), 3.42-3.55 (m, 2H), 3.89 (dd, J = 11.6, 3.1 Hz, 1H), 4.24 (s, 2H), 4.32-4.48 (m, 3H), 7.16 (dd, 2H), 7.61 (dd, 2H), 9.17 (s, 1H). m/z (ES+), [M + H]$^+$ = 438; HPLC $t_R$ = 1.697 min (99.9%). |
| 56 | 4-{[4-(butan-2-yl)phenyl]amino}-2-[(2R)-2-methylmorpholin-4-yl]-6-(propan-2-yl)-5,6-dihydro-7H-pyrrolo[3,4-d]pyrimidin-7-one | 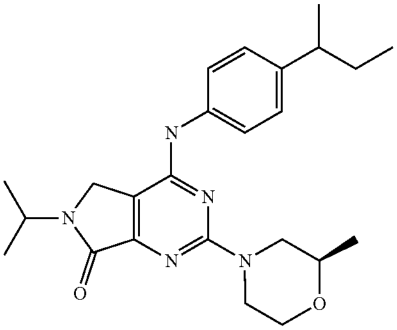 [SMILES: CCC(C)c1ccc(Nc2nc(N3CCO[C@H](C)C3)nc3c2CN(C(C)C)C3=O)cc1] | $^1$H NMR (400 MHz, DMSO) δ 0.78 (t, J = 7.4 Hz, 3H), 1.13-1.26 (m, 12H), 1.49-1.61 (m, 2H), 2.54-2.65 (m, 2H), 2.90-3.01 (m, 1H), 3.43-3.54 (m, 2H), 3.86-3.93 (m, 1H), 4.24 (s, 2H), 4.33-4.49 (m, 3H), 7.18 (d, J = 8.6 Hz, 2H), 7.65 (d, J = 8.6 Hz, 2H), 9.19 (s, 1H). m/z (ES+), [M + H]$^+$: 424.3; HPLC $t_R$ = 1.854 min (96.8%). |

TABLE 3-continued

| Example | Name | Structure | Analytical Data |
|---|---|---|---|
| 57 | 4-[(4-(benzyloxy)phenyl]amino}-2-[(2R)-2-methylmorpholin-4-yl]-6-(propan-2-yl)-5,6-dihydro-7H-pyrrolo[3,4-d]pyrimidin-7-one | 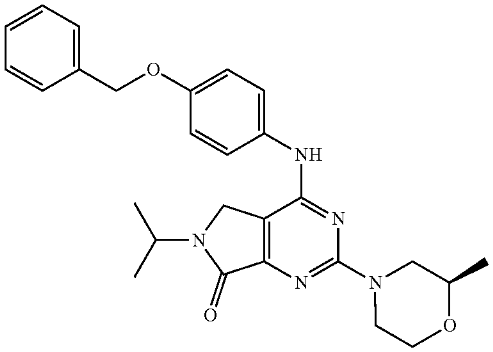 [SMILES: CC(C)N1Cc2c(Nc3ccc(OCc4ccccc4)cc3)nc(N3CCO[C@H](C)C3)nc2C1=O] | $^{1}$H NMR (400 MHz, DMSO) δ 1.15 (d, J = 6.1 Hz, 3H), 1.22 (d, J = 6.7 Hz, 6H), 2.59 (dd, J = 13.2, 10.4 Hz, 1H), 2.92 (td, 1H), 3.41-3.54 (m, 2H), 3.88 (d, J = 9.3 Hz, 1H), 4.22 (s, 2H), 4.30-4.46 (m, 3H), 5.09 (s, 2H), 6.98-7.06 (m, 2H), 7.31-7.36 (m, 1H), 7.37-7.43 (m, 2H), 7.44-7.48 (m, 2H), 7.55-7.64 (m, 2H), 9.14 (s, 1H). m/z (ES+), [M + H]$^{+}$: 474; HPLC $t_R$ = 1.883 min (95%). |
| 58 | 2-(2-cyclopropylmorpholin-4-yl)-4-{[4-(pentafluoroethyl)phenyl]amino}-6-(propan-2-yl)-5,6-dihydro-7H-pyrrolo[3,4-d]pyrimidin-7-one | 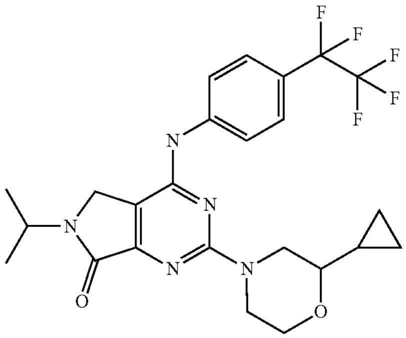 [SMILES: CC(C)N1Cc2c(Nc3ccc(C(F)(F)C(F)(F)F)cc3)nc(N3CCOC(C4CC4)C3)nc2C1=O] | $^{1}$H NMR (400 MHz, DMSO) δ 0.30 (d, 2H), 0.49 (dd, 2H), 0.85-0.96 (m, 1H), 1.24 (d, J = 6.7 Hz, 6H), 2.71-2.80 (m, 1H), 2.86 (t, 1H), 3.02 (td, J = 10.7 Hz, 1H), 3.17 (d, J = 4.3 Hz, 1H), 3.44 (s, 1H), 3.93 (d, J = 11.3 Hz, 1H), 4.31 (s, 3H), 4.38-4.46 (m, 1H), 4.51 (d, J = 12.8 Hz, 1H), 7.66 (d, J = 8.7 Hz, 2H), 8.01 (d, J = 8.6 Hz, 2H), 9.64 (s, 1H). m/z (ES+), [M + H]$^{+}$: 512; HPLC $t_R$ = 2.033 min (97%). |
| 59 | 2-(2-cyclopropylmorpholin-4-yl)-6-(propan-2-yl)-4-[(4-propylphenyl)amino]-5,6-dihydro-7H-pyrrolo[3,4-d]pyrimidin-7-one | 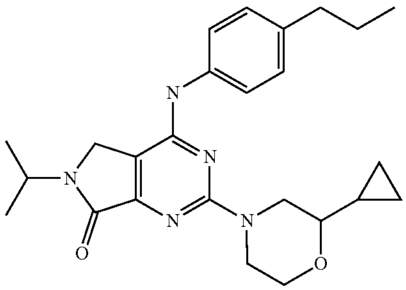 [SMILES: CCCc1ccc(Nc2nc(N3CCOC(C4CC4)C3)nc3c2CN(C(C)C)C3=O)cc1] | $^{1}$H NMR (400 MHz, DMSO) δ 0.23-0.29 (m, 1H), 0.29-0.38 (m, 1H), 0.46-0.55 (m, 2H), 0.90 (t, J = 7.3 Hz, 4H), 1.23 (d, J = 6.8 Hz, 6H), 1.53-1.66 (m, 2H), 2.54 (d, J = 7.5 Hz, 2H), 2.70-2.86 (m, 2H), 2.97 (td, 1H), 3.41 (td, J = 11.6, 2.7 Hz, 1H), 3.91 (dd, 1H), 4.25 (s, 2H), 4.33 (d, J = 13.2 Hz, 1H), 4.36-4.47 (m, 1H), 4.52 (d, J = 12.5 Hz, 1H), 7.16 (d, 2H), 7.63 (d, 2H), 9.20 (s, 1H). m/z (ES+), [M + H]$^{+}$: 436; HPLC $t_R$ = 1.838 min (99%). |
| 60 | 2-[(2R)-2-methylmorpholin-4-yl]-6-(propan-2-yl)-4-[(4-propylphenyl)amino]-5,6-dihydro-7H-pyrrolo[3,4-d]pyrimidin-7-one | 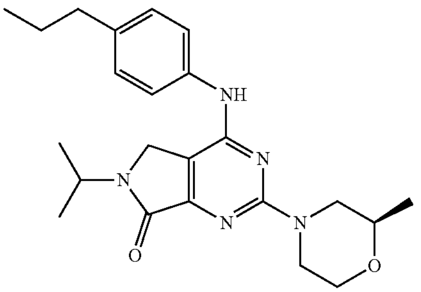 [SMILES: CCCc1ccc(Nc2nc(N3CCO[C@H](C)C3)nc3c2CN(C(C)C)C3=O)cc1] | $^{1}$H NMR (400 MHz, DMSO) δ 0.90 (t, J = 7.3 Hz, 3H), 1.15 (d, J = 6.2 Hz, 3H), 1.23 (d, J = 6.8 Hz, 6H), 1.52-1.66 (m, 2H), 2.56 (d, J = 14.3 Hz, 2H), 2.59-2.69 (m, 1H), 2.94 (td, J = 12.6, 3.5 Hz, 1H), 3.43-3.55 (m, 2H), 3.89 (dd, J = 11.4, 3.2 Hz, 1H), 4.25 (s, 2H), 4.32-4.49 (m, 3H), 7.17 (d, 2H), 7.63 (d, 2H), 9.21 (s, 1H). m/z (ES+), [M + H]$^{+}$: 410; HPLC $t_R$ = 1.977 min (99%). |

TABLE 3-continued

| Example | Name | Structure | Analytical Data |
|---|---|---|---|
| 61 | 2-[(2R)-2-methylmorpholin-4-yl]-4-{[4-(pentafluoroethyl) phenyl]amino}-6-(propan-2-yl)-5,6-dihydro-7H-pyrrolo[3,4-d]pyrimidin-7-one | 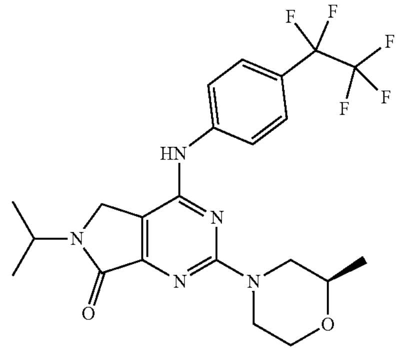 [SMILES: CC(C)N1Cc2c(Nc3ccc(C(F)(F)C(F)(F)F)cc3)nc(N3CCO[C@H](C)C3)nc2C1=O] | $^1$H NMR (400 MHz, DMSO) δ 1.18 (d, J = 6.2 Hz, 3H), 1.25 (d, J = 6.8 Hz, 6H), 2.66 (dd, J = 13.1, 10.4 Hz, 1H), 3.00 (td, 1H), 3.45-3.57 (m, 2H), 3.92 (dd, 1H), 4.32 (s, 2H), 4.34-4.49 (m, 3H), 7.69 (d, J = 8.7 Hz, 2H), 8.03 (d, J = 8.7 Hz, 2H), 9.62 (s, 1H). m/z (ES+), [M + H]$^+$: 486; HPLC $t_R$ = 1.975 min (98%). |
| 62 | 2-(2-cyclopropylmorpholin-4-yl)-6-(propan-2-yl)-4-({4-[(propan-2-yl)oxy]phenyl}amino)-5,6-dihydro-7H-pyrrolo[3,4-d]pyrimidin-7-one | 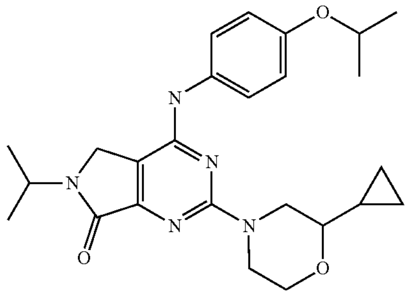 [SMILES: CC(C)Oc1ccc(Nc2nc(N3CCOC(C4CC4)C3)nc3c2CN(C(C)C)C3=O)cc1] | $^1$H NMR (400 MHz, DMSO) δ 0.21-0.28 (m, 1H), 0.28-0.37 (m, 1H), 0.44-0.57 (m, 2H), 0.84-0.97 (m, 1H), 1.23 (d, J = 6.7 Hz, 6H), 1.27 (d, J = 6.0 Hz, 6H), 2.69-2.85 (m, 2H), 2.96 (td, J = 12.4, 11.8, 3.5 Hz, 1H), 3.40 (td, J = 11.6, 2.7 Hz, 1H), 3.90 (dd, 1H), 4.22 (s, 2H), 4.32 (d, J = 13.2 Hz, 1H), 4.36-4.47 (m, 1H), 4.48-4.61 (m, 2H), 6.90 (d, 2H), 7.58 (d, 2H), 9.12 (s, 1H). m/z (ES+), [M + H]$^+$: 452.15; HPLC $t_R$ = 1.438 min (99.6%). |
| 63 | 4-[(4-cyclobutylphenyl) amino]-2-(morpholin-4-yl)-6-(propan-2-yl)-5,6-dihydro-7H-pyrrolo[3,4-d]pyrimidin-7-one | 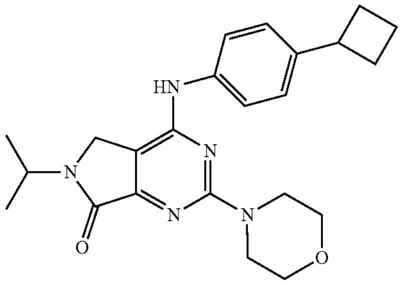 [SMILES: CC(C)N1Cc2c(Nc3ccc(C4CCC4)cc3)nc(N3CCOCC3)nc2C1=O] | $^1$H NMR (400 MHz, DMSO) δ 1.23 (d, J = 6.7 Hz, 6H), 1.76-2.02 (m, 2H), 2.03-2.15 (m, 2H), 2.22-2.34 (m, 2H), 3.42-3.55 (m, 1H), 3.62-3.73 (m, 8H), 4.36-4.49 (m, 1H), 7.22 (d, 2H), 7.66 (d, 2H), 9.20 (s, 1H). m/z (ES+), [M + H]$^+$: 408; HPLC $t_R$ = 1.622 min (98%). |
| 64 | 4-{[4-(cyclopentyloxy)phenyl] amino}-2-[(2R)-2-methylmorpholin-4-yl]-6-(propan-2-yl)-5,6-dihydro-7H-pyrrolo[3,4-d]pyrimidin-7-one | 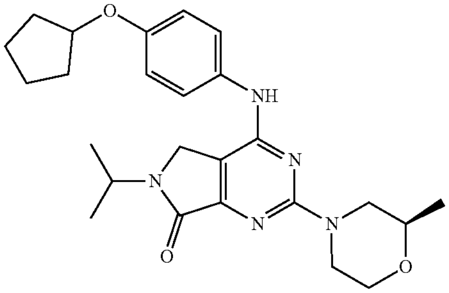 [SMILES: CC(C)N1Cc2c(Nc3ccc(OC4CCCC4)cc3)nc(N3CCO[C@H](C)C3)nc2C1=O] | $^1$H NMR (400 MHz, DMSO) δ 1.15 (d, J = 6.2 Hz, 3H), 1.22 (d, J = 6.7 Hz, 6H), 1.52-1.65 (m, 2H), 1.65-1.77 (m, 4H), 1.85-1.97 (m, 2H), 2.59 (dd, J = 13.1, 10.4 Hz, 1H), 2.92 (td, 1H), 3.42-3.54 (m, 2H), 3.88 (dd, J = 11.4, 3.3 Hz, 1H), 4.22 (s, 2H), 4.31-4.47 (m, 3H), 4.79 (t, J = 5.8 Hz, 1H), 6.89 (d, 2H), 7.57 (d, 2H), 9.13 (s, 1H). m/z (ES+), [M + H]$^+$: 452; HPLC $t_R$ = 2.005 min (99%). |
| 65 | 2-[(2R)-2-methylmorpholin-4-yl]-6-(propan-2-yl)-4-{[4-(2,2,2-trifluoroethyl)phenyl] amino}-5,6-dihydro-7H-pyrrolo[3,4-d]pyrimidin-7-one | 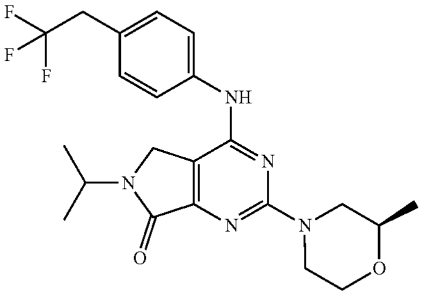 [SMILES: CC(C)N1Cc2c(Nc3ccc(CC(F)(F)F)cc3)nc(N3CCO[C@H](C)C3)nc2C1=O] | $^1$H NMR (400 MHz, DMSO) δ 1.15 (d, J = 6.2 Hz, 3H), 1.23 (d, J = 6.7 Hz, 6H), 2.63 (dd, J = 13.1, 10.3 Hz, 1H), 2.96 (td, 1H), 3.43-3.66 (m, 4H), 3.89 (dd, 1H), 4.27 (s, 2H), 4.32-4.48 (m, 3H), 7.33 (d, J = 8.3 Hz, 2H), 7.74 (d, 2H), 9.30 (s, 1H). m/z (ES+), [M + H]$^+$: 450; HPLC $t_R$ = 1.811 min (95%). |

TABLE 3-continued

| Example | Name | Structure | Analytical Data |
|---|---|---|---|
| 66 | tert-butyl {2-[(4'-{[2-(2-cyclopropylmorpholin-4-yl)-7-oxo-6-(propan-2-yl)-6,7-dihydro-5H-pyrrolo[3,4-d]pyrimidin-4-yl]amino}[1,1'-biphenyl]-4-yl)oxy]ethyl}carbamate | 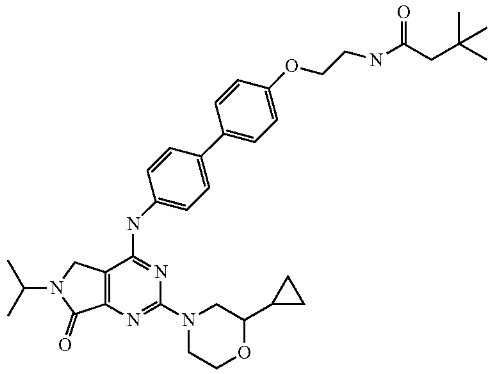 [SMILES: CC(C)N1Cc2c(Nc3ccc(-c4ccc(OCCNC(=O)CC(C)(C)C)cc4)cc3)nc(N3CCOC(C4CC4)C3)nc2C1=O] | $^1$H NMR (400 MHz, DMSO) δ 0.25-0.37 (m, 2H), 0.49-0.55 (m, 2H), 0.94 (s, 1H), 1.25 (d, J = 6.7 Hz, 6H), 1.40 (s, 9H), 2.72-2.91 (m, 2H), 3.01 (t, J = 11.4 Hz, 1H), 3.31 (s, 2H), 3.43 (t, J = 11.1 Hz, 1H), 3.93 (d, J = 11.4 Hz, 1H), 4.00 (t, J = 5.8 Hz, 2H), 4.29 (s, 2H), 4.32-4.48 (m, 2H), 4.55 (d, J = 12.5 Hz, 1H), 6.98-7.06 (m, 3H), 7.57-7.65 (m, 4H), 7.81 (d, J = 8.6 Hz, 2H), 9.34 (s, 1H). m/z (ES+), $[M + H]^+$: 630; HPLC $t_R$ = 2.57 min (95.5%). |
| 67 | 6-ethyl-2-[(2R)-2-methylmorpholin-4-yl]-4-{[4-(propan-2-yl)phenyl]amino}-5,6-dihydro-7H-pyrrolo[3,4-d]pyrimidin-7-one | 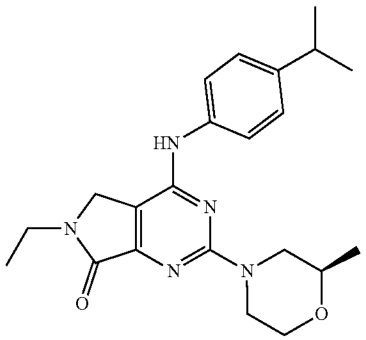 [SMILES: CCN1Cc2c(Nc3ccc(C(C)C)cc3)nc(N3CCO[C@H](C)C3)nc2C1=O] | $^1$H NMR (400 MHz, DMSO) δ 1.13-1.24 (m, 12H), 2.62 (dd, J = 13.0, 10.4 Hz, 1H), 2.83-2.91 (m, 1H), 2.95 (t, J = 11.0 Hz, 1H), 3.44-3.60 (m, 4H), 3.90 (dd, 1H), 4.30 (s, 2H), 4.37 (d, J = 13.3 Hz, 1H), 4.45 (d, J = 13.3 Hz, 1H), 7.22 (d, J = 8.5 Hz, 2H), 7.65 (d, J = 8.6 Hz, 2H), 9.19 (s, 1H). m/z (ES+), $[M + H]^+$: 396; HPLC $t_R$ = 1.708 min (97%). |
| 68 | 4-[(4-cyclohexylphenyl)amino]-6-ethyl-2-[(2R)-2-methylmorpholin-4-yl]-5,6-dihydro-7H-pyrrolo[3,4-d]pyrimidin-7-one | 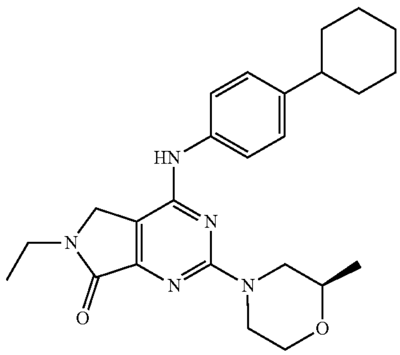 [SMILES: CCN1Cc2c(Nc3ccc(C4CCCCC4)cc3)nc(N3CCO[C@H](C)C3)nc2C1=O] | $^1$H NMR (400 MHz, DMSO) δ 1.04-1.22 (m, 7H), 1.32-1.43 (m, 4H), 1.74 (dd, J = 34.6, 11.5 Hz, 5H), 2.46 (s, 1H), 2.61 (dd, J = 13.2, 10.4 Hz, 1H), 2.94 (td, J = 12.5, 11.9, 3.5 Hz, 1H), 3.42-3.59 (m, 4H), 3.89 (dd, J = 11.4, 3.3 Hz, 1H), 4.29 (s, 2H), 4.40 (dd, J = 34.4, 13.2 Hz, 2H), 7.19 (d, J = 9.0, 2.4 Hz, 2H), 7.63 (d, 2H), 9.17 (s, 1H). m/z (ES+), $[M + H]^+$: 436; HPLC $t_R$ = 2.217 min (96.3%). |

Example 69: tert-Butyl (2-((4'-((6-isopropyl-2-morpholino-7-oxo-6,7-dihydro-5H-pyrrolo[3,4-d]pyrimidin-4-yl)amino)-[1,1'-biphenyl]-4-yl)oxy)ethyl)carbamate

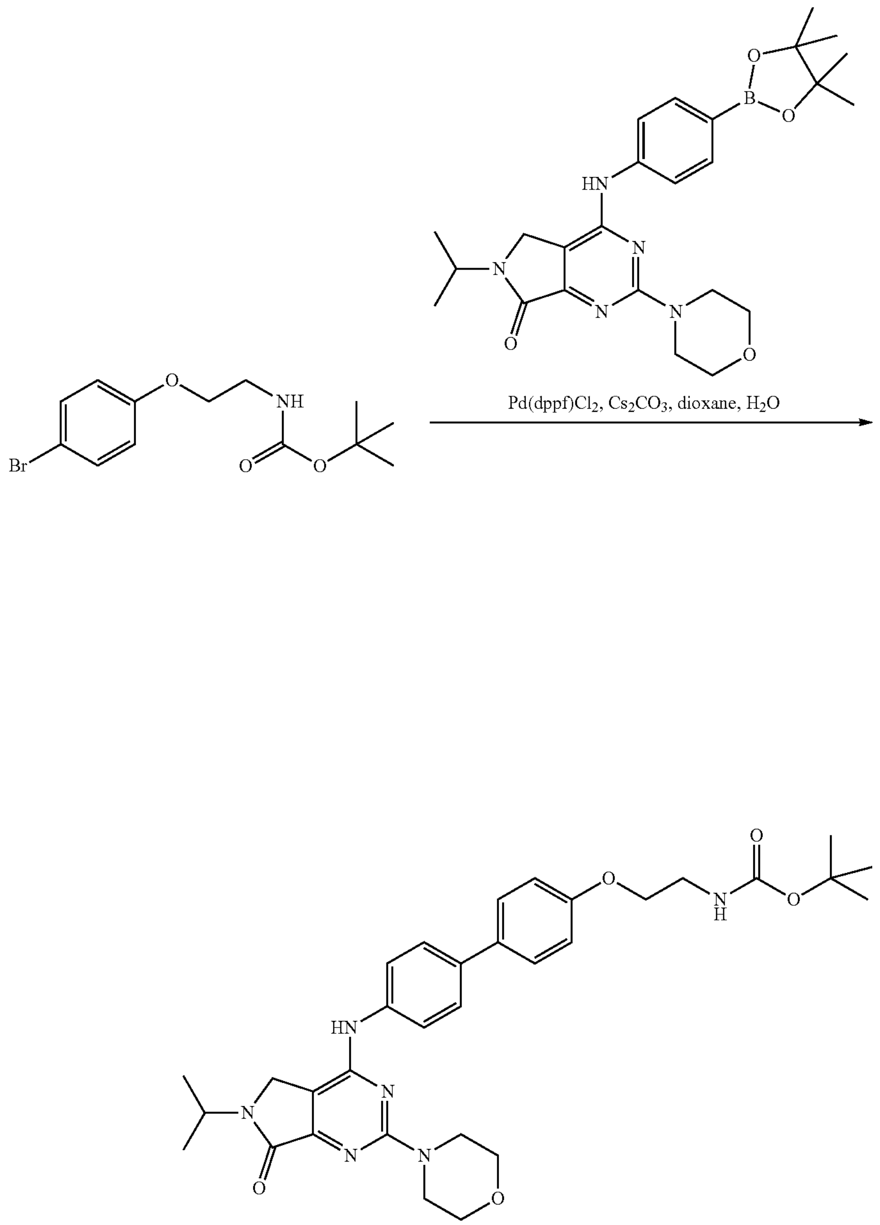

Pd(dppf)$Cl_2$ (15.26 mg, 0.02 mmol) was added to $Cs_2CO_3$ (136 mg, 0.42 mmol), tert-butyl (2-(4-bromophenoxy)ethyl) carbamate (99 mg, 0.31 mmol) and 6-isopropyl-2-morpholino-4-((4-(4,4,5,5-tetraethyl-1,3,2-dioxaborolan-2-yl) phenyl)amino)-5,6-dihydro-7H-pyrrolo[3,4-d]pyrimidin-7-one (100 mg, 0.21 mmol) in dioxane (5 mL) and water (1.000 mL) at 25° C. under air. The resulting mixture was stirred at 100° C. for 2 hours.

The solvent was removed under reduced pressure. The crude product was purified by flash silica chromatography, elution gradient 0 to 8% MeOH in DCM to give a yellow oil. The oil product was purified by preparative HPLC conditions C. Fractions containing the desired compound were evaporated to dryness to afford tert-butyl (2-((4'-((6-isopropyl-2-morpholino-7-oxo-6,7-dihydro-5H-pyrrolo[3,4-d]pyrimidin-4-yl)amino)-[1,1'-biphenyl]-4-yl)oxy)ethyl)carbamate (56.5 mg, 46.0%) as a grey solid. $^1$H NMR (400 MHz, DMSO) δ 1.25 (d, J=6.8 Hz, 6H), 1.40 (s, 9H), 3.13 (d, J=5.8 Hz, 2H), 3.70 (dd, J=12.4, 4.4 Hz, 8H), 4.00 (t, J=5.8 Hz, 2H), 4.30 (s, 2H), 4.29-4.43 (m, 1H), 6.96-7.09 (m, 3H), 7.62 (t, J=8.6 Hz, 4H), 7.77-7.85 (m, 2H), 9.34 (s, 1H). m/z (ES+), $[M+H]^+$: 589; HPLC $t_R$=1.79 min (99.4%).

The Examples in Table 4 were made from Intermediate 11 and the appropriate bromide, according to the procedure for Example 69.

TABLE 4

| Example | Name | Structure | Analytical data |
| --- | --- | --- | --- |
| 70 | 4-[(4'-{2-[3-(but-3-yn-1-yl)-3H-diaziren-3-yl]ethoxy}[1,1'-biphenyl]-4-yl)amino]-2-(morpholin-4-yl)-6-(propan-2-yl)-5,6-dihydro-7H-pyrrolo[3,4-d]pyrimidin-7-one | 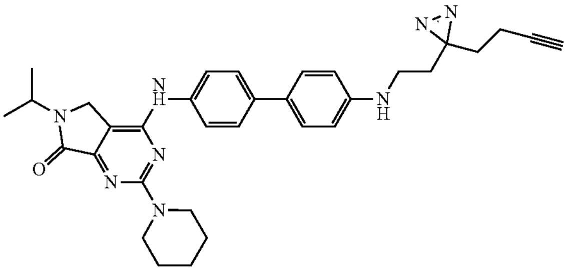 [SMILES: C#CCCC1(CCNc2ccc(-c3ccc(Nc4nc(N5CCCCC5)nc5c4CN(C(C)C)C5=O)cc3)cc2)N=N1] | $^1$H NMR (400 MHz, DMSO) δ 1.25 (d, J = 6.8 Hz, 6H), 1.68 (t, J = 7.4 Hz, 2H), 1.90 (t, J = 6.0 Hz, 2H), 2.02-2.11 (m, 2H), 2.86 (s, 1H), 3.69 (d, J = 10.4 Hz, 8H), 3.87 (t, J = 6.0 Hz, 2H), 4.30 (s, 2H), 4.39-4.47 (m, 1H), 7.00 (d, J = 8.5 Hz, 2H), 7.62 (t, J = 8.0 Hz, 4H), 7.81 (d, J = 8.6 Hz, 2H), 9.34 (s, 1H). m/z (ES+), $[M + H]^+$: 566; HPLC $t_R$ = 1.84 min (95.8%). |
| 71 | 2-(morpholin-4-yl)-6-(propan-2-yl)-4-({4'-[(prop-2-yn-1-yl)oxy][1,1'-biphenyl]-4-yl}amino)-5,6-dihydro-7H-pyrrolo[3,4-d]pyrimidin-7-one | 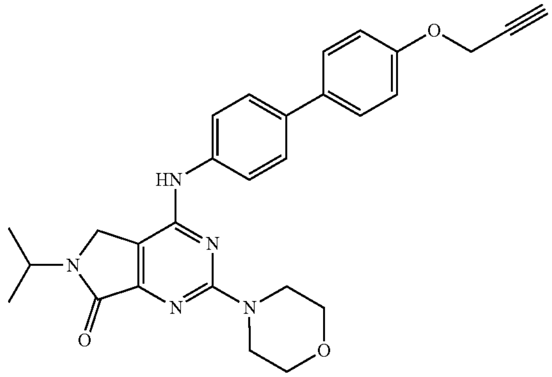 [SMILES: C#CCOc1ccc(-c2ccc(Nc3nc(N4CCOCC4)nc4c3CN(C(C)C)C4=O)cc2)cc1] | $^1$H NMR (400 MHz, DMSO) δ 1.25 (d, J = 6.7 Hz, 6H), 3.61 (t, J = 2.4 Hz, 1H), 3.65-3.81 (m, 8H), 4.30 (s, 2H), 4.37-4.49 (m, 1H), 4.85 (d, J = 2.4 Hz, 2H), 7.07 (d, J = 8.7 Hz, 2H), 7.64 (dd, J = 8.8, 2.4 Hz, 4H), 7.82 (d, J = 8.5 Hz, 2H), 9.35 (s, 1H). m/z (ES+), $[M + H]^+$: 484; HPLC $t_R$ = 1.722 min (99.6%). |

Example 72: (R)-4-((4-cyclohexylphenyl)amino)-6-(3-(dimethylamino)propyl)-2-(2-methylmorpholino)-5,6-dihydro-7H-pyrrolo[3,4-d]pyrimidin-7-one

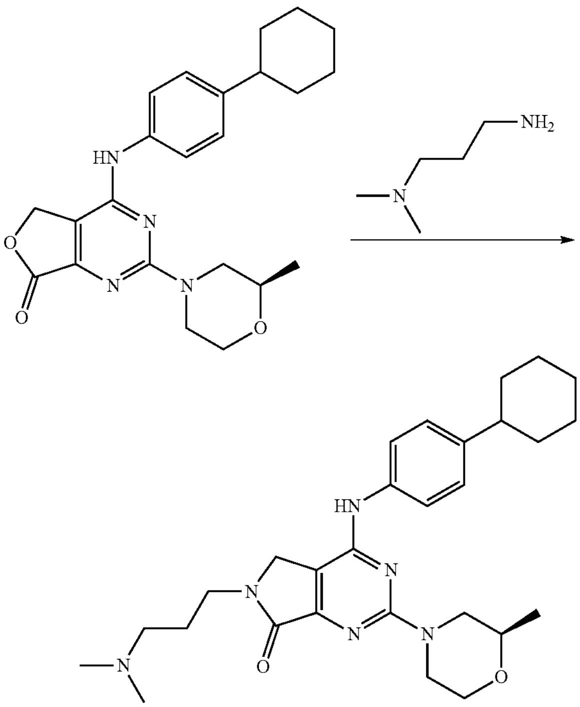

HCl (0.191 mL, 2.20 mmol) was added to N1,N1-dimethylpropane-1,3-diamine (75 mg, 0.73 mmol), and (R)-4-((4-cyclohexylphenyl)amino)-2-(2-methylmorpholino)furo[3,4-d] pyrimidin-7(5H)-one (100 mg, 0.24 mmol) in 2-(2-methoxyethoxy) ethanol (2 mL). The resulting mixture was stirred at 190° C. for 4 hours. The reaction mixture was diluted with water (100 mL), extracted with DCM (3×200 mL), and washed sequentially with water (100 mL) and saturated brine (100 mL). The organic layer was dried over $Na_2SO_4$, filtered and evaporated to afford crude product. The crude product was purified by preparative HPLC conditions A. Fractions containing the desired compound were evaporated to dryness to afford (R)-4-((4-cyclohexylphenyl)amino)-6-(3-(dimethylamino)propyl)-2-(2-methylmorpholino)-5,6-dihydro-7H-pyrrolo[3,4-d]pyrimidin-7-one (21.0 mg, 14%) as a yellow solid. $^1$H NMR (400 MHz, DMSO) δ 1.16 (d, J=6.2 Hz, 3H), 1.23 (d, J=10.9 Hz, 1H), 1.32-1.47 (m, 4H), 1.71 (d, J=12.7 Hz, 1H), 1.79 (d, J=9.9 Hz, 4H), 1.92-2.02 (m, 2H), 2.47 (s, 1H), 2.53-2.68 (m, 1H), 2.78 (d, 6H), 2.95 (td, J=12.6, 12.1, 3.4 Hz, 1H), 3.01-3.11 (m, 2H), 3.42-3.55 (m, 2H), 3.61 (t, J=12.9 Hz, 2H), 3.90 (dd, 1H), 4.33 (s, 3H), 4.43 (s, 1H), 7.20 (d, 2H), 7.63 (d, 2H), 9.28 (s, 1H), 9.43 (s, 1H). m/z (ES+), $[M+H]^+$: 493; HPLC $t_R$=1.614 min (95%).

The Examples in Table 5 were made by procedures analogous to that used for Example 72, using Intermediates 15, 16 or 17.

TABLE 5

| Example | Name | Structure | Analytical data |
|---|---|---|---|
| 73 | 4-[(4-cyclohexylphenyl)amino]-6-[2-(dimethylamino)ethyl]-2-[(2R)-2-methylmorpholin-4-yl]-5,6-dihydro-7H-pyrrolo[3,4-d]pyrimidin-7-one | 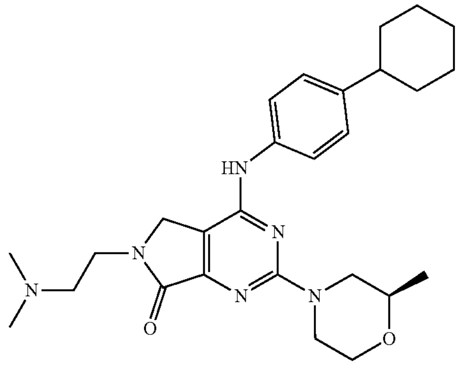 [SMILES: C[C@@H]1CN(c2nc(Nc3ccc(C4CCCCC4)cc3)c3c(n2)C(=O)N(CCN(C)C)C3)CCO1] | $^1$H NMR (400 MHz, DMSO) δ 1.04-1.28 (m, 5H), 1.29-1.47 (m, 4H), 1.71 (d, J = 12.8 Hz, 1H), 1.79 (d, J = 9.7 Hz, 4H), 2.19 (s, 6H), 2.47 (d, J = 5.6 Hz, 2H), 2.62 (dd, J = 13.1, 10.4 Hz, 1H), 2.96 (td, 1H), 3.44-3.55 (m, 2H), 3.62 (t, J = 6.2 Hz, 2H), 3.90 (dd, 1H), 4.32-4.49 (m, 4H), 7.19 (d, 2H), 7.63 (d, 2H), 9.19 (s, 1H). m/z (ES+), [M + H]$^+$: 479; HPLC $t_R$ = 2.406 min (97%). |
| 74 | 4-[(4-cyclobulylphenyl)amino]-6-[3-(dimethylamino)propyl]-2-[(2R)-2-methylmorpholin-4-yl]-5,6-dihydro-7H-pyrrolo[3,4-d]pyrimidin-7-one | 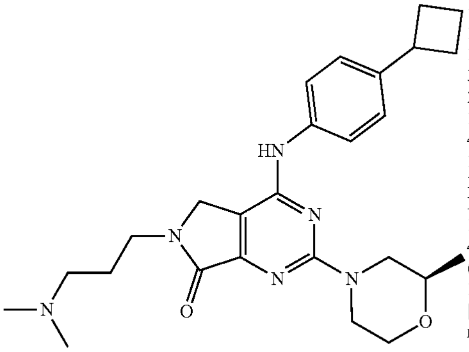 | $^1$H NMR (400 MHz, DMSO) δ 1.16 (d, J = 6.1 Hz, 3H), 1.75-1.86 (m, 1H), 1.88-2.00 (m, 3H), 2.00-2.16 (m, 2H), 2.22-2.34 (m, 2H), 2.63 (dd, J = 13.1, 10.4 Hz, 1H), 2.78 (d, J = 4.8 Hz, 6H), 2.90-3.01 (m, 1H), 3.01-3.11 (m, 2H), 3.43-3.53 (m, 3H), 3.61 (t, J = 6.4 Hz, 2H), 3.91 (d, J = 9.4 Hz, 1H), 4.36 (d, J = 20.0 Hz, 3H), 4.45 (d, J = 12.8 Hz, 1H), 7.23 (d, 2H), 7.65 (d, 2H), 9.29 (s, 1H), 9.38 (s, 1H). m/z (ES+), [M + H]$^+$: 465; HPLC $t_R$ = 1.492 min (97%). |
| 75 | 4-[(4-cyclobutylphenyl)amino]-6-[2-(dimethylamino)ethyl]-2-[(2R)-2-methylmorpholin-4-yl]-5,6-dihydro-7H-pyrrolo[3,4-d]pyrimidin-7-one | 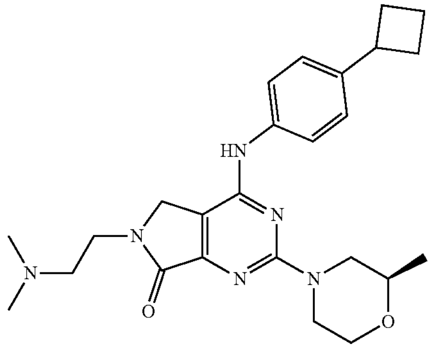 | $^1$H NMR (400 MHz, DMSO) δ 1.16 (d, J = 6.2 Hz, 3H), 1.82 (t, J = 9.2 Hz, 1H), 1.92-2.02 (m, 1H), 2.03-2.15 (m, 2H), 2.22-2.34 (m, 8H), 2.54-2.66 (m, 3H), 2.89-3.01 (m, 1H), 3.45-3.54 (m, 3H), 3.65 (t, J = 6.0 Hz, 2H), 3.90 (dd, 1H), 4.37 (d, J = 10.1 Hz, 3H), 4.45 (d, J = 13.0 Hz, 1H), 7.22 (d, J = 8.5 Hz, 2H), 7.61-7.69 (m, 2H), 8.15 (d, J = 2.3 Hz, 1H), 9.22 (s, 1H). m/z (ES+), [M + H]$^+$: 451; HPLC $t_R$ = 1.574 min (96%). |
| 76 | 2-(morpholin-4-yl)-4-{[4-(propan-2-yl)phenyl]amino}-6-(prop-2-yn-1-yl)-5,6-dihydro-7H-pyrrolo[3,4-d]pyrimidin-7-one | 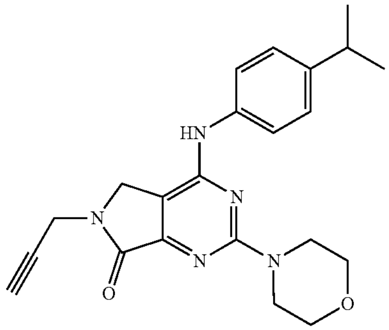 [SMILES: C#CCN1Cc2c(Nc3ccc(C(C)C)cc3)nc(N3CCOCC3)nc2C1=O] | $^1$H NMR (400 MHz, DMSO) δ 1.21 (d, J = 6.9 Hz, 6H), 2.81-2.93 (m, 1H), 3.41 (1, J = 5.0 Hz, 1H), 3.63-3.73 (m, 8H), 4.39 (1, 4H), 7.23 (d, 2H), 7.66 (d, 2H), 9.25 (s, 1H). m/z (ES+), [M + H]$^+$: 392; HPLC $t_R$ = 1.815 min (97.1%). |

Example 78: 4-((4-cyclohexylphenyl)amino)-6-isopropyl-2-(tetrahydro-2H-pyran-4-yl)-5,6-dihydro-7H-pyrrolo[3,4-d]pyrimidin-7-one

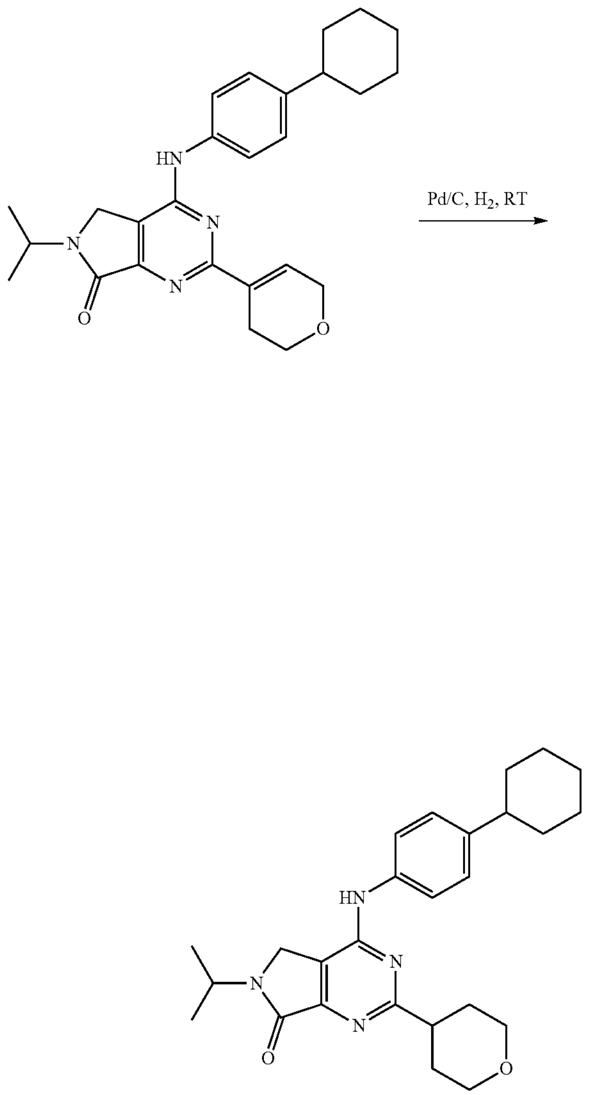

Palladium on carbon (73.8 mg, 0.07 mmol) was added to 4-((4-cyclohexylphenyl)amino)-2-(3,6-dihydro-2H-pyran-4-yl)-6-isopropyl-5,6-dihydro-7H-pyrrolo[3,4-d]pyrimidin-7-one (300 mg, 0.69 mmol) in MeOH (10 mL) at RT under hydrogen. The resulting mixture was stirred at RT for 6 hours. The reaction mixture was filtered through celite. The crude product was purified by preparative HPLC conditions C. Fractions containing the desired compound were evaporated to dryness to afford 4-((4-cyclohexylphenyl)amino)-6-isopropyl-2-(tetrahydro-2H-pyran-4-yl)-5,6-dihydro-7H-pyrrolo[3,4-d]pyrimidin-7-one (68.0 mg, 22%) as a white solid. $^1$H NMR (400 MHz, DMSO) δ 1.25 (d, J=6.7 Hz, 7H), 1.32-1.48 (m, 4H), 1.71 (d, J=12.6 Hz, 1H), 1.75-1.91 (m, 8H), 2.46 (d, J=10.7 Hz, 1H), 2.92-3.04 (m, 1H), 3.40-3.51 (m, 2H), 3.90-3.99 (m, 2H), 4.35 (s, 2H), 4.44 (p, J=6.7 Hz, 1H), 7.18-7.26 (m, 2H), 7.71-7.79 (m, 2H), 9.42 (s, 1H). ES+ m/z $[M+H]^+$: 435, HPLC $t_R$=1.855 min (99.8%).

Example 79: 4-((4-cyclohexylphenyl)amino)-2-(1H-imidazol-1-yl)-6-isopropyl-5,6-dihydro-7H-pyrrolo[3,4-d]pyrimidin-7-one

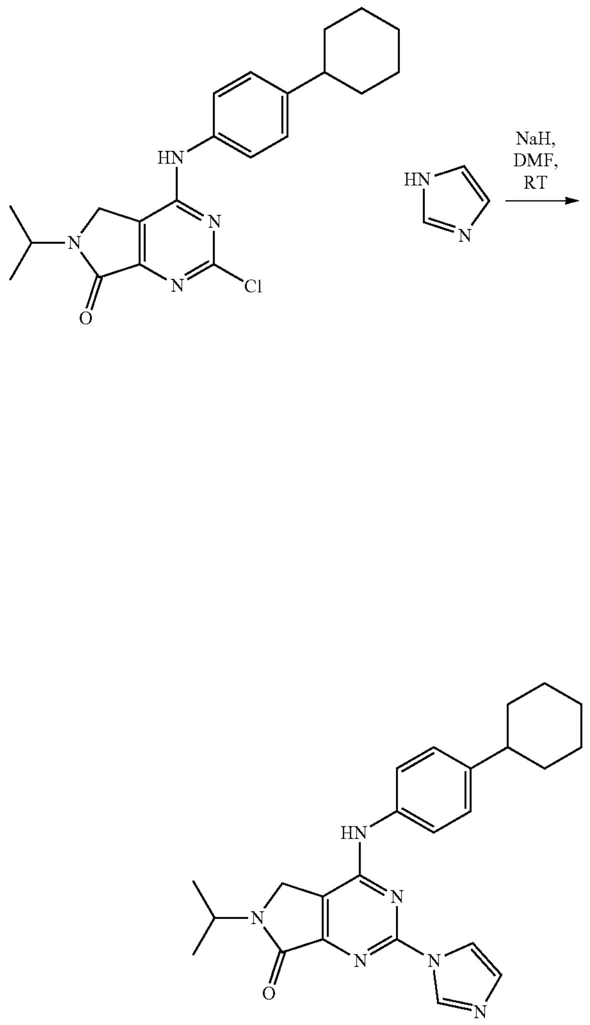

NaH (31.2 mg, 0.78 mmol) was added to 1H-imidazole (53 mg, 0.78 mmol) and 2-chloro-4-((4-cyclohexylphenyl)amino)-6-isopropyl-5,6-dihydro-7H-pyrrolo[3,4-d]pyrimidin-7-one (100 mg, 0.26 mmol) in DMF (2 mL) at 0° C. The resulting mixture was stirred at R T for 14 hours. The crude product was purified by preparative HPLC Column: XBridge Shield RP18 OBD Column, 19×250 mm, 10 um; Mobile Phase A: Water (10 mM $NH_4HCO_3$+0.1% $NH_3 \cdot H_2O$), Mobile Phase B: acetonitrile; Flow rate: 25 mL/min; Gradient elution with detection at 254/220 nm. Fractions containing the desired compound were evaporated to dryness to afford 4-((4-cyclohexylphenyl)amino)-2-(1H-imidazol-1-yl)-6-isopropyl-5,6-dihydro-7H-pyrrolo[3,4-d]pyrimidin-7-one (10.0 mg, 9%) as a white solid. $^1$H NMR (DMSO-d6, 400 MHz) δ 1.28 (d, J=6.8 Hz, 7H), 1.31-1.51 (m, 4H), 1.72 (d, J=12.5 Hz, 1H), 1.83 (d, J=9.0 Hz, 4H), 2.51 (s, 1H), 4.41-4.52 (m, 3H), 7.13 (d, J=1.2 Hz, 1H), 7.28-7.36 (m, 2H), 7.65-7.72 (m, 2H), 7.86 (t, J=1.4, 1.4 Hz, 1H), 8.47 (d, J=1.1 Hz, 1H), 9.91 (s, 1H). ES+ m/z $[M+H]^+$: 417, HPLC $t_R$=1.655 min (99.3%).

Example 80: 2-(3,6-dihydro-2H-pyran-4-yl)-6-isopropyl-4-((2'-methyl-[1,1'-biphenyl]-4-yl)amino)-5,6-dihydro-7H-pyrrolo[3,4-d]pyrimidin-7-one

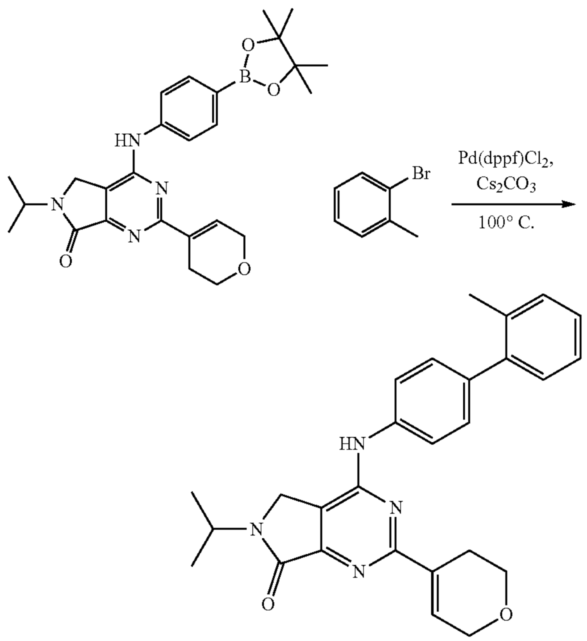

Pd(dppf)$Cl_2$ (30.7 mg, 0.04 mmol) was added to 2-(3,6-dihydro-2H-pyran-4-yl)-6-isopropyl-4-((4-(4,4,5,5-tetramethyl-1,3,2-dioxaborolan-2-yl)phenyl)amino)-5,6-dihydro-7H-pyrrolo[3,4-d]pyrimidin-7-one (200 mg, 0.42 mmol), 1-bromo-2-methylbenzene (108 mg, 0.63 mmol) and $Cs_2CO_3$ (274 mg, 0.84 mmol) in 1,4-dioxane (5 mL) and water (1 mL) at RT under nitrogen. The resulting mixture was stirred at 100° C. for 2 hours. The solvent was removed by distillation under vacuum. The crude product was purified by flash silica chromatography, elution gradient 0 to 5% MeOH in DCM. Pure fractions were evaporated to dryness to afford yellow oil. The crude product was purified by preparative HPLC conditions A. Fractions containing the desired compound were evaporated to dryness to afford 2-(3,6-dihydro-2H-pyran-4-yl)-6-isopropyl-4-((2'-methyl-[1,1'-biphenyl]-4-yl)amino)-5,6-dihydro-7H-pyrrolo[3,4-d]pyrimidin-7-one (25.0 mg, 13%) as a white solid. $^1$H NMR (400 MHz, DMSO-d6) δ 1.28 (d, J=6.7 Hz, 6H), 2.29 (s, 3H), 2.62 (s, 2H), 3.83 (t, J=5.4, 5.4 Hz, 2H), 4.32 (q, J=2.8, 2.8, 2.8 Hz, 2H), 4.38-4.58 (m, 3H), 7.19 (d, J=2.8 Hz, 1H), 7.20-7.34 (m, 4H), 7.34-7.42 (m, 2H), 7.90-7.97 (m, 2H), 9.59 (s, 1H). ES+ m/z $[M+H]^+$: 441, HPLC $t_R$=1.796 min (98.6%).

Example 81: 4-((4'-(2-(3-(but-3-yn-1-yl)-3H-diazirin-3-yl)ethoxy)-[1,1'-biphenyl]-4-yl)amino)-2-(3,6-dihydro-2H-pyran-4-yl)-6-isopropyl-5,6-dihydro-7H-pyrrolo[3,4-d]pyrimidin-7-one

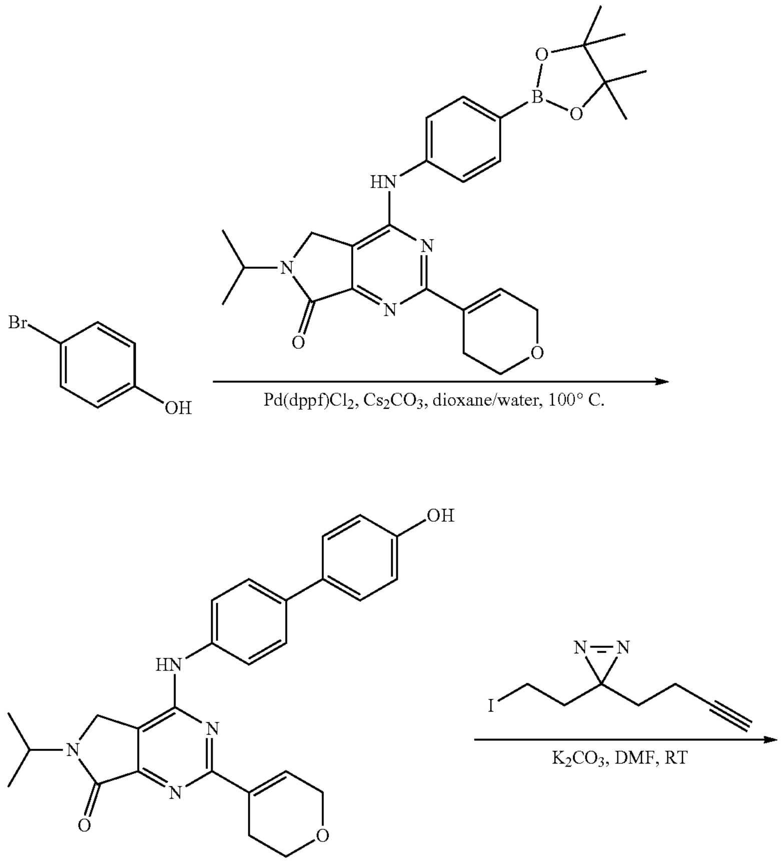

-continued

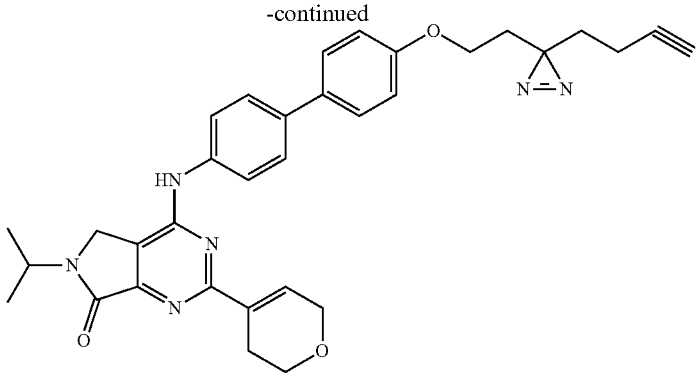

Example 81, Step 1: 2-(3,6-dihydro-2H-pyran-4-yl)-4-((4'-hydroxy-[1,1'-biphenyl]-4-yl)amino)-6-isopropyl-5,6-dihydro-7H-pyrrolo[3,4-d]pyrimidin-7-one

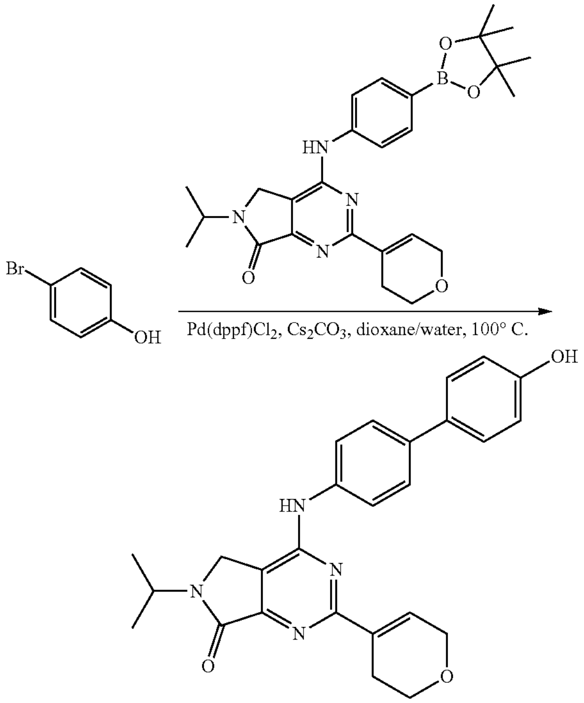

$Pd(dppf)Cl_2$ (100 mg, 0.14 mmol) was added to 2-(3,6-dihydro-2H-pyran-4-yl)-6-isopropyl-4-((4-(4,4,5,5-tetramethyl-1,3,2-dioxaborolan-2-yl)phenyl)amino)-5,6-dihydro-7H-pyrrolo[3,4-d]pyrimidin-7-one (650 mg, 1.36 mmol), 4-bromophenol (283 mg, 1.64 mmol) and $Cs_2CO_3$ (889 mg, 2.73 mmol) in 1,4-dioxane (5 mL) and water (1 mL) at RT under nitrogen. The resulting mixture was stirred at 100° C. for 2.5 hours under nitrogen. The crude product was purified by flash silica chromatography, elution gradient 0 to 5% MeOH in DCM. Pure fractions were evaporated to dryness to afford 2-(3,6-dihydro-2H-pyran-4-yl)-4-((4'-hydroxy-[1,1'-biphenyl]-4-yl)amino)-6-isopropyl-5,6-dihydro-7H-pyrrolo[3,4-d]pyrimidin-7-one (210 mg, 35%) as a yellow solid. $^1$H NMR (400 MHz, DMSO) δ 1.28 (d, J=6.7 Hz, 6H), 2.62 (s, 2H), 3.84 (t, J=5.4 Hz, 2H), 3.94 (s, 2H), 4.33 (d, J=2.8 Hz, 2H), 4.44 (m, 1H), 6.84 (d, J=8.7 Hz, 2H), 7.19 (d, J=2.7 Hz, 1H), 7.49-7.56 (m, 2H), 7.62 (d, J=8.7 Hz, 2H), 7.87-7.93 (m, 2H), 9.50 (s, 1H), 9.54 (s, 1H). $ES^+$ m/z $[M+H]^+$: 443; HPLC $t_R$=1.175 min (95.4%).

Example 81, Step 2: 4-((4'-(2-(3-(but-3-yn-1-yl)-3H-diazirin-3-yl)ethoxy)-[1,1'-biphenyl]-4-yl)amino)-2-(3,6-dihydro-2H-pyran-4-yl)-6-isopropyl-5,6-dihydro-7H-pyrrolo[3,4-d]pyrimidin-7-one

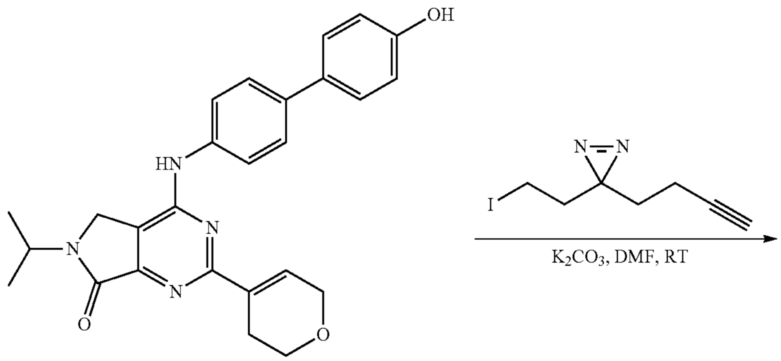

-continued

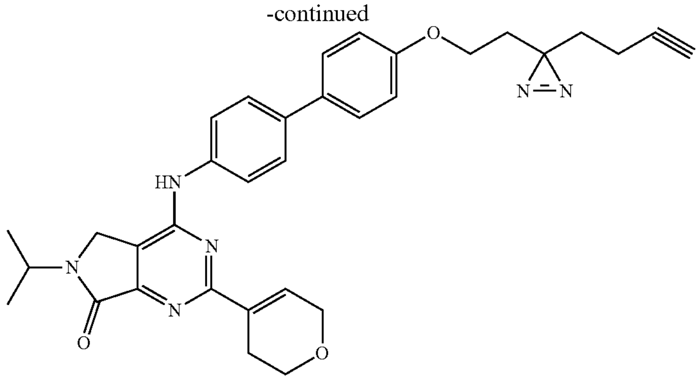

3-(But-3-yn-1-yl)-3-(2-iodoethyl)-3H-diazirine (188 mg, 0.76 mmol) was added to $K_2CO_3$ (105 mg, 0.76 mmol) and 2-(3,6-dihydro-2H-pyran-4-yl)-4-((4'-hydroxy-[1,1'-biphenyl]-4-yl)amino)-6-isopropyl-5,6-dihydro-7H-pyrrolo[3,4-d]pyrimidin-7-one (168 mg, 0.38 mmol) in DMF (2 mL) at RT under air. The resulting mixture was stirred at RT overnight. The solvent was removed under reduced pressure. The crude product was purified by flash silica chromatography, elution gradient 0 to 30% EtOAc in petroleum ether. Pure fractions were evaporated to dryness to afford crude product. The crude product was purified by preparative HPLC Column:)(Bridge Shield RP18 OBD Column 19×250 mm, 10 um; Mobile Phase A: Water (10 mM ammonium formate), Mobile Phase B: acetonitrile; Flow rate: 25 mL/min; Gradient elution with detection at 254/220 nm. Fractions containing the desired compound were evaporated to dryness to afford 4-((4'-(2-(3-(but-3-yn-1-yl)-3H-diazirin-3-yl)ethoxy)-[1,1'-biphenyl]-4-yl)amino)-2-(3,6-dihydro-2H-pyran-4-yl)-6-isopropyl-5,6-dihydro-7H-pyrrolo[3,4-d]pyrimidin-7-one (6.2 mg, 2.9%) as a yellow solid. $^1H$ NMR (400 MHz, MeOD) δ 1.38 (d, J=6.7 Hz, 6H), 1.73 (t, J=7.5 Hz, 2H), 1.91 (t, J=6.0 Hz, 2H), 2.05-2.15 (m, 2H), 2.30 (t, J=2.7 Hz, 1H), 2.73 (s, 2H), 3.86-3.96 (m, 4H), 4.34-4.47 (m, 4H), 4.53-4.66 (m, 1H), 6.98 (d, J=8.7 Hz, 2H), 7.27 (s, 1H), 7.57 (dd, J=8.6, 7.0 Hz, 4H), 7.87 (d, J=8.5 Hz, 2H). ES+ m/z $[M+H]^+$: 563, HPLC $t_R$=3.053 min (95.9%).

Example 82: 2-(3,6-dihydro-2H-pyran-4-yl)-4-((2-fluoro-[1,1'-biphenyl]-4-yl)amino)-6-isopropyl-5,6-dihydro-7H-pyrrolo[3,4-d]pyrimidin-7-one -continued

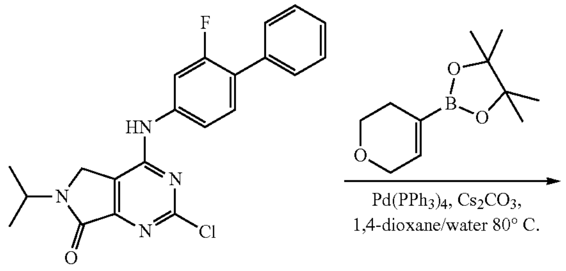

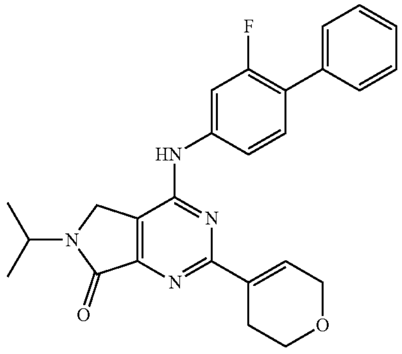

Example 82, Step 1: 2-chloro-4-((2-fluoro-[1,1'-biphenyl]-4-yl)amino)-6-isopropyl-5,6-dihydro-7H-pyrrolo[3,4-d]pyrimidin-7-one

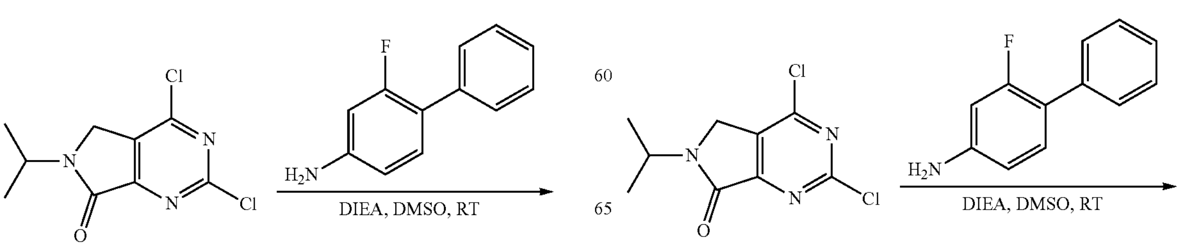

-continued

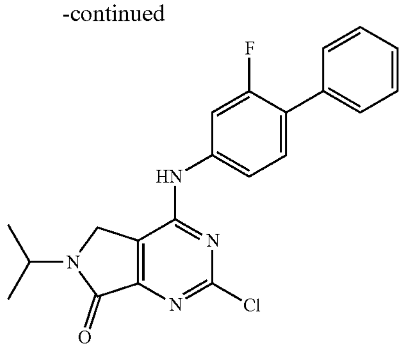

DIEA (0.426 mL, 2.44 mmol) was added to 2-fluoro-[1,1'-biphenyl]-4-amine (228 mg, 1.22 mmol) and 2,4-dichloro-6-isopropyl-5,6-dihydro-7H-pyrrolo[3,4-d]pyrimidin-7-one (300 mg, 1.22 mmol) in DMSO (2 mL). The resulting mixture was stirred at RT for 16 hours. The crude product was purified by C18-flash chromatography, elution gradient 90 to 100% MeOH in water (0.1% formic acid). Pure fractions were evaporated to dryness to afford 2-chloro-4-((2-fluoro-[1,1'-biphenyl]-4-yl)amino)-6-isopropyl-5,6-dihydro-7H-pyrrolo[3,4-d]pyrimidin-7-one (150 mg, 31.0%) as a white solid. m/z (ES+), $[M+H]^+$=397; HPLC $t_R$=1.402 min.

Example 82, Step 2: 2-(3,6-dihydro-2H-pyran-4-yl)-4-((2-fluoro-[1,1'-biphenyl]-4-yl)amino)-6-isopropyl-5,6-dihydro-7H-pyrrolo[3,4-d]pyrimidin-7-one

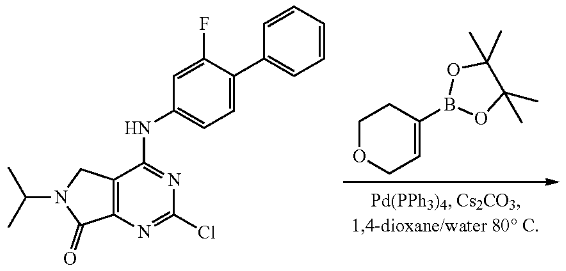

-continued

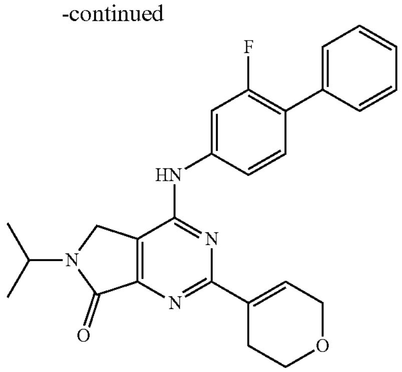

$Pd(PPh_3)_4$ (43.7 mg, 0.04 mmol) was added to 2-(3,6-dihydro-2H-pyran-4-yl)-4,4,5,5-tetramethyl-1,3,2-dioxaborolane (95 mg, 0.45 mmol), 2-chloro-4-((2-fluoro-[1,1'-biphenyl]-4-yl)amino)-6-isopropyl-5,6-dihydro-7H-pyrrolo[3,4-d]pyrimidin-7-one (150 mg, 0.38 mmol) and $Cs_2CO_3$ (246 mg, 0.76 mmol) in 1,4-dioxane (5 mL) and water (1 mL) at RT under nitrogen. The resulting mixture was stirred at 80° C. for 3 hours. The crude product was purified by flash silica chromatography, elution gradient 0 to 5% MeOH in DCM. Pure fractions were evaporated to dryness to afford a yellow solid. The crude product was purified by preparative HPLC: XSelect CSH Prep C18 OBD column, 5 μm, 50 mm diameter, 150 mm length, using decreasingly polar mixtures of water (containing 0.1% Formic acid) and acetonitrile as eluents. Fractions containing the desired compound were evaporated to dryness to afford 2-(3,6-dihydro-2H-pyran-4-yl)-4-((2-fluoro-[1,1'-biphenyl]-4-yl)amino)-6-isopropyl-5,6-dihydro-7H-pyrrolo[3,4-d]pyrimidin-7-one (20.0 mg, 12%) as a white solid. $^1$H NMR (400 MHz, DMSO) δ 1.28 (d, J=6.7 Hz, 6H), 2.64 (s, 2H), 3.85 (t, J=5.4 Hz, 2H), 4.34 (d, J=3.0 Hz, 2H), 4.47 (d, J=6.1 Hz, 3H), 7.20 (s, 1H), 7.34-7.43 (m, 1H), 7.48 (dd, J=8.4, 6.9 Hz, 2H), 7.53-7.62 (m, 3H), 7.73 (dd, J=8.6, 2.1 Hz, 1H), 8.02 (dd, J=14.0, 2.1 Hz, 1H), 9.79 (s, 1H). ES' m/z $[M+H]^+$: 445, HPLC $t_R$=2.977 min (98.6%).

The Examples in Table 6 were prepared by procedures analogous to those described above.

TABLE 6

| Example | Name | Structure | m/z (ES+), $[M + H]^+$ |
|---|---|---|---|
| 83 | 2-(morpholin-4-yl)-4-{[4-(pentafluoroethyl)phenyl]amino}-6-(propan-2-yl)-5,6-dihydro-7H-pyrrolo[3,4-d]pyrimidin-7-one | 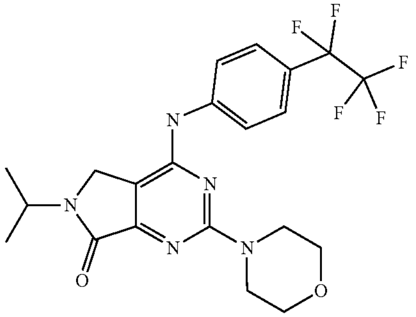 [SMILES: CC(C)N1Cc2c(Nc3ccc(C(F)(F)C(F)(F)F)cc3)nc(N3CCOCC3)nc2C1=O] | 472 |

TABLE 6-continued

| Example | Name | Structure | m/z (ES+), [M + H]+ |
|---|---|---|---|
| 84 | 4-[(2-fluoro[1,1'-biphenyl]-4-yl)amino]-2-(morpholin-4-yl)-6-(propan-2-yl)-5,6-dihydro-7H-pyrrolo [3,4-d]pyrimidin-7-one | 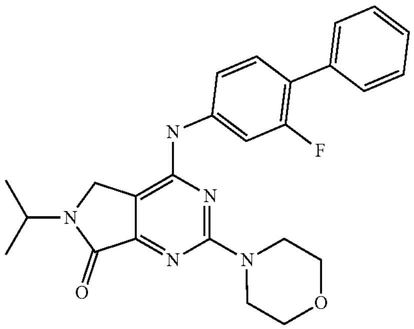 [SMILES: CC(C)N1Cc2c(Nc3ccc(-c4ccccc4)c(F)c3)nc(N3CCOCC3)nc2C1=O] | 448 |
| 85 | 4-[(3',4'-dichloro[1,1'-biphenyl]-4-yl)amino]-2-(morpholin-4-yl)-6-(propan-2-yl)-5,6-dihydro-7H-pyrrolo [3,4-d]pyrimidin-7-one | 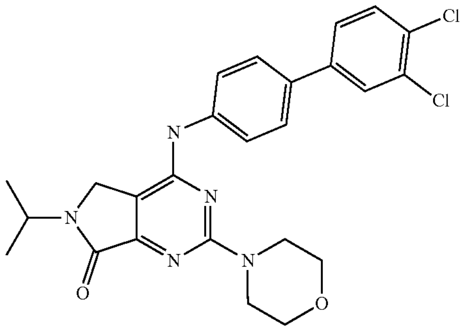 [SMILES: CC(C)N1Cc2c(Nc3ccc(-c4ccc(Cl)c(Cl)c4)cc3)nc(N3CCOCC3)nc2C1=O] | 498 |
| 86 | 2-(morpholin-4-yl)-6-(propan-2-yl)-4-{[4-(propan-2-yl)phenyl]amino}-5,6-dihydro-7H-pyrrolo[3,4-d]pyrimidin-7-one | 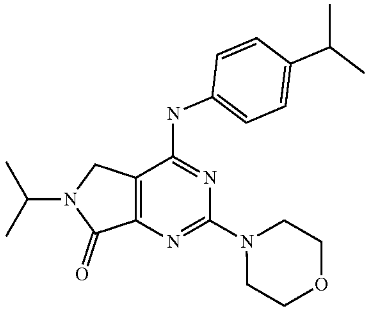 [SMILES: CC(C)c1ccc(Nc2nc(N3CCOCC3)nc3c2CN(C(C)C)C3=O)cc1] | 396 |
| 87 | 4-[(4-tert-butylphenyl)amino]-2-(morpholin-4-yl)-6-(propan-2-yl)-5,6-dihydro-7H-pyrrolo[3,4-d]pyrimidin-7-one | 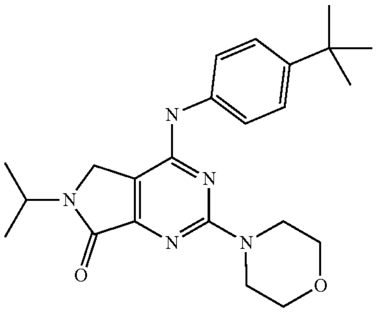 [SMILES: CC(C)N1Cc2c(Nc3ccc(C(C)(C)C)cc3)nc(N3CCOCC3)nc2C1=O] | 410 |

TABLE 6-continued

| Example | Name | Structure | m/z (ES+), [M + H]+ |
|---|---|---|---|
| 88 | 4-[(2-methyl[1,1'-biphenyl]-4-yl)amino]-2-(morpholin-4-yl)-6-(propan-2-yl)-5,6-dihydro-7H-pyrrolo[3,4-d]pyrimidin-7-one | 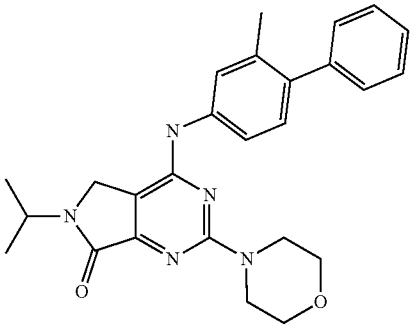 [SMILES: Cc1cc(Nc2nc(N3CCOCC3)nc3c2CN(C(C)C)C3=O)ccc1-c1ccccc1] | 444 |
| 89 | 4-[(4'-chloro[1,1'-biphenyl]-4-yl)amino]-2-(morpholin-4-yl)-6-(propan-2-yl)-5,6-dihydro-7H-pyrrolo[3,4-d]pyrimidin-7-one | 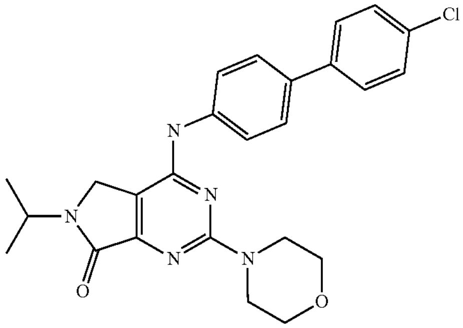 [SMILES: CC(C)N1Cc2c(Nc3ccc(-c4ccc(Cl)cc4)cc3)nc(N3CCOCC3)nc2C1=O] | 464 |
| 113 | 2-(morpholin-4-yl)-6-(propan-2-yl)-4-{[4-(thiophen-2-yl)phenyl]amino}-5,6-dihydro-7H-pyrrolo[3,4-d]pyrimidin-7-one | 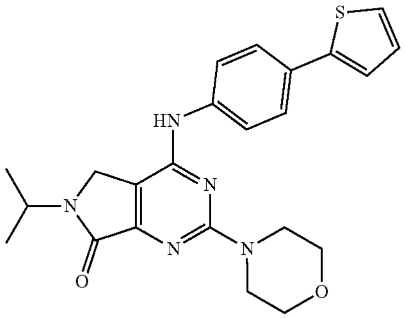 [SMILES: CC(C)N1Cc2c(Nc3ccc(-c4cccs4)cc3)nc(N3CCOCC3)nc2C1=O] | 436 |
| 114 | 2-(morpholin-4-yl)-6-(propan-2-yl)-4-{[4-(thiophen-3-yl)phenyl]amino}-5,6-dihydro-7H-pyrrolo[3,4-d]pyrimidin-7-one | 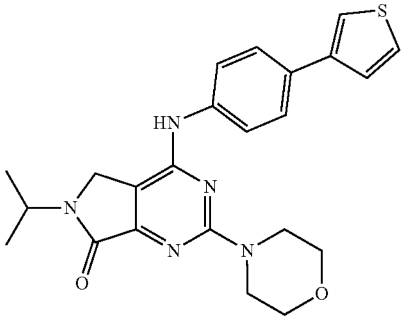 [SMILES: CC(C)N1Cc2c(Nc3ccc(-c4ccsc4)cc3)nc(N3CCOCC3)nc2C1=O] | 436 |

Example 90: (R)—N-(4-cyclohexylphenyl)-2-(2-methylmorpholino)-5,7-dihydrofuro[3,4-d]pyrimidin-4-amine

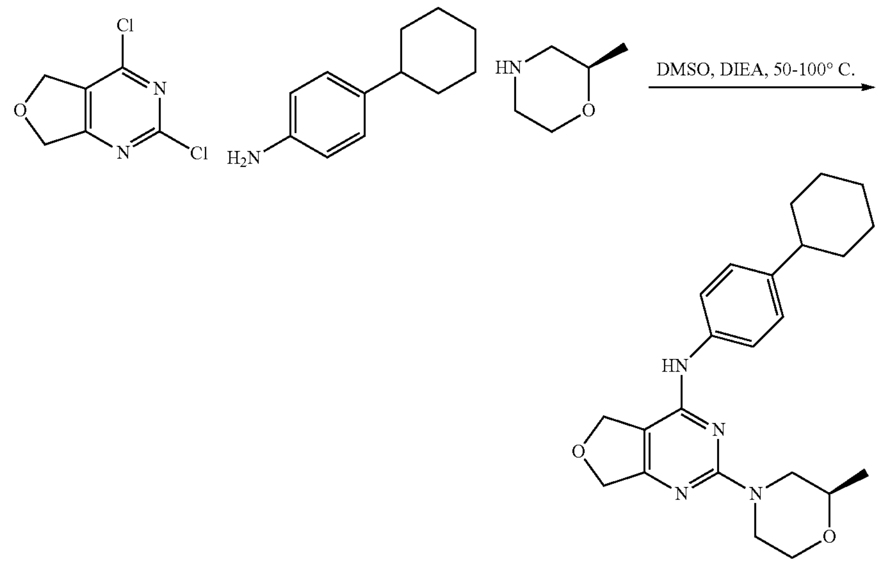

4-Cyclohexylaniline (0.918 g, 5.24 mmol) was added to 2,4-dichloro-5, 7-dihydrofuro[3,4-d]pyrimidine (1 g, 5.24 mmol) and DIEA (2.74 mL, 15.71 mmol) in DMSO (15 mL) at RT. The resulting mixture was stirred at 50° C. for 7 hours. (R)-2-methylmorpholine (0.635 g, 6.28 mmol) was added to above mixture and stirred at 100° C. for 16 hours. The reaction mixture was purified by flash C18-flash chromatography with elution gradient 10 to 85% MeCN in water (0.1% FA). Pure fractions were evaporated to dryness to afford (R)—N-(4-cyclohexylphenyl)-2-(2-methylmorpholino)-5,7-dihydrofuro[3,4-d]pyrimidin-4-amine (0.932 g, 45.1%) as a white solid. $^1H$ NMR (400 MHz, DMSO) δ 1.13 (d, J=6.1 Hz, 3H), 1.18-1.25 (m, 1H), 1.27-1.44 (m, 4H), 1.70 (d, J=12.7 Hz, 1H), 1.78 (d, J=9.7 Hz, 4H), 2.42-2.46 (m, 1H), 2.57 (dd, J=13.0, 10.3 Hz, 1H), 2.90 (td, J=12.4, 3.5 Hz, 1H), 3.37-3.56 (m, 2H), 3.86 (dd, J=11.3, 3.2 Hz, 1H), 4.30 (d, J=13.2 Hz, 1H), 4.38 (d, J=12.6 Hz, 1H), 4.68 (t, J=2.3 Hz, 2H), 4.87 (t, J=2.4 Hz, 2H), 7.12-7.19 (m, 2H), 7.52-7.60 (m, 2H), 8.76 (s, 1H). $ES^+$ m/z $[M+H]^+$: 395, HPLC $t_R$=1.78 min (99.6%).

Example 91: N-(4-cyclobutylphenyl)-2-(3,6-dihydro-2H-pyran-4-yl)-5,7-dihydrofuro[3,4-d]pyrimidin-4-amine

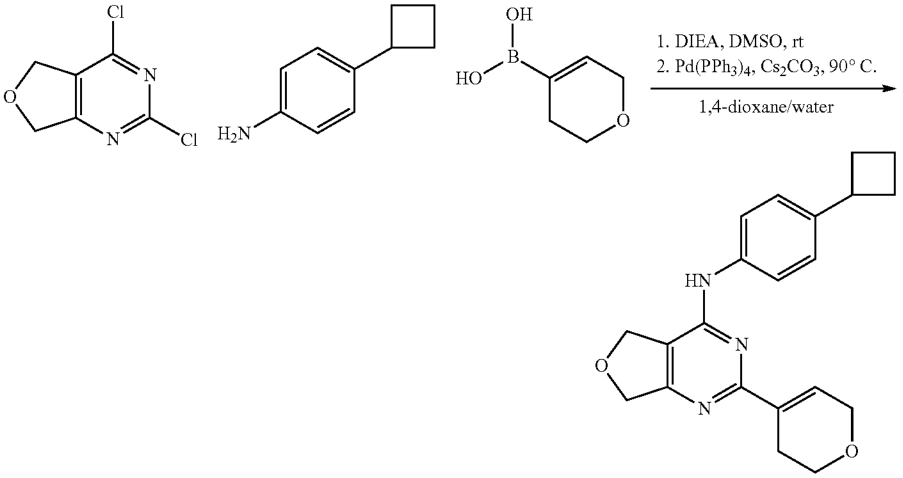

DIEA (0.069 mL, 0.39 mmol) was added to 2,4-dichloro-5,7-dihydrofuro[3,4-d]pyrimidine (50 mg, 0.26 mmol) and 4-cyclobutylaniline (38.5 mg, 0.26 mmol) in DMSO (2 mL) at rt. The resulting mixture was stirred at rt for 16 hours. The reaction mixture was quenched with water (50 mL), extracted with EtOAc (2×25 mL), the organic layer was dried over $Na_2SO_4$, filtered and evaporated to the afford crude intermediate. $Pd(PPh_3)_4$ (30.2 mg, 0.03 mmol) was added to $Cs_2CO_3$ (171 mg, 0.52 mmol), (3,6-dihydro-2H-pyran-4-yl)boronic acid (50.2 mg, 0.39 mmol) and crude intermediate in 1,4-dioxane (2.0 mL) and water (0.4 mL) at 25° C. under nitrogen. The resulting mixture was stirred at 90° C. for 3 hours. The reaction mixture was diluted with water (100 mL), extracted with EtOAc (2×50 mL), the organic layer was dried over $Na_2SO_4$, filtered and evaporated to afford crude product. The crude product was purified by preparative HPLC conditions A. Fractions containing the desired compound were evaporated to dryness to afford N-(4-cyclobutylphenyl)-2-(3,6-dihydro-2H-pyran-4-yl)-5,7-dihydrofuro[3,4-d]pyrimidin-4-amine (40.0 mg, 43.7%) as a pale yellow solid. $^1H$ NMR (400 MHz, DMSO-d6) δ 1.75-1.87 (m, 1H), 1.88-2.02 (m, 1H), 2.02-2.16 (m, 2H), 2.28 (qt, J=7.8, 2.4 Hz, 2H), 2.55 (s, 2H), 3.49 (p, J=8.8 Hz, 1H), 3.80 (t, J=5.4 Hz, 2H), 4.29 (q, J=2.8 Hz, 2H), 4.85 (t, J=2.5 Hz, 2H), 5.01 (t, J=2.5 Hz, 2H), 7.06-7.12 (m, 1H), 7.17-7.25 (m, 2H), 7.65-7.73 (m, 2H), 9.03 (s, 1H). $ES^+$ m/z $[M+H]^+$: 350, HPLC $t_R$=1.72 min (98.4%).

The compounds in Table 7 are made using the appropriate intermediates in a manner analogous to Example 91 and the examples above.

TABLE 7

| Example | Name | Structure | Analytical Data |
|---|---|---|---|
| 92 | N-(4-cyclohexylphenyl)-2-(2-cyclopropyl-morpholin-4-yl)-5,7-dihydrofuro[3,4-d]pyrimidin-4-amine | 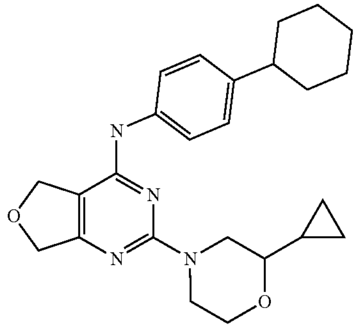 [SMILES: c1cc(C2CCCCC2)ccc1Nc1nc(N2CCOC(C3CC3)C2)nc2c1COC2] | $^1H$ NMR (400 MHz, DMSO) δ 0.20-0.27 (m, 1H), 0.28-0.37 (m, 1H), 0.45-0.52 (m, 2H), 0.83-0.92 (m, 1H), 1.21-1.26 (m, 1H), 1.35 (q, J = 13.0, 14.4 Hz, 4H), 1.70 (d, J = 12.9 Hz, 1H), 1.78 (d, J = 9.3 Hz, 4H), 2.43-2.47 (m, 1H), 2.67-2.82 (m, 2H), 2.87-2.99 (m, 1H), 3.34-3.45 (m, 1H), 3.88 (d, J = 12.1 Hz, 1H), 4.26 (d, J = 13.2 Hz, 1H), 4.46 (d, J = 11.6 Hz, 1H), 4.69 (t, J = 2.4 Hz, 2H), 4.87 (d, J = 2.6 Hz, 2H), 7.11-7.18 (m, 2H), 7.51-7.59 (m, 2H), 8.78 (s, 1H). $ES^+$ m/z $[M + H]^+$: 421, HPLC $t_R$ = 2.18 min (97.8%). |
| 93 | 2-(2-cyclopropyl-morpholin-4-yl)-N-[4'-(heptyloxy)[1,1']-biphenyl]-4-yl]-5,7-dihydrofuro[3,4-d]pyrimidin-4-amine | 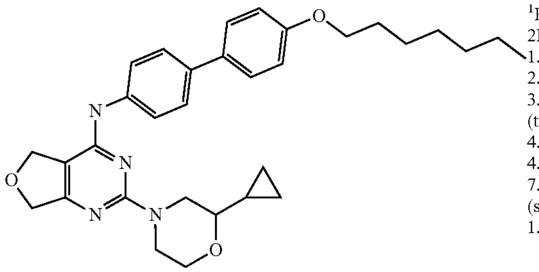 | $^1H$ NMR (400 MHz, DMSO) δ 0.25-0.36 (m, 2H), 0.45-0.55 (m, 2H), 0.84-0.94 (m, 4H), 1.22-1.51 (m, 8H), 1.67-1.78 (m, 2H), 2.71-2.86 (m, 2H), 2.91-3.02 (m, 1H), 3.36-3.47 (m, 1H), 3.90 (d, J = 10.6 Hz, 1H), 3.99 (t, J = 6.5 Hz, 2H), 4.30 (d, J = 13.1 Hz, 1H), 4.49 (d, J = 11.8 Hz, 1H), 4.69-4.74 (m, 2H), 4.94 (d, J = 2.6 Hz, 2H), 6.95-7.03 (m, 2H), 7.53-7.62 (m, 4H), 7.70-7.78 (m, 2H), 8.93 (s, 1H). $ES^+$ m/z $[M + H]^+$: 529, HPLC $t_R$ = 1.26 min (98.4%). |
| 94 | 2-[(2R)-2-methylmorpholin-4-yl]-N-{4'-[(6,6,6-trifluorohexyl)oxy][1,1'-biphenyl]-4-yl}-5,7-dihydrofuro[3,4-d]pyrimidin-4-amine | 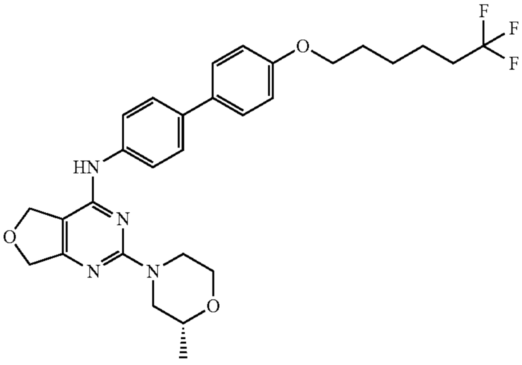 [SMILES: C[C@@H]1CN(c2nc3c(c(Nc4ccc(-c5ccc(OCCCCCC(F)(F)F)cc5)cc4)n2)COC3)CCO1] | $^1H$ NMR (300 MHz, DMSO) δ 1.13 (d, J = 6.1 Hz, 3H), 1.52 (q, J = 3.4, 4.8 Hz, 4H), 1.74 (p, J = 6.5 Hz, 2H), 2.26 (dt, J = 7.6, 11.5 Hz, 2H), 2.57 (dd, J = 10.5, 13.1 Hz, 1H), 2.83-2.98 (m, 1H), 3.40-3.54 (m, 2H), 3.75-4.03 (m, 3H), 4.35 (dd, J = 13.1, 22.2 Hz, 2H), 4.69 (d, J = 2.4 Hz, 2H), 4.91 (d, J = 2.4 Hz, 2H), 6.92-7.02 (m, 2H), 7.51-7.61 (m, 4H), 7.67-7.76 (m, 2H), 8.90 (s, 1H). $ES^+$ m/z $[M + H]^+$: 543, HPLC $t_R$ = 1.92 min (98.5%). |
| 95 | N-(4-cyclohexylphenyl)-2-(2-methylpyridin-4-yl)-5,7-dihydrofuro[3,4-d]pyrimidin-4-amine | 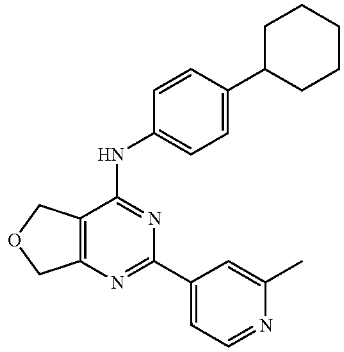 [SMILES: Cc1cc(-c2nc3c(c(Nc4ccc(C5CCCCC5)cc4)n2)COC3)ccn1] | $^1H$ NMR (400 MHz, DMSO) δ 1.18-1.31 (m, 1H), 1.32-1.51 (m, 4H), 1.68-1.76 (m, 1H), 1.77-1.86 (m, 5H), 2.56 (s, 3H), 4.94 (t, J = 2.6 Hz, 2H), 5.04 (t, J = 2.6 Hz, 2H), 7.23-7.30 (m, 2H), 7.66-7.73 (m, 2H), 7.95 (dd, J = 1.6, 5.1 Hz, 1H), 8.04 (s, 1H), 8.59 (d, J = 5.2 Hz, 1H), 9.26 (s, 1H). ES+ m/z $[M + H]^+$: 387, HPLC $t_R$ = 1.71 min (99.4%) |

TABLE 7-continued

| Example | Name | Structure | Analytical Data |
|---|---|---|---|
| 96 | N-(4-cyclohexylphenyl)-2-[(2R)-2-methylmorpholin-4-yl]pyrido[2,3-d]pyrimidin-4-amine | 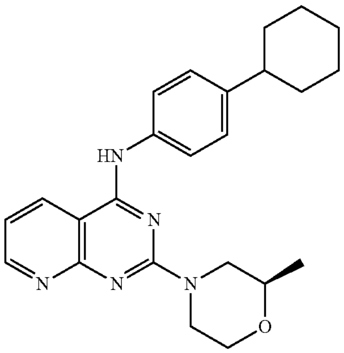 [SMILES: C[C@@H]1CN(c2nc(Nc3ccc(C4CCCCC4)cc3)c3cccnc3n2)CCO1] | $^1$H NMR (400 MHz, DMSO) δ 1.16 (d, J = 6.2 Hz, 3H), 1.24 (d, J = 10.8 Hz, 1H), 1.31-1.49 (m, 4H), 1.71 (d, J = 12.7 Hz, 1H), 1.81 (d, J = 9.2 Hz, 4H), 2.50-2.51 (m, 1H), 2.67 (dd, J = 13.2, 10.4 Hz, 1H), 2.94-3.06 (m, 1H), 3.49 (dd, J = 12.2, 9.4 Hz, 2H), 3.91 (dd, J = 11.5, 3.2 Hz, 1H), 4.54 (dd, J = 34.4, 12.9 Hz, 2H), 7.18 (dd, J = 8.1, 4.4 Hz, 1H), 7.22-7.28 (m, 2H), 7.67-7.73 (m, 2H), 8.66-8.76 (m, 2H), 9.70 (s, 1H). $ES^+$ m/z $[M + H]^+$: 404, HPLC $t_R$ = 1.35 min (99.4%). |
| 97 | 6-bromo-N-(4-cyclohexylphenyl)-2-[(2R)-2-methylmorpholin-4-yl]pyrido[2,3-d]pyrimidin-4-amine | 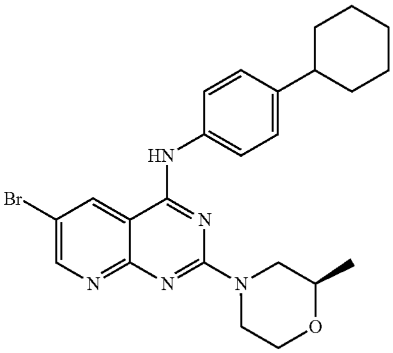 [SMILES: C[C@@H]1CN(c2nc(Nc3ccc(C4CCCCC4)cc3)c3cc(Br)cnc3n2)CCO1] | $^1$H NMR (400 MHz, DMSO) δ 1.16 (d, J = 6.1 Hz, 3H), 1.25 (s, 1H), 1.30-1.49 (m, 4H), 1.72 (d, J = 12.6 Hz, 1H), 1.81 (d, J = 9.4 Hz, 4H), 2.68 (t, J = 11.9 Hz, 1H), 3.02 (1, J = 11.1 Hz, 1H), 3.34 (s, 1H), 3.43-3.54 (m, 2H), 3.91 (d, J = 11.4 Hz, 1H), 4.47-4.52 (m, 2H), 7.26 (d, J = 8.5 Hz, 2H), 7.69 (d, J = 8.6 Hz, 2H), 8.77 (d, J = 2.4 Hz, 1H), 9.00 (d, J = 2.5 Hz, 1H), 9.77 (s, 1H). $ES^+$ m/z $[M + H]^+$: 482, HPLC $t_R$ = 1.92 min (99.9%). |
| 98 | N-(4-cyclohexylphenyl)-2-(3,6-dihydro-2H-pyran-4-yl)pyrido[2,3-d]pyrimidin-4-amine | 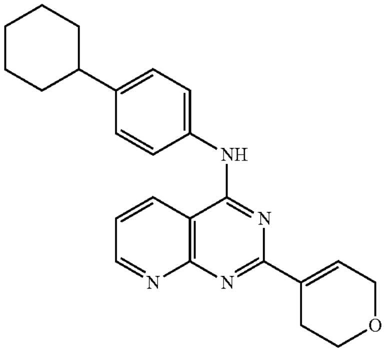 [SMILES: C1=C(c2nc(Nc3ccc(C4CCCCC4)cc3)c3cccnc3n2)CCOC1] | $^1$H NMR (300 MHz, DMSO-d6) δ 1.22-1.49 (m, 5H), 1.63-1.87 (m, 5H), 2.48 (d, J = 1.8 Hz, 1H), 2.62 (s, 2H), 3.81 (t, J = 5.4, 5.4 Hz, 2H), 4.28-4.37 (m, 2H), 7.16-7.30 (m, 3H), 7.56 (dd, J = 8.2, 4.4 Hz, 1H), 7.75-7.86 (m, 2H), 8.94 (dd, J = 8.3, 1.9 Hz, 1H), 8.99 (dd, J = 4.4, 1.8 Hz, 1H), 9.88 (s, 1H). $ES^+$ m/z $[M + H]^+$:: 387, HPLC $t_R$ = 1.74 min (99.0%). |

Example 99: (R)-4-((4-cyclohexylphenyl)amino)-2-(2-methylmorpholino)pyrido [2,3-d]pyrimidine 8-oxide

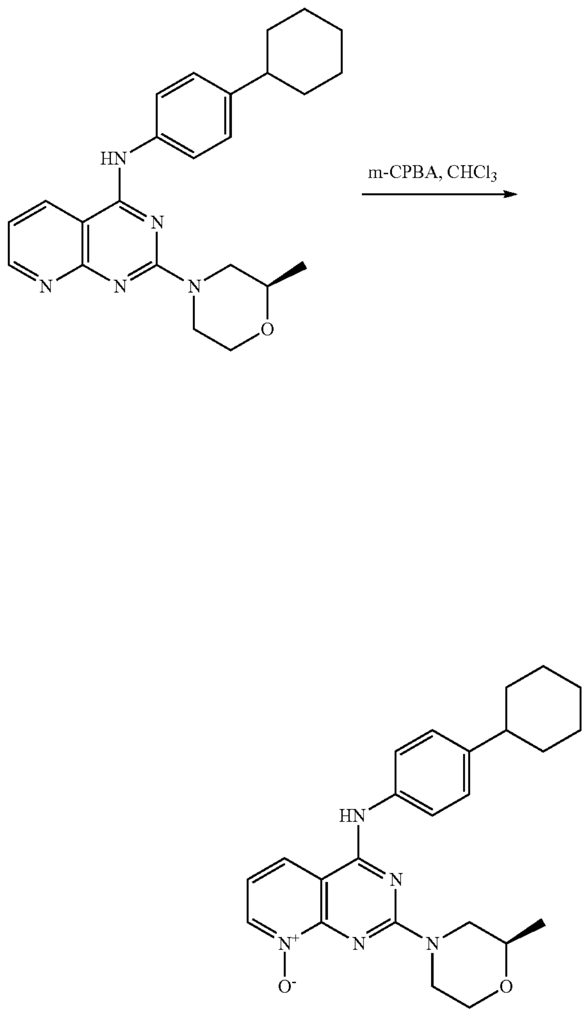

m-CPBA (222 mg, 1.29 mmol) was added to (R)—N-(4-cyclohexylphenyl)-2-(2-methyl morpholino)pyrido[2,3-d] pyrimidin-4-amine (130 mg, 0.32 mmol) in $CHCl_3$ (3 mL) at RT under nitrogen. The resulting mixture was stirred at 60° C. for 5 hours. The crude product was purified by flash silica chromatography, elution gradient 0 to 6% MeOH in DCM. Pure fractions were evaporated to afford a yellow liquid. The crude product was purified by preparative HPLC conditions B. Fractions containing the desired compound were evaporated to dryness to afford (R)-4-((4-cyclohexylphenyl) amino)-2-(2-methylmorpholino)pyrido[2,3-d]pyrimidine 8-oxide (11.0 mg, 8%) as a yellow solid. $^1$H NMR (400 MHz, MeOD) δ 1.15-1.39 (m, 5H), 1.44-1.57 (m, 4H), 1.80 (d, J=12.6 Hz, 1H), 1.90 (d, J=8.3 Hz, 4H), 2.56 (s, 1H), 2.76 (dd, J=13.4, 10.3 Hz, 1H), 3.11 (d, J=11.3 Hz, 1H), 3.60 (s, 2H), 3.97 (d, J=11.0 Hz, 1H), 4.61 (s, 1H), 4.88-5.10 (m, 1H), 7.14 (dd, J=8.2, 6.3 Hz, 1H), 7.28 (d, J=8.5 Hz, 2H), 7.61 (d, J=8.4 Hz, 2H), 8.33-8.39 (m, 1H), 8.59 (dd, J=6.4, 1.3 Hz, 1H). ES$^+$ m/z [M+H]$^+$: 420, HPLC $t_R$=1.73 min (99.4%).

Example 100: (R)—N-(4-cyclohexylphenyl)-6-ethyl-2-(2-methylmorpholino) pyrido[2,3-d]pyrimidin-4-amine

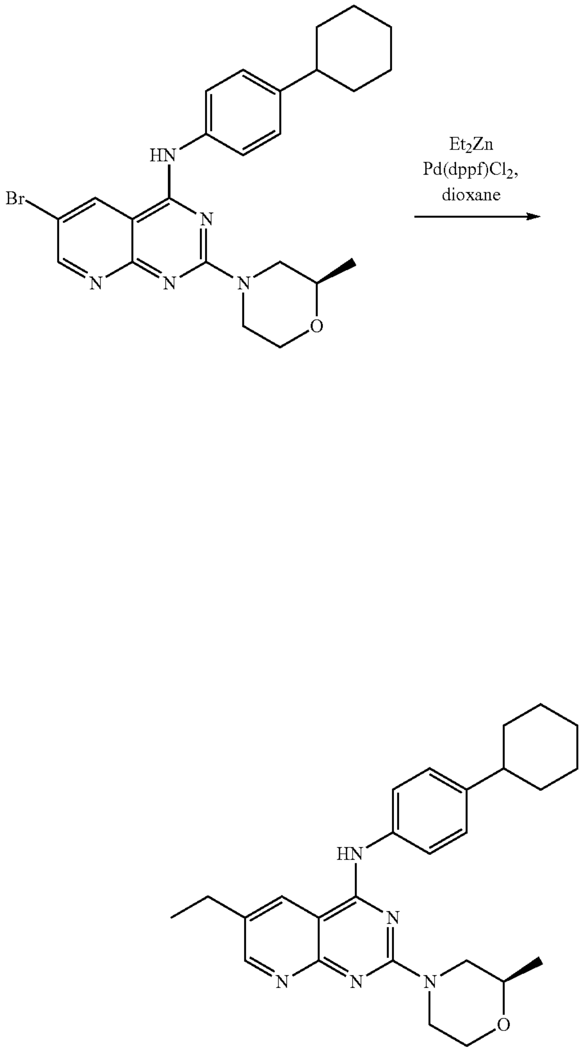

Diethylzinc (0.118 mL, 0.41 mmol) was added to (R)-6-bromo-N-(4-cyclohexylphenyl)-2-(2-methylmorpholino) pyrido[2,3-d]pyrimidin-4-amine (200 mg, 0.41 mmol), Pd(dppf)$Cl_2$ (303 mg, 0.41 mmol) in dioxane (2 mL) and at RT under nitrogen. The resulting solution was stirred at 70° C. for 5 hours. The reaction mixture was added to a silica gel column and was eluted with 0-10% MeOH in DCM to give the crude product as a yellow solid. The crude was purified by preparative HPLC conditions B. Fractions containing the desired compound were evaporated to dryness to afford (R)—N-(4-cyclohexylphenyl)-6-ethyl-2-(2-methylmorpholino)pyrido[2,3-d]pyrimidin-4-amine (50.0 mg, 28%) as a white solid. $^1$H NMR (400 MHz, DMSO-$d_6$) δ 1.16 (d, J=6.2 Hz, 3H), 1.21-1.29 (m, 2H), 1.26-1.49 (m, 6H), 1.71 (d, J=12.4 Hz, 1H), 1.81 (d, J=8.8 Hz, 4H), 2.43-2.50 (m, 1H), 2.60-2.76 (m, 3H), 2.92-3.04 (m, 1H), 3.43-3.56 (m, 2H), 3.90 (dd, J=11.5, 3.0 Hz, 1H), 4.47 (d, J=13.0 Hz, 1H), 4.56 (d, J=13.1 Hz, 1H), 7.21-7.28 (m, 2H), 7.66-7.73 (m, 2H), 8.55 (d, J=2.4 Hz, 1H), 8.64 (d, J=2.3 Hz, 1H), 9.65 (s, 1H). ES$^+$ m/z [M+H]$^+$: 432, HPLC $t_R$=1.70 min (99.9%).

Example 101: (R)-4-((4-cyclohexylphenyl)amino)-2-(2-methylmorpholino)pyrido[2,3-d]pyrimidine-6-carbonitrile

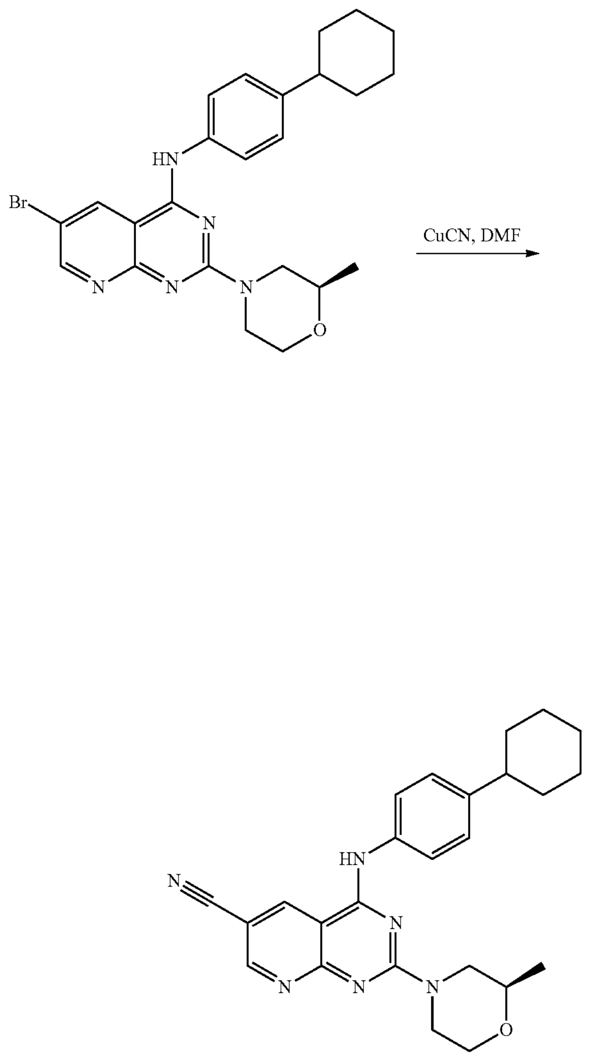

Copper cyanide (111 mg, 1.24 mmol) was added to (R)-6-bromo-N-(4-cyclohexyl-phenyl)-2-(2-methylmorpholino)pyrido[2,3-d]pyrimidin-4-amine (200 mg, 0.41 mmol) in DMF (2 mL) at R T under nitrogen. The resulting mixture was stirred at 150° C. for 6 hours. The reaction mixture was added to a silica gel column and was eluted with 0-10% MeOH in DCM to give the crude product as a yellow solid. The crude product was purified by preparative HPLC conditions A. Fractions containing the desired compound were evaporated to dryness to afford (R)-4-((4-cyclohexylphenyl)amino)-2-(2-methylmorpholino)pyrido[2,3-d]pyrimidine-6-carbonitrile (80 mg, 45.0%) as a yellow solid. $^1$H NMR (400 MHz, DMSO) δ 1.07-1.30 (m, 4H), 1.30-1.61 (m, 4H), 1.72 (d, J=12.4 Hz, 1H), 1.81 (d, J=9.3 Hz, 4H), 2.34-2.52 (m, 1H), 2.73-2.87 (m, 1H), 3.05-3.17 (m, 1H), 3.37-3.66 (m, 2H), 3.90-3.98 (m, 1H), 4.32-4.77 (m, 2H), 7.29 (d, J=8.6 Hz, 2H), 7.67 (d, J=8.3 Hz, 2H), 9.04 (d, J=2.2 Hz, 1H), 9.22 (d, J=2.3 Hz, 1H), 10.07 (s, 1H). ES$^+$ m/z [M+H]$^+$: 429, HPLC $t_R$=3.35 min (98.3%).

Example 102: methyl (R)-4-((4-cyclohexylphenyl) amino)-2-(2-methylmorpholino) pyrido[2,3-d]pyrimidine-6-carboxylate

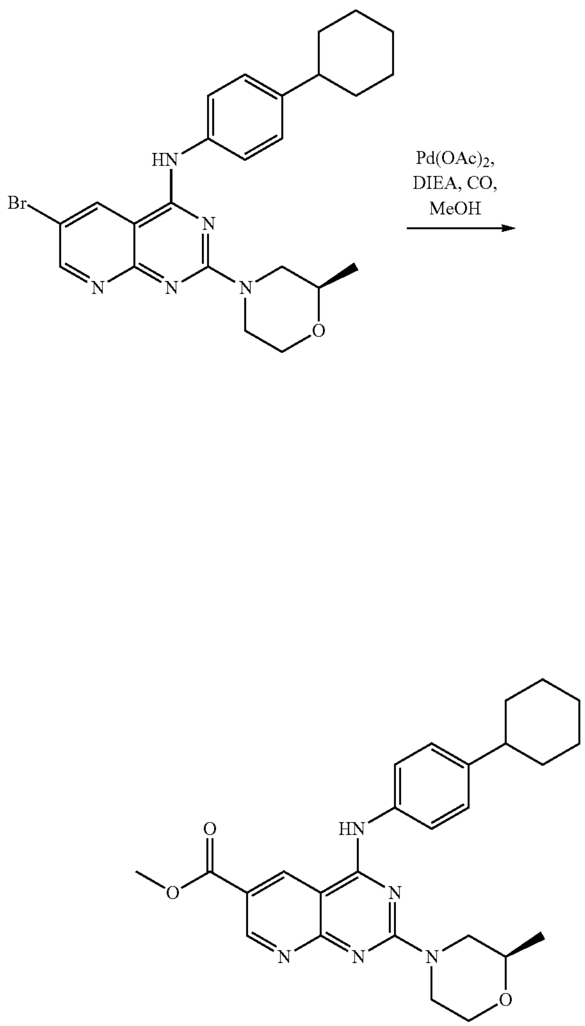

Palladium acetate (0.023 g, 0.10 mmol) was added to DIEA (1.086 mL, 6.22 mmol), (R)-6-bromo-N-(4-cyclohexylphenyl)-2-(2-methylmorpholino)pyrido[2,3-d]pyrimidin-4-amine (1.0 g, 2.07 mmol) in MeOH (5.0 mL) and toluene (5.00 mL) at RT under carbon monoxide (60 atm). The resulting solution was stirred at 100° C. for 36 hours. The reaction mixture was purified by flash silica chromatography, elution gradient 0 to 5% MeOH in DCM. Pure fractions were evaporated to dryness to afford a yellow solid.

The crude product was purified by preparative HPLC conditions B. Fractions containing the desired compound were evaporated to dryness to afford methyl (R)-4-((4-cyclohexylphenyl)amino)-2-(2-methylmorpholino)pyrido[2,3-d]pyrimidine-6-carboxylate (25.0 mg, 42%) as a yellow solid. $^1$H NMR (400 MHz, DMSO) δ 1.08-1.30 (m, 4H), 1.31-1.50 (m, 4H), 1.65-1.88 (m, 5H), 2.49-2.51 (m, 1H), 2.70-2.77 (m, 1H), 3.01-3.07 (m, 1H), 3.44-3.56 (m, 2H), 3.92 (s, 4H), 4.38-4.79 (m, 2H), 7.22-7.29 (m, 2H), 7.65-7.74 (m, 2H), 9.14 (d, J=2.3 Hz, 1H), 9.33 (d, J=2.3 Hz, 1H), 10.14 (s, 1H). ES$^+$ m/z [M+H]$^+$: 462, HPLC $t_R$=1.74 min (99.8%).

Example 103: (R)-4-((4-cyclohexylphenyl)amino)-2-(2-methylmorpholino)pyrido[2,3-d]pyrimidine-6-carboxylic acid

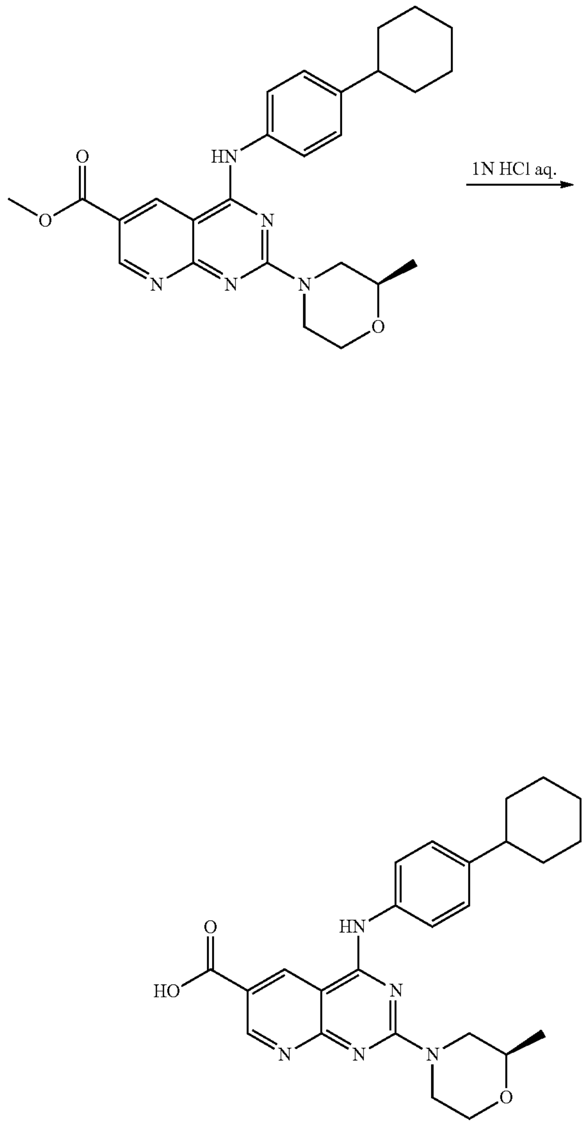

Methyl (R)-4-((4-cyclohexylphenyl)amino)-2-(2-methylmorpholino)pyrido[2,3-d]pyrimidine-6-carboxylate (150 mg, 0.32 mmol) was added to 1N HCl (2 mL) at RT under nitrogen. The resulting solution was stirred at 60° C. for 16 hours. The crude product was purified by preparative HPLC conditions B. Fractions containing the desired compound were evaporated to dryness to afford (R)-4-((4-cyclohexylphenyl) amino)-2-(2-methylmorpholino)pyrido[2,3-d]pyrimidine-6-carboxylic acid (20.00 mg, 34.4%) as a yellow solid. $^1$H NMR (400 MHz, DMSO) δ 1.16 (d, J=6.2 Hz, 3H), 1.22-1.27 (m, 1H), 1.34-1.49 (m, 4H), 1.64-1.89 (m, 5H), 2.49-2.51 (m, 1H), 2.69-2.74 (m, 1H), 3.02-3.10 (m, 1H), 3.44-3.54 (m, 2H), 3.92 (d, J=9.8 Hz, 1H), 4.48-4.66 (m, 2H), 7.25 (d, J=8.5 Hz, 2H), 7.67-7.74 (m, 2H), 9.13 (d, J=2.2 Hz, 1H), 9.32 (d, J=2.3 Hz, 1H), 10.11 (s, 1H), 13.16 (s, 1H). ES$^+$ m/z [M+H]$^+$:448, HPLC $t_R$=1.74 min (98.1%).

Example 104: (R)-4-((4-cyclohexylphenyl)amino)-2-(2-methylmorpholino)pyrido[2,3-d]pyrimidine-6-carboxamide

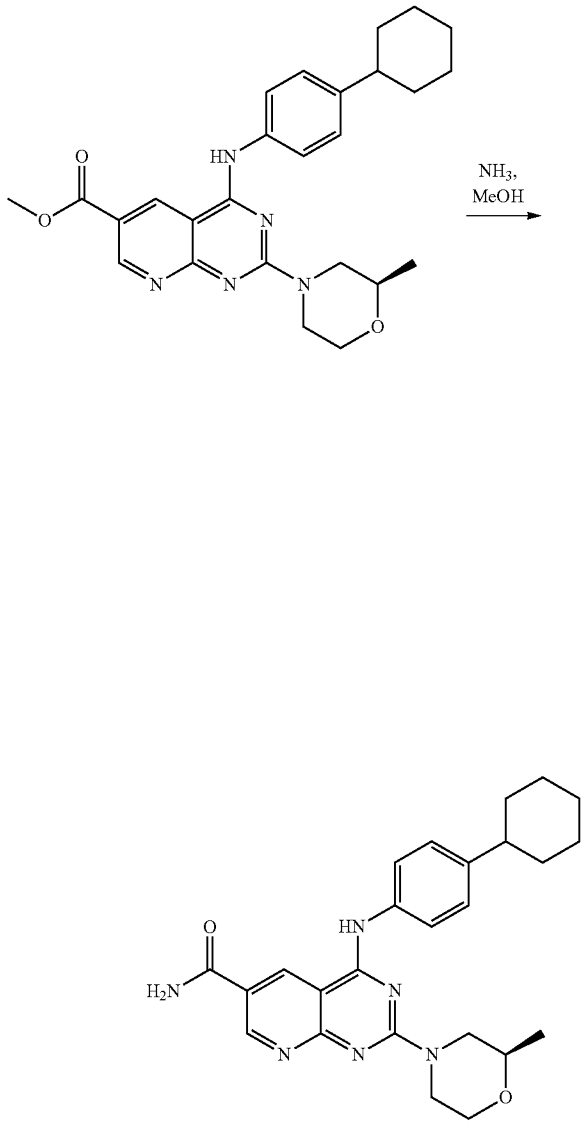

Methyl (R)-4-((4-cyclohexylphenyl)amino)-2-(2-methylmorpholino)pyrido[2,3-d]pyrimidine-6-carboxylate (150 mg, 0.32 mmol) was added to $NH_3$ in MeOH (4 mL) at RT under nitrogen. The resulting solution was stirred at 60° C. for 16 hours. The reaction crude was purified by preparative HPLC conditions B. Fractions containing the desired compound were evaporated to dryness to afford (R)-4-((4-cyclohexylphenyl)amino)-2-(2-methylmorpholino)pyrido [2,3-d]pyrimidine-6-carboxamide (20.0 mg, 35%) as a yellow solid. $^1$H NMR (400 MHz, DMSO) δ 1.10-1.27 (m, 4H), 1.31-1.49 (m, 4H), 1.76 (dd, J=10.9, 37.6 Hz, 5H), 2.33-2.50 (m, 1H), 2.72 (d, J=11.7 Hz, 1H), 3.01-3.06 (m, 1H), 3.42-3.59 (m, 2H), 3.93 (s, 1H), 4.53 (s, 2H), 7.25 (d, J=8.5 Hz, 2H), 7.55 (s, 1H), 7.71 (d, J=8.5 Hz, 2H), 8.04 (s, 1H), 9.19 (dd, J=2.3, 23.8 Hz, 2H), 9.98 (s, 1H). ES$^+$ m/z [M+H]$^+$: 447, HPLC $t_R$=1.42 min (99.5%).

Example 105: 4-((4-cyclohexylphenyl)amino)-2-(2-cyclopropylmorpholino) pyrido[2,3-d]pyrimidine-6-carboxamide

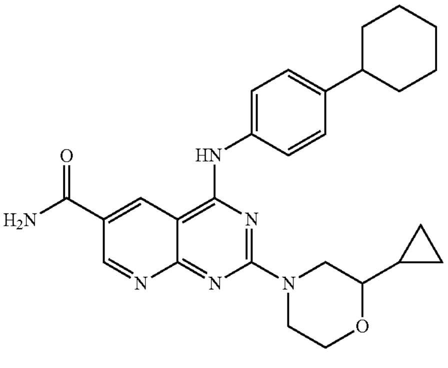 [SMILES: NC(=O)c1cnc2nc(N3CCOC(C4CC4)C3)nc(Nc3ccc(C4CCCCC4)cc3)c2c1]

The title compound was made using the method described above for (R)-4-((4-cyclohexylphenyl)amino)-2-(2-methylmorpholino)pyrido[2,3-d]pyrimidine-6-carboxamide. $^{1}$H NMR (300 MHz, DMSO) δ 0.28 (d, J=20.5 Hz, 2H), 0.49 (d, J=8.3 Hz, 2H), 0.89 (s, 1H), 1.30 (d, J=47.9 Hz, 5H), 1.70 (d, J=12.7 Hz, 1H), 1.79 (d, J=7.9 Hz, 4H), 2.43-2.49 (m, 1H), 2.71 (s, 1H), 2.85-2.93 (m, 1H), 3.02-3.09 (m, 1H), 3.31-3.45 (m, 1H), 3.91 (d, J=11.4 Hz, 1H), 4.48 (s, 1H), 4.64 (s, 1H), 7.22 (d, J=8.4 Hz, 2H), 7.52 (s, 1H), 7.68 (d, J=8.2 Hz, 2H), 8.01 (s, 1H), 9.13 (d, J=2.2 Hz, 1H), 9.18 (d, J=2.3 Hz, 1H), 9.97 (s, 1H). ES$^{+}$ m/z [M+H]$^{+}$: 473, HPLC $t_R$=1.66 min (99.4%).

Example 106: (R)—N-(4-cyclohexylphenyl)-6-methoxy-2-(2-methylmorpholino) pyrido[2,3-d]pyrimidin-4-amine

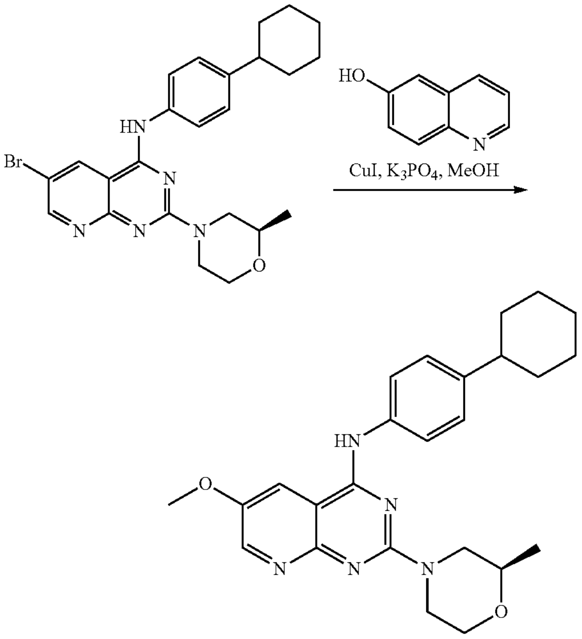

Quinolin-6-ol (60.2 mg, 0.41 mmol) was added to (R)-6-bromo-N-(4-cyclohexylphenyl)-2-(2-methylmorpholino) pyrido[2,3-d]pyrimidin-4-amine (200 mg, 0.41 mmol), copper (I) iodide (3.95 mg, 0.02 mmol) and tripotassium phosphate (176 mg, 0.83 mmol) in MeOH (6 mL) at RT under argon. The resulting mixture was stirred at 110° C. for 24 hours. The reaction mixture was evaporated to dryness. The crude product was purified by flash C18-flash chromatography, elution gradient 50 to 100% MeOH in water (0.1% $NH_4HCO_3$). Pure fractions were evaporated to dryness to afford a yellow liquid. The obtained yellow liquid was purified by preparative HPLC conditions B. Fractions containing the desired compound were evaporated to dryness to afford (R)—N-(4-cyclohexylphenyl)-6-methoxy-2-(2-methylmorpholino)pyrido[2,3-d]pyrimidin-4-amine (10.0 mg, 5.5%) as a yellow solid. $^{1}$H NMR (400 MHz, DMSO) δ 1.16 (d, J=6.2 Hz, 3H), 1.25 (d, J=9.7 Hz, 1H), 1.31-1.50 (m, 4H), 1.72 (d, J=12.5 Hz, 1H), 1.81 (d, J=8.6 Hz, 4H), 2.32-2.49 (m, 1H), 2.62 (dd, J=13.1, 10.4 Hz, 1H), 2.90-3.01 (m, 1H), 3.43-3.54 (m, 2H), 3.91 (s, 4H), 4.43 (d, J=13.2 Hz, 1H), 4.51 (d, J=12.9 Hz, 1H), 7.26 (d, J=8.6 Hz, 2H), 7.65-7.72 (m, 2H), 8.24 (d, J=3.1 Hz, 1H), 8.55 (d, J=3.0 Hz, 1H), 9.60 (s, 1H). ES$^{+}$ m/z [M+H]$^{+}$: 434, HPLC $t_R$=1.89 min (99.6%).

Example 107: (R)—N-(4-((4-cyclohexylphenyl) amino)-2-(2-methylmorpholino) pyrido[2,3-d]pyrimidin-6-yl)acetamide

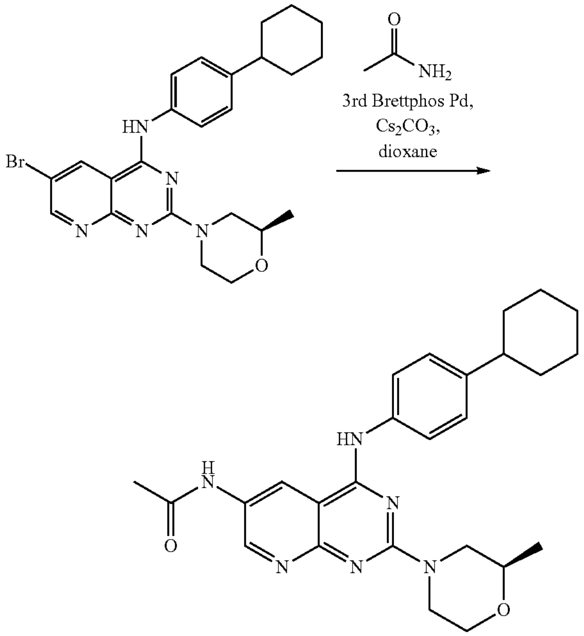

3rd Generation Brettphos Pd catalyst (96 mg, 0.10 mmol) was added to $Cs_2CO_3$ (675 mg, 2.07 mmol), acetamide (184 mg, 3.11 mmol) and (R)-6-bromo-N-(4-cyclohexyl phenyl)-2-(2-methylmorpholino)pyrido[2,3-d]pyrimidin-4-amine (500 mg, 1.04 mmol) in 1,4-dioxane (5 mL) at RT under nitrogen. The resulting mixture was stirred at 100° C. for 5 hours. The crude product was purified by flash silica chromatography, elution gradient 0 to 10% MeOH in DCM. Pure fractions were evaporated to dryness to afford (R)—N-(4-((4-cyclohexylphenyl)amino)-2-(2-methylmorpholino) pyrido[2,3-d]pyrimidin-6-yl)acetamide (275 mg) as a yellow solid. The obtained crude product (125 mg) was purified by preparative HPLC Column:)(Bridge Prep OBD C18

Column 19×250 mm, 5um; Mobile Phase A: Water (10 mM $NH_4HCO_3$+0.1% $NH_3 \cdot H_2O$), Mobile Phase B: acetonitrile; Flow rate: 25 mL/min; Gradient elution, detecting at 254/220 nm. Fractions containing the desired compound were evaporated to dryness to afford (R)—N-(4-((4-cyclohexylphenyl)amino)-2-(2-methylmorpholino)pyrido[2,3-d]pyrimidin-6-yl)acetamide (25 mg, 5%) as a yellow solid. $^1$H NMR (400 MHz, DMSO) δ 1.15 (d, J=6.2 Hz, 3H), 1.20-1.49 (m, 5H), 1.76 (dd, J=38.0, 10.7 Hz, 5H), 2.10 (s, 3H), 2.49-2.51 (m, 1H), 2.64 (dd, J=13.3, 10.4 Hz, 1H), 2.91-3.02 (m, 1H), 3.48 (dd, J=12.0, 9.3 Hz, 2H), 3.85-3.93 (m, 1H), 4.49 (dd, J=33.9, 13.2 Hz, 2H), 7.19-7.26 (m, 2H), 7.63-7.71 (m, 2H), 8.68 (d, J=2.6 Hz, 1H), 8.84 (d, J=2.7 Hz, 1H), 9.76 (s, 1H), 10.14 (s, 1H). ES$^+$ m/z [M+H]$^+$: 461, HPLC $t_R$=1.59 min (97.7%).

Example 108: (R)—N4-(4-cyclohexylphenyl)-2-(2-methylmorpholino)pyrido[2,3-d]pyrimidine-4,6-diamine

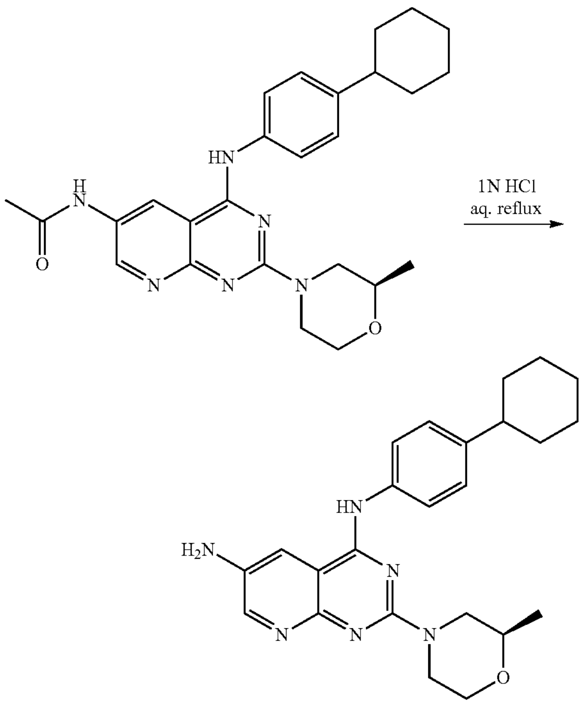

(R)—N-(4-((4-cyclohexylphenyl)amino)-2-(2-methylmorpholino)pyrido[2,3-d]pyrimidin-6-yl)acetamide (100 mg, 0.22 mmol) was added to 1N HCl aqueous solution (1 mL) at RT. The resulting mixture was stirred at 100° C. for 16 hours. The crude product was purified by preparative HPLC conditions B. Fractions containing the desired compound were evaporated to dryness to afford (R)—N4-(4-cyclohexylphenyl)-2-(2-methylmorpholino)pyrido[2,3-d]pyrimidine-4,6-diamine (35.0 mg, 38.5%) as a yellow solid. $^1$H NMR (400 MHz, DMSO) δ 1.15 (d, J=6.2 Hz, 3H), 1.24 (s, 1H), 1.30-1.49 (m, 4H), 1.71 (d, J=12.6 Hz, 1H), 1.80 (d, J=9.6 Hz, 4H), 2.46-2.51 (m, 1H), 2.57 (dd, J=13.0, 10.3 Hz, 1H), 2.85-2.97 (m, 1H), 3.43-3.56 (m, 2H), 3.89 (dd, J=11.3, 3.1 Hz, 1H), 4.37 (d, J=13.0 Hz, 1H), 4.46 (d, J=12.9 Hz, 1H), 5.25 (s, 2H), 7.21 (d, J=8.5 Hz, 2H), 7.67-7.74 (m, 3H), 8.34 (d, J=2.8 Hz, 1H), 9.42 (s, 1H). ES$^+$ m/z [M+H]$^+$: 419, HPLC $t_R$=2.30 min (99.8%).

Example 109: N-(4-cyclohexylphenyl)-6-isopropyl-2-morpholino-6,7-dihydro-5H-pyrrolo[3,4-d]pyrimidin-4-amine

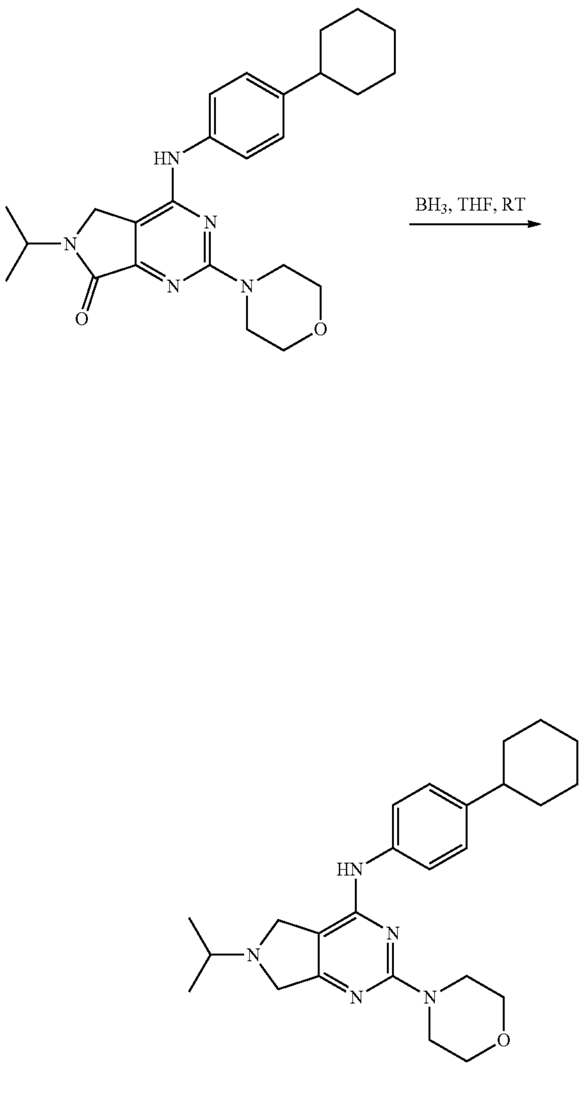

Borane-THF complex (3 mL, 3.00 mmol) was added dropwise to 4-((4-cyclohexylphenyl)amino)-6-isopropyl-2-morpholino-5,6-dihydro-7H-pyrrolo[3,4-d]pyrimidin-7-one (120 mg, 0.28 mmol) in THF (3 mL) at rt under nitrogen. The resulting mixture was stirred at rt for 18 hours. The reaction mixture was quenched with MeOH (5 mL) and the solvent was removed under reduced pressure. The crude product was purified by preparative HPLC conditions A. Fractions containing the desired compound were evaporated to dryness to afford N-(4-cyclohexylphenyl)-6-isopropyl-2-morpholino-6,7-dihydro-5H-pyrrolo[3,4-d]pyrimidin-4-amine formate (37.0 mg, 29.8%) as a white solid. $^1$H NMR (400 MHz, DMSO) δ 1.10 (d, J=6.2 Hz, 6H), 1.19-1.30 (m, 1H), 1.31-1.44 (m, 4H), 1.70 (d, J=12.8 Hz, 1H), 1.78 (d, J=10.0 Hz, 4H), 2.41-2.46 (m, 1H), 2.72 (q, J=6.2 Hz, 1H), 3.57-3.69 (m, 10H), 3.75 (d, J=2.2 Hz, 2H), 7.11-7.17 (m, 2H), 7.55-7.63 (m, 2H), 8.20 (s, 1H), 8.56 (s, 1H). ES+ m/z [M+H]$^+$: 422, HPLC $t_R$=2.30 min (98.2%).

Example 110: (R)—N-(4-cyclohexylphenyl)-6-isopropyl-2-(2-methylmorpholino)-6,7-dihydro-5H-pyrrolo[3,4-d]pyrimidin-4-amine

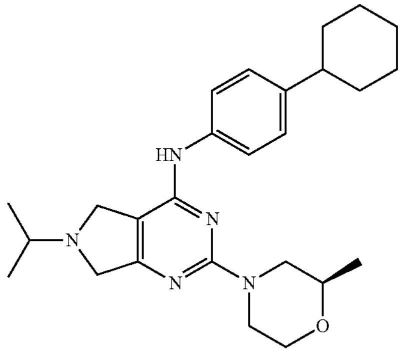 [SMILES: CC(C)N1Cc2nc(N3CCO[C@H](C)C3)nc(Nc3ccc(C4CCCCC4)cc3)c2C1]

(R)—N-(4-cyclohexylphenyl)-6-isopropyl-2-(2-methylmorpholino)-6,7-dihydro-5H-pyrrolo[3,4-d]pyrimidin-4-amine formate was made using the described method for N-(4-cyclohexylphenyl)-6-isopropyl-2-morpholino-6,7-dihydro-5H-pyrrolo[3,4-d]pyrimidin-4-amine. $^1$H NMR (400 MHz, DMSO) δ 1.12 (dd, J=6.2, 16.1 Hz, 9H), 1.19-1.29 (m, 1H), 1.35-1.40 (m, 4H), 1.70 (d, J=12.8 Hz, 1H), 1.78 (d, J=9.8 Hz, 4H), 2.65-2.76 (m, 1H), 2.87 (t, J=12.2 Hz, 1H), 3.41-3.56 (m, 3H), 3.70 (d, J=35.7 Hz, 5H), 3.87 (d, J=11.3 Hz, 1H), 4.32 (dd, J=12.9, 32.2 Hz, 2H), 7.14 (d, J=8.3 Hz, 2H), 7.59 (d, J=8.3 Hz, 2H), 8.23 (s, 1H), 8.56 (s, 1H). ES+ m/z $[M+H]^+$: 436, HPLC $t_R$=1.47 min (99.0%).

Example 111: 2-{4-[(4-cyclohexylphenyl)amino]-2-(3,6-dihydro-2H-pyran-4-yl)-5,7-dihydro-6H-pyrrolo[3,4-d]pyrimidin-6-yl}-N,N-dimethylacetamide

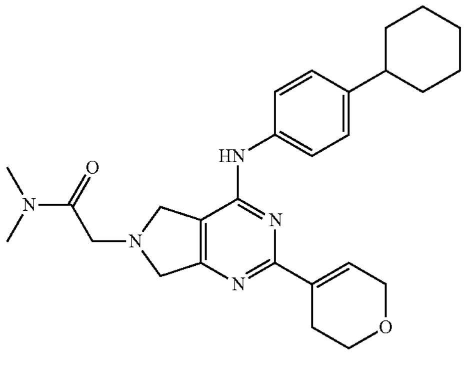 [SMILES: CN(C)C(=O)CN1Cc2nc(C3=CCOCC3)nc(Nc3ccc(C4CCCCC4)cc3)c2C1]

Example 111, Step 1: tert-butyl 2-chloro-4-((4-cyclohexylphenyl)amino)-5,7-dihydro-6H-pyrrolo[3,4-d]pyrimidine-6-carboxylate

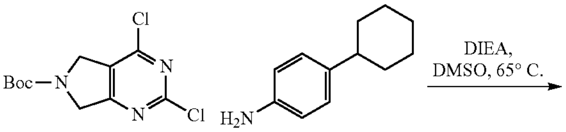

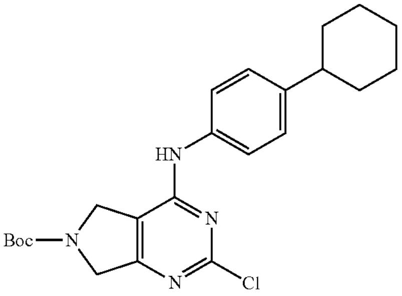

4-cyclohexylaniline (3.02 g, 17.23 mmol) was added to DIEA (3.61 mL, 20.68 mmol), and tert-butyl 2,4-dichloro-5,7-dihydro-6H-pyrrolo[3,4-d]pyrimidine-6-carboxylate (5 g, 17.23 mmol) in DMSO (25 mL). The resulting mixture was stirred at 65° C. for 16 hours. The crude product was purified by flash silica chromatography, elution gradient 0 to 20% MeOH in DCM. Pure fractions were evaporated to dryness to afford tert-butyl 2-chloro-4-((4-cyclohexylphenyl)amino)-5,7-dihydro-6H-pyrrolo[3,4-d]pyrimidine-6-carboxylate (7.78 g, 105%). $^1$H NMR (400 MHz, DMSO) δ 1.20-1.26 (m, 1H), 1.26-1.41 (m, 4H), 1.47 (d, J=4.7 Hz, 9H), 1.71 (d, J=12.9 Hz, 1H), 1.80 (d, J=9.8 Hz, 4H), 2.50-2.51 (m, 1H), 4.39-4.49 (m, 4H), 7.22 (d, J=8.3 Hz, 2H), 7.52 (t, J=8.1 Hz, 2H), 9.49 (d, J=12.3 Hz, 1H). ES+ m/z $[M+H]^+$: 429, HPLC $t_R$=1.71 min (96.7%).

Example 111, Step 2: tert-butyl 4-((4-cyclohexylphenyl)amino)-2-(3,6-dihydro-2H-pyran-4-yl)-5,7-dihydro-6H-pyrrolo[3,4-d]pyrimidine-6-carboxylate

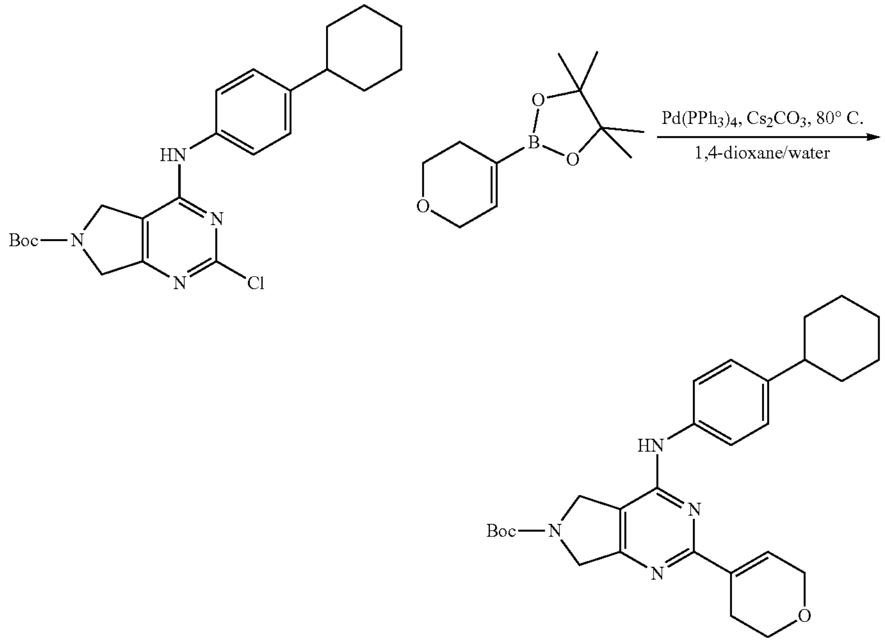

$Pd(PPh_3)_4$ (1.347 g, 1.17 mmol) was added to $Cs_2CO_3$ (7.60 g, 23.31 mmol), 2-(3,6-dihydro-2H-pyran-4-yl)-4,4,5,5-tetramethyl-1,3,2-dioxaborolane (2.69 g, 12.82 mmol) and tert-butyl 2-chloro-4-((4-cyclohexylphenyl)amino)-5,7-dihydro-6H-pyrrolo[3,4-d]pyrimidine-6-carboxylate (5 g, 11.66 mmol) in water (10 mL) and 1,4-dioxane (50 mL). The resulting mixture was stirred at 80° C. for 14 hours. The reaction mixture was concentrated and diluted with EtOAc (100 mL) and washed sequentially with water (2×100 mL) and saturated brine (75 mL). The organic layer was dried over $Na_2SO_4$, filtered and evaporated to afford crude product. The crude product was purified by flash silica chromatography, elution gradient 0 to 20% MeOH in DCM. Pure fractions were evaporated to dryness to afford tert-butyl 4-((4-cyclohexylphenyl)amino)-2-(3,6-dihydro-2H-pyran-4-yl)-5,7-dihydro-6H-pyrrolo[3,4-d]pyrimidine-6-carboxylate (6.62 g, 119%) as a white solid. ES+ m/z $[M+H]^+$: 477, HPLC $t_R$=1.42 min (92.7%).

Example 111, Step 3: N-(4-cyclohexylphenyl)-2-(3,6-dihydro-2H-pyran-4-yl)-6,7-dihydro-5H-pyrrolo[3,4-d]pyrimidin-4-amine

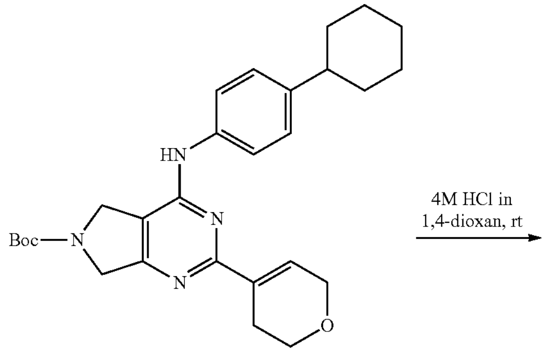

-continued

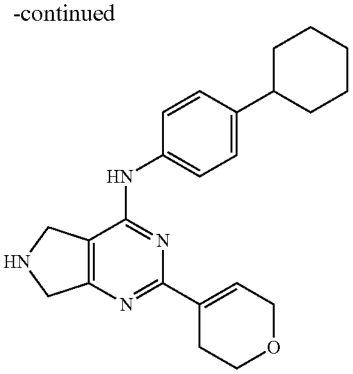

tert-Butyl 4-((4-cyclohexylphenyl)amino)-2-(3,6-dihydro-2H-pyran-4-yl)-5,7-dihydro-6H-pyrrolo[3,4-d]pyrimidine-6-carboxylate (6.622 g, 13.89 mmol) was added to HCl in 1, 4-dioxane (4 M, 20 mL). The resulting mixture was stirred at RT for 4 hours.

The mixture was filtered to afford N-(4-cyclohexylphenyl)-2-(3,6-dihydro-2H-pyran-4-yl)-6,7-dihydro-5H-pyrrolo[3,4-d]pyrimidin-4-amine hydrochloride (3.69 g, 64%) as a white solid. $^1H$ NMR (400 MHz, DMSO) δ 1.14-1.29 (m, 1H), 1.32-1.43 (m, 4H), 1.70 (d, J=12.6 Hz, 1H), 1.79 (d, J=9.3 Hz, 4H), 2.38-2.49 (m, 1H), 2.49-2.56 (m, 3H), 3.36 (s, 1H), 3.78 (t, J=5.5 Hz, 2H), 4.27 (q, J=2.8 Hz, 2H), 4.42 (d, J=10.2 Hz, 2H), 4.51 (s, 2H), 7.05 (s, 1H), 7.16 (d, J=8.2 Hz, 2H), 7.65-7.73 (m, 2H), 8.96 (d, J=7.0 Hz, 1H). ES+ m/z $[M+H]^+$: 377, HPLC $t_R$=1.18 min (95.1%).

Example 111, Step 4: 2-(4-((4-cyclohexylphenyl) amino)-2-(3,6-dihydro-2H-pyran-4-yl)-5,7-dihydro-6H-pyrrolo[3,4-d]pyrimidin-6-yl)-N,N-dimethylacetamide

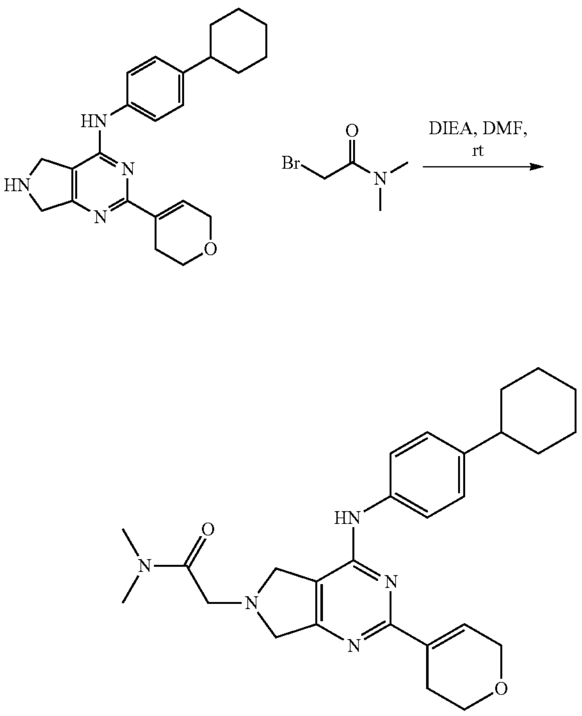

2-Bromo-N,N-dimethylacetamide (88 mg, 0.53 mmol) was added to N-(4-cyclohexylphenyl)-2-(3,6-dihydro-2H-pyran-4-yl)-6,7-dihydro-5H-pyrrolo[3,4-d]pyrimidin-4-amine (200 mg, 0.53 mmol) and DIEA (0.278 mL, 1.59 mmol) in DMF (2 mL) at RT. The resulting mixture was stirred at RT for 16 hours. The reaction mixture was purified by preparative HPLC: Column)(Bridge Shield RP18 OBD Column 19×250 mm, 10 um; Mobile Phase A: Water (0.1% formic acid), Mobile Phase B: acetonitrile; Flow rate: 25 mL/min; Gradient elution with detection at 254/220 nm. Fractions containing the desired compound were evaporated to dryness to afford 2-(4-((4-cyclohexylphenyl)amino)-2-(3,6-dihydro-2H-pyran-4-yl)-5,7-dihydro-6H-pyrrolo[3,4-d]pyrimidin-6-yl)-N,N-dimethylacetamide formate (13.0 mg, 5%) as a pale yellow solid. $^1$H NMR (400 MHz, DMSO) δ 1.19-1.27 (m, 1H), 1.32-1.47 (m, 4H), 1.71 (d, J=12.6 Hz, 1H), 1.79 (d, J=9.8 Hz, 4H), 2.49-2.50 (m, 2H), 2.85 (s, 3H), 3.01 (s, 3H), 3.63 (s, 2H), 3.80 (t, J=5.4 Hz, 2H), 3.94 (s, 2H), 4.00 (d, J=2.7 Hz, 2H), 4.28 (d, J=3.0 Hz, 2H), 7.04 (s, 1H), 7.13-7.20 (m, 2H), 7.65-7.72 (m, 2H), 8.29 (s, 1H), 8.78 (s, 1H). ES+ m/z $[M+H]^+$: 462, HPLC $t_R$=2.34 min (96.0%).

Example 112: N-(4-cyclohexylphenyl)-2-(2-cyclopropylmorpholino)-6-(1-methyl piperidin-4-yl)-6,7-dihydro-5H-pyrrolo[3,4-d]pyrimidin-4-amine

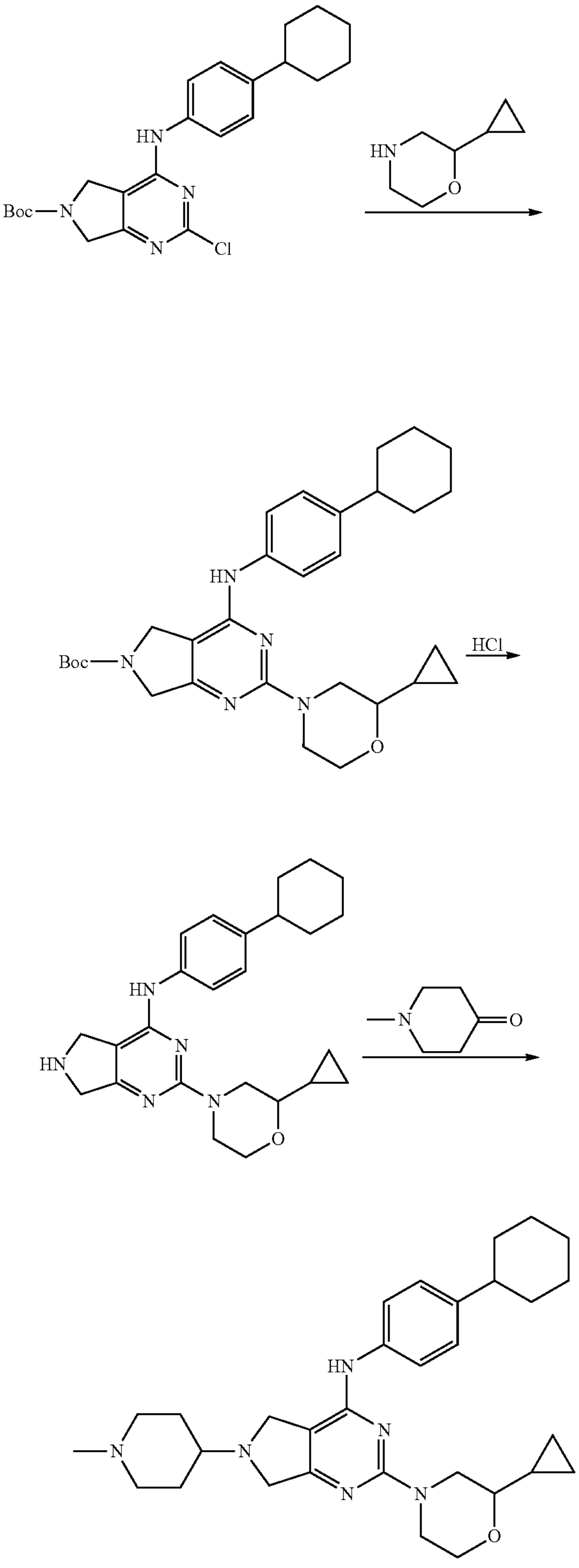

Example 112, Step 1: tert-butyl 4-((4-cyclohexylphenyl)amino)-2-(2-cyclopropyl morpholino)-5,7-dihydro-6H-pyrrolo[3,4-d]pyrimidine-6-carboxylate

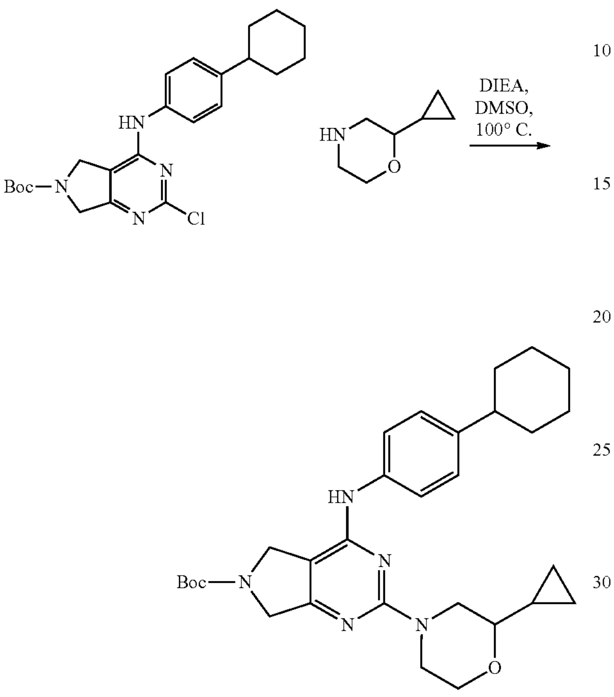

2-cyclopropylmorpholine (178 mg, 1.40 mmol) was added to tert-butyl 2-chloro-4-((4-cyclohexylphenyl)amino)-5,7-dihydro-6H-pyrrolo[3,4-d]pyrimidine-6-carboxylate (600 mg, 1.40 mmol) and DIEA (0.489 mL, 2.80 mmol) in DMSO (3 mL) at rt. The resulting mixture was stirred at 100° C. for 16 hours. The crude product was purified by flash C18-flash chromatography, elution gradient 80 to 100% MeOH in water (0.1% $NH_4HCO_3$). Pure fractions were evaporated to dryness to afford tert-butyl 4-((4-cyclohexylphenyl)amino)-2-(2-cyclopropylmorpholino)-5,7-dihydro-6H-pyrrolo[3,4-d]pyrimidine-6-carboxylate (625 mg, 86%) as a white solid. $^1$H NMR (400 MHz, MeOD) δ 0.29 (dd, J=4.6, 9.6 Hz, 1H), 0.35-0.44 (m, 1H), 0.49-0.63 (m, 2H), 0.84-0.96 (m, 1H), 1.31 (d, J=7.9 Hz, 2H), 1.37-1.50 (m, 4H), 1.54 (s, 9H), 1.77 (d, J=12.7 Hz, 1H), 1.87 (d, J=8.7 Hz, 4H), 2.49 (s, 1H), 2.73 (ddd, J=2.3, 8.1, 10.4 Hz, 1H), 2.83 (dd, J=10.4, 12.9 Hz, 1H), 3.00 (ddd, J=3.5, 11.7, 13.3 Hz, 1H), 3.52 (td, J=2.8, 11.6 Hz, 1H), 3.90-3.98 (m, 1H), 4.30-4.39 (m, 3H), 4.41 (t, J=2.2 Hz, 1H), 4.46 (d, J=2.2 Hz, 1H), 4.51-4.59 (m, 1H), 7.15 (dd, J=1.9, 8.6 Hz, 2H), 7.49-7.56 (m, 2H). ES+ m/z $[M+H]^+$: 520, HPLC $t_R$=1.79 min (97.8%).

Example 112, Step 2: N-(4-cyclohexylphenyl)-2-(2-cyclopropylmorpholino)-6,7-dihydro-5H-pyrrolo[3,4-d]pyrimidin-4-amine

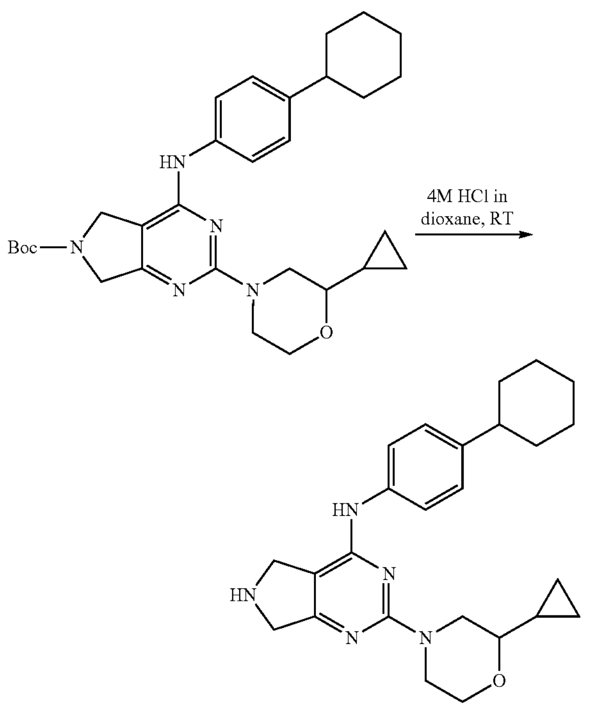

tert-Butyl 4-((4-cyclohexylphenyl)amino)-2-(2-cyclopropylmorpholino)-5,7-dihydro-6H-pyrrolo[3,4-d]pyrimidine-6-carboxylate (615 mg, 1.18 mmol) was added in HCl in 1,4-dioxane (8 mL) at rt. The resulting mixture was stirred at rt for 1 hour. The reaction mixture was filtered through EA to afford N-(4-cyclohexylphenyl)-2-(2-cyclopropylmorpholino)-6,7-dihydro-5H-pyrrolo[3,4-d]pyrimidin-4-amine hydrochloride (510 mg, 103%) as a yellow solid. $^1$H NMR (400 MHz, DMSO) δ 0.24-0.28 (m, 1H), 0.28-0.37 (m, 1H), 0.43-0.53 (m, 2H), 0.82-0.95 (m, 1H), 1.22-1.27 (m, 1H), 1.30-1.47 (m, 4H), 1.67-1.75 (m, 1H), 1.79 (d, J=9.2 Hz, 4H), 2.76 (t, J=9.7 Hz, 1H), 2.90 (dd, J=10.4, 13.1 Hz, 1H), 3.07 (t, J=12.1 Hz, 1H), 3.42 (td, J=2.7, 11.6 Hz, 1H), 3.57 (s, 1H), 3.91 (dd, J=3.1, 11.4 Hz, 1H), 4.23-4.52 (m, 6H), 7.18-7.24 (m, 2H), 7.54-7.61 (m, 2H), 9.72 (s, 1H), 10.14 (s, 2H). ES+ m/z $[M+H]^+$: 420, HPLC $t_R$=1.14 min (99.8%).

Example 112, Step 3: N-(4-cyclohexylphenyl)-2-(2-cyclopropylmorpholino)-6-(1-methylpiperidin-4-yl)-6,7-dihydro-5H-pyrrolo[3,4-d]pyrimidin-4-amine

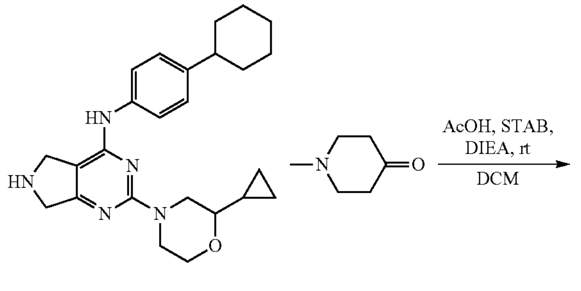

-continued

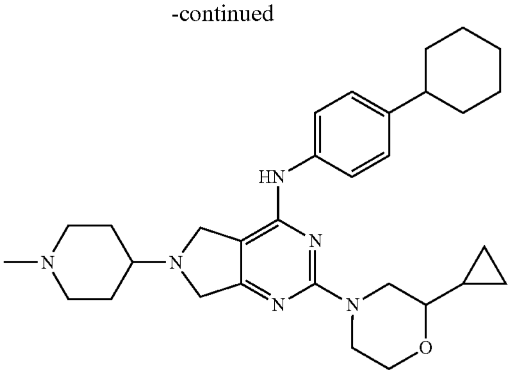

AcOH (0.126 mL, 2.19 mmol) was added to N-(4-cyclohexylphenyl)-2-(2-cyclopropylmorpholino)-6,7-dihydro-5H-pyrrolo[3,4-d]pyrimidin-4-amine hydrochloride (100 mg, 0.22 mmol), 1-methylpiperidin-4-one (74.4 mg, 0.66 mmol) and DIEA (0.115 mL, 0.66 mmol) in DCM (3 mL) at rt. The resulting mixture was stirred at rt for 30 min. Sodium triacetoxyborohydride (139 mg, 0.66 mmol) was added to above mixture at rt. The resulting mixture was stirred at rt for 16 hours. The solvent was removed under reduced pressure. The crude product was dissolved in MeOH (5 mL). The crude product was purified by flash C18-flash chromatography, elution gradient 90 to 100% MeOH in water (0.1% $NH_4HCO_3$). Pure fractions were evaporated to dryness to afford product as a white solid. The obtained product was purified by preparative HPLC: Kinetex EVO C18 Column 30×150, Sum; Mobile Phase A: Water (10 mM $NH_4HCO_3$), Mobile Phase B: acetonitrile; Flow rate: 60 mL/min; Gradient elution with detection at 254/220 nm. Fractions containing the desired compound were evaporated to dryness to afford N-(4-cyclohexylphenyl)-2-(2-cyclopropylmorpholino)-6-(1-methylpiperidin-4-yl)-6,7-dihydro-5H-pyrrolo[3,4-d]pyrimidin-4-amine (32.5 mg, 28.7%) as a white solid. $^1$H NMR (400 MHz, DMSO) δ 0.19-0.37 (m, 2H), 0.45-0.52 (m, 2H), 0.87 (s, 1H), 1.23 (s, 1H), 1.27-1.53 (m, 6H), 1.63-1.86 (m, 7H), 1.95 (t, J=10.9 Hz, 2H), 2.15 (s, 3H), 2.38 (m, 2H), 2.69-2.76 (m, 4H), 2.84-2.94 (m, 1H), 3.33-3.43 (m, 1H), 3.64 (s, 2H), 3.73 (s, 2H), 3.87 (d, J=11.9 Hz, 1H), 4.24 (d, J=13.0 Hz, 1H), 4.44 (d, J=10.1 Hz, 1H), 7.13 (d, J=8.4 Hz, 2H), 7.57 (d, J=8.5 Hz, 2H), 8.56 (s, 1H). ES+ m/z $[M+H]^+$: 517, HPLC $t_R$=1.05 min (97.4%).

Biological Assay

A thallium transport FLIPR-based assay was used to measure the ability of compounds to activate KCC2. KCC2 activity is assessed by measuring KCC2-dependent $Tl^+$ influx in a KCC2-expressing cell. The assay protocol was based on those described by Delpire et al (Proc Natl Acad Sci USA. 2009 Mar. 31; 106(13): 5383-5388) and Zhang et al (Journal of Biomolecular Screening 15(2): 2010).

Preparation of HEK cells expressing KCC2

KCC2 was synthesised and codon optimised by GeneArt based on the Uniprot sequence Q9H2X9. The final sequence was subcloned into pcDNA3.1.

HEK293 cells were grown in 10 layer cell stacks at 37° C., 5% $CO_2$, in DMEM, 10% fetal calf serum and 2 mM Glutamine. The cells were detached by removing the media and washing the cell stack with 100 ml of PBS. The PBS was removed and 100 ml of 1× TrypLE was added and the cell stack returned to 37° C. for 5 min. The detached cells were then counted in a Vi Cell counter and spun for 10 min at 1250 rpm in a Sorval Legend centrifuge. The cells were diluted down in Maxcyte electroporation buffer at 4× the final concentration and spun as before. The cell pellet was resuspended at $1\times10^8$/cells per ml and electroporated in a Maxcyte Cl 2.2 bag on a Maxcyte STX machine via the HEK293 programme with 200 ug/ml of plasmid DNA. The cells were then allowed to recover for 30 min before adding to 500 ml of PBS and then counted again on the Vi Cell. The cells were then frozen down in planer controlled rate freeze in 90% complete media, 10% DMSO.

Procedure for KCC2 Thallium Assay

All reagents were dispensed using a Mulitdrop Combi unless stated otherwise. All FluXOR Invitrogen propriety buffer compositions are mentioned in tables below.

HEK293 KCC2 cells were harvested at a density of $3.33\times10^5$ cells/mL in complete media (DMEM, Sigma, D6546, 10% fetal calf serum and 1% Glutamax) and 30 μL per well seeded into 384-well PDL coated black-clear plates (Corning, 354663). Leave cells at RT for 20 mins to settle before incubating for 48 h at 37° C., 5% $CO_2$. Following incubation, perform three wash steps in HBSS (Sigma, H6648) using a Biotek cell washer with the final aspiration leaving 20 μL HBSS residual volume in each well. A further 20 μL per well of thallium loading dye is then added (1 h, RT, protect from light). 5 μL of test compounds (100 μM top concentration, 1:2 dilutions, 12 point curve) were added using the FLIPR TETRA and incubated at RT for 90 min in the dark. Following compound incubation, the thallium flux response is read on FLIPR TETRA (ex. 515-575 nm) which is initiated by FLIRR TETRA dispensing 5 μL stimulus buffer into each well. Recordings are measured every 1 second for 120 seconds. Thallium flux at 120 s used to determine $EC_{50}$.

Reagents for KCC2 Assay:

| Assay Buffer For 100 ml | | |
|---|---|---|
| Material/Reagent | Details | Source |
| Kit assay buffer (10 x; component B) | 10 ml | Life Tech (F10017) |
| Deionised water | 86 ml | Media prep |
| HEPES (1M) | 2 ml | Sigma (H0887) |
| Ouabain (10 mM in deionised water) | 200 μL (Note TH-4) | Sigma (O3125) |

pH adjusted to 7.4 using NaOH

| Loading Buffer For 10 ml | | |
|---|---|---|
| Material/Reagent | Details | Source |
| FluxOR dye (component A) | 10 μl | Life Tech (F10017) |
| Assay Buffer | 9 ml | as above |
| Back drop suppressor | 1 ml | Life Tech (B10512) |
| Bumetanide (100 mM in DMSO) | 2 μl | Sigma (B3023) |

Loading buffer must be made up fresh on the day of assay.

Compound buffer: Assay buffer with 1 μL of bumetanide per 10 ml.

| Stimulus Buffer For 10 ml | | |
|---|---|---|
| Material/Reagent | Details | Source |
| FluxOR Cl− free buffer (component E) | 1.5 ml | Life Tech (F10017) |
| Deionised water | 6 ml | Media prep |
| $K^+$ ($K_2SO_4$) solution (component F) | 2 ml | Life Tech (F10017) |
| Tl+ ($Tl_2SO_4$) solution (component G) | 0.5 ml | Life Tech (F10017) |
| Bumetanide (100 mM in DMSO) | 1 μl | Sigma (D129) |

Activity of Examples in KCC2 Thallium Assay.

All compounds showed $E_{max}$>140% of DMSO signal.

| Example | Activity KCC2 EC50 (μM) |
|---|---|
| 1 | 1.71 |
| 2 | 0.672 |
| 3 | 3.00 |
| 4 | 3.76 |
| 5 | 3.77 |
| 6 | 6.82 |
| 7 | 4.50 |
| 8 | 5.43 |
| 9 | 6.14 |
| 10 | 2.99 |
| 11 | 2.01 |
| 12 | 1.35 |
| 13 | 1.71 |
| 14 | 0.707 |
| 15 | 0.769 |
| 16 | 0.749 |
| 17 | 1.09 |
| 18 | 1.39 |
| 19 | 2.04 |
| 20 | 2.35 |
| 21 | 2.64 |
| 22 | 2.79 |
| 23 | 2.92 |
| 24 | 2.92 |
| 25 | 3.41 |
| 26 | 3.50 |
| 27 | 3.58 |
| 29 | 3.89 |
| 30 | 4.05 |
| 31 | 4.81 |
| 32 | 4.89 |
| 33 | 5.01 |
| 34 | 5.21 |
| 35 | 6.30 |
| 36 | 6.30 |
| 37 | 6.30 |
| 38 | 9.34 |
| 39 | 9.90 |
| 40 | 6.36 |
| 41 | 0.518 |
| 42 | 0.633 |
| 43 | 0.738 |
| 44 | 0.901 |
| 45 | 1.15 |
| 46 | 1.29 |
| 47 | 3.16 |
| 48 | 6.30 |
| 49 | 6.30 |
| 50 | 7.98 |
| 51 | 0.973 |
| 52 | 0.146 |
| 53 | 0.215 |
| 54 | 0.253 |
| 55 | 2.30 |
| 56 | 3.28 |
| 57 | 3.60 |

-continued

| Example | Activity KCC2 EC50 (μM) |
|---|---|
| 58 | 3.78 |
| 59 | 4.46 |
| 60 | 4.82 |
| 61 | 5.51 |
| 62 | 5.66 |
| 63 | 5.71 |
| 64 | 5.76 |
| 65 | 7.65 |
| 66 | 0.917 |
| 67 | 4.07 |
| 68 | 1.94 |
| 69 | 1.56 |
| 70 | 1.83 |
| 71 | 4.13 |
| 72 | 1.53 |
| 73 | 2.73 |
| 74 | 3.70 |
| 75 | 3.77 |
| 76 | 6.89 |
| 78 | 3.08 |
| 79 | 6.30 |
| 80 | 1.80 |
| 81 | 2.47 |
| 82 | 2.29 |
| 83 | 3.88 |
| 84 | 2.09 |
| 85 | 8.41 |
| 86 | 5.83 |
| 87 | 8.18 |
| 88 | 3.52 |
| 89 | 3.51 |
| 90 | 1.71 |
| 91 | 9.92 |
| 92 | 2.37 |
| 93 | 1.41 |
| 94 | 1.30 |
| 95 | 3.22 |
| 96 | 2.92 |
| 97 | 1.35 |
| 98 | 5.53 |
| 99 | 3.79 |
| 100 | 6.30 |
| 101 | 1.01 |
| 102 | 0.700 |
| 103 | 3.99 |
| 104 | 1.63 |
| 105 | 1.17 |
| 106 | 1.85 |
| 107 | 6.30 |
| 108 | 1.97 |
| 109 | 6.34 |
| 110 | 7.31 |
| 111 | 5.35 |
| 112 | 3.57 |
| 113 | 4.74 |
| 114 | 7.30 |

What is claimed is:

1. A compound of Formula (I):

(I)

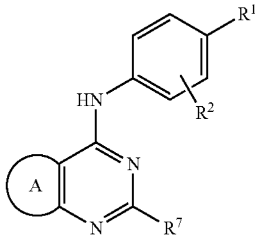

or a pharmaceutically acceptable salt or stereoisomer thereof, wherein:

$R^1$ is $C_{2-6}$ alkyl, $C_{2-6}$ alkenyl, $C_{2-6}$ alkynyl, $OC_{2-6}$ alkyl, $OCH_2C_{6-10}$ aryl, $OC_{2-6}$ alkenyl, $OC_{2-6}$ alkynyl, $OC_{3-7}$ cycloalkyl, $OC_{6-10}$ aryl, $C_{3-7}$ cycloalkyl, $C_{6-10}$ aryl, thiophenyl, or 6-membered heteroaryl;

wherein the $C_{2-6}$ alkyl, $C_{2-6}$ alkenyl, $C_{2-6}$ alkynyl, $OC_{2-6}$ alkyl, $OC_{2-6}$ alkenyl, $OC_{2-6}$ alkynyl, or $C_{3-7}$ cycloalkyl is optionally substituted with 1, 2, or 3 substituents independently selected from the group consisting of F and $CF_3$;

wherein the $C_{6-10}$ aryl of $OCH_2C_{6-10}$ aryl, $OC_{6-10}$ aryl, $C_{6-10}$ aryl, or 6-membered heteroaryl is optionally substituted with 1 or 2 substituents independently selected from the group consisting of halo, $C_{1-3}$ alkyl, $OC_{1-8}$ alkyl, and $OC_{2-8}$ alkynyl; and wherein each $C_{1-3}$ alkyl, $OC_{1-8}$ alkyl, and $OC_{2-8}$ alkynyl substituent is optionally and independently substituted with 1, 2, or 3 substituents independently selected from the group consisting of F, $CF_3$, and $NHC(O)OC_{1-6}$ alkyl; or any two $R^1$ substituents, together with the carbon atom to which they are attached, form diazirinyl;

$R^2$ is H, halo, or $C_{1-3}$ alkyl, wherein the $C_{1-3}$ alkyl is optionally substituted with 1, 2, or 3 substituents independently selected from the group consisting of F and $CF_3$;

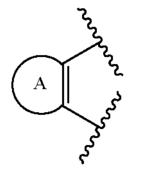

is:

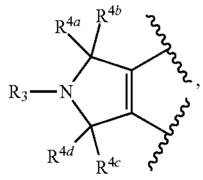
,
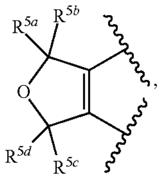
,
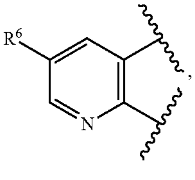
, or
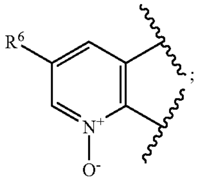
;

$R^3$ is H, $C_{1-6}$ alkyl, $C_{2-6}$ alkenyl, $C_{2-6}$ alkynyl, $C_{3-7}$ cycloalkyl, or 5- or 6-membered heterocycloalkyl;

wherein the $C_{1-6}$ alkyl, $C_{2-6}$ alkenyl, $C_{2-6}$ alkynyl, $C_{3-7}$ cycloalkyl, or 5- or 6-membered heterocycloalkyl is optionally substituted with 1, 2, or 3 substituents independently selected from the group consisting of F, $CF_3$, $C_{1-3}$ alkyl, $C(O)NR^8R^9$, and $NR^8R^9$; and wherein each $C_{1-3}$ alkyl substituent is optionally and independently substituted with 1, 2, or 3 substituents independently selected from the group consisting of F and $CF_3$;

$R^{4a}$ is H or $C_{1-3}$ alkyl, wherein the $C_{1-3}$ alkyl is optionally substituted with 1, 2, or 3 substituents independently selected from the group consisting of F and $CF_3$;

$R^{4b}$ is H or $C_{1-3}$ alkyl, wherein the $C_{1-3}$ alkyl is optionally substituted with 1, 2, or 3 substituents independently selected from the group consisting of F and $CF_3$;

$R^{4c}$ is H or $C_{1-3}$ alkyl, wherein the $C_{1-3}$ alkyl is optionally substituted with 1, 2, or 3 substituents independently selected from the group consisting of F and $CF_3$;

$R^{4d}$ is H or $C_{1-3}$ alkyl, wherein the $C_{1-3}$ alkyl is optionally substituted with 1, 2, or 3 substituents independently selected from the group consisting of F and $CF_3$; or $R^{4c}$ and $R^{4d}$, taken together with the carbon atom to which they are attached, form —C(O)—;

$R^{5a}$ is H or $C_{1-3}$ alkyl, wherein the $C_{1-3}$ alkyl is optionally substituted with 1, 2, or 3 substituents independently selected from the group consisting of F and $CF_3$;

$R^{5b}$ is H or $C_{1-3}$ alkyl, wherein the $C_{1-3}$ alkyl is optionally substituted with 1, 2, or 3 substituents independently selected from the group consisting of F and $CF_3$;

$R^{5c}$ is H or $C_{1-3}$ alkyl, wherein the $C_{1-3}$ alkyl is optionally substituted with 1, 2, or 3 substituents independently selected from the group consisting of F and $CF_3$;

$R^{5d}$ is H or $C_{1-3}$ alkyl, wherein the $C_{1-3}$ alkyl is optionally substituted with 1, 2, or 3 substituents independently selected from the group consisting of F and $CF_3$;

$R^6$ is H, halo, CN, $C_{1-3}$ alkyl, $C(O)NR^8R^9$, C(O)OH, $C(O)OC_{1-3}$ alkyl, $NH_2$, $NHC(O)C_{1-3}$ alkyl, or $OC_{1-3}$ alkyl, wherein the $C_{1-3}$ alkyl or $OC_{1-3}$ alkyl is optionally substituted with 1, 2, or 3 substituents independently selected from the group consisting of F and $CF_3$;

$R^7$ is $NR^{10}R^{11}$, monocyclic 5- to 7-membered heterocycloalkyl, or monocyclic 5- or 6-membered heteroaryl;

wherein the 5- to 7-membered heterocycloalkyl is optionally substituted with 1, 2, or 3 substituents independently selected from the group consisting of CN, $C_{1-6}$ alkyl, $C_{1-3}$ alkylene-$NHC(O)C_{1-6}$ alkyl, $C_{1-3}$ alkylene-$NHC(O)OC_{1-6}$ alkyl, C(O)OH, $OC_{1-3}$ alkyl, and $C_{3-5}$ cycloalkyl; or wherein the 5- to 7-membered heterocycloalkyl is optionally substituted with 2 substituents on the same ring carbon, which together with the carbon atom to which they are attached, form a monocyclic 5- to 7-membered heterocycloalkyl;

wherein the 5- or 6-membered heteroaryl is optionally substituted with 1, 2, or 3 substituents independently selected from the group consisting of CN, $C_{1-6}$ alkyl, $C_{1-3}$ alkylene-$NHC(O)C_{1-6}$ alkyl, $C_{1-3}$ alkylene-$NHC(O)OC_{1-6}$ alkyl, C(O)OH, $OC_{1-3}$ alkyl, and $C_{3-5}$ cycloalkyl;

wherein each $C_{1-6}$ alkyl substituent is optionally and independently substituted with 1, 2, or 3 substituents independently selected from the group consisting of F, $CF_3$, and OH; and wherein each $OC_{1-3}$ alkyl substituent is optionally and independently substituted with 1, 2, or 3 substituents independently selected from the group consisting of F and $CF_3$;

each $R^8$ is independently H or $C_{1-6}$ alkyl;

each $R^9$ is independently H or $C_{1-6}$ alkyl;

$R^{10}$ is $C_{1-6}$ alkyl;

$R^{11}$ is $C_{1-6}$ alkyl or $(CH_2)_nR^{12}$, wherein the $C_{1-6}$ alkyl is optionally substituted with 1 or 2 substituents independently selected from the group consisting of F and $OC_{1-3}$ alkyl;

$R^{12}$ is $C_{3-5}$ cycloalkyl, 3- to 6-membered heterocycloalkyl, or 5- or 6-membered heteroaryl; and n is 1, 2, or 3;

with the proviso that if $R^1$ is unsubstituted phenyl and $R^7$ is morpholinyl, then $R^2$ is not H.

2. The compound according to claim 1, or a pharmaceutically acceptable salt or stereoisomer thereof, wherein $R^1$ is $C_{2-6}$ alkyl, $OC_{2-6}$ alkyl, $OCH_2C_{6-10}$ aryl, $OC_{3-7}$ cycloalkyl, $OC_{6-10}$ aryl, $C_{3-7}$ cycloalkyl, $C_{6-10}$ aryl, or thiophenyl;

wherein the $C_{2-6}$ alkyl, $OC_{2-6}$ alkyl, or $C_{3-7}$ cycloalkyl is optionally substituted with 1, 2, or 3 substituents independently selected from the group consisting of F and $CF_3$;

wherein the $C_{6-10}$ aryl of $OCH_2C_{6-10}$ aryl, $OC_{6-10}$ aryl, or $C_{6-10}$ aryl is optionally substituted with 1 or 2 substituents independently selected from the group consisting of halo, $C_{1-3}$ alkyl, $OC_{1-8}$ alkyl, and $OC_{2-8}$ alkynyl; and wherein each $C_{1-3}$ alkyl, $OC_{1-3}$ alkyl, and $OC_{2-s}$ alkynyl substituent is optionally and independently substituted with 1, 2, or 3 substituents independently selected from the group consisting of F, $CF_3$, and $NHC(O)OC_{1-6}$ alkyl; or any two $R^1$ substituents, together with the carbon atom to which they are attached, form diazirinyl.

3. The compound according to claim 2, or a pharmaceutically acceptable salt or stereoisomer thereof, wherein $R^1$ is $CH_2CF_3$, $CH_2CH_2CH_3$, $CH_2CH_2CH_2CH_3$, $CH_2CH_2CH_2CH_2CH_3$, $OCH_2CH_2CH_3$, $OCH_2$phenyl, Ocyclopentyl, Ophenyl, cyclobutyl, cyclohexyl, phenyl, or thiophenyl;

wherein the Ophenyl is optionally substituted with 1 or 2 F substituents; and wherein the phenyl is optionally substituted with 1 or 2 substituents independently selected from the group consisting of F, Cl, $CH_3$, $O(CH_2)_5CF_3$, $O(CH_2)_7CH_3$, $OCH_2C{\equiv}CH$, $O(CH_2)_5C{\equiv}CH$, $O(CH_2)_2NHC(O)OC(CH_3)_3$, and $O(CH_2)_2{-}C(N{=}N){-}CH_2C{\equiv}CH$.

4. The compound according to claim 1, or a pharmaceutically acceptable salt or stereoisomer thereof, wherein $R^2$ is H, F, or $CH_3$.

5. The compound according to claim 1, or a pharmaceutically acceptable salt or stereoisomer thereof, wherein

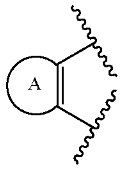

is:

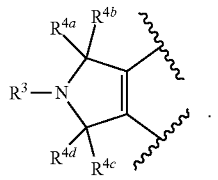

6. The compound according to claim 1, wherein the compound is of Formula (II):

(II)

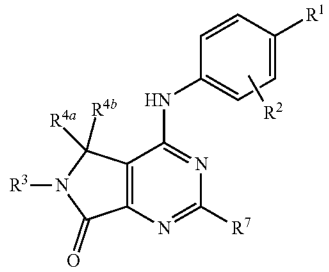

or a pharmaceutically acceptable salt or stereoisomer thereof.

7. The compound according to claim 1, or a pharmaceutically acceptable salt or stereoisomer thereof, wherein $R^3$ is $CH_2CH_3$, $CH_2C(O)N(CH_3)_2$, $CH_2CH_2N(CH_3)_2$, $CH_2CH_2CH_2N(CH_3)_2$, $CH(CH_3)_2$, $C{\equiv}CCH_3$, $CH_2C{\equiv}CH$, or N-methylpiperidinyl.

8. The compound according to claim 1, or a pharmaceutically acceptable salt or stereoisomer thereof, wherein:

$R^{4a}$ is H; and $R^{4b}$ is H.

9. The compound according to claim 1, or a pharmaceutically acceptable salt or stereoisomer thereof, wherein $R^{4c}$ and $R^{4d}$, taken together with the carbon atom to which they are attached, form —C(O)—.

10. The compound according to claim 1, or a pharmaceutically acceptable salt or stereoisomer thereof, wherein

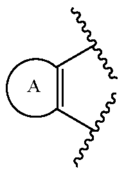

is:

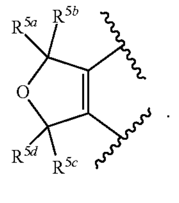

11. The compound according to claim 1, wherein the compound is of Formula (III):

(III)

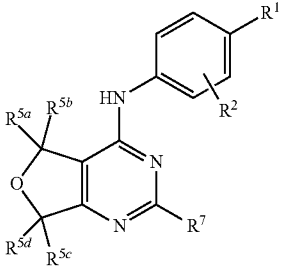

or a pharmaceutically acceptable salt or stereoisomer thereof.

12. The compound according to claim 1, or a pharmaceutically acceptable salt or stereoisomer thereof, wherein:

$R^{5a}$ is H;

$R^{5b}$ is H;

$R^{5c}$ is H; and $R^{5d}$ is H.

13. The compound according to claim 1, or a pharmaceutically acceptable salt or stereoisomer thereof, wherein

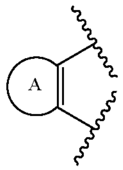

is:

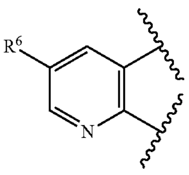

or

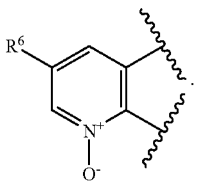

14. The compound according to claim 1, wherein the compound is of Formula (IV):

(IV)

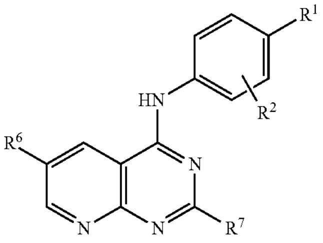

or a pharmaceutically acceptable salt or stereoisomer thereof.

15. The compound according to claim 1, or a pharmaceutically acceptable salt or stereoisomer thereof, wherein $R^6$ is H, Br, CN, $CH_2CH_3$, $C(O)NH_2$, C(O)OH, $C(O)OCH_3$, $NH_2$, $NHC(O)CH_3$, or $OCH_3$.

16. The compound according to claim 1, or a pharmaceutically acceptable salt or stereoisomer thereof, wherein $R^7$ is thiazolidinyl, 3,4-dihydro-2H-pyranyl, tetrahydropyranyl, morpholinyl, thiomorpholinyl, pyrrolyl, imidazolyl, oxazolyl, thiazolyl, or pyridinyl;

wherein the thiazolidinyl, 3,4-dihydro-2H-pyranyl, tetrahydropyranyl, morpholinyl, or thiomorpholinyl is optionally substituted with 1, 2, or 3 substituents independently selected from the group consisting of CN, $C_{1-6}$ alkyl, $C_{1-3}$ alkylene-NHC(O)$C_{1-6}$ alkyl, $C_{1-3}$ alkylene-NHC(O)O$C_{1-6}$ alkyl, C(O)OH, O$C_{1-3}$ alkyl, and $C_{3-5}$ cycloalkyl; or wherein the thiazolidinyl, 3,4-dihydro-2H-pyranyl, tetrahydropyranyl, morpholinyl, or thiomorpholinyl is optionally substituted with 2 substituents on the same ring carbon, which together with the carbon atom to which they are attached, form a monocyclic 5- to 7-membered heterocycloalkyl;

wherein the pyrrolyl, imidazolyl, oxazolyl, thiazolyl, or pyridinyl is optionally substituted with 1, 2, or 3 substituents independently selected from the group consisting of CN, $C_{1-6}$ alkyl, $C_{1-3}$ alkylene-NHC(O)$C_{1-6}$ alkyl, $C_{1-3}$ alkylene-NHC(O)O$C_{1-6}$ alkyl, C(O)OH, O$C_{1-3}$ alkyl, and $C_{3-5}$ cycloalkyl;

wherein each $C_{1-6}$ alkyl substituent is optionally and independently substituted with 1, 2, or 3 substituents independently selected from the group consisting of F, $CF_3$, and OH; and wherein each O$C_{1-3}$ alkyl substituent is optionally and independently substituted with 1, 2, or 3 substituents independently selected from the group consisting of F and $CF_3$.

17. The compound according to claim 16, or a pharmaceutically acceptable salt or stereoisomer thereof, wherein $R^7$ is thiazolidinyl, 3,4-dihydro-2H-pyranyl, tetrahydropyranyl, morpholinyl, thiomorpholinyl, pyrrolyl, imidazolyl, oxazolyl, thiazolyl, or pyridinyl;

wherein the thiazolidinyl, 3,4-dihydro-2H-pyranyl, tetrahydropyranyl, morpholinyl, or thiomorpholinyl is optionally substituted with 1, 2, or 3 substituents independently selected from the group consisting of CN, $CH_3$, $CH_2NHC(O)OC(CH_3)_3$, $CH_2OH$, $CH_2CH_3$, $CH_2CF_3$, $CH_2CH_2NHC(O)CH_3$, $CH_2CH_2OH$, $CH_2CH_2CH_3$, C(O)OH, $OCH_3$, and cyclopropyl; or wherein the thiazolidinyl, 3,4-dihydro-2H-pyranyl, tetrahydropyranyl, morpholinyl, or thiomorpholinyl is optionally substituted with 2 substituents on the same ring carbon, which together with the carbon atom to which they are attached, form a tetrahydropyranyl; and wherein the pyrrolyl, imidazolyl, oxazolyl, thiazolyl, or pyridinyl is optionally substituted with 1, 2, or 3 substituents independently selected from the group consisting of CN, $CH_3$, $CH_2NHC(O)OC(CH_3)_3$, $CH_2OH$, $CH_2CH_3$, $CH_2CF_3$, $CH_2CH_2NHC(O)CH_3$, $CH_2CH_2OH$, $CH_2CH_2CH_3$, C(O)OH, $OCH_3$, and cyclopropyl.

18. The compound according to claim 1, or a pharmaceutically acceptable salt or stereoisomer thereof, wherein $R^7$ is $NR^{10}R^{11}$.

19. The compound according to claim 1, or a pharmaceutically acceptable salt or stereoisomer thereof, wherein:

(i) each $R^8$ is independently H; and
each $R^9$ is independently H; or (ii) each R is independently $CH_3$; and
each $R^9$ is independently $CH_3$.

20. The compound according to claim 1, or a pharmaceutically acceptable salt or stereoisomer thereof, wherein $R^{10}$ is $CH_3$, $CH_2CH_3$, or $CH_2CH_2CH_3$.

21. The compound according to claim 1, or a pharmaceutically acceptable salt or stereoisomer thereof, wherein $R^{11}$ is $CH_2CH_3$, $CH_2CHF_2$, $CH_2CH_2OCH_2CH_3$, $CH_2CH_2CH_3$, or $(CH_2)_nR^{12}$.

22. The compound according to claim 1, or a pharmaceutically acceptable salt or stereoisomer thereof, wherein $R^{12}$ is cyclopropyl, tetrahydrofuranyl, isoxazolyl, oxadiazolyl, pyridinyl, or pyrazinyl.

23. The compound according to claim 1, or a stereoisomer thereof, wherein the compound, or stereoisomer thereof, is:

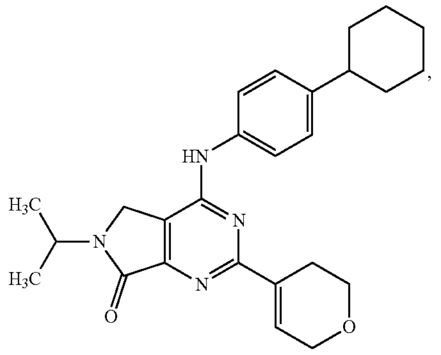 [SMILES: CC(C)N1Cc2c(Nc3ccc(C4CCCCC4)cc3)nc(C3=CCOCC3)nc2C1=O]

or a pharmaceutically acceptable salt thereof.

24. The compound according to claim 1, or a stereoisomer thereof, wherein the compound, or stereoisomer thereof, is:

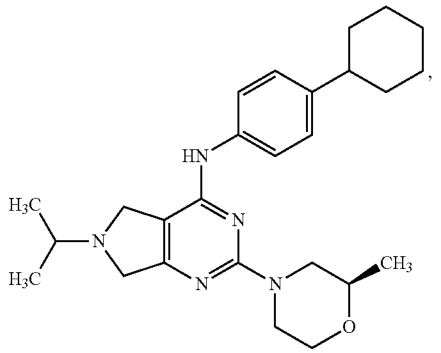 [SMILES: CC(C)N1Cc2nc(N3CCO[C@H](C)C3)nc(Nc3ccc(C4CCCCC4)cc3)c2C1]

or a pharmaceutically acceptable salt thereof.

25. The compound according to claim 1, or a stereoisomer thereof, wherein the compound, or stereoisomer thereof, is:

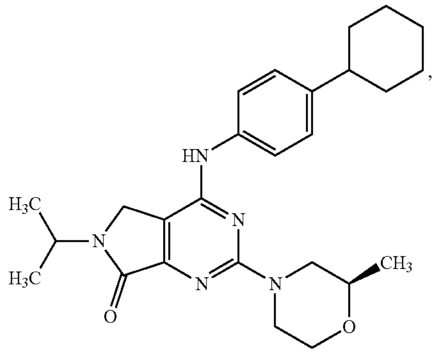 [SMILES: CC(C)N1Cc2c(Nc3ccc(C4CCCCC4)cc3)nc(N3CCO[C@H](C)C3)nc2C1=O]

or a pharmaceutically acceptable salt thereof.

26. The compound according to claim 1, or a stereoisomer thereof, wherein the compound, or stereoisomer thereof, is:

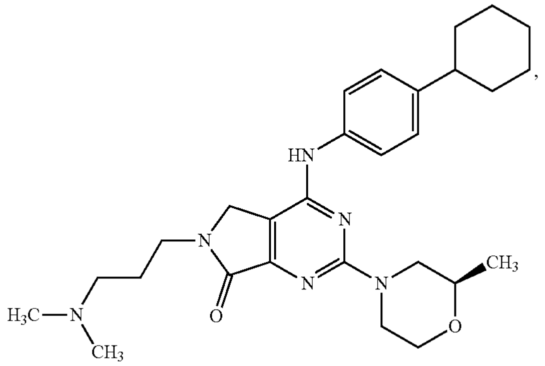 [SMILES: C[C@@H]1CN(c2nc(Nc3ccc(C4CCCCC4)cc3)c3c(n2)C(=O)N(CCCN(C)C)C3)CCO1]

or a pharmaceutically acceptable salt thereof.

27. The compound according to claim 1, or a stereoisomer thereof, wherein the compound, or stereoisomer thereof, is:

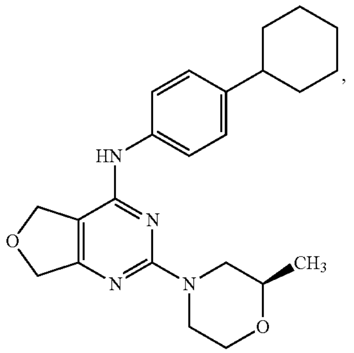 [SMILES: C[C@@H]1CN(c2nc3c(c(Nc4ccc(C5CCCCC5)cc4)n2)COC3)CCO1]

or a pharmaceutically acceptable salt thereof.

28. The compound according to claim 1, or a stereoisomer thereof, wherein the compound, or stereoisomer thereof, is:

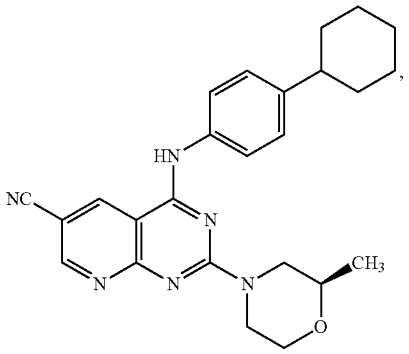 [SMILES: C[C@@H]1CN(c2nc(Nc3ccc(C4CCCCC4)cc3)c3cc(C#N)cnc3n2)CCO1]

or a pharmaceutically acceptable salt thereof.

29. The compound according to claim 1, or a stereoisomer thereof, wherein the compound, or stereoisomer thereof, is:

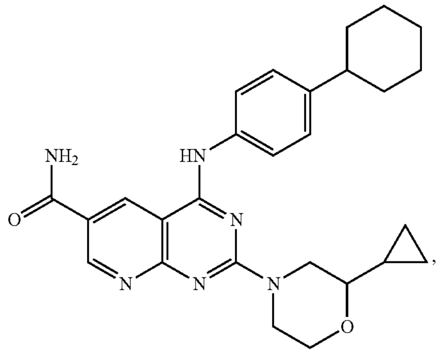 [SMILES: NC(=O)c1cnc2nc(N3CCOC(C4CC4)C3)nc(Nc3ccc(C4CCCCC4)cc3)c2c1]

or a pharmaceutically acceptable salt thereof.

30. The compound according to claim 1, or a stereoisomer thereof, wherein the compound, or stereoisomer thereof, is:

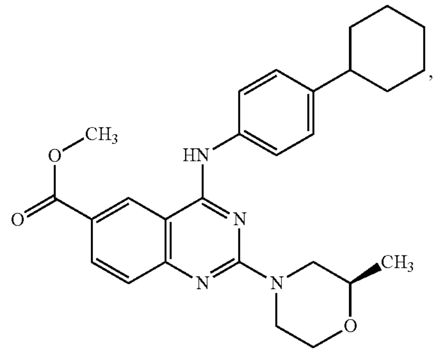 [SMILES: COC(=O)c1ccc2nc(N3CCO[C@H](C)C3)nc(Nc3ccc(C4CCCCC4)cc3)c2c1]

or a pharmaceutically acceptable salt thereof.

31. A pharmaceutical composition comprising at least one pharmaceutically acceptable excipient and a compound according to claim 1, or a pharmaceutically acceptable salt or stereoisomer thereof.

32. A method for treating a neurological disorder in a patient in need thereof, wherein the method comprises administering to the patient a therapeutically effective amount of a compound according to claim 1, or a pharmaceutically acceptable salt or stereoisomer thereof.

33. The method according to claim 32, wherein the neurological disorder is selected from the group consisting of amyotrophic lateral sclerosis, anxiety, an autism spectrum disorder, cognition, epilepsy, and pain.

34. A method for treating epilepsy in a patient in need thereof, wherein the method comprises administering to the patient a therapeutically effective amount of a compound according to claim 1, or a pharmaceutically acceptable salt or stereoisomer thereof.

35. A compound selected from the group consisting of:

2-(diethylamino)-6-(propan-2-yl)-4-{[4-(propan-2-yl) phenyl]amino}-5,6-dihydro-7H-pyrrolo[3,4-d]pyrimidin-7-one;

4-[(4-cyclohexylphenyl)amino]-2-(2-cyclopropylmorpholin-4-yl)-6-(propan-2-yl)-5,6-dihydro-7H-pyrrolo[3,4-d]pyrimidin-7-one;

6-(propan-2-yl)-4-{[4-(propan-2-yl)phenyl]amino}-2-(1,3-thiazolidin-3-yl)-5,6-dihydro-7H-pyrrolo[3,4-d]pyrimidin-7-one;

2-[(2R,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one;

6-(propan-2-yl)-4-{[4-(propan-2-yl)phenyl]amino}-2-(thiomorpholin-4-yl)-5,6-dihydro-7H-pyrrolo[3,4-d]pyrimidin-7-one;

2-[(2S)-2-methylmorpholin-4-yl]-6-(propan-2-yl)-4-{[4-(propan-2-yl)phenyl]amino}-5,6-dihydro-7H-pyrrolo[3,4-d]pyrimidin-7-one;

2-[(2R)-2-methylmorpholin-4-yl]-6-(propan-2-yl)-4-{[4-(propan-2-yl)phenyl]amino}-5,6-dihydro-7H-pyrrolo[3,4-d]pyrimidin-7-one;

2-[(2S,6S)-2,6-dimethylmorpholin-4-yl]-6-(propan-2-yl)-4-{[4-(propan-2-yl)phenyl]amino}-5,6-dihydro-7H-pyrrolo[3,4-d]pyrimidin-7-one;

2-(3-methylmorpholin-4-yl)-6-(propan-2-yl)-4-{[4-(propan-2-yl)phenyl]amino}-5,6-dihydro-7H-pyrrolo[3,4-d]pyrimidin-7-one;

2-(2-cyclopropylmorpholin-4-yl)-6-(propan-2-yl)-4-{[4-(propan-2-yl)phenyl]amino}-5,6-dihydro-7H-pyrrolo[3,4-d]pyrimidin-7-one;

4-[(4-cyclohexylphenyl)amino]-2-(morpholin-4-yl)-6-(propan-2-yl)-5,6-dihydro-7H-pyrrolo[3,4-d]pyrimidin-7-one;

4-[(4-cyclohexylphenyl)amino]-2-(2-methylmorpholin-4-yl)-6-(propan-2-yl)-5,6-dihydro-7H-pyrrolo[3,4-d]pyrimidin-7-one;

4-[(4-cyclohexylphenyl)amino]-2-[(2R)-2-methylmorpholin-4-yl]-6-(propan-2-yl)-5,6-dihydro-7H-pyrrolo[3,4-d]pyrimidin-7-one;

4-[(4-cyclohexylphenyl)amino]-2-((2R)-cyclopropylmorpholin-4-yl)-6-(propan-2-yl)-5,6-dihydro-7H-pyrrolo[3,4-d]pyrimidin-7-one;

4-[(4-cyclohexylphenyl)amino]-2-((2S)-cyclopropylmorpholin-4-yl)-6-(propan-2-yl)-5,6-dihydro-7H-pyrrolo[3,4-d]pyrimidin-7-one;

4-[(4-cyclohexylphenyl)amino]-6-(propan-2-yl)-2-[2-(2,2,2-trifluoroethyl) morpholin-4-yl]-5,6-dihydro-7H-pyrrolo[3,4-d]pyrimidin-7-one;

tert-butyl {(2R)-4-{4-[(4-cyclohexylphenyl)amino]-7-oxo-6-(propan-2-yl)-6,7-dihydro-5H-pyrrolo[3,4-d]pyrimidin-2-yl}morpholin-2-yl]methyl}carbamate;

4-[(4-cyclohexylphenyl)amino]-6-(propan-2-yl)-2-[2-(propan-2-yl) morpholin-4-yl]-5,6-dihydro-7H-pyrrolo[3,4-d]pyrimidin-7-one;

4-[(4-cyclohexylphenyl)amino]-6-(propan-2-yl)-2-(1,3-thiazolidin-3-yl)-5,6-dihydro-7H-pyrrolo[3,4-d]pyrimidin-7-one;

4-[(4-cyclohexylphenyl)amino]-2-[(2-ethoxyethyl)(methyl)amino]-6-(propan-2-yl)-5,6-dihydro-1H-pyrrolo[3,4-d]pyrimidin-7-one;

4-[(4-cyclohexylphenyl)amino]-2-(2-ethylmorpholin-4-yl)-6-(propan-2-yl)-5,6-dihydro-7H-pyrrolo[3,4-d]pyrimidin-7-one;

4-[(4-cyclohexylphenyl)amino]-2-{methyl[(1,2-oxazol-3-yl)methyl]amino}-6-(propan-2-yl)-5,6-dihydro-7H-pyrrolo[3,4-d]pyrimidin-7-one;

4-[(4-cyclohexylphenyl)amino]-2-{methyl[2-(1,2,4-oxadiazol-3-yl)ethyl]amino}-6-(propan-2-yl)-5,6-dihydro-7H-pyrrolo[3,4-d]pyrimidin-7-one;

4-[(4-cyclohexylphenyl)amino]-2-(1,4-oxazepan-4-yl)-6-(propan-2-yl)-5,6-dihydro-7H-pyrrolo[3,4-d]pyrimidin-7-one;

4-[(4-cyclohexylphenyl)amino]-2-(1,9-dioxa-4-azaspiro[5.5]undecan-4-yl)-6-(propan-2-yl)-5,6-dihydro-7H-pyrrolo[3,4-d]pyrimidin-7-one;

4-[(4-cyclohexylphenyl)amino]-2-(3-methoxypyrrolidin-1-yl)-6-(propan-2-yl)-5,6-dihydro-7H-pyrrolo[3,4-d]pyrimidin-7-one;

4-[(4-cyclohexylphenyl)amino]-2-[2-(2-hydroxyethyl)morpholin-4-yl]-6-(propan-2-yl)-5,6-dihydro-7H-pyrrolo[3,4-d]pyrimidin-7-one;

4-[(4-cyclohexylphenyl)amino]-2-(dipropylamino)-6-(propan-2-yl)-5,6-dihydro-7H-pyrrolo[3,4-d]pyrimidin-7-one;

4-[(4-cyclohexylphenyl)amino]-2-[(cyclopropylmethyl)(methyl)amino]-6-(propan-2-yl)-5,6-dihydro-7H-pyrrolo[3,4-d]pyrimidin-7-one;

4-[(4-cyclohexylphenyl)amino]-2-[2-(hydroxymethyl)morpholin-4-yl]-6-(propan-2-yl)-5,6-dihydro-7H-pyrrolo[3,4-d]pyrimidin-7-one;

4-[(4-cyclohexylphenyl)amino]-2-[3-(hydroxymethyl)morpholin-4-yl]-6-(propan-2-yl)-5,6-dihydro-7H-pyrrolo[3,4-d]pyrimidin-7-one;

4-[(4-cyclohexylphenyl)amino]-2-{methyl[(pyrazin-2-yl)methyl]amino}-6-(propan-2-yl)-5,6-dihydro-7H-pyrrolo[3,4-d]pyrimidin-7-one;

4-[(4-cyclohexylphenyl)amino]-2-(diethylamino)-6-(propan-2-yl)-5,6-dihydro-7H-pyrrolo[3,4-d]pyrimidin-7-one;

4-[(4-cyclohexylphenyl)amino]-2-{methyl[(oxolan-2-yl)methyl]amino}-6-(propan-2-yl)-5,6-dihydro-7H-pyrrolo[3,4-d]pyrimidin-7-one;

4-[(4-cyclohexylphenyl)amino]-2-[(2,2-difluoroethyl)(methyl)amino]-6-(propan-2-yl)-5,6-dihydro-7H-pyrrolo[3,4-d]pyrimidin-7-one;

4-[(4-cyclohexylphenyl)amino]-2-(methyl[2-(pyridin-2-yl)ethyl]amino)-6-(propan-2-yl)-5,6-dihydro-1H-pyrrolo[3,4-d]pyrimidin-7-one;

(3S)-4-{4-[(4-cyclohexylphenyl)amino]-7-oxo-6-(propan-2-yl)-6,7-dihydro-5H-pyrrolo[3,4-d]pyrimidin-2-yl}morpholine-3-carboxylic acid;

N-[2-(4-{4-[(4-cyclohexylphenyl)amino]-7-oxo-6-(propan-2-yl)-6,7-dihydro-5H-pyrrolo[3,4-d]pyrimidin-2-yl}morpholin-2-yl)ethyl]acetamide;

6-(propan-2-yl)-4-{[4-(propan-2-yl)phenyl]amino}-2-(pyridin-4-yl)-5,6-dihydro-7H-pyrrolo[3,4-d]pyrimidin-7-one;

4-{4-[(4-cyclohexylphenyl)amino]-7-oxo-6-(propan-2-yl)-6,7-dihydro-5H-pyrrolo[3,4-d]pyrimidin-2-yl}pyridine-2-carbonitrile;

4-[(4-cyclohexylphenyl)amino]-2-(2-cyclopropylpyridin-4-yl)-6-(propan-2-yl)-5,6-dihydro-7H-pyrrolo[3,4-d]pyrimidin-7-one;

4-[(4-cyclohexylphenyl)amino]-2-(2-methoxypyridin-4-yl)-6-(propan-2-yl)-5,6-dihydro-7H-pyrrolo[3,4-d]pyrimidin-7-one;

4-[(4-cyclohexylphenyl)amino]-2-(2-methylpyridin-4-yl)-6-(propan-2-yl)-5,6-dihydro-7H-pyrrolo[3,4-d]pyrimidin-7-one;

4-[(4-cyclohexylphenyl)amino]-2-(3,6-dihydro-2H-pyran-4-yl)-6-(propan-2-yl)-5,6-dihydro-7H-pyrrolo[3,4-d]pyrimidin-7-one;

4-[(4-cyclohexylphenyl)amino]-6-(propan-2-yl)-2-(pyridin-4-yl)-5,6-dihydro-7H-pyrrolo[3,4-d]pyrimidin-7-one;

4-[(4-cyclohexylphenyl)amino]-2-(1-methyl-1H-pyrazol-4-yl)-6-(propan-2-yl)-5,6-dihydro-7H-pyrrolo[3,4-d]pyrimidin-7-one;

4-[(4-cyclohexylphenyl)amino]-2-(1,3-oxazol-5-yl)-6-(propan-2-yl)-5,6-dihydro-7H-pyrrolo[3,4-d]pyrimidin-7-one;

4-[(4-cyclohexylphenyl)amino]-6-(propan-2-yl)-2-(1,3-thiazol-S-yl)-5,6-dihydro-7H-pyrrolo[3,4-d]pyrimidin-7-one;

2-(3,6-dihydro-2H-pyran-4-yl)-6-(propan-2-yl)-4-[[4-(propan-2-yl)phenyl]amino]-5,6-dihydro-7H-pyrrolo[3,4-d]pyrimidin-7-one;

4-{[4-(4-fluorophenoxy)phenyl]amino}-2-[(2R)-2-methylmorpholin-4-yl]-6-(propan-2-yl)-5,6-dihydro-7H-pyrrolo[3,4-d]pyrimidin-7-one;

2-(2-cyclopropylmorpholin-4-yl)-4-({4'-[(hept-6-yn-1-yl)oxy][1,1'-biphenyl]-4-yl}amino)-6-(propan-2-yl)-5,6-dihydro-7H-pyrrolo[3,4-d]pyrimidin-7-one;

2-(2-cyclopropylmorpholin-4-yl)-4-{[4'-(heptyloxy)[1,1'-biphenyl]-4-yl]amino}-6-(propan-2-yl)-5,6-dihydro-7H-pyrrolo[3,4-d]pyrimidin-7-one;

4-[(4'-{2-[3-(but-3-yn-1-yl)-3H-diaziren-3-yl]ethoxy}[1,1'-biphenyl]-4-yl)amino]-2-(2-cyclopropyl-morpholin-4-yl)-6-(propan-2-yl)-5,6-dihydro-7H-pyrrolo[3,4-d]pyrimidin-7-one;

2-[(2R)-2-methylmorpholin-4-yl]-4-[(4-pentylphenyl)amino]-6-(propan-2-yl)-5,6-dihydro-7H-pyrrolo[3,4-d]pyrimidin-7-one;

4-{[4-(butan-2-yl)phenyl]amino}-2-[(2R)-2-methylmorpholin-4-yl]-6-(propan-2-yl)-5,6-dihydro-7H-pyrrolo[3,4-d]pyrimidin-7-one;

4-{[4-(benzyloxy)phenyl]amino}-2-[(2R)-2-methylmorpholin-4-yl]-6-(propan-2-yl)-5,6-dihydro-7H-pyrrolo[3,4-d]pyrimidin-7-one;

2-(2-cyclopropylmorpholin-4-yl)-4-{[4-(pentafluoroethyl)phenyl]amino}-6-(propan-2-yl)-5,6-dihydro-7H-pyrrolo[3,4-d]pyrimidin-7-one;

2-(2-cyclopropylmorpholin-4-yl)-6-(propan-2-yl)-4-[(4-propylphenyl)amino]-5,6-dihydro-7H-pyrrolo[3,4-d]pyrimidin-7-one;

2-[(2R)-2-methylmorpholin-4-yl]-6-(propan-2-yl)-4-[(4-propylphenyl)amino]-5,6-dihydro-7H-pyrrolo[3,4-d]pyrimidin-7-one;

2-[(2R)-2-methylmorpholin-4-yl]-4-{[4-(pentafluoroethyl)phenyl]amino}-6-(propan-2-yl)-5,6-dihydro-7H-pyrrolo[3,4-d]pyrimidin-7-one;

2-(2-cyclopropylmorpholin-4-yl)-6-(propan-2-yl)-4-({4-[(propan-2-yl)oxy]phenyl}amino)-5,6-dihydro-7H-pyrrolo[3,4-d]pyrimidin-7-one;

4-[(4-cyclobutylphenyl)amino]-2-(morpholin-4-yl)-6-(propan-2-yl)-5,6-dihydro-7H-pyrrolo[3,4-d]pyrimidin-7-one;

4-{[4-(cyclopentyloxy)phenyl]amino}-2-[(2R)-2-methylmorpholin-4-yl]-6-(propan-2-yl)-5,6-dihydro-7H-pyrrolo[3,4-d]pyrimidin-7-one;

2-[(2R)-2-methylmorpholin-4-yl]-6-(propan-2-yl)-4-{[4-(2,2,2-trifluoroethyl)phenyl]amino}-5,6-dihydro-7H-pyrrolo[3,4-d]pyrimidin-7-one;

tert-butyl {2-[(4'-{[2-(2-cyclopropylmorpholin-4-yl)-7-oxo-6-(propan-2-yl)-6,7-dihydro-5H-pyrrolo[3,4-d]pyrimidin-4-yl]amino}[1,1'-biphenyl]-4-yl)oxy]ethyl}carbamate;

6-ethyl-2-[(2R)-2-methylmorpholin-4-yl]-4-{[4-(propan-2-yl)phenyl]amino}-5,6-dihydro-7H-pyrrolo[3,4-d]pyrimidin-7-one;

4-[(4-cyclohexylphenyl)amino]-6-ethyl-2-[(2R)-2-methylmorpholin-4-yl]-5,6-dihydro-7H-pyrrolo[3,4-d]pyrimidin-7-one;

tert-butyl {2-[(4'-{[2-(morpholin-4-yl)-7-oxo-6-(propan-2-yl)-6,7-dihydro-5H-pyrrolo[3,4-d]pyrimidin-4-yl]amino}[1,1'-biphenyl]-4-yl)oxy]ethyl}carbamate;

4-[(4'-{2-[3-(but-3-yn-1-yl)-3H-diaziren-3-yl]ethoxy}[1,1'-biphenyl]-4-yl)amino]-2-(morpholin-4-yl)-6-(propan-2-yl)-5,6-dihydro-7H-pyrrolo[3,4-d]pyrimidin-7-one;

2-(morpholin-4-yl)-6-(propan-2-yl)-4-({4'-[(prop-2-yn-1-yl)oxy][1,1'-biphenyl]-4-yl}amino)-5,6-dihydro-7H-pyrrolo[3,4-d]pyrimidin-7-one;

4-[(4-cyclohexylphenyl)amino]-6-[3-(dimethylamino)propyl]-2-[(2R)-2-methylmorpholin-4-yl]-5,6-dihydro-7H-pyrrolo[3,4-d]pyrimidin-7-one;

4-[(4-cyclohexylphenyl)amino]-6-[2-(dimethylamino)ethyl]-2-[(2R)-2-methylmorpholin-4-yl]-5,6-dihydro-7H-pyrrolo[3,4-d]pyrimidin-7-one;

4-[(4-cyclobutylphenyl)amino]-6-[3-(dimethylamino)propyl]-2-[(2R)-2-methylmorpholin-4-yl]-5,6-dihydro-7H-pyrrolo[3,4-d]pyrimidin-7-one;

4-[(4-cyclobutylphenyl)amino]-6-[2-(dimethylamino)ethyl]-2-[(2R)-2-methylmorpholin-4-yl]-5,6-dihydro-7H-pyrrolo[3,4-d]pyrimidin-7-one;

2-(morpholin-4-yl)-4-{[4-(propan-2-yl)phenyl]amino}-6-(prop-2-yn-1-yl)-5,6-dihydro-7H-pyrrolo[3,4-d]pyrimidin-7-one;

4-[(4-cyclohexylphenyl)amino]-2-(oxan-4-yl)-6-(propan-2-yl)-5,6-dihydro-7H-pyrrolo[3,4-d]pyrimidin-7-one;

4-[(4-cyclohexylphenyl)amino]-2-(1H-imidazol-1-yl)-6-(propan-2-yl)-5,6-dihydro-7H-pyrrolo[3,4-d]pyrimidin-7-one;

2-(3,6-dihydro-2H-pyran-4-yl)-4-[(2'-methyl[1,1'-biphenyl]-4-yl)amino]-6-(propan-2-yl)-5,6-dihydro-7H-pyrrolo[3,4-d]pyrimidin-7-one;

4-[(4'-{2-[3-(but-3-yn-1-yl)-3H-diaziren-3-yl]ethoxy}[1,1'-biphenyl]-4-yl)amino]-2-(3,6-dihydro-2H-pyran-4-yl)-6-(propan-2-yl)-5,6-dihydro-7H-pyrrolo[3,4-d]pyrimidin-7-one;

2-(3,6-dihydro-2H-pyran-4-yl)-4-[(2-fluoro[1,1'-biphenyl]-4-yl)amino]-6-(propan-2-yl)-5,6-dihydro-7H-pyrrolo[3,4-d]pyrimidin-7-one;

2-(morpholin-4-yl)-4-{[4-(pentafluoroethyl)phenyl]amino}-6-(propan-2-yl)-5,6-dihydro-7H-pyrrolo[3,4-d]pyrimidin-7-one;

4-[(2-fluoro[1,1'-biphenyl]-4-yl)amino]-2-(morpholin-4-yl)-6-(propan-2-yl)-5,6-dihydro-7H-pyrrolo[3,4-d]pyrimidin-7-one;

4-[(3',4'-dichloro[1,1'-biphenyl]-4-yl)amino]-2-(morpholin-4-yl)-6-(propan-2-yl)-5,6-dihydro-7H-pyrrolo[3,4-d]pyrimidin-7-one;

2-(morpholin-4-yl)-6-(propan-2-yl)-4-{[4-(propan-2-yl)phenyl]amino}-5,6-dihydro-7H-pyrrolo[3,4-d]pyrimidin-7-one;

4-[(4-tert-butylphenyl)amino]-2-(morpholin-4-yl)-6-(propan-2-yl)-5,6-dihydro-7H-pyrrolo[3,4-d]pyrimidin-7-one;

4-[(2-methyl[1,1'-biphenyl]-4-yl)amino]-2-(morpholin-4-yl)-6-(propan-2-yl)-5,6-dihydro-7H-pyrrolo[3,4-d]pyrimidin-7-one;

4-[(4'-chloro[1,1'-biphenyl]-4-yl)amino]-2-(morpholin-4-yl)-6-(propan-2-yl)-5,6-dihydro-7H-pyrrolo[3,4-d]pyrimidin-7-one;

N-(4-cyclohexylphenyl)-2-[(2R)-2-methylmorpholin-4-yl]-5,7-dihydrofuro[3,4-d]pyrimidin-4-amine;

N-(4-cyclobutylphenyl)-2-(3,6-dihydro-2H-pyran-4-yl)-5,7-dihydrofuro[3,4-d]pyrimidin-4-amine;

N-(4-cyclohexylphenyl)-2-(2-cyclopropylmorpholin-4-yl)-5,7-dihydrofuro[3,4-d]pyrimidin-4-amine;

2-(2-cyclopropylmorpholin-4-yl)-N-[4'-(heptyloxy)[1,1'-biphenyl]-4-yl]-5,7-dihydrofuro[3,4-d]pyrimidin-4-amine;

2-[(2R)-2-methylmorpholin-4-yl]-N-{4'-[(6,6,6-trifluorohexyl)oxy][1,1'-biphenyl]-4-yl}-5,7-dihydrofuro[3,4-d]pyrimidin-4-amine;

N-(4-cyclohexylphenyl)-2-(2-methylpyridin-4-yl)-5,7-dihydrofuro[3,4-d]pyrimidin-4-amine;

N-(4-cyclohexylphenyl)-2-[(2R)-2-methylmorpholin-4-yl]pyrido[2,3-d]pyrimidin-4-amine;

6-bromo-N-(4-cyclohexylphenyl)-2-[(2R)-2-methylmorpholin-4-yl]pyrido[2,3-d]pyrimidin-4-amine;

N-(4-cyclohexylphenyl)-2-(3,6-dihydro-2H-pyran-4-yl)pyrido[2,3-d]pyrimidin-4-amine;

N-(4-cyclohexylphenyl)-2-[(2R)-2-methylmorpholin-4-yl]-8-oxo-8lambda~5~-pyrido[2,3-d]pyrimidin-4-amine;

N-(4-cyclohexylphenyl)-6-ethyl-2-[(2R)-2-methylmorpholin-4-yl]pyrido[2,3-d]pyrimidin-4-amine;

4-[(4-cyclohexylphenyl)amino]-2-[(2R)-2-methylmorpholin-4-yl]pyrido[2,3-d]pyrimidine-6-carbonitrile;

methyl 4-[(4-cyclohexylphenyl)amino]-2-[(2R)-2-methylmorpholin-4-yl]pyrido[2,3-d]pyrimidine-6-carboxylate;

4-[(4-cyclohexylphenyl)amino]-2-[(2R)-2-methylmorpholin-4-yl]pyrido[2,3-d]pyrimidine-6-carboxylic acid;

4-[(4-cyclohexylphenyl)amino]-2-[(2R)-2-methylmorpholin-4-yl]pyrido[2,3-d]pyrimidine-6-carboxamide;

4-[(4-cyclohexylphenyl)amino]-2-(2-cyclopropylmorpholin-4-yl)pyrido[2,3-d]pyrimidine-6-carboxamide;

N-(4-cyclohexylphenyl)-6-methoxy-2-[(2R)-2-methylmorpholin-4-yl]pyrido[2,3-d]pyrimidin-4-amine;

N-{4-[(4-cyclohexylphenyl)amino]-2-[(2R)-2-methylmorpholin-4-yl]pyrido[2,3-d']pyrimidin-6-yl}acetamide;

N-4-(4-cyclohexylphenyl)-2-[(2R)-2-methylmorpholin-4-yl]pyrido[2,3-d]pyrimidine-4,6-diamine;

N-(4-cyclohexylphenyl)-2-(morpholin-4-yl)-6-(propan-2-yl)-6,7-dihydro-5H-pyrrolo[3,4-d]pyrimidin-4-amine;

N-(4-cyclohexylphenyl)-2-[(2R)-2-methylmorpholin-4-yl]-6-(propan-2-yl)-6,7-dihydro-5H-pyrrolo[3,4-d]pyrimidin-4-amine;

2-{4-[4-cyclohexylphenyl)amino]-2-(3,6-dihydro-2H-pyran-4-yl)-5,7-dihydro-6H-pyrrolo[3,4-d]pyrimidin-6-yl}-N,N-dimethylacetamide;

N-(4-cyclohexylphenyl)-2-(2-cyclopropylmorpholin-4-yl)-6-(1-methylpiperidin-4-yl)-6,7-dihydro-5H-pyrrolo[3,4-d]pyrimidin-4-amine;

2-(morpholin-4-yl)-6-(propan-2-yl)-4-{[4-(thiophen-2-yl)phenyl]amino}-5,6-dihydro-7H-pyrrolo[3,4-d]pyrimidin-7-one; and 2-(morpholin-4-yl)-6-(propan-2-yl)-4-{[4-(thiophen-3-yl)phenyl]amino}-5,6-dihydro-7H-pyrrolo[3,4-d]pyrimidin-7-one, or a pharmaceutically acceptable salt thereof.

* * * * *